United States Patent
Kriesel et al.

(10) Patent No.: US 8,110,679 B2
(45) Date of Patent: Feb. 7, 2012

(54) NANOFILM AND MEMBRANE COMPOSITIONS

(75) Inventors: Joshua W. Kriesel, San Francisco, CA (US); Timothy B. Karpishin, Castro Valley, CA (US); Donald B. Bivin, Oakland, CA (US); Grant Merrill, San Francisco, CA (US); Martin S. Edelstein, Foster City, CA (US); Thomas H. Smith, San Carlos, CA (US); Jeffery A. Whiteford, Belmont, CA (US); Robert T. Jonas, Palo Alto, CA (US); Mark Micklatcher, Hayward, CA (US); Serena Joshi, San Jose, CA (US)

(73) Assignee: Covalent Partners LLC, Burlingame, CA (US)

( * ) Notice: Subject to any disclaimer, the term of this patent is extended or adjusted under 35 U.S.C. 154(b) by 860 days.

(21) Appl. No.: 12/183,469

(22) Filed: Jul. 31, 2008
(Under 37 CFR 1.47)

(65) Prior Publication Data

US 2009/0114596 A1   May 7, 2009

Related U.S. Application Data

(63) Continuation of application No. 10/359,894, filed on Feb. 7, 2003, now Pat. No. 7,432,371, and a continuation-in-part of application No. 10/226,400, filed on Aug. 23, 2002, now abandoned, which is a continuation-in-part of application No. 10/071,377, filed on Feb. 7, 2002, now abandoned.

(60) Provisional application No. 60/383,236, filed on May 22, 2002.

(51) Int. Cl.
*C07D 291/00* (2006.01)

(52) U.S. Cl. ........ 540/474; 540/460; 540/467; 540/471; 544/238; 544/294; 544/333; 502/64; 210/636

(58) Field of Classification Search .................. 540/474, 540/460, 467, 471; 544/238, 294, 333; 502/64; 210/636
See application file for complete search history.

(56) References Cited

U.S. PATENT DOCUMENTS 3,847,949 A   11/1974   Pedersen et al.
(Continued)

FOREIGN PATENT DOCUMENTS

DE   40 35 378   5/1992
(Continued)

OTHER PUBLICATIONS

Fuhrhop J.-H.et al., "A Macrocylic Tetraether Bolaamphiphilic and an Oligoamino Dicarboxylate Combine to Form Monolayered, Porous Vesicle Membranes, Which are Reversibily Sealed by EDTA and Other Bulky Anions," J. Am. Chem. Soc., vol. 110, pp. 6840-6845, (1988).*

(Continued)

*Primary Examiner* — Peter D. Mulcahy
*Assistant Examiner* — Henry Hu
(74) *Attorney, Agent, or Firm* — Finnegan, Henderson, Farabow, Garrett & Dunner, LLP

(57) ABSTRACT

Nanofilms useful for filtration are prepared from oriented amphiphilic molecules and oriented macrocyclic modules. The amphiphilic species may be oriented on an interface or surface. The nanofilm may be prepared by depositing or attaching an oriented layer to a substrate. A nanofilm may also be prepared by coupling the oriented macrocyclic modules to provide a membrane.

44 Claims, 19 Drawing Sheets

U.S. PATENT DOCUMENTS

| | | | |
|---|---|---|---|
| 4,031,111 | A | 6/1977 | Pedersen et al. |
| 4,438,251 | A | 3/1984 | Herweh |
| 4,554,076 | A | 11/1985 | Speaker |
| 4,828,917 | A | 5/1989 | Wegner et al. |
| 4,948,506 | A | 8/1990 | Lonsdale et al. |
| 5,059,510 | A | 10/1991 | Jones, Jr. et al. |
| 5,143,784 | A | 9/1992 | Mita |
| 5,196,257 | A | 3/1993 | Barraud et al. |
| 5,342,934 | A | 8/1994 | Still et al. |
| 5,357,029 | A | 10/1994 | Takekoshi et al. |
| 5,384,168 | A | 1/1995 | Dübal et al. |
| 5,405,550 | A | 4/1995 | Michl et al. |
| 5,405,552 | A | 4/1995 | Jüngbauer et al. |
| 5,447,635 | A * | 9/1995 | Viscardi et al. ............... 210/636 |
| 5,622,945 | A | 4/1997 | Sessler et al. |
| 5,702,777 | A | 12/1997 | Rösch et al. |
| 5,831,087 | A | 11/1998 | Haubs et al. |
| 5,876,830 | A | 3/1999 | Michl et al. |
| 5,883,246 | A | 3/1999 | Brückner et al. |
| 6,033,773 | A | 3/2000 | Yang et al. |
| 6,045,821 | A | 4/2000 | Garrity et al. |
| 6,210,551 | B1 | 4/2001 | Osman et al. |
| 6,262,257 | B1 | 7/2001 | Gale et al. |
| 6,326,215 | B1 * | 12/2001 | Keen .............................. 436/518 |
| 6,380,347 | B1 | 4/2002 | Lau et al. |
| 7,368,564 | B2 * | 5/2008 | Whiteford et al. ............ 540/145 |
| 7,491,669 | B2 * | 2/2009 | Johnson et al. ................. 502/64 |
| 7,595,368 | B2 * | 9/2009 | Kriesel et al. ................. 526/201 |
| 2002/0026047 | A1 | 2/2002 | Gale et al. |
| 2003/0199688 | A1 | 10/2003 | Kriesel et al. |
| 2004/0034223 | A1 | 2/2004 | Karpishin et al. |
| 2004/0106741 | A1 | 6/2004 | Kriesel et al. |
| 2004/0260085 | A1 | 12/2004 | Kriesel et al. |
| 2005/0154199 | A1 | 7/2005 | Whiteford et al. |
| 2006/0041077 | A1 | 2/2006 | Kriesel et al. |
| 2006/0128680 | A1 | 6/2006 | Kriesel et al. |
| 2006/0270846 | A1 | 11/2006 | Karpishin et al. |

FOREIGN PATENT DOCUMENTS

| | | |
|---|---|---|
| DE | 196 36 337 A1 | 3/1998 |
| DE | 196 46 537 A1 | 5/1998 |
| DE | 197 11 078 | 9/1998 |
| SU | 1139730 | 2/1985 |
| SU | 1139731 | 2/1985 |
| SU | 1266849 | 10/1986 |
| SU | 1532560 | 12/1989 |
| WO | WO 92/12708 | 8/1992 |
| WO | WO 95/11449 | 4/1995 |
| WO | WO 96/39402 | 12/1996 |
| WO | WO 97/37995 | 10/1997 |
| WO | WO 99/51570 | 10/1999 |
| WO | WO 03/066646 A1 | 8/2003 |
| WO | WO 03/067286 A1 | 8/2003 |
| WO | WO-03/067286 A2 * | 8/2003 |

OTHER PUBLICATIONS

Markowitz et al. "Perforated Monolayers: Design and Synthesis of Porous and Cohesive Monorayers From Mercurated Calix[n]arenes," J, Am. Chem, Soc. 111(21): 8192-8200 (1989).*

Akine et al., "Synthesis and Crystal Structure of a Novel Triangular Macrocyclic Molecule, Tris(H2saloph), and its Water Complex," *Tetrahedron Letters* 42:8861-8864 (2001).

Alston et al., "Second Sphere Coordination of Tetraammineplatinum(II) by a Macropolycyclic Crown Ether Bisamide Receptor," *Angew. Chem. Int. Ed Engl.* 26(7):692-693 (1987).

Arslanov, V.V., "Monolayers and Langmuir-Blodgett Films of Monomers and Polymers Polyreactions, Structural Transformations, Properties and Applications," *Advances in Colloid and Interface Science* 40:307-370 (1992).

Asfari et al., "Synthesis and Properties of Double-Calix[4]arenes, Doubly-Crowned Calix[4]arenes, and Double-Calix-Crowns," *Pure & Appl. Chem.* 65(3):585-590 (1993).

Baguley et al., "Heterocyclic Imines and Amines. Part VIII. Identification of "o-Cyanothiobenzamide" as 1-Imino-3-Thioisoindoline, and its Conversion With Amines Into Macrocycles and Intermediates," *The Journal of the Chemical Society* Part I: 709-719 (1957).

Belanger et al., "Chloroplast Biogenesis—47:Spectroscopic Study of Net Spectral Shifts Induced by Axial Ligand Coordination in Metalated Tetrapyrroles," *Spectrochim. Acta*, 40A(9):807-827 (1984).

Böhmer V., "Calixarenes, Macrocycles With (Almost) Unlimited Possibilities," *Angew Chem. Eng. Int*. Ed. 34(7):713-745 (1995).

Busch et al., "Molecular Template Effect: Historical View, Principles, and Perspectives" Chapter 1 *In Compr. Supramol. Chem*. Atwood, J.L. et al. eds. *Elsevier Science Inc.*: New York, NY 9:1-43 (1996).

Chadim et al., "(3+3)-Cyclocondensation of the Enantiopure and Racemic Forms of Trans-1, 2-Diaminocyclohexane with Terephthaldehyde. Formation of Diasteromeric Molecular Triangles and Their Stereoselective Solid-State Stacking into Microporous Chiral Columns," *Tetrahedron: Asymmetry* 12:127-133 (2001).

Conner et al., "Perforated Monolayers," *Advanced Materials* 6(11):872-874 (1994).

Conner et al., "Perforated Monolayers: Fabrication of Calix[6]arene-Based Composite Membranes That Function as Molecular Sieves," *Langmuir* 9:2389-2397 (1993).

Dutta et al., "Stoichiometric and Metal-Deficient Copper (II) Complexes of a Dinucleating Macrocyclic Ligand. Structural Studies," *Inorg. Chem*. 37(19):5029-5032 (1998).

Endo et al., "Synthesis of Novel Peptidomimetics, Cyclic Hexamers of Unnatural Amino Acids, 2,5-Disubstituted 3-Aminobenzoic Acids," *Heterocycles* 51(2):337-344 (1999).

Gawronski et al., "Designing Large Triangular Chiral Macrocycles Efficient [3+3] Diamine-Dialdehyde Condensations Based on Conformational Bias," *J. Org. Chem*. 65:5768-5773 (2000).

Hendel et al., "Assembly and Disassembly of Langmuir-Blodgett Films on Poly[1-(trimethylsilyl)-1-Propyne]:The Uniqueness of Calix[6]arene Multilayers as Permeation-Selective Membranes," *J. Am. Chem. Soc*. 119(29):6909-6918 (1997).

Hendel et al., "Extraordinary Cohesiveness of a Boronic Acid-Based Calix[6]arene Monolayer at the Air-Water Interface," *Langmuir* 12(23):5745-5746 (1996).

Hendel et al., "Insight Into The Fabrication Of Highly Permselective Polymer/Surfactant Composite Membranes," *Polymeric Materials Science and Engineering (PMSE) Proceedings of the American Chemical Society, Division of Polymeric Materials, Science and Engineering*, (Sep. 8-11, 1997) Las Vegas: NV 77:318-319 (1997).

Höger et al., "High-Yield Macrocyclization via Glaser Coupling of Temporary Covalent Templated Bisacetylenes," *J. Org. Chem*. 62:4556-4557 (1997).

Höger et al., "Shape-Persistent Macrocycles: Building Blocks for Comply Organic and Polymeric Architectures," *Macromol. Symp*. 177:185-191 (2002).

Höger et al., "Solvent Triggering Between Conformational States in Amphiphilec Shape-Persistent Macrocycles," *JACS*. 124(23):6734-6736 (2002).

Höger et al., "Template-Direoted Synthesis of Shape-persistent Macrocyclic Amphiphiles with Convergently Arranged Functionalities," *Chem. Eur. J*. 5(6):1686-1691 (1999).

Höger S., "Highly Efficient Template-Based Preparation of Shape-Persistent Macrocyclics," *Macromol. Symp*. 142:185-191 (1999).

Holliday et al., "Strategies for the Construction of Supramolecular Compounds Through Coordination Chemistry," *Angew. Chem. Int. Ed*. 40(11):2022-2043 (2001).

Hosokawa et al., "8,16,24,32,40,48-Hexamethoxy[$2_6$]Metacyclophane-1,9,17,25,33,41-Hexayne: A Novel Near Planar Ammonium-Selective Ionophore," *Chem. Commun*. 1948-1949 (2001).

Ishida et al., "Molecular. Design and Synthesis of Artifical Ion Channels Based on Cyclic Peptides Containing Unnatural Amino Acids," *J. Org. Chem*. 66(9):2978-2989 (2001).

Ito et al., "Syntheses of Chiral Homoazacalix[4]arenes Incorporating Amino Acid Residues: Molecular Recognition for Racemic Quaternary Ammonium Ions," *J. Org. Chem*. 67(21):7519-7522 (2002).

Kanamathareddy et al., "Conformational Characteristics of p-tert-Butylcalix[6]arene Ethers," *J. Org. Chem*., 59:3871-3879 (1994).

Kim et al., "$CaCl_3$ or $Ca_2Cl_4$ Complexing Cyclic Aromatic Amide. Template Effect on Cyclization," *J. Am. Chem. Soc*. 118(6):1545-1546 (1996).

Kim et al., "Pyrene-Armed Calix[4]azacrowns as New Fluorescent Ionophores: "Molecular Taekowndo" Process via-Fluorescence Change," *J. Org. Chem.* 67:2348-2351 (2002).

Kon et al., "Synthesis of Macrocyclic Cage Compounds by Diamine-Dihalide One-Step Coupling-Reaction," *J. Org. Chem.* 65:3708-3715 (2000).

Korupoju et al., Formation of Dinuclear Macrocyclic and Mononuclear Acyclic Complexes of a New Trinucleating Hexaaza Triphenoiic Schiff Base Macrocycle: Structure and NLO Properties, *J. Chem. Soc. Dalton Trans.* pp. 2845-2852 (2000).

Korupoju et al., "New Optically Active Hexaaza Triphenolic Macrocycles: Synthesis, Molecular Structure and Crystal Packing Features," *Chemical Communications* 12:1267-1268 (1998).

Korupoju et al., "Synthesis, Structure, and DNA Cleavage Activity of New Trinuclear $Zn_3$ and $Zn_2Cu$ Complexes of a Chiral Macrocycle: Structural Correlation with the Active Center of P1 Nuclease" *Inorganic Chemistry* 41:(6)4099-4101 (2002).

Kraft et al., "Regioselective Synthesis of Calixcrowns Derived From p-tert-Butylcalix[5]arene," *Tetrahedron* 49(27):6019-6024 (1993).

Kuhnert et al., "Synthesis of Novel Chiral Non-Racemic Substituted Trianglimine and Trianglamine Macrocycles," *Tetrahedron Letters* 43:3329-3332 (2002).

Kuhnert et al., "Synthesis of Novel Enantiomerically Pure Trianglimine and Trianglamine Macrocycles," *Tetrahedron: Asymmetry* 13:123-128 (2002).

Kuroda et al., "Syntheses and Redox Behavior of Novel Cyclic Hosts Having Multiple Redox Centers of NAD+ Analogue," *Tetrahedron Letters* 38:3939-3942 (1997).

Kwit et al., "Chiral Calixsalen-Type Macrocycles From *trans*-1,2-diaminocyclohexane," *Tetrahedron: Asymmetry* 14:1303-1308 (2003).

Lee et al., "Membrane Composites Derived from Porous Versus Nonporous Surfactants: Evidence for Uniqueness of Calix[6]arene-Based Surfactants," *J. Am. Chem. Soc.* 117(25):6793-6794 (1995).

Lee et al., "Unusual Pressure Effects on the Permeation Properties of a Langmuir-Blodgett Composite Membrane," *J. Am. Chem. Soc.* 117(42)10599-10600 (1995).

Li et al., "Synthesis and Characterization of 'Calixsalens': A New Class of Macrocyclic Chiral Ligands," *Chem. Commun.* pp. 1531-1532 (1999).

Lin et al., "Hydrogen-Bond-Assisted π-Stacking of Shape-Persistent Cyclopbanes," *J. Org. Chem.* 67(21):7761-7768 (2002).

Markowitz et al., "Perforated Monolayers: Design and Synthesis of Porous and Cohesive Monolayers From Mercurated Calix[*n*]arenes," *J. Am. Chem. Soc.* 111(21):8192-8200 (1989).

Markowitz et al., "Perforated Monolayers: Porous and Cohesive Monolayers from Mercurated Calix[6]arenes," *J. Am. Chem. Soc.* 110:7545-7546 (1988).

Mohanta et al., "Macrocydic $Cu^{II}_2$, $Cu^{II}_4$, $Ni^{II}_3$, and $Ni^{II}_4$ Complexes: Magnetic Properties of Tetranuclear Systems," *Inorg. Chem.* 36(21):4656-4664 (1997).

Molina et al., "A Generalized and Efficient Preparation of a Novel Class of Macrocyclic Bis(guanidines) From Cyclic Bis(carbodiimides)," *J. Org.Chem.* 63:2922-2927 (1998).

Morrison et al., "Shape-Persistent Macrocyclic Amphiphiles: Molecular Reversible Coats," *Chem Commun.* 20:2313-2314 (1996).

Murakami et al., "Supramolecutar Effects and Molecular Discrimination by Macrocyclic Hosts Embedded in Synthetic Bilayer Membranes," *Proc. Natl. Acad. Sci. USA* 90:1140-1145 (1993).

Nakamoto et al., Langmuir Monolayers of *p*-Octadecylcalix[4]arene, *American Chemical Society*, 5(4):1116-17 (1989).

Notti et al., "Calix[4]-and Calix[5]arene-Based Multicavity Macrocyles," *J. Org. Chem.* 67(21):7569-7572 (2002).

O'Connor et al., "Calixarenes in Electroanalysis," *Electroanalysis* 7(3):205-215 (1995).

Perrin et al., "Industrial Applications of Calixarenes," *In Calixarenes: A Versatile Class of Macrocyclic Compounds*, Vicens, J. et al. eds, 3:235-259 (1991).

Pigge et al., "An Enaminone-Directed Benzannulation/Macrocyclization Approach to Cyclophane Ring Systems," *J. Org. Chem.* 67(13):4547-4552 (2002).

Qian et al., "Spectroscopic Studies of the Multiporphyrin Arrays at the Air-Water Interface and in Langmuir-Blodgett Films," *Thin Solid Film* 397:266-275 (2001).

Rajca et al., "Biphenylene dimer. Molecular fragment of a two-dimensional carbon net and double-stranded polymer," *J. Am. Chem. Soc.*, 118:7272-7279 (1996).

Ruaudel-Teixier A., "Supermolecutar Architecture in Langmuir-Blodgett Films: Control and Chemistry," *Heterogeneous Chemistry Reviews*. 3:1-15 (1996).

Rudkevich et al., "Calix[4]arene Salenes: A Bifunctional Receptor for $NaH_2PO_4$," *J.Org. Chem.* 59(13):3683-3686 (1994).

Schrader et al., "Towards Synthetic Adrenaline Receptors," *Materials Science & Engineering*, C18:147-155 (2001).

Shetty et al., "Assembly of Amphiphilic Phenylacetylene Macrocycles at the Air-Water Interface and on Solid Surfaces," *J. Am. Chem. Soc.* 118(39):9409-9414 (1996).

Timmerman et al., "A Novel Type of Stereoisomerism in Calix[4]arene-Based Carceplexes," *Angew. Chem.* 33(22):2345-2348 (1994).

Tsukruk V.V., "Assembly of Supramolecular Polymers in Ultrathin Films," *Prog. Polym. Sci.* 22(2):247-311 (1997).

Van der Heyden et al., "Probing Inter- and Intramolecular Interactions of Six New *p-tert*-Butylcalix[4]arene-Based Bipyridyl Podands with Langmuir Monolayers," *Langmuir* 18:8854-8861 (2002).

van Nostrum et al., "Supramolecular Architectures From Phthalocyanine Building Blocks," *Polym. Prepr.* 34(1):164-165 (1993).

van Nostrum et al., "Supramolecular Architectures From Phthalocyanine Building Blocks," *Macromol. Symp.* 77:267-276 (1994).

Wilkop et al., "Smart Structures for Sensing Environmental Pollution," *Proceedings of SPIE-The International Society for Optical Engineering(Smart Electronics and MEMS)*, Mar. 1-3, 1999 Newport Beach, CA 3673:327-334 (1999).

Yan et al., "Selective Dampening of the Gas Permeability of a Langmuir-Blodgett Film Using Moist Permeants," *J. Am. Chem. Soc.* 122:11944-11947 (2002).

Yatsimirskii et al., "Interphase Transport of Iron (III) Chloride by Means of Macrocyclic Ligands," *Theoretical and Experimental Chemistry* 22(10):162-167 with Table of Contents, *A translation of the article published in Teoreticheskaya I Ekspermental' naya Khimiya* (Jan.-Feb. 1986) 22(1):174-180 (1986).

Yoshino et al., "An Artificial Ion Channel Formed by a Macrocyclic Resorcin[4]arene With Amphiphilic Cholic Acid Ether Groups," *Angew. Chem. Int. Ed. Engl.* 40(2):457-459 (2001).

Zhao et al., "Synthesis and Self-Association of an Imine-Containing *m*-Phenylene Ethynylene Macrocycle," *J. Org. Chem.* 67(11):3548-3554 (2002).

Foreign language article, "Macrocyclic Compounds with Selective Molecular Recognition Functions and Application Thereto," f(1):85-8 (1991).

Foreign language article, "Calixarene-A macrocyclic Compound with Bright Prospect," *Chemical Research and Application*, 2(2):8-21 (1990).

Foreign language article, "Synthesis and Application of Calix[4]pyrrole Macrocyclic Compounds," *Hecheng Huaxue*, 9(5):436-438 (2001).

International Search Report mailed Dec. 18, 2003, issued in PCT Application No. PCT/US03/03830.

International Search Report mailed Feb. 23, 2004, issued in PCT Application No. PCT/US03/03829.

International Search Report mailed Jul. 6, 2005, issued in PCT Application No. PCT/US03/22749.

Supplementary European Search Report mailed May 13, 2005, in European Patent Application No. 03709017.2-1211.

Supplementary European Search Report mailed May 13, 2005, in European Patent Application No. 03709018.0-1211.

Office Action mailed Jan. 23, 2004, in U.S. Appl. No. 10/071,377, filed Feb. 7, 2002.

Office Action mailed Jul. 6, 2004, in U.S. Appl. No. 10/071,377, filed Feb. 7, 2002.

Office Action mailed Apr. 18, 2005, in U.S. Appl. No. 10/071,377, filed Feb. 7, 2002.

Office Action mailed Jan. 23, 2004, in U.S. Appl. No. 10/226,400, filed Aug. 23, 2002.
Office Action mailed Jul. 6, 2004, in U.S. Appl. No. 10/226,400, filed Aug. 23, 2002.
Office Action mailed Apr. 7, 2005, in U.S. Appl. No. 10/226,400, filed Aug. 23, 2002.
Office Action mailed Dec. 19, 2005, in U.S. Appl. No. 10/359,894, filed Feb. 7, 2003.
Office Action mailed Sep. 27, 2006, in U.S. Appl. No. 10/359,894, filed Feb. 7, 2003.
Office Action mailed May 4, 2007, in U.S. Appl. No. 10/359,894, filed Feb. 7, 2003.
Advisory Action mailed Oct. 3, 2007, in U.S. Appl. No. 10/359,894, filed Feb. 7, 2003.
Notice of Allowance mailed Apr. 30, 2008, in U.S. Appl. No. 10/359,894, filed Feb. 7, 2003.
Office Action mailed Dec. 23, 2004, in U.S. Appl. No. 10/426,475, filed Apr. 29, 2003.
Office Action mailed Mar. 10, 2005, in U.S. Appl. No. 10/426,475, filed Apr. 29, 2003.
Office Action mailed Nov. 9, 2006, in U.S. Appl. No. 10/913,634, filed Aug. 6, 2004.
Office Action mailed Mar. 29, 2007, in U.S. Appl. No. 10/913,634, filed Aug. 6, 2004.
Notice of Allowance mailed Dec. 27, 2007, in U.S. Appl. No. 10/913,634, filed Aug. 6, 2004.
Office Action mailed Feb. 11, 2008, in U.S. Appl. No. 11/199,913, filed Aug. 8, 2005.
Office Action mailed Oct. 10, 2008, in U.S. Appl. No. 11/199,913, filed Aug. 8, 2005.
Office Action mailed Aug. 2, 2007, in U.S. Appl. No. 11/207,383, filed Aug. 18, 2005.
Office Action mailed Feb. 11, 2008, in U.S. Appl. No. 11/207,383, filed Aug. 18, 2005.
Office Action mailed Sep. 26, 2008, in U.S. Appl. No. 11/207,383, filed Aug. 18, 2005.
Office Action mailed Jan. 12, 2006, in U.S. Appl. No. 11/202,322, filed Aug. 10, 2005.
Office Action mailed Jun. 21, 2006, in U.S. Appl. No. 11/202,322, filed Aug. 10, 2005.
Office Action mailed Oct. 12, 2006, in U.S. Appl. No. 11/202,322, filed Aug. 10, 2005.
Office Action mailed Jan. 16, 2007, in U.S. Appl. No. 11/202,322, filed Aug. 10, 2005.
Office Action mailed May 16, 2007, in U.S. Appl. No. 11/202,322, filed Aug. 10, 2005.
Office Action mailed Jan. 11, 2008, in U.S. Appl. No. 11/202,322, filed Aug. 10, 2005.
Office Action mailed Aug. 25, 2008, in U.S. Appl. No. 11/202,322, filed Aug. 10, 2005.
EPO Examination Report mailed Aug. 24, 2009, issued in European Patent Application No. 03709017.2.
Capuzzi et al., "Counterion Complexation of Calixarene Ligands in Monolayers and Micellar Solutions," *Colloids and Surfaces A: Physicochem. Eng. Aspects* 167:105-113 (2000).
Moreira et al., "Spectroscopic Characterization and the Effect of Metal Ions on Langmuir-Blodgett Films of Octasubstituted Calix[4]resorcinarenes," *Langmuir* 11:3137-3144 (1995).
Orthmann et al., "Herstellung ultradünner Schichten mit molekular kontrolliertem Aufbau aus polymeren Phthalocyaninen mit der Langmuir-Blodgett-Technik," *Angew. Chem.* 98:1114-1115 (1986).

* cited by examiner

NANOFILM AND MEMBRANE COMPOSITIONS

CROSS REFERENCE TO RELATED APPLICATIONS

This application is a continuation of U.S. patent application Ser. No. 10/359,894, filed Feb. 7, 2003 now U.S. Pat. No. 7,432,371, which claims benefit of U.S. Provisional Application No. 60/383,236, filed May 22, 2002 and is a continuation-in-part of U.S. patent application Ser. No. 10/226,400, filed Aug. 23, 2002, now abandoned, which is a continuation-in-part of U.S. patent application Ser. No. 10/071,377, filed Feb. 7, 2002, now abandoned. Each of these applications is incorporated herein by reference for all purposes.

TECHNICAL FIELD

This invention relates variously to thin layer compositions of coupled oriented amphiphilic macrocyclic modules, nanofilms having particular permeation properties, and nanofilms for filtration and separation. The thin layer nanofilms may be applied to a variety of selective permeation processes.

BACKGROUND OF THE INVENTION

Nanotechnology involves the ability to engineer novel structures at the atomic and molecular level. One area of nanotechnology is to develop chemical building blocks from which hierarchical molecules of predicted properties can be assembled. An approach to making chemical building blocks or nanostructures begins at the atomic and molecular level by designing and synthesizing starting materials with highly tailored properties. Precise control at the atomic level is the foundation for development of rationally tailored synthesis-structure-property relationships which can provide materials of unique structure and predictable properties. This approach to nanotechnology is inspired by nature. For example, biological organization is based on a hierarchy of structural levels: atoms formed into biological molecules which are arranged into organelles, cells, and ultimately, into organisms. These building block capabilities are unparalleled conventional materials and methods such as polymerizations which produce statistical mixtures or confinement of reactants to enhance certain reaction pathways. For example, from twenty common amino acids found in natural proteins, more than $10^5$ stable and unique proteins are made.

One field that will benefit from nanotechnology is filtration using membranes. Conventional membranes used in a variety of separation processes can be made selectively permeable to various molecular species. The permeation properties of conventional membranes generally depend on the pathways of transport of species through the membrane structure. While the diffusion pathway in conventional selectively permeable materials can be made tortuous in order to control permeation, porosity is not well defined or controlled by conventional methods. The ability to fabricate regular or unique pore structures of membranes is a long-standing goal of separation technology.

Resistance to flow of species through a membrane may also be governed by the flow path length. Resistance can be greatly reduced by using a very thin film as a membrane, at the cost of reduced mechanical strength of the membrane material. Conventional membranes may have a barrier thickness of at least one to two hundred nanometers, and often up to millimeter thickness. In general, a thin film of membrane barrier material can be deposited on a porous substrate of greater thickness to restore material strength.

Membrane separation processes are used to separate components from a fluid in which atomic or molecular components having sizes smaller than a certain "cut-off" size can be separated from components of larger size. Normally, species smaller than the cut-off size are passed by the membrane. The cut-off size may be an approximate empirical value which reflects the phenomenon that the rate of transport of components smaller than the cut-off size is merely faster than the rate of transport of larger components. In conventional pressure-driven membrane separation processes, the primary factors affecting separation of components are size, charge, and diffusivity of the components in the membrane structure. In dialysis, the driving force for separation is a concentration gradient, while in electrodialysis electromotive force is applied to ion selective membranes.

In all these methods what is required is a selectively permeable membrane barrier to components of the fluid to be separated.

SUMMARY OF THE INVENTION

In one aspect, this invention relates to a nanofilm comprising coupled oriented amphiphilic macrocyclic modules. The modules of the nanofilm may be coupled through reactive functional groups of the modules, or may be coupled through a linker molecule. The coupling may be initiated by chemical, thermal, photochemical, electrochemical, or irradiative methods.

In some variations, the thickness of a nanofilm is less than about 30 nanometers, sometimes less than about 4 nanometers, and sometimes less than about 1 nanometer.

A nanofilm may have a filtration function that may be used to describe the species that pass through the nanofilm. A nanofilm may be permeable only to a particular species in a particular fluid and species smaller than the particular species. A nanofilm may have a molecular weight cut-off.

A particular nanofilm may have high permeability for certain species in a certain solvent. A nanofilm may have low permeability for certain species in a certain solvent. A nanofilm may have high permeability for certain species and low permeability for other species in a certain solvent.

A nanofilm barrier can be made up of layers of nanofilm. A spacing layer may be used between any two nanofilm layers. Spacing layers may include layers of polymer, gel, and other substances.

A nanofilm may be deposited on a substrate, which in turn may be porous or non-porous. A nanofilm may have surface attachment groups, and may be covalently bonded to a substrate through surface attachment groups, or bonded to a substrate through ionic interactions.

In another variation, this invention relates to a method for filtration comprising using a nanofilm to separate components or species from a fluid or solution.

In some instances, a nanofilm is composed of oriented macrocyclic modules deposited on a substrate using a Langmuir trough. In other variations, a nanofilm may be made up of coupled oriented amphiphilic molecules and oriented amphiphilic macrocyclic modules.

In one variation, a nanofilm is composed of oriented amphiphilic molecules coupled through a hydrophilic group.

DETAILED DESCRIPTION OF THE INVENTION

Macrocyclic Modules and Nanofilm Compositions

Figures 1A, 1B:
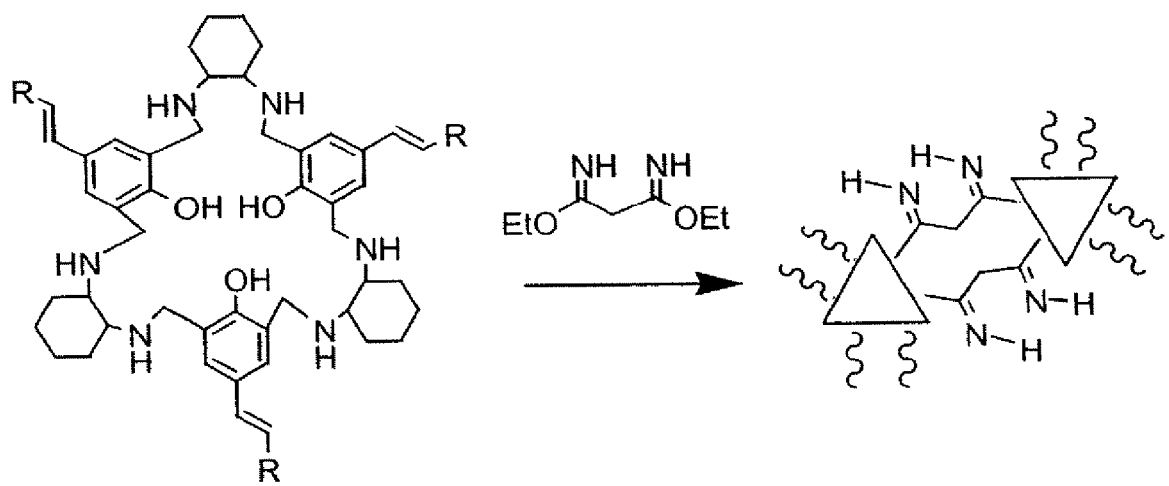
FIG. 1A illustrates a Hexamer 1dh macrocyclic module, which may be reacted with diethyl malonimidate and at least one other macrocyclic module to yield the nanofilm illustrated in FIG. 1B.

In one aspect, this invention relates to nanotechnology in the preparation of porous structures and materials having pores that are of atomic to molecular size. These materials may have unique structures which repeat at regular intervals to provide a lattice of pores having substantially uniform dimensions. The unique structures may have a variety of shapes and sizes, thereby providing pores of various shapes and sizes. Because the unique structures may be formed in a monolayer of molecular thickness, the pores defined by the unique structures may include a cavity, opening, or chamber-like structure of molecular size. In general, pores of atomic to molecular size defined by those unique structures may be used for selective permeation or molecular sieving functions. Some aspects of nanotechnology are given in *Nanostructured Materials*, J. Ying, ed., Academic Press, San Diego, 2001.

This invention further includes the rational design of molecules that may be assembled as building blocks for further assembly into larger species. Standardized molecular subunits or modules may be used from which hierarchical molecules of predicted properties can be assembled. Coupling reactions can be employed to combine or attach modules in directed syntheses.

Nanotechnology involves the assembly of molecular building blocks to form intermediate size hierarchical molecules having built-in directionality. Ideally, a nanoassembly begins with a set of synthons which may be assembled to make a module. Synthons are individual molecules which are the primary starting material. The module may have a set of "arms" destined for interconnection with other modules. Modules are covalently-bonded combinations of synthons. Modules may be used as building blocks for larger molecular species, including uniquely structured species and compositions. A wide variety of real-world applications, such as membranes or porous materials, may be derived from nano-chemical tools, compositions and processes.

Molecular modules may be prepared from cyclic organic synthons. Synthons may be coupled or bonded together to form modules. For example, a macrocyclic module may be prepared with the cyclic organic synthons R,R-1,2-transdiaminocyclohexane and 4-substituted 2,6-diformyl phenol. These synthons may be coupled to form a hexameric macrocyclic module having the following arrangement:

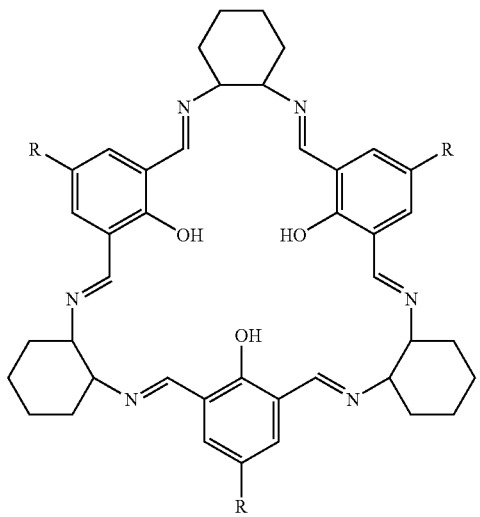

where each R group may be different.

This hexameric module and others are useful as building blocks to provide structures having certain controlled and predictable properties. Macrocyclic modules and amphiphilic macrocyclic modules prepared from cyclic organic synthons are described in U.S. patent application Ser. Nos. 10/071,377 and 10/226,400, and in the PCT Application entitled "Macrocyclic module compositions" filed Feb. 7, 2003, herein incorporated by reference. Examples of synthons, macrocyclic modules, and amphiphilic macrocyclic modules and their syntheses are further described hereinbelow.

Examples of modules useful as building blocks are shown in Table 1.

TABLE 1
Examples of macrocyclic modules
| MODULE | STRUCTURE |
| --- | --- |
| Hexamer 1a | 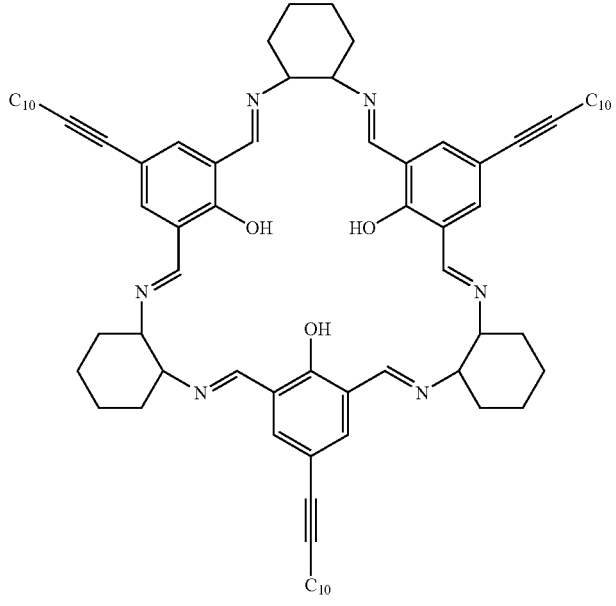 |
| Hexamer 1dh | 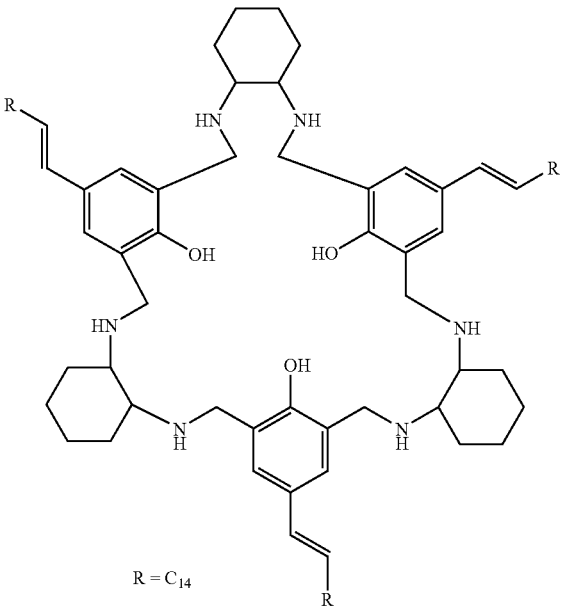 |

TABLE 1-continued
Examples of macrocyclic modules
| MODULE | STRUCTURE |
|---|---|
| Hexamer 3j-amine | 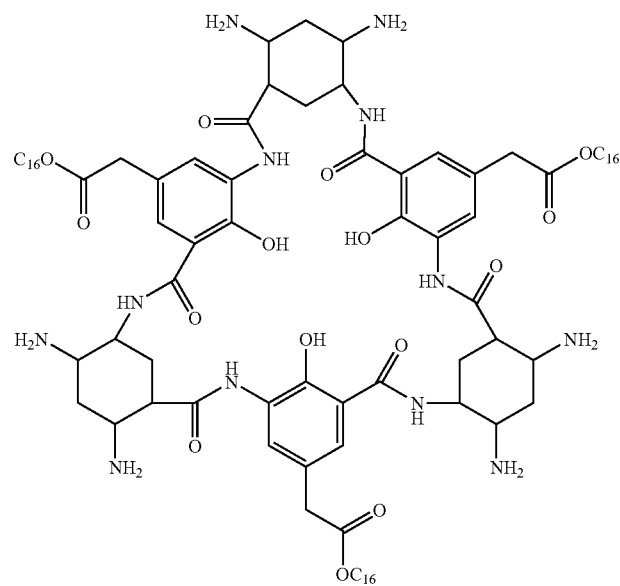 |
| Hexamer 1jh | 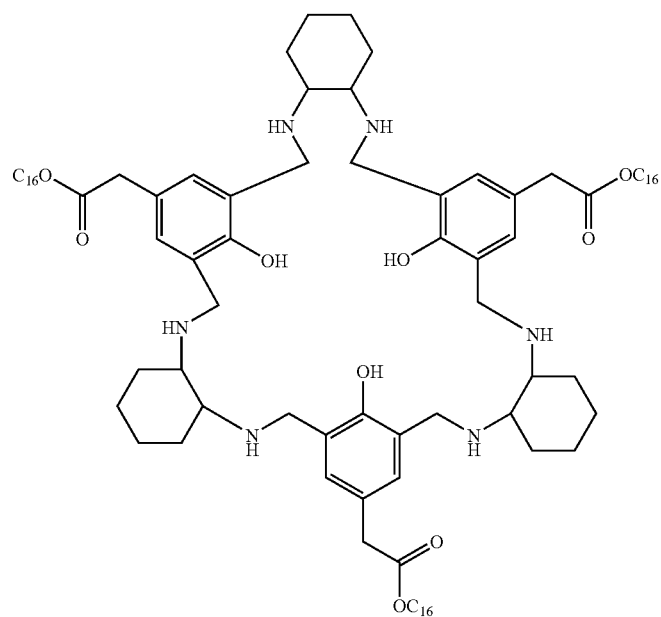 |

TABLE 1-continued
Examples of macrocyclic modules
| MODULE | STRUCTURE |
|---|---|
| Hexamar 1jh-AC | 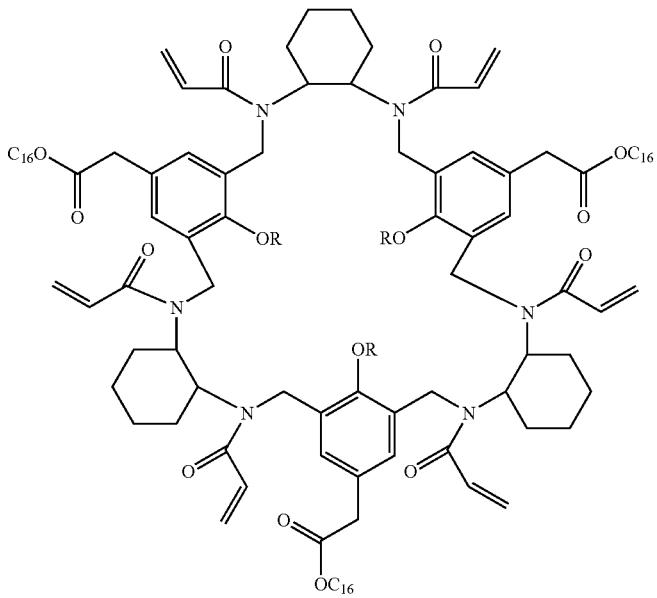<br>Hexamer 1jh-AC |
| Hexamer 2j-amine/ester | 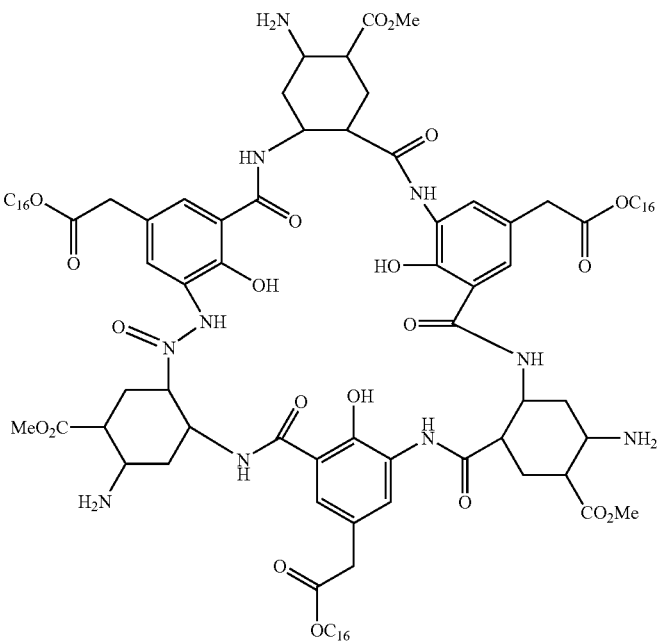 |

TABLE 1-continued
Examples of macrocyclic modules
| MODULE | STRUCTURE |
| --- | --- |
| Hexamer 1dh-acryl | 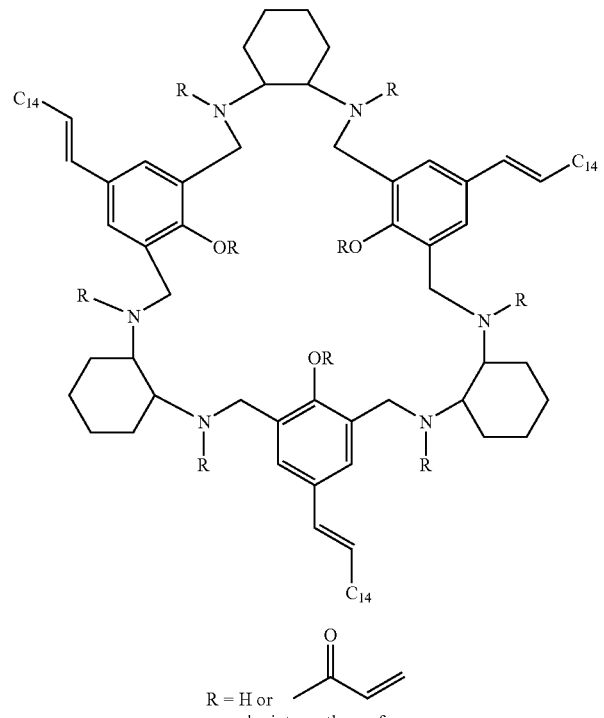 |
| Octamer 5jh-aspartic | 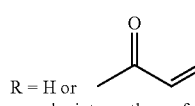 |

TABLE 1-continued

Examples of macrocyclic modules

| MODULE | STRUCTURE |
|---|---|
| Octamer 4jh-acryl | 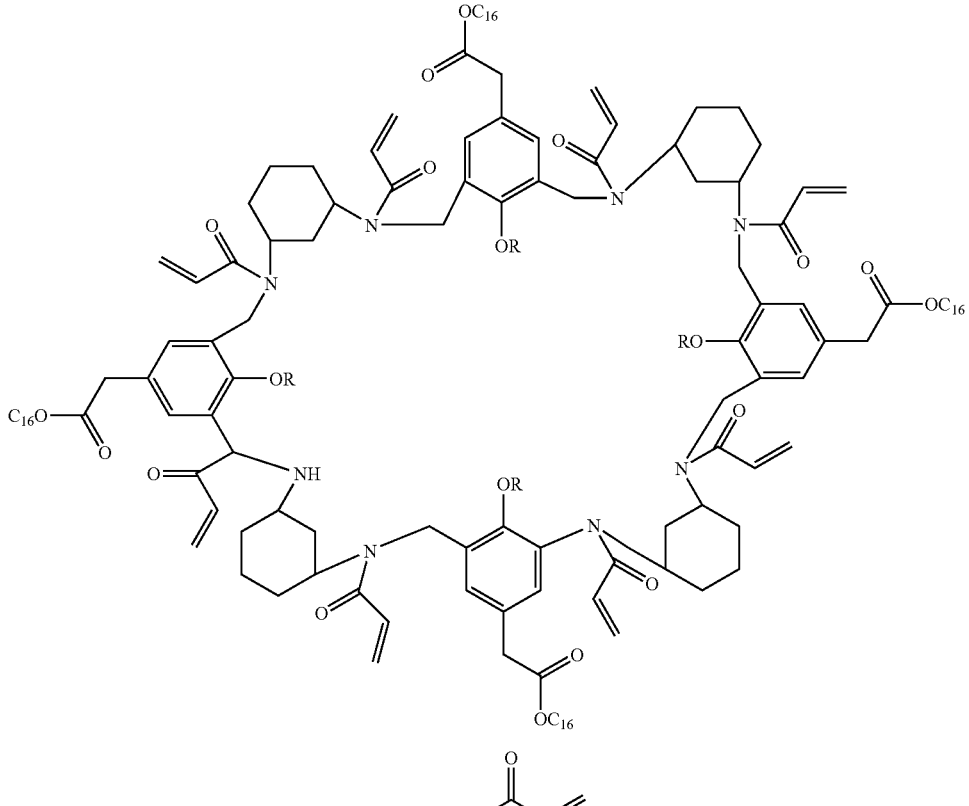 |

R = H or 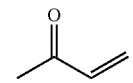
and mixtures there of

Macrocyclic modules can be oriented on a surface by providing functional groups on the modules which impart amphiphilic character to the modules. For example, when the module is deposited on a hydrophilic surface, hydrophobic substituent groups or hydrophobic tails attached to the module may cause the module to reorient on the surface so that the hydrophobic substituents are oriented away from the surface, leaving a more hydrophilic facet of the module oriented toward the surface. Examples of hydrophobic groups include lower alkyl groups, alkyl groups having 7, 8, 9, 10, 11, 12, or more carbon atoms, including alkyl groups with 14-30, or 30 or more carbon atoms, substituted alkyl groups, aryl groups, substituted aryl, saturated or unsaturated cyclic hydrocarbons, heteroaryl, heteroarylalkyl, heterocyclic, and corresponding substituted groups. A hydrophobic group may contain some hydrophilic groups or substituents insofar as the hydrophobic character of the group is not outweighed. In further variations, a hydrophobic group may include substituted silicon atoms, and may include fluorine atoms.

In another instance, hydrophilic groups may be included in the modules to cause orientation of the modules on surfaces. Examples of hydrophilic groups include hydroxyl, methoxy, phenol, carboxylic acids and salts thereof, methyl, ethyl, and vinyl esters of carboxylic acids, amides, amino, cyano, ammonium salts, sulfonium salts, phosphonium salts, polyethylene glycols, epoxy groups, acrylates, sulfonamides, nitro, —OP(O)(OCH$_2$CH$_2$N$^+$RR'R")O$^-$, guanidinium, aminate, acrylamide, pyridinium, piperidine, and combinations thereof, wherein R, R' and R" are each independently selected from H or alkyl.

The conformation of a molecule on a surface may depend on the loading, density, or state of the phase or layer in which the molecule resides on the surface. Surfaces which may be used to orient modules include interfaces such as gas-liquid, air-water, immiscible liquid-liquid, liquid-solid, or gas-solid interfaces. The thickness of the oriented layer may be substantially a monomolecular layer thickness.

A nanofilm is a thin film and may be prepared from macrocyclic modules. A nanofilm may also be prepared from macrocyclic modules in combination with other non-modular molecules. In some instances, a nanofilm may be prepared from non-modular molecules. The modules forming a nanofilm may be deposited on a surface. In some instances, the nanofilm is prepared from coupled modules.

A nanofilm composition may be prepared by orienting amphiphilic macrocyclic modules on a surface. Surface-oriented macrocyclic modules arranged in a nanofilm layer may provide a unique composition. The composition of a nanofilm prepared from surface-oriented macrocyclic modules may be solid, gel, or liquid. The modules of the nanofilm may be in an expanded state, a liquid state, or a liquid-expanded state. The state of the modules of the nanofilm may be condensed, collapsed, or may be a solid phase or close-packed state. The modules of the nanofilm may interact with each other by weak forces of attraction. The modules of a nanofilm prepared from surface-oriented macrocyclic modules need not be linked by any strong interaction or coupling. Alternatively, the modules of the nanofilm may be linked through, for example, covalent bonds or ionic interactions.

As used herein, the term "coupling," with respect to molecular moieties or species, molecules, and modules refers to their attachment or association with other molecular moieties or species, molecules, or modules, whether the attachment or association is specific or non-specific, reversible or non-reversible, is the result of chemical reaction, or the result of direct or indirect physical interactions, weak interactions, or hydrophobic/hydrophilic interactions, or as the result of magnetic, electrostatic, or electromagnetic interaction. Coupling may be specific or non-specific, and the bonds formed by a coupling reaction are often covalent bonds, or polar-covalent bonds, or mixed ionic-covalent bonds, and may sometimes be hydrogen bonds, Van der Waals forces, London forces, ionic or electrostatic forces or interactions, dipole-dipole or dispersive, or other types of binding.

Modules oriented on a surface may be coupled to form a thin layer composition or nanofilm. Surface-oriented modules may be coupled in a two-dimensional array to form a substantially monomolecular layer nanofilm. The two-dimensional array is generally one molecule thick throughout the thin layer composition, and may vary locally due to physical and chemical forces. Coupling of modules may be done to form a substantially two-dimensional thin film by orienting the modules on a surface before or during the process of coupling.

Macrocyclic modules can be prepared to possess reactive functional groups which permit coupling of the modules. The nature of the products formed by coupling modules depends, in one variation, on the relative orientations of the reactive functional groups with respect to the module structure, and in other instances on the arrangement of complementary functional groups on different modules which can form covalent, non-covalent or other binding attachments with each other.

In one variation, a module includes reactive functional groups which couple directly to complementary reactive functional groups of other modules to form linkages between modules. The reactive functional groups may contribute to the amphiphilic character of the module before or after coupling, and may be covalently or non-covalently attached to the modules. The reactive functional groups may be attached to the modules before, during, or after orientation of the modules on the surface.

Examples of reactive functional groups of modules and the linkages formed in coupling modules include those shown in Table 2. Each module may have 1 to 30 or more reactive functional groups often selected to couple to another module.

In making nanofilm from macrocyclic modules and other components, one or more coupling linkages may be formed between macrocyclic modules, and coupling may occur between macrocyclic modules and other components. The linkage formed between macrocyclic modules may be the product of the coupling of one functional group from each macrocyclic module. For example, a hydroxyl group of a first macrocyclic module may couple with an acid group or acid halide group of a second macrocyclic module to form an ester linkage between the two macrocyclic modules. Another example is an imine linkage, —CH=N—, resulting from the reaction of an aldehyde, —CH=O, on one macrocyclic module with an amine, —$NH_2$, on another macrocyclic module. Examples of linkages between macrocyclic modules are shown in Table 2.

TABLE 2

Examples of reactive functional groups of modules

| Functional Group A | Functional Group B | Linkage Formed |
|---|---|---|
| —$NH_2$ | —C(O)H | —N=CH— |
| —$NH_2$ | —$CO_2$H | —NHC(O)— |
| —NHR | —$CO_2$H | —NRC(O)— |
| —OH | —$CO_2$H | —OC(O)— |
| —X | —O Na | —O— |
| —SH | —SH | —S—S— |
| —X | —(NR)Li | —NR— |
| —X | —S Na | —S— |
| —X | —NHR | —NR— |
| —X | —$CH_2$CuLi | —$CH_2$— |
| —X | —$(CRR')_{n=1-6}$CuLi | —$(CRR')_n$— |
| module-X | module-X | module-module |
| —$CH_2$X | —$CH_2$X | —$CH_2CH_2$— |
| —ONa | —C(O)OR | —C(O)O— |
| —SNa | —C(O)OR | —C(O)S— |
| —X | —C≡CH | —C≡C— |
| —C≡CH | —C≡CH | —C≡C—C≡C— |
| —MgX | —C(O)H | —CH(OH)— |
| module-$NH_2$ | module—△(O) (epoxide) | module—CH(OH)—CH$_2$—NH—module |
| module-MgX | module—△(O) (epoxide) | module—CH(OH)—CH$_2$—module |
| module—C(=CH$_2$)— (vinyl, —C(O)H) | module-X | module—C(=CH-module)— |
| —C(O)H | —C(O)H | —HC=CH— |

TABLE 2-continued

Examples of reactive functional groups of modules

| Functional Group A | Functional Group B | Linkage Formed |
|---|---|---|
| $(CH_3)_2C=CH$-module | module-$C(O)Cl$ | (ketone linkage structure) |
| —N=C=O<br>—N=C=O<br>—C(O)H<br>—OH | —$NH_2$<br>HO—<br>—$NHNH_2$<br>—OC(O)X | —NHC(O)NH—<br>—NHC(O)O—<br>—CH=N—NH—<br>—OC(O)O— |
| $(CH_3)_2C=CH$-module | module-SH | (thioether linkage structure) |
| $(CH_3)_2CHC(O)O$-module | module-CH(O) | (ester/hydroxyl linkage structure) |
| module-$CH_2C(O)OH$ | module-$CH_2C(O)OH$ | (diketone/carboxylic linkage structure) |
| module—CH=CH$_2$ | $R_2SiH$-module | module—CH$_2$CH$_2$—Si$R_2$—module |
| module—CH=CH$_2$ | module—CH=CH$_2$ | module—(cyclobutane)—module |
| (module A) CH$_2$=CR— | (module B) CH$_2$=CR— | R,R-cyclobutane with (module A) and (module B) |
| (module A) PhCH=CH— | (module B) PhCH=CH— | Ph,Ph-cyclobutane with (module A) and (module B) |
| —N(—)—C(O)—CH=CH$_2$ | CH$_2$=CH—C(O)—N(—)— | —N(—)—C(O)—(cyclobutane)—C(O)—N(—)— |
| —NH—C(O)—CH=CH$_2$ | CH$_2$=CH—C(O)—NH— | —NH—C(O)—(cyclobutane)—C(O)—NH— |
| —NH—C(O)—C(CH$_3$)=CH$_2$ | CH$_2$=C(CH$_3$)—C(O)—NH— | —NH—C(O)—(dimethyl cyclobutane)—C(O)—NH— |

TABLE 2-continued

Examples of reactive functional groups of modules

| Functional Group A | Functional Group B | Linkage Formed |
|---|---|---|

[Chemical structures showing various functional group combinations and their resulting linkages, including reactions involving —OP(O)(OH)₂ and —OH groups forming —OP(O)(OH)O— linkages, along with multiple structural diagrams depicting amide, ester, and related linkage formations with spacer groups indicated by (...)ₙ where n = 0-5]

In Table 2, R and R' represent hydrogen or alkyl groups, and X is halogen or other good leaving group.

These functional groups may be separated from the module by a spacer group. Examples of spacer groups are alkylene, aryl, acyl, alkoxy, saturated or unsaturated cyclic hydrocarbon, heteroaryl, heteroarylalkyl, or heterocyclic groups, and the corresponding substituted groups. Further examples of spacer groups are polymer, copolymer, or oligomer chains, for example, polyethylene oxides, polypropylene oxides, polysaccharides, polylysines, polypeptides, poly(amino acids), polyvinylpyrrolidones, polyesters, polyacrylates, polyamines, polyimines, polystyrenes, poly(vinyl acetate)s, polytetrafluoroethylenes, polyisoprenes, neopropene, polycarbonate, polyvinylchlorides, polyvinylidene fluorides, polyvinylalcohols, polyurethanes, polyamides, polyimides, polysulfones, polyethersulfones, polysulfonamides, polysulfoxides, and copolymers thereof. Examples of polymer chain spacer structures include linear, branched, comb and dendrimeric polymers, random and block copolymers, homo-and heteropolymers, flexible and rigid chains. The spacer may be any group which does not interfere with formation of the linkage. A spacer group may be substantially longer or shorter than the reactive functional group to which it is attached.

Coupling of surface-oriented modules to each other may occur through coupling of reactive functional groups of the modules to linker molecules. The reactive functional groups involved may be those exemplified in Table 2. Modules may couple to at least one other module through a linker molecule. A linker molecule is a discrete molecular species used to couple at least two modules. Each module may have 1 to 30 or more reactive functional groups which may couple to a linker molecule. Linker molecules may have 1 to 20 or more reactive functional groups which may couple to a module.

In one instance, a linker molecule has at least two reactive functional groups, each of which can couple to a module. In these variations, linker molecules may include a variety of reactive functional groups for coupling modules. Examples of reactive functional groups of modules and linker molecules are illustrated in Table 3.

TABLE 3

Examples of reactive functional groups of modules and linker molecules

| Reactive Functional Group of Module A | Reactive Functional Group of Module B | Linker Molecule | Linkage |
|---|---|---|---|
| —NHR or NH₂ | —NHR or NH₂ | [structure: NH=C(O—)—(CH₂)ₘ—C(=NH)O—] | [structure: NH=C(NH—)—(CH₂)ₘ—C(=NH)NH—] |

TABLE 3-continued

Examples of reactive functional groups of modules and linker molecules

| Reactive Functional Group of Module A | Reactive Functional Group of Module B | Linker Molecule | Linkage |
|---|---|---|---|
| —NHR or NH$_2$ | —NHR or NH$_2$ | [structure] | [structure] |
| —NHR or NH$_2$ | —NHR or NH$_2$ | [structure] | [structure] |
| —NHR or NH$_2$ | —NHR or NH$_2$ | [structure] | [structure] |
| —OH | —OH | [structure] | [structure] |
| —OH | —OH | [structure] | [structure] |
| —OH, —NHR or NH$_2$ | —OH, —NHR or NH$_2$ | (RO)$_2$BR'B(OR)$_2$ (RO)$_2$BR'B(OR)$_2$ | —O(HO)BR'B(OH)O— —NH(HO)BR'B(OH)NH— |
| —OH | —OH | X—(CH$_2$)$_n$—X | —O—(CH$_2$)$_n$—O— |
| —OH | —OH | ClC(O)—(CH$_2$)$_n$—C(O)Cl | [structure] |
| —NHR or NH$_2$ | —NHR or NH$_2$ | [structure] | [structure] |
| —NHR or NH$_2$ | —NHR or NH$_2$ | [structure] | [structure] |
| [structure] | [structure] | [structure] | [structure] |
| [structure] | [structure] | [structure] | [structure] |

TABLE 3-continued

Examples of reactive functional groups of modules and linker molecules

| Reactive Functional Group of Module A | Reactive Functional Group of Module B | Linker Molecule | Linkage |
|---|---|---|---|
| [structure] | [structure] | [structure] | [structure] |
| [structure] | [structure] | [structure] | [structure] |

In Table 3, n=1-6, m=1-10, R=$CH_3$ or H, R'=—$(CH_2)_n$— or Phenyl, R''=—$(CH_2)$—, polyethylene glycol (PEG), or polypropylene glycol (PPG), and X is Br, Cl, I, or other good leaving groups which are organic groups consisting only of carbon, oxygen, nitrogen, halogen, silicon, phosphorous, sulfur, and hydrogen atoms, and having from 1 to 20 carbon atoms. A module may have a combination of the various reactive functional groups exemplified in Table 3.

Methods of initiating coupling of the modules to linker molecules include chemical, thermal, photochemical, electrochemical, and irradiative methods.

Figures 2A, 2B:
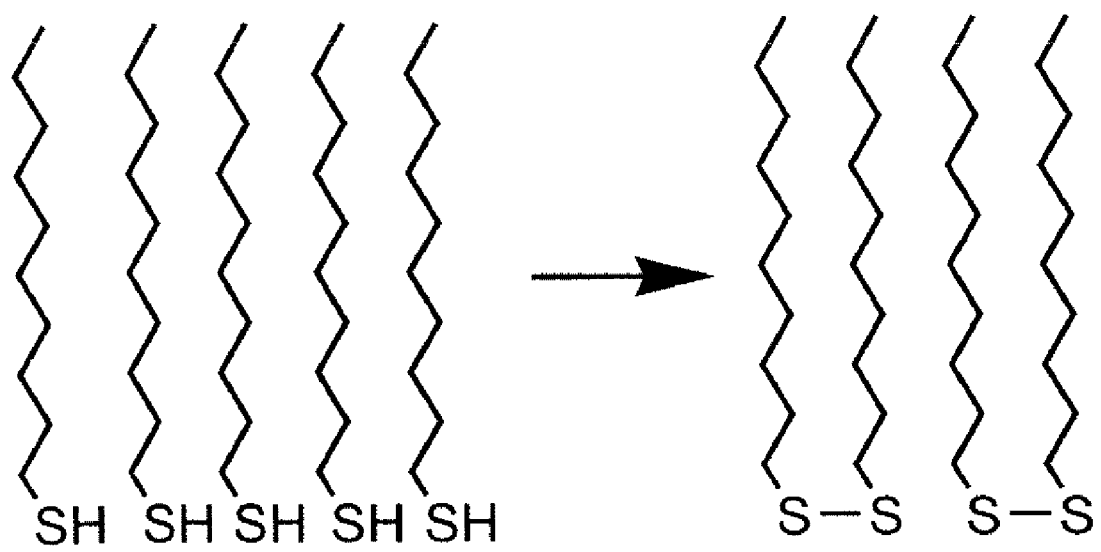
FIG. 2A illustrates amphiphilic alkythiol molecules, which may be reacted to yield the nanofilm illustrated in FIG. 2B.

In one variation, illustrated in FIG. 1A, module Hexamer 1dh is coupled to a second module through diethyl malonimidate linkers to yield the nanofilm illustrated in FIG. 2B.

A nanofilm comprising interlinked modules can be made by coupling together one or more members of the collection of modules, perhaps with other bulky or flexible components, to form a thin layer nanofilm material or composition. Coupling of modules may be complete or incomplete, providing a variety of structural variations useful as nanofilm membranes. The nanofilm may have a unique molecular structure. The compositional structure of a nanofilm made from oriented and coupled modules may include a unique molecular structure along with other component structures. The structure of the nanofilm may be a substantially crystalline structure having precise ordering of the coupled modules over distances which are long compared to the size of the modules. Nanofilms may also be prepared having the structure of a glass. Other nanofilms will have less long range ordering of the modules and be amorphous in molecular form. In some variations, the nanofilm is an elastomeric composition of coupled modules. In other instances, the nanofilm is a brittle thin film. A particular nanofilm may be found to have regions with more than one of these structural variations.

The thickness of a nanofilm made from surface-oriented molecular species or modules is exceptionally small, often being less than about 30 nanometers, sometimes less than about 20 nanometers, and sometimes less than about 15, 14, 13, 12, 11, 10, 9, 8, 7, 6, 5, 4, 3, 2, or 1. The thickness of a nanofilm depends partly on the structure and nature of the groups on the modules which impart amphiphilic character to the modules. The thickness may be dependent on temperature, and the presence of solvent on the surface or located within the nanofilm. The thickness may be modified if the groups on the modules which impart amphiphilic character to the modules are removed or modified after the modules have been coupled, or at other points during or after the process of preparation of a nanofilm. The thickness of a nanofilm may also depend on the structure and nature of the surface attachment groups on the modules. The thickness may be modified if the surface attachment groups on the modules are removed or modified after the modules have been coupled, or at other points during or after the process of preparation of a nanofilm. The thickness of nanofilms made from surface-oriented molecular species or modules may be less than about 300, 200, 250, 200, 150, 100, 90, 80, 70, 60, 50, 40, 30, 20, 10, or 5 Å.

In some instances, the nanofilm may be derivatized to provide biocompatability or reduce fouling of the nanofilm by attachment or adsorption of biomolecules.

The nanofilm composition may include uniquely structured regions in which modules are interlinked. Coupling of modules provides a nanofilm in which unique structures may be formed. Nanofilm structures define pores through which atoms, molecules, or particles of only up to a certain size and composition may pass. One variation of a nanofilm structure includes an area of nanofilm able to face a fluid medium, either liquid or gaseous, and provide pores or openings through which atoms, ions, small molecules, biomolecules, or other species are able to pass. The dimensions of the pores defined by nanofilm structures may be exemplified by quantum mechanical calculations and evaluations, and physical tests.

The dimensions of the pores defined by nanofilm structures are described by actual atomic and chemical structural features of the nanofilm. The approximate diameters of pores formed in the structure of a nanofilm are from about 1-150 Å, or more. In some embodiments, the dimensions of the pores are about 1-10 Å, about 3-15 Å, about 10-15 Å, about 15-20 Å, about 20-30 Å, about 30-40 Å, about 40-50 Å, about 50-75 Å, about 75-100 Å, about 100-125 Å, about 125-150 Å, about 150-300 Å, about 300-600 Å, about 600-1000 Å. The approximate dimensions of pores formed in the structure of a nanofilm are useful to understand the porosity of the nanofilm. On the other hand, the porosity of conventional membranes is normally quantified by empirical results such as molecular weight cut-off, which reflects complex diffusive and other transport characteristics.

In one variation, a nanofilm structure may be an array of coupled modules which provides an array of pores of substantially uniform size. The pores of uniform size may be defined by the individual modules themselves. Each module defines a pore of a particular size, depending on the conformation and state of the module. For example, the conformation of the interlinked module of the nanofilm may be different from the nascent, pure macrocyclic module in a solvent, and both may be different from the conformation of the amphiphilic module oriented on a surface before coupling. A nanofilm structure including an array of coupled modules can provide a matrix or lattice of pores of substantially uniform dimension based on the structure and conformation of the coupled modules.

Modules of various composition and structure may be prepared which define pores of different sizes. A nanofilm prepared from coupled modules may be made from any one of a variety of modules. Thus, nanofilms having pores of various dimensions are provided, depending on the particular module used to prepare the nanofilm.

In other instances, nanofilm structures define pores in the matrix of interlinked modules. Pores defined by nanofilm structures may have a wide range of dimensions, for example, dimensions capable of selectively blocking the passage of small molecules or large molecules. Nanofilm structures may be formed from the coupling of two or more modules, in which an interstitial pore is defined by the combined structure of the linked modules. A nanofilm may have an extended matrix of pores of various dimensions and characteristics. Interstitial pores may be, for example, less than about 5 Å, less than about 10 Å, about 3-15 Å, about 10-15 Å, about 15-20 Å, about 20-30 Å, about 30-40 Å, about 40-50 Å, about 50-75 Å, about 75-100 Å, about 100-125 Å, about 125-150 Å, about 150-300 Å, about 300-600 Å, about 600-1000 Å.

The coupling process may result in a nanofilm in which regions of the nanofilm are not precisely monomolecular layers. Various types of local structures are possible which do not prevent use of the nanofilm in a variety of applications. Local structural features may include amphiphilic modules which are flipped over relative to neighboring modules, or turned in a different orientation, having their hydrophobic and hydrophilic facets oriented differently than neighboring modules. Local structural features may also include overlaying of modules in which the nanofilm is two or more molecular layers thick, local regions in which the coupling of the modules is not complete so that some of the coupling groups of the modules are not coupled to other modules, or local regions in which there is an absence of modules. In one variation, the nanofilm has a thickness of up to 30 nanometers due to the layering of nanofilm structures.

As used herein, a nanofilm comprising "oriented macrocyclic modules" indicates that the macrocyclic modules are substantially uniformly oriented within the film, but may comprise regions of local structural features as indicated hereinabove. Local structural features may comprise, for example, greater than about 30%, less than about 30%, less than about 20%, less than about 15%, less than about 10%, less than about 5%, less than about 3%, less than about 1% of the surface area of the nanofilm. Analogously, a nanofilm comprising "oriented amphiphilic molecules" indicates that the amphiphilic molecules are substantially uniformly oriented within the film, but may comprise regions of local structural features as indicated hereinabove. Local structural features may comprise, for example, greater than about 30%, less than about 30%, less than about 20%, less than about 15%, less than about 10%, less than about 5%, less than about 3%, less than about 1% of the surface area of the nanofilm.

A nanofilm may also be prepared with mixtures of different modules, or with mixtures of macrocyclic modules and other amphiphilic molecules. These nanofilms may have an array of coupled modules and other amphiphilic molecules in which the positional ordering of the modules and other amphiphilic molecules is random, or is non-random with regions in which one type of species is predominant. Nanofilms made from mixtures of different modules, or with mixtures of macrocyclic modules and other amphiphilic molecules may also have interspersed arrays of pores of various sizes.

In Langmuir film methods, a monolayer of oriented amphiphilic species is formed on the surface of a liquid subphase. Typically, movable plates or barriers are used to compress the monolayer and decrease its surface area to form a more dense monolayer. At various degrees of compression, having corresponding surface pressures, the monolayer may reach various condensed states. In some cases, the film reaches a collapse point at which a condensed phase of the monolayer is produced at reduced surface pressure.

Surface pressure versus film area isotherms are obtained by the Wilhelmy balance method to monitor the state of the film. Extrapolation of the isotherm to zero surface pressure reveals the average surface area per module before the modules are coupled. When the hydrophobic groups used to orient the molecules of a Langmuir film monolayer are fatty acid groups, the collapse typically occurs at a molecular surface area of about 20 $Å^2$/molecule. Thus, the isotherm gives empirical indication of the state of the thin film.

Nanofilms of oriented species may be deposited on a substrate by various methods to provide a porous membrane. For example, description of Langmuir films and substrates is given in U.S. Pat. Nos. 6,036,778, 4,722,856, 4,554,076, and 5,102,798, and in R. A. Hendel et al., Vol. 119, *J. Am. Chem. Soc.* 6909-18 (1997). Description of films on substrates is given in Munir Cheryan, *Ultrafiltration and Microfiltration Handbook* (1998).

A substrate may be any surface of any material. Substrates may be porous and non-porous. Examples of porous substrates are polymers, track-etch polycarbonate, track-etch polyester, polyethersulfone, polysulfone, gels, hydrogels, cellulose acetate, polyamide, PVDF, ceramics, anodic alumina, laser ablated polyimide, and UV etched polyacrylate. Examples of non-porous substrates are silicon, metals, gold, glass, silicates, aluminosilicates, non-porous polymers, and mica.

In forming a nanofilm with Langmuir film methods, a linker molecule, when present, may be added to the solution containing the modules which is deposited on the surface of the Langmuir subphase. Alternatively, the linker molecules may be added to the subphase of the Langmuir trough, and subsequently transfer to the module layer phase to couple to modules. In some instances, modules may be added to the subphase of the Langmuir trough, and subsequently transfer to the module layer phase to couple to other modules.

Amphiphilic molecules may be oriented on a surface such as an air-water interface in a Langmuir trough. The surface oriented amphiphilic molecules may be compressed to form a Langmuir thin film. The amphiphilic molecules of the Langmuir thin film may be coupled to each other or interlinked to form a substantially monomolecular layer thin film material. The polar groups of the amphiphilic molecules of the Langmuir thin film may be coupled together by coupling reactions to form a thin film material. The lengths of the hydrophobic tails of the amphiphilic molecules may be from about 8 to 28 carbon atoms. Examples of hydrophobic tails of the amphiphilic molecules include the hydrophobic groups which may be attached to macrocyclic modules to impart amphiphilic character to the modules.

Examples of polar groups of the amphiphilic molecules include amide, amino, ester, —SH, acrylate, acrylamide, epoxy, and the hydrophilic groups as defined above. The polar groups of the amphiphilic molecules may be linked directly to each other. For example, sulfhydryl groups may be coupled to form disulfide links between the amphiphilic molecules of the Langmuir thin film. Examples of polar groups include —OH, —OCH$_3$, —NH$_2$, —C≡N, —NO$_2$, —$^+$NRR'R", —SO$_3^-$, —OPO$_2^{2-}$, —OC(O)CH=CH$_2$, —SO$_2$NH$_2$, SO$_2$NRR', —OP(O)(OCH$_2$CH$_2$N$^+$RR'R")O$^-$, —C(O)OH, —C(O)O$^-$, guanidinium, aminate, pyridinium, —C(O)OCH$_3$, —C(O)OCH$_2$CH$_3$,

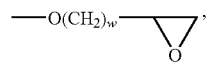

where w is 1-6, —C(O)OCH=CH$_2$, —O(CH$_2$)$_x$C(O)NH$_2$, where x is 1-6, —O(CH$_2$)$_y$C(O)NHR, where y is 1-6, and —O(CH$_2$CH$_2$O)$_z$R, where z is 1-6.

The coupling may attach two amphiphilic molecules, such as the alkylthiols of FIG. 2A, by a disulfide link, as illustrated in FIG. 2B. The coupling may attach more than two amphiphilic molecules, for example, by extended amide linkages. A portion of the amphiphilic molecules of the nanofilm may be coupled, while the rest are not coupled. The amphiphilic molecules of the nanofilm, both those which are coupled and those which are not coupled, may also interact through weak nonbonding or bonding interactions such as hydrogen bonding and other interactions.

Pores and barrier properties are found in the structure of the nanofilm made by coupling amphiphilic molecules. The pores and barrier properties may be modified by the degree or extent of coupling or interaction of the amphiphilic molecules, and for example, by the length of the linker molecules.

Figures 3A, 3B:
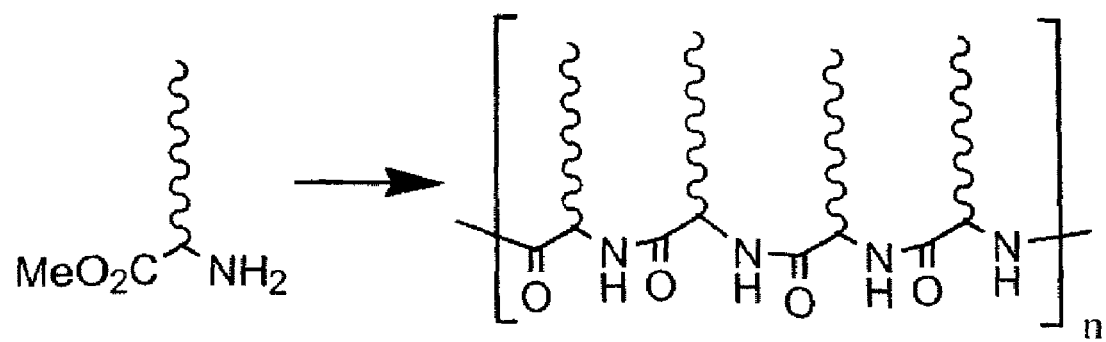
FIG. 3A illustrates an exemplary scheme for preparing a nanofilm comprising amphiphilic methyl 2-amino(alkan)oate molecules, which may be reacted to yield the nanofilm illustrated in FIG. 3B.

Polar groups having ester and amino groups may couple to attach the amphiphilic molecules of FIG. 3A, through amide linkages, to form the nanofilm illustrated in FIG. 3B.

Figures 4A, 4B:
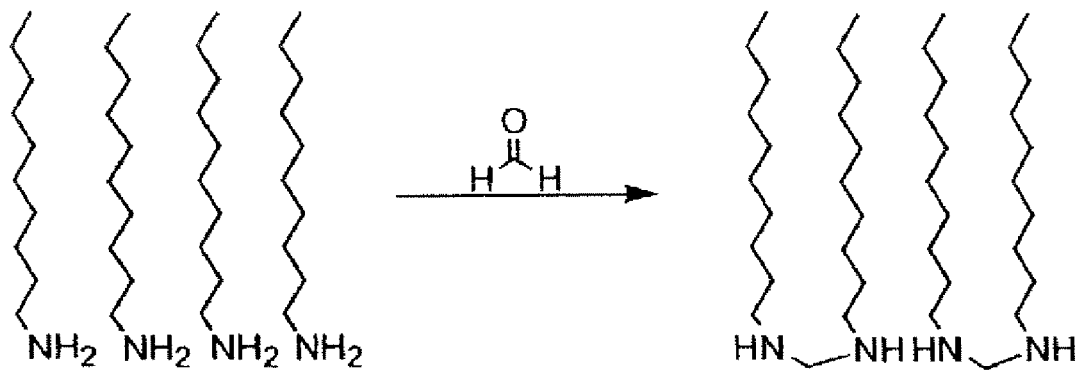
FIG. 4A illustrates amphiphilic alkylamine molecules, which may be reacted with formaldehyde to yield the nanofilm illustrated in FIG. 4B comprising dialkylmethandiamine units.
Figures 4C, 4D:
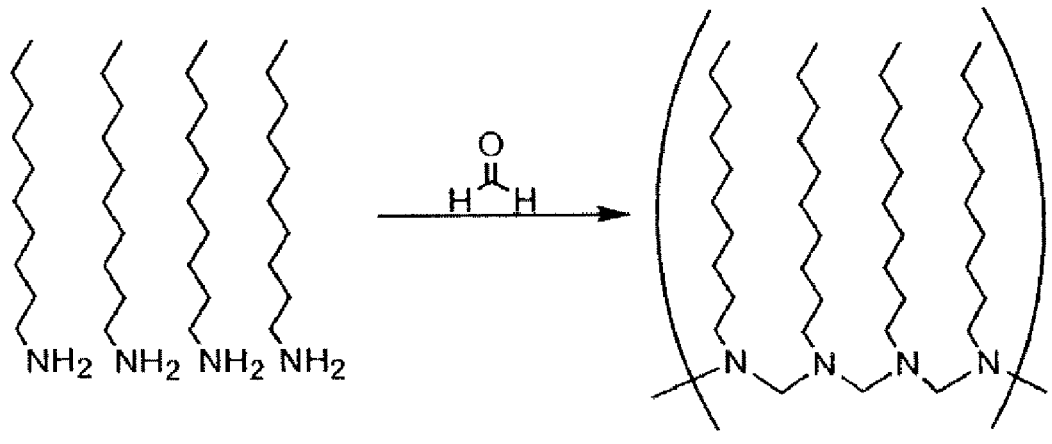
FIG. 4C illustrates amphiphilic alkylamine molecules, which may be reacted with formaldehyde to yield the nanofilm illustrated in FIG. 4D comprising alkylamine polymers.
Figures 4E, 4F:
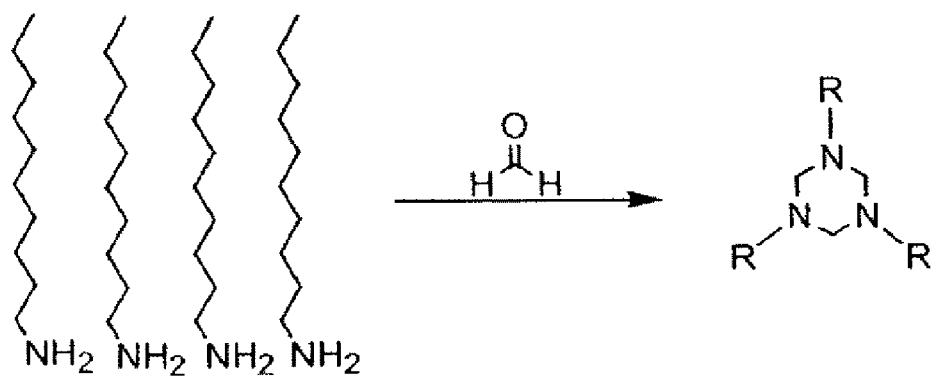
FIG. 4E illustrates amphiphilic alkylamine molecules, which may be reacted with formaldehyde to yield the nanofilm illustrated in FIG. 4F comprising 1,3,5-trialkyl-1.3,5-triazinane units.

The polar groups of the amphiphilic molecules may be linked to each other with a linker molecule. For example, amino groups of the amphiphilic molecules of the Langmuir thin film may be coupled by Mannich reaction with formaldehyde, as illustrated in FIGS. 4A, 4C and 4E. FIGS. 4A, 4C and 4E illustrate a Langmuir film of the amphiphiles, and FIGS. 4B, 4D and 4F illustrate the structures of the linkages formed in the nanofilm upon coupling the amphiphiles. The thin film material formed by coupling amphiphilic molecules of a Langmuir thin film may have barrier properties useful for filtration.

A nanofilm may be prepared from amphiphilic macrocyclic modules oriented on a surface, such as an air-subphase interface in a Langmuir trough, without coupling the modules. Amphiphilic modules may be prepared by attaching groups having interaction with the surface which cause orientation of the modules. A substantially uniform monolayer of oriented amphiphilic modules, such as a Langmuir film, may be formed on a hydrophilic surface. The surface-oriented macrocyclic modules may be arranged in a nanofilm layer, providing a unique composition, which may be an expanded state, a liquid state, or a liquid-expanded state, or may be condensed, collapsed, or a solid phase or close-packed state. The nanofilm of oriented amphiphilic macrocyclic modules may be deposited on a substrate by various methods to provide a porous membrane.

A nanofilm may be prepared by orienting amphiphilic macrocyclic modules and coupling the modules. Modules may be directly coupled, or may be coupled through linker molecules. Modules may be dissolved in a solvent and deposited on an air-subphase interface in a Langmuir trough. The amphiphilic modules can be oriented at the interface and may be compressed to a condensed thin film.

Linker molecules may be added to the subphase or to the solvent containing the modules which is deposited on the subphase.

Coupling of modules may be initiated by chemical, thermal, photochemical, electrochemical, and irradiative methods.

The coupling of modules in a nanofilm may attach two or more modules by a linkage or linkages. The coupling may attach more than two modules, for example, by an array of linkages each formed between two modules. Each module may form more than one linkage to another module, and each module may form several types of linkages, including those exemplified in Tables 2 and 3. A module may have direct linkages, linkages through a linker molecule, and linkages which include spacers, in any combination. A linkage may connect any portion of a module to any portion of another module. An array of linkages and an array of modules may be described in terms of the theory of Bravais lattices and theories of symmetry.

A portion of the modules of a nanofilm may be coupled, while the rest are not coupled. The modules of the nanofilm, both those which are coupled and those which are not coupled, may also interact through weak non-bonding or bonding interactions such as hydrogen bonding, van der Waals, and other interactions. The arrangement of linkages formed in a nanofilm may be represented by a type of symmetry, or may be substantially unordered.

Functional groups added to the modules to impart amphiphilic character to the modules may be removed after formation of the nanofilm. The method of removal depends on the functional group. For example, lipophilic groups or tails which are attached to modules may be selectively removed. The groups attached to the modules which impart amphiphilic character to the modules may include reactive functional groups which can be used to remove the groups at some point during or after the process of formation of a nanofilm. Acid or base hydrolysis may be used to remove groups attached to the module via a carboxylate or amide linkage. An unsaturated group located in the functional group which imparts amphiphilic character to the module may be oxidized and cleaved by hydrolysis. Photolytic cleavage of the functional group which imparts amphiphilic character to the module may also be done. Examples of cleavable functional groups include

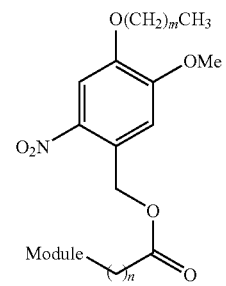

where n is zero to four, which is cleavable by light activation, and

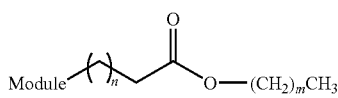

where n is zero to four, and m is 7 to 27, which is cleavable by acid or base catalyzed hydrolysis.

Examples of functional groups added to the modules to impart amphiphilic character to the modules include 8C-28C alkyl groups, —O(8C-28C)alkyl, —NH(8C-28C)alkyl, —OC(O)-(8C-28C)alkyl, —C(O)O-(8C-28C)alkyl, —NHC(O)-(8C-28C)alkyl, —C(O)NH-(8C-28C)alkyl, —CH=CH-(8C-28C)alkyl, and —C≡C-(8C-28C)alkyl, where the carbon atoms of the (8C-28C)alkyl groups may be interrupted by one or more —S—, double bond, triple bond or —SiR'R"— groups, substituted with one or more fluorine atoms or any combination of these, and the R' and R" independently comprise (1C-18C)alkyl.

Membranes and Filtration

A membrane is a medium which is brought into contact with a fluid or solution, separating a species or component from that fluid or solution, for example, for purposes of filtration. Normally, a membrane is a substance which acts as a barrier to block the passage of some species, while allowing restricted or regulated passage of other species. In general, permeants may traverse the membrane if they are smaller than a cut-off size, or have a molecular weight smaller than a so-called cut-off molecular weight. The membrane may be called impermeable to species which are larger than the cut-off molecular weight. The cut-off size or molecular weight is a characteristic property of the membrane. Selective permeation is the ability of the membrane to cut-off, restrict, or regulate passage of some species, while allowing smaller species to pass. Thus, the selective permeation of a membrane may be described functionally in terms of the largest species able to pass the membrane under given conditions. The size or molecular weight of various species may also be dependent on the conditions in the fluid to be separated, which may determine the form of the species. For example, species may have a sphere of hydration or solvation in a fluid, and the size of the species in relation to membrane applications may or may not include the water of hydration or the solvent molecules. Thus, a membrane is permeable to a species of a fluid if the species can traverse the membrane in the form in which it normally would be found in the fluid. Permeation and permeability may be affected by interaction between the species of a fluid and the membrane itself. While various theories may describe these interactions, the empirical measurement of pass/no-pass information relating to a nanofilm, membrane, or module is a useful tool to describe permeation properties. A membrane is impermeable to a species if the species cannot pass through the membrane.

The nanofilms may have molecular weight species cut offs of, for example, greater than about 15 kDa, greater than about 10 kDa, greater than about 5 kDa, greater that about 1 kDa, greater than about 800 Da, greater than about 600 Da, greater than about 400 Da, greater than about 200 Da, greater than about 100 Da, greater than about 50 Da, greater than about 20 Da, less than about 15 kDa, less than about 10 kDa, less than about 5 kDa, less that about 1 kDa, less than about 800 Da, less than about 600 Da, less than about 400 Da, less than about 200 Da, less than about 100 Da, less than about 50 Da, less than about 20 Da, about 13 kDa, about 190 Da, about 100 Da, about 45 Da, about 20 Da.

"High permeability" indicates a clearance of, for example, greater than about 70%, greater than about 80%, greater than about 90% of the solute. "Medium permeability" indicates a clearance of, for example, less than about 50%, less than about 60%, less than about 70% of the solute. "Low permeability" indicates a clearance of less than, for example, about 10%, less than about 20%, less than about 30% of the solute. A membrane is impermeable to a species if it has a very low clearance (for example, less than about 5%, less than about 3%) for the species, or if it has very high rejection for the species (for example, greater than about 95%, greater than about 98%). The passage or exclusion of a solute is measured by its clearance, which reflects the portion of solute that actually passes through the membrane. For example, the no pass symbol in Tables 13-14 indicates that the solute is partly excluded by the module, sometimes less than 90% rejection, often at least 90% rejection, sometimes at least 98% rejection. The pass symbol indicates that the solute is partly cleared by the module, sometimes less than 90% clearance, often at least 90% clearance, sometimes at least 98% clearance.

A nanofilm may be deposited on a substrate. The deposition may result in non-covalent or weak attachment of the membrane to the substrate through physical interactions and weak chemical forces such as van der Waals forces and weak hydrogen bonding. The membrane may be bound to the substrate through ionic or covalent interaction, or other coupling. A nanofilm deposited on a substrate may serve as a membrane. Any number of layers of nanofilm may be deposited on the substrate to form a membrane.

A layer or layers of various spacing materials may be deposited or attached in between layers of a nanofilm, and a spacing layer may also be used in between the substrate and the first deposited layer of nanofilm. Examples of spacing layer compositions include polymeric compositions, hydrogels (acrylates, poly vinyl alcohols, polyurethanes, silicones), thermoplastic polymers (polyolefins, polyacetals, polycarbonates, polyesters, cellulose esters), polymeric foams, thermosetting polymers, hyperbranched polymers, biodegradable polymers such as polylactides, liquid crystalline polymers, polymers made by atom transfer radical polymerization (ATRP), polymers made by ring opening metathesis polymerization (ROMP), polyisobutylenes and polyisobutylene star polymers, and amphiphilic polymers (e.g. Poly(maleic anhydride octadecene). Examples of amphiphilic molecules include amphiphiles containing polymerizable groups such as diynes, enes, or amino-esters. The spacing layers may serve to modify barrier properties of the nanofilm, or may serve to modify transport, flux, or flow characteristics of the membrane or nanofilm. Spacing layers may serve to modify functional characteristics of the membrane or nanofilm, such as strength, modulus, or other properties.

Deposition of a nanofilm on a substrate may be done by Langmuir-Schaefer, Langmuir-Blodgett, or other methods used with Langmuir systems. In one variation, a nanofilm is deposited on a substrate in a Langmuir tank by locating the substrate in the subphase beneath the air-water interface, and lowering the level of the subphase until the nanofilm lands gently on the substrate and is therefore deposited.

Nanofilms deposited on a substrate may be cured or annealed by radiation, thermal treatment, or drying methods during or after deposition on a substrate.

A nanofilm may be attached to a substrate surface by covalent or non-covalent chemical binding. Surface attachment groups may be provided on the macrocyclic modules which may be used to couple to the substrate to attach the membrane to the substrate. Coupling of some, but not all of the surface attachment groups may be done to attach the nanofilm to the substrate. Examples of reactive functional groups of modules which can be used as surface attachment groups to couple the nanofilm to a substrate include amine, carboxylic acid, carboxylic ester, alcohol, glycol, vinyl, styrene, epoxide, thiol, magnesium halo or Grignard, acrylate, acrylamide, diene, aldehyde, and mixtures thereof. Table 4 illustrates complementary functional groups of the nanofilm and the substrate surface which are used to couple the nanofilm to the substrate.

TABLE 4

Examples of complementary functional groups of a nanofilm and a substrate surface indicating linkage formed

| Nanofilm group | Substrate group | Linkage Formed |
|---|---|---|
| —NH$_2$ | —C(O)H | —N=CH— |
| —NH$_2$ | —CO$_2$H | —NHC(O)— |
| —NHR | —CO$_2$H | —NRC(O)— |
| —OH | —CO$_2$H | —OC(O)— |
| —X | —O Na | —O— |
| —SH | —SH | —S—S— |
| —X | —(NR)Li | —NR— |
| —X | —S Na | —S— |
| —X | —NHR | —NR— |
| —X | —CH$_2$CuLi | —CH$_2$— |
| —X | —(CRR')$_{n=1-6}$CuLi | —(CRR')$_n$— |
| module-X | module-X | module-module |
| —CH$_2$X | —CH$_2$X | —CH$_2$CH$_2$— |
| —ONa | —C(O)OR | —C(O)O— |
| —SNa | —C(O)OR | —C(O)S— |
| —X | —C≡CH | —C≡C— |
| —C≡CH | —C≡CH | —C≡C—C≡C— |
| —MgX | —C(O)H | —CH(OH)— |
| module-NH$_2$ | 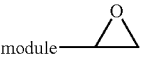 | 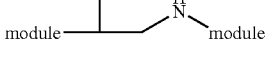 |
| module-MgX |  | 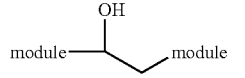 |
| 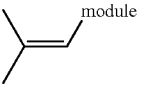 | module-X | 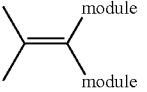 |
| —C(O)H | —C(O)H | —HC=CH— |
| (CH$_3$)$_2$C=CH-module | module-C(O)Cl | 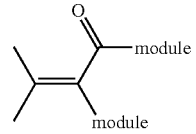 |
| —N=C=O | —NH$_2$ | —NHC(O)NH— |
| —N=C=O | HO— | —NHC(O)O— |
| —C(O)H | —NHNH$_2$ | —CH=N—NH— |
| —OH | —OC(O)X | —OC(O)O— |
| (CH$_3$)$_2$C=CH-module | module-SH | 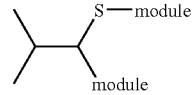 |
| (CH$_3$)$_2$CHC(O)O-module | module-CH(O) | 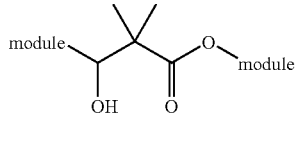 |
| module-CH$_2$C(O)OH | module-CH$_2$C(O)OH | 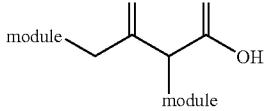 |

TABLE 4-continued
Examples of complementary functional groups of a nanofilm and a substrate surface indicating linkage formed
| Nanofilm group | Substrate group | Linkage Formed |
|---|---|---|
| 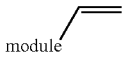 | R₂SiH-module | 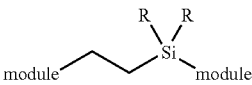 |
| 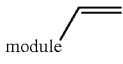 | 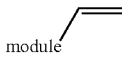 | 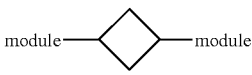 |
| 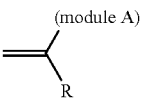 | 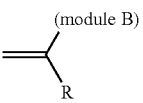 | 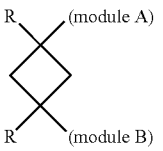 |
| 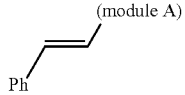 | 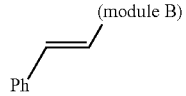 | 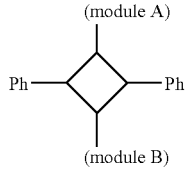 |
| —OP(O)(OH)₂ | —OH | —OP(O)(OH)O— |
| 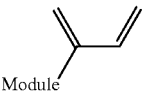 | 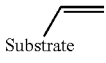 | 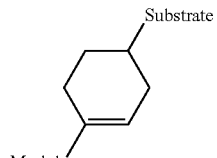 |
| 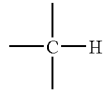 | 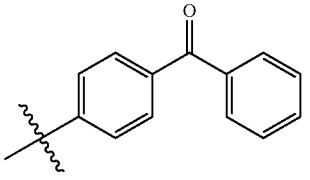 | 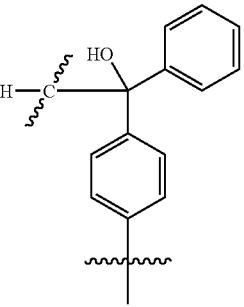 |
|  | —NH₂ | 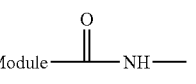 |
| 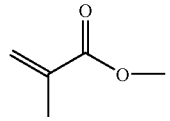 | 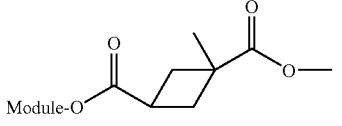 | 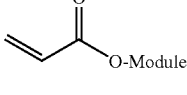 |
| 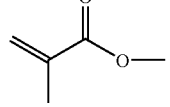 | 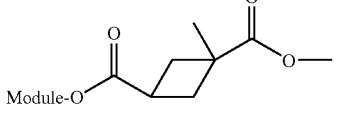 | 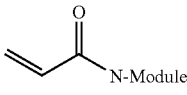 |

In Table 4, X is halogen or another group leaving group, and R and R' represent hydrogen or alkyl groups. It is to be understood that the functional groups listed in Table 4 may be reversed, for example, substrate-$NH_2$ could couple with nanofilm-C(O)H to form a —N=CH— linkage. It is to be further understood that the functional groups listed in Table 4 may be used in linking modules together, and that the functional groups listed in Table 2 may be used to link the nanofilm to the substrate.

Figures 5A, 5B, 5C:
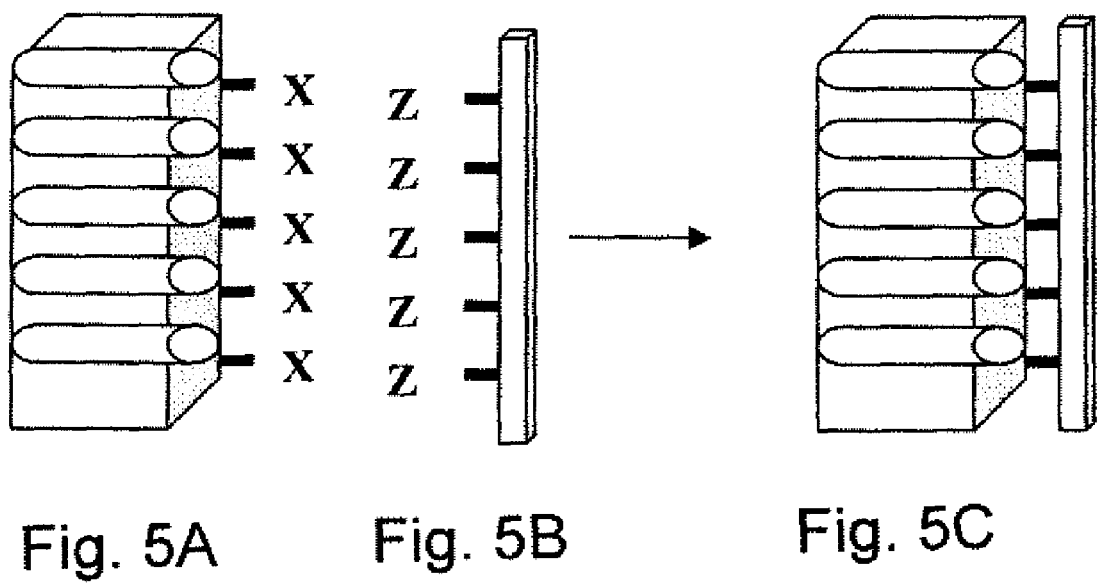
FIG. 5A illustrates a nanofilm, which may be attached to the substrate of FIG. 5B, showing examples of surface attachment groups, to yield the complex illustrated in FIG. 5C.

As illustrated, the substrate in FIG. 5B may have reactive functional groups which couple to the reactive functional groups of the modules of FIG. 5A to attach the membrane to the substrate. The functional groups of the substrate may be surface groups or linking groups bound to the substrate, which may be formed by reactions which bind the surface groups or linking groups to the substrate. Surface groups may also be created on the substrate by a variety of treatments such as cold plasma treatment, surface etching methods, solid abrasion methods, or chemical treatments. Some methods of plasma treatment are given in Inagaki, *Plasma Surface Modification and Plasma Polymerization*, Technomic, Lancaster, Pa., 1996. In one variation, a photoreactive group such as a benzophenone group is bound to the surface or substrate. The photoreactive group may be activated with light, for example, ultraviolet light to provide a reactive species which couples to a macrocyclic module.

The reactive functional groups of the modules and the surface may be blocked with protecting groups until needed. After formation of the coupled module nanofilm layer, the protecting groups of the reactive functional groups which are to be used for attaching the module membrane layer to the substrate surface may be removed, thereby allowing the attachment step to proceed.

Spacer groups may be used to connect reactive functional groups on the nanofilm to the substrate. Spacer groups for surface attachment groups may be polymer chains. Examples of polymer chain spacers include polyethylene oxides, polypropylene oxides, polysaccharides, polylysines, polypeptides, poly(amino acids), polyvinylpyrrolidones, polyesters, polyvinylchlorides, polyvinylidene fluorides, polyvinylalcohols, polyurethanes, polyamides, polyimides, polysulfones, polyethersulfones, polysulfonamides, and polysulfoxides. Examples of polymer chain spacer structures include linear, branched, comb and dendrimeric polymers, random and block copolymers, homo- and heteropolymers, flexible and rigid chains. Spacer groups for surface attachment groups may also include bifunctional linker groups or heterobifunctional linker groups used to couple biomolecules and other chemical species.

Methods of initiating coupling of the modules to the substrate include chemical, thermal, photochemical, electrochemical, and irradiative methods.

In one instance, a photoreactive group is bound to the substrate. The photoreactive group may be activated with light, for example, ultraviolet light to provide a reactive species which couples to a nanofilm. The photoreactive species may couple to an atom or group of the hydrophilic portion of the nanofilm amphiphiles, or to a hydrophobic portion of the nanofilm amphiphiles. The photoreactive species may couple to a linkage group of the nanofilm, or other atoms or groups which were initially part of the amphiphile or module from which the nanofilm was prepared.

Surface attachment of modules may also be achieved through ligand-receptor mediated interactions, such as biotin-streptavidin. For example, the substrate may be coated with streptavidin, and biotin may be attached to the modules, for example, through linker groups such as PEG or alkyl groups.

Examples of processes in which nanofilms may be useful include processes involving liquid or gas as a continuous fluid phase, filtration, clarification, fractionation, pervaporation, reverse osmosis, dialysis, hemodialysis, affinity separation, oxygenation, and other processes. Filtration applications may include ion separation, desalinization, gas separation, small molecule separation, ultrafiltration, microfiltration, hyperfiltration, water purification, sewage treatment, removal of toxins, removal of biological species such as bacteria, viruses, or fungus.

Synthons and Macrocyclic Modules

As used herein, the term "alkyl" refers to a branched or unbranched monovalent hydrocarbon radical. An "n-mC" alkyl or "(nC-mC)alkyl" refers to all alkyl groups containing from n to m carbon atoms. For example, a 1-4C alkyl refers to a methyl, ethyl, propyl, or butyl group. All possible isomers of an indicated alkyl are also included. Thus, propyl includes isopropyl, butyl includes n-butyl, isobutyl and t-butyl, and so on. An alkyl group with from 1-6 carbon atoms is referred to as "lower alkyl." The term alkyl includes substituted alkyls. As used herein, the term "substituted alkyl" refers to an alkyl group with an additional group or groups attached to any carbon of the alkyl group. Additional groups may include one or more functional groups such as alkyl, lower alkyl, aryl, acyl, halogen, alkylhalo, hydroxy, amino, alkoxy, alkylamino, acylamino, acyloxy, aryloxy, aryloxyalkyl, mercapto, both saturated and unsaturated cyclic hydrocarbons, heterocycles, and others.

As used herein, the term "alkenyl" refers to any structure or moiety having the unsaturation C=C. As used herein, the term "alkynyl" refers to any structure or moiety having the unsaturation C≡C.

As used herein, the terms "R," "R'," "R''", and "R'''" in a chemical formula refer to a hydrogen or a functional group, each independently selected, unless stated otherwise.

As used herein, the term "aryl" refers to an aromatic group which may be a single aromatic ring or multiple aromatic rings which are fused together, linked covalently, or linked to a common group such as a methylene, ethylene, or carbonyl, and includes polynuclear ring structures. An aromatic ring or rings may include substituted or unsubstituted phenyl, naphthyl, biphenyl, diphenylmethyl, and benzophenone groups, among others. The term "aryl" includes substituted aryls.

As used herein, the term "substituted aryl" refers to an aryl group with an additional group or groups attached to any carbon of the aryl group. Additional groups may include one or more functional groups such as lower alkyl, aryl, acyl, halogen, alkylhalos, hydroxy, amino, alkoxy, alkylamino, acylamino, acyloxy, aryloxy, aryloxyalkyl, thioether, heterocycles, both saturated and unsaturated cyclic hydrocarbons which are fused to the aromatic ring(s), linked covalently or linked to a common group such as a methylene or ethylene group, or a carbonyl linking group such as in cyclohexyl phenyl ketone, and others.

As used herein, the term "heteroaryl" refers to an aromatic ring(s) in which one or more carbon atoms of the aromatic ring(s) are substituted by a heteroatom such as nitrogen, oxygen, or sulfur. Heteroaryl refers to structures which may include a single aromatic ring, multiple aromatic rings, or one or more aromatic rings coupled to one or more nonaromatic rings. It includes structures having multiple rings, fused or unfused, linked covalently, or linked to a common group such as a methylene or ethylene group, or linked to a carbonyl as in phenyl pyridyl ketone. As used herein, the term "heteroaryl"

includes rings such as thiophene, pyridine, isoxazole, phthalimide, pyrazole, indole, furan, or benzo-fused analogues of these rings.

As used herein, the term "acyl" refers to a carbonyl substituent, —C(O)R, where R is alkyl or substituted alkyl, aryl or substituted aryl, which may be called an alkanoyl substituent when R is alkyl.

As used herein, the term "amino" refers to a group —NRR', where R and R' may independently be hydrogen, lower alkyl, substituted lower alkyl, aryl, substituted aryl or acyl.

As used herein, the term "alkoxy" refers to an —OR group, where R is an alkyl, substituted lower alkyl, aryl, substituted aryl. Alkoxy groups include, for example, methoxy, ethoxy, phenoxy, substituted phenoxy, benzyloxy, phenethyloxy, t-butoxy, and others.

As used herein, the term "thioether" refers to the general structure R—S—R' in which R and R' are the same or different and may be alkyl, aryl or heterocyclic groups. The group —SH may also be referred to as "sulfhydryl" or "thiol" or "mercapto."

As used herein, the term "saturated cyclic hydrocarbon" refers to ring structures cyclopropyl, cyclobutyl, cyclopentyl groups, and others, including substituted groups. Substituents to saturated cyclic hydrocarbons include substituting one or more carbon atoms of the ring with a heteroatom such as nitrogen, oxygen, or sulfur. Saturated cyclic hydrocarbons include bicyclic structures such as bicycloheptanes and bicyclooctanes, and multicyclic structures.

As used herein, the term "unsaturated cyclic hydrocarbon" refers to a monovalent nonaromatic group with at least one double bond, such as cyclopentene, cyclohexene, and others, including substituted groups. Substituents to unsaturated cyclic hydrocarbons include substituting one or more carbon atoms of the ring with a heteroatom such as nitrogen, oxygen, or sulfur. As used herein, the term "cyclic hydrocarbon" includes substituted and unsubstituted, saturated and unsaturated cyclic hydrocarbons, and multicyclic structures. Unsaturated cyclic hydrocarbons include bicyclic structures such as bicycloheptenes and bicyclooctenes, and multicyclic structures.

As used herein, the term "heteroarylalkyl" refers to alkyl groups in which the heteroaryl group is attached through an alkyl group.

As used herein, the term "heterocyclic" refers to a monovalent saturated or unsaturated nonaromatic group having a single ring or multiple condensed rings from 1-12 carbon atoms and from 1-4 heteroatoms selected from nitrogen, phosphorous, sulfur, or oxygen within the ring. Examples of heterocycles include tetrahydrofuran, morpholine, piperidine, pyrrolidine, and others.

As used herein, each chemical term described above expressly includes the corresponding substituted group. For example, the term "heterocyclic" includes substituted heterocyclic groups.

As used herein, the terms "amphiphile" or "amphiphilic" refer to a species which exhibits both hydrophilic and lipophilic character. In general, an amphiphile contains a lipophilic moiety and a hydrophilic moiety. An amphiphile may form a Langmuir film.

Examples of hydrophilic moieties include, without limitation, hydroxyl, methoxy, phenol, carboxylic acids and salts thereof, methyl and ethyl esters of carboxylic acids, amides, amino, cyano, ammonium salts, monoalkyl-substituted amino groups, di-alkyl-substituted amino groups, —NRR', —N≡C, —NHR, sulfonium salts, phosphonium salts, polyethyleneglycols, polypropyleneglycols, epoxy groups, acrylates, sulfonamides, nitro, —OP(O)(OCH$_2$CH$_2$N$^+$RR'R")O$^-$, guanidinium, aminate, acrylamide, and pyridinium. Such hydrophilic moieties may include groups such as polyethylene glycols, or for example, polymethylene chains substituted with alcohol, carboxylate, acrylate, methacrylate, or

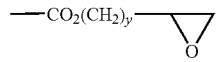

groups, where y is 1-6. Hydrophilic moieties may also include alkyl chains having internal amino or substituted amino groups, for example, internal —NH—, —NC(O)R—, or —NC(O)CH═CH$_2$— groups. Hydrophilic moieties may also include polycaprolactones, polycaprolactone diols, poly(acetic acid)s, poly(vinyl acetates)s, poly(2-vinyl pyridine)s, cellulose esters, cellulose hydroxyl ethers, poly(L-lysine hydrobromide)s, poly(itaconic acid)s, poly(maleic acid)s, poly(styrenesulfonic acid)s, poly(aniline)s, or poly(vinyl phosphonic acid)s.

Examples of lipophilic moieties include, without limitation, linear or branched alkyls, including 1-28C hydrocarbons. Examples of groups which may be coupled to a synthon or macrocyclic module as a lipophilic group include alkyls, —CH═CH—R, —C≡C—R, —OC(O)—R, —C(O)O—R, —NHC(O)—R, —C(O)NH—R, and —O—R, where R is 4-18C alkyl. Each chain may independently comprise, without limitation, alkenyl, alkynyl, saturated and unsaturated cyclic hydrocarbons, or aromatic groups. Each chain may also contain, interspersed among the carbons of the chain, one or more silicon atoms substituted with alkyl, alkenyl, alkynyl, saturated and unsaturated cyclic hydrocarbons, or aryl groups. The carbon atoms of each chain may independently be substituted with one or more fluorine atoms. The carbon atoms of an alkyl group may be interrupted by one or more functional groups such as, for example, —S—, double bond, triple bond or —SiR'R"— groups (where R' and R" are independently H or alkyl), any of which may be substituted with one or more fluorine atoms, and any combination of such functional groups may be used.

As used herein, the term "functional group" includes, but is not limited to, chemical groups, organic groups, inorganic groups, organometallic groups, aryl groups, heteroaryl groups, cyclic hydrocarbon groups, amino (—NH$_2$), hydroxyl (—OH), cyano (—C≡N), nitro (NO$_2$), carboxyl (—COOH), formyl (—CHO), keto (—CH$_2$C(O)CH$_2$—), alkenyl (—C═C—), alkynyl, (—C≡C—), and halo (F, Cl, Br and I) groups.

As used herein, the term "activated acid" refers to a —C(O)X moiety, where X is a leaving group, in which the X group is readily displaced by a nucleophile to form a covalent bond between the —C(O)— and the nucleophile. Examples of activated acids include acid chlorides, acid fluorides, p-nitrophenyl esters, pentafluorophenyl esters, and N-hydroxysuccinimide esters.

As used herein, the term "amino acid residue" refers to the product formed when a species comprising at least one amino (—NH$_2$) and at least one carboxyl (—C(O)O—) group couples through either of its amino or carboxyl groups with an atom or functional group of a synthon. Whichever of the amino or carboxyl groups is not involved in the coupling may be blocked with a removable protective group.

Synthons

As used herein, the term "synthon" refers to a molecule used to make a macrocyclic module. A synthon may be substantially one isomeric configuration, for example, a single enantiomer. A synthon may be substituted with functional groups which are used to couple a synthon to another synthon or synthons, and which are part of the synthon. A synthon may be substituted with an atom or group of atoms which are used to impart hydrophilic, lipophilic, or amphiphilic character to the synthon or to species made from the synthon. A synthon may be substituted with an atom or group of atoms to form one or more functional groups on the synthon which may be used to couple the synthon to another synthon or synthons. The synthon before being substituted with functional groups or groups used to impart hydrophilic, lipophilic, or amphiphilic character may be called the core synthon. As used herein, the term "synthon" refers to a core synthon, and also refers to a synthon substituted with functional groups or groups used to impart hydrophilic, lipophilic, or amphiphilic character.

As used herein, the term "cyclic synthon" refers to a synthon having one or more ring structures. Examples of ring structures include aryl, heteroaryl, and cyclic hydrocarbon structures including bicyclic ring structures and multicyclic ring structures. Examples of core cyclic synthons include, but are not limited to, benzene, cyclohexadiene, cyclopentadiene, naphthalene, anthracene, phenylene, phenanthracene, pyrene, triphenylene, phenanthrene, pyridine, pyrimidine, pyridazine, biphenyl, bipyridyl, cyclohexane, cyclohexene, decalin, piperidine, pyrrolidine, morpholine, piperazine, pyrazolidine, quinuclidine, tetrahydropyran, dioxane, tetrahydrothiophene, tetrahydrofuran, pyrrole, cyclopentane, cyclopentene, triptycene, adamantane, bicyclo[2.2.1]heptane, bicyclo[2.2.1]heptene, bicyclo[2.2.2]octane, bicyclo[2.2.2]octene, bicyclo[3.3.0]octane, bicyclo[3.3.0]octene, bicyclo[3.3.1]nonane, bicyclo[3.3.1]nonene, bicyclo[3.2.2]nonane, bicyclo[3.2.2]nonene, bicyclo[4.2.2]decane, 7-azabicyclo[2.2.1]heptane, 1,3-diazabicyclo[2.2.1]heptane, and spiro[4.4]nonane. A core synthon comprises all isomers or arrangements of coupling the core synthon to other synthons. For example, the core synthon benzene includes synthons such as 1,2- and 1,3-substituted benzenes, where the linkages between synthons are formed at the 1,2- and 1,3-positions of the benzene ring, respectively. For example, the core synthon benzene includes 1,3-substituted synthons such as

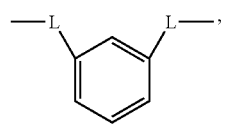

where L is a linkage between synthons and the 2,4,5,6 positions of the benzene ring may also have substituents. A condensed linkage between synthons involves a direct coupling between a ring atom of one cyclic synthon to a ring atom of another cyclic synthon, for example, where synthons M-X and M-X couple to form M-M, where M is a cyclic synthon and X is halogen; as for example when M is phenyl resulting in the condensed linkage

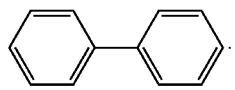

Macrocyclic Modules

A macrocyclic module is a closed ring of coupled synthons. To make a macrocyclic module, synthons may be substituted with functional groups to couple the synthons to form a macrocyclic module. Synthons may also be substituted with functional groups which will remain in the structure of the macrocyclic module. Functional groups which remain in the macrocyclic module may be used to couple the macrocyclic module to other macrocyclic modules.

A macrocyclic module may contain from three to about twenty-four cyclic synthons. In the closed ring of a macrocyclic module, a first cyclic synthon may be coupled to a second cyclic synthon, the second cyclic synthon may be coupled to a third cyclic synthon, the third cyclic synthon may be coupled to a fourth cyclic synthon, if four cyclic synthons are present in the macrocyclic module, the fourth to a fifth, and so on, until an $n^{th}$ cyclic synthon may be coupled to its predecessor, and the $n^{th}$ cyclic synthon may be coupled to the first cyclic synthon to form a closed ring of cyclic synthons. In one variation, the closed ring of the macrocyclic module may be formed with a linker molecule.

A macrocyclic module may be an amphiphilic macrocyclic module when hydrophilic and lipophilic functional groups exist in the structure. The amphiphilic character of a macrocyclic module may arise from atoms in the synthons, in the linkages between synthons, or in functional groups coupled to the synthons or linkages.

In some variations, one or more of the synthons of a macrocyclic module may be substituted with one or more lipophilic moieties, while one or more of the synthons may be substituted with one or more hydrophilic moieties, thereby forming an amphiphilic macrocyclic module. Lipophilic and hydrophilic moieties may be coupled to the same synthon or linkage in an amphiphilic macrocyclic module. Lipophilic and hydrophilic moieties may be coupled to the macrocyclic module before or after formation of the closed ring of the macrocyclic module. For example, lipophilic or hydrophilic moieties may be added to the macrocyclic module after formation of the closed ring by substitution of a synthon or linkage.

The amphiphilicity of a macrocyclic module may be characterized in part by its ability to form a stable Langmuir film. A Langmuir film may be formed on a Langmuir trough at a particular surface pressure measured in milliNewtons per meter (mN/m) with a particular barrier speed measured in millimeters per minute (mm/min), and the isobaric creep or change in film area at constant surface pressure can be measured to characterize stability of the film. For example, a stable Langmuir film of macrocyclic modules on a water subphase may have an isobaric creep at 5-15 mN/m such that the majority of the film area is retained over a period of time of about one hour. Examples of stable Langmuir films of macrocyclic modules on a water subphase may have isobaric creep at 5-15 mN/m such that about 70% of the film area is retained over a period of time of about 30 minutes, sometimes about 70% of the film area is retained over a period of time of about 40 minutes, sometimes about 70% of the film area is retained over a period of time of about 60 minutes, and sometimes about 70% of the film area is retained over a period of time of about 120 minutes. Other examples of stable Langmuir films of macrocyclic modules on a water subphase may have isobaric creep at 5-15 mN/m such that about 80% of the film area is retained over a period of time of about thirty minutes, sometimes about 85% of the film area is retained over a period of time of about thirty minutes, sometimes about 90% of the film area is retained over a period of time of about thirty minutes, sometimes about 95% of the film area is retained over a period of time of about thirty minutes, and sometimes about 98% of the film area is retained over a period of time of about thirty minutes.

In one aspect, an individual macrocyclic module may include a pore in its structure. Each macrocyclic module may define a pore of a particular size, depending on the conformation and state of the module. Various macrocyclic modules may be prepared which define pores of different sizes.

A macrocyclic module may include a flexibility in its structure. Flexibility may permit a macrocyclic module to more easily form linkages with other macrocyclic modules by coupling reactions. Flexibility of a macrocyclic module may also play a role in regulating passage of species through the pore of the macrocyclic module. For example, flexibility may affect the dimension of the pore of an individual macrocyclic module since various conformations may be available to the structure. For example, the macrocyclic module may have a certain pore dimension in one conformation when no substituents are located at the pore, and the same macrocyclic module may have a different pore dimension in another conformation when one or more substituents of that macrocycle are located at the pore. Likewise, a macrocyclic module may have a certain pore dimension in one conformation when one group of substituents are located at the pore, and have a different pore dimension in a different conformation when a different group of substituents are located at the pore. For example, the "one group" of substituents located at the pore may be three alkoxy groups arranged in one regioisomer, while the "different group" of substituents may be two alkoxy groups arranged in another regioisomer. The effect of the "one group" of substituents located at the pore and the "different group" of substituents located at the pore is to provide a macrocyclic module composition which may regulate transport and filtration, in conjunction with other regulating factors.

In making macrocyclic modules from synthons, the synthons may be used as a substantially pure single isomer, for example, as a pure single enantiomer.

In making macrocyclic modules from synthons, one or more coupling linkages are formed between adjacent synthons. The linkage formed between synthons may be the product of the coupling of one functional group on one synthon to a complementary functional group on a second synthon. For example, a hydroxyl group of a first synthon may couple with an acid group or acid halide group of a second synthon to form an ester linkage between the two synthons. Another example is an imine linkage, —CH=N—, resulting from the reaction of an aldehyde, —CH=O, on one synthon with an amine, —NH$_2$, on another synthon. Examples of complementary functional groups and linkages between synthons are shown in Table 5.

TABLE 5

EXAMPLES OF FUNCTIONAL GROUPS OF SYNTHONS AND SYNTHON LINKAGES

| Functional Group A | Functional Group B | Linkage Formed |
|---|---|---|
| —NH$_2$ | —C(O)H | —N=CH— |
| —NH$_2$ | —CO$_2$H | —NHC(O)— |
| —NHR | —CO$_2$H | —NRC(O)— |
| —OH | —CO$_2$H | —OC(O)— |
| —X | —O Na | —O— |
| —SH | —SH | —S—S— |
| —X | —(NR)Li | —NR— |
| —X | —S Na | —S— |
| —X | —NHR | —NR— |
| —X | —CH$_2$CuLi | —CH$_2$— |
| —X | —(CRR')$_{n-1-6}$CuLi | —(CRR')$_n$— |
| synthon-X | synthon-X | synthon-synthon |
| —CH$_2$X | —CH$_2$X | —CH$_2$CH$_2$— |
| —ONa | —C(O)OR | —C(O)O— |
| —SNa | —C(O)OR | —C(O)S— |
| —X | —C≡CH | —C≡C— |
| —C≡CH | —C≡CH | —C≡C—C≡C— |
| —MgX | —C(O)H | —CH(OH)— |
| synthon-NH$_2$ | synthon—epoxide | synthon—CH(OH)—CH$_2$—NH—synthon |
| synthon-MgX | synthon—epoxide | synthon—CH(OH)—CH$_2$—synthon |
| (CH$_3$)$_2$C=CH-synthon | synthon-X | synthon$_2$C=C(synthon)$_2$ |
| —C(O)H | —C(O)H | —HC=CH— |
| (CH$_3$)$_2$C=CH-synthon | synthon-C(O)Cl | (CH$_3$)$_2$C=C(synthon)C(O)-synthon |
| —N=C=O | —NH$_2$ | —NHC(O)NH— |

TABLE 5-continued

EXAMPLES OF FUNCTIONAL GROUPS OF SYNTHONS
AND SYNTHON LINKAGES

| Functional Group A | Functional Group B | Linkage Formed |
|---|---|---|
| —N=C=O | HO— | —NHC(O)O— |
| —C(O)H | —NHNH$_2$ | —CH=N—NH— |
| —OH | —OC(O)X | —OC(O)O— |
| (CH$_3$)$_2$C=CH-synthon | synthon-SH | 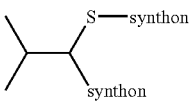 |
| (CH$_3$)$_2$CHC(O)O—synthon | synthon-CH(O) | 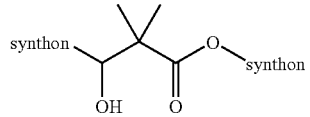 |
| synthon-CH$_2$C(O)OH | synthon-CH$_2$C(O)OH | 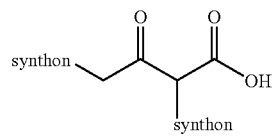 |
| 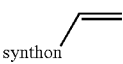 | R$_2$SiH-synthon | 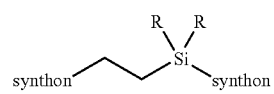 |
| 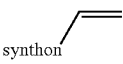 |  | 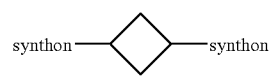 |
| 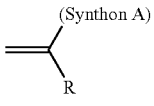 | 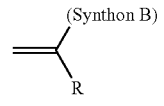 | 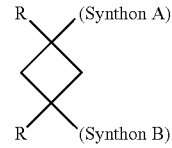 |
| 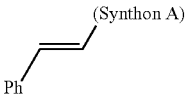 | 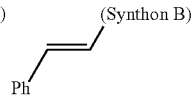 | 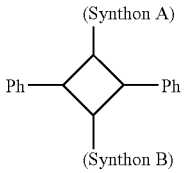 |
| —OP(O)(OH)$_2$ | —OH | —OP(O)(OH)O— |

In Table 5, R and R' represent hydrogen or a functional group, and X is halogen or other good leaving groups.

In another variation, a macrocyclic module may have functional groups for coupling to other macrocyclic modules which were coupled to the macrocyclic module after initial preparation of the closed ring. For example, an imine linkage of a macrocyclic module may be substituted with one of various functional groups to produce additional macrocyclic modules. Examples of linkages between synthons having functional groups for coupling macrocyclic modules are shown in Table 6.

TABLE 6

EXAMPLES OF FUNCTIONAL GROUPS OF SYNTHONS AND SYNTHON LINKAGES

| Functional Group of Macrocyclic Module Linkage | Reagent | Substituted Linkage |
|---|---|---|
| $Q_1\text{—NH—}Q_2$ | acryloyl chloride | $Q_1\text{—N}(C(O)CH=CH_2)\text{—}Q_2$ |
| $Q_1\text{—CH}_2\text{—NH—}Q_2$ | acryloyl chloride | $Q_1\text{—CH}_2\text{—N}(C(O)CH=CH_2)\text{—}Q_2$ |
| $Q_1\text{—CH(OH)—}Q_2$ | acryloyl chloride | $Q_1\text{—CH}(OC(O)CH=CH_2)\text{—}Q_2$ |
| $Q_1\text{—CH(X)—}Q_2$ | $X\text{—C}{\equiv}\text{C—H}$ | $Q_1\text{—CH}(C{\equiv}CH)\text{—}Q_2$ |
| $Q_1\text{—CH(X)—}Q_2$ | $X\text{—C}_6H_4\text{—CH=CH}_2$ | $Q_1\text{—CH}(C_6H_4\text{CH=CH}_2)\text{—}Q_2$ |
| $Q_1\text{—NH—}Q_2$ | $\alpha$-R-acryloyl chloride, R = alk | $Q_1\text{—N}(C(O)C(R)=CH_2)\text{—}Q_2$ |
| $Q_1\text{—CH(OH)—}Q_2$ | $\alpha$-R-acryloyl chloride, R = alk | $Q_1\text{—CH}(OC(O)C(R)=CH_2)\text{—}Q_2$ |
| $Q_1\text{—NH—}Q_2$ | cinnamoyl chloride | $Q_1\text{—N}(C(O)CH=CHPh)\text{—}Q_2$ |
| $Q_1\text{—CH(OH)—}Q_2$ | cinnamoyl chloride | $Q_1\text{—CH}(OC(O)CH=CHPh)\text{—}Q_2$ |

In Table 6, X is halogen, and $Q_1$ and $Q_2$ are independently selected synthons which are part of a module.

The functional groups of synthons used to form linkages between synthons or other macrocyclic modules may be separated from the synthon by a spacer. A spacer can be any atom or group of atoms which couples the functional group to the synthon, and does not interfere with the linkage-forming reaction. A spacer is part of the functional group, and becomes part of the linkage between synthons. An example of a spacer is a methylene group, —$CH_2$—. The spacer may be said to extend the linkage between synthons. For example, if one methylene spacer were inserted in an imine linkage, —CH=N—, the resulting imine linkage may be —$CH_2$CH=N—.

A linkage between synthons may also contain one or more atoms provided by an external moiety other than the two functional groups of the synthons. An external moiety may be a linker molecule which may couple with the functional group of one synthon to form an intermediate which couples with a functional group on another synthon to form a linkage between the synthons, such as, for example, to form a closed ring of synthons from a series of coupled synthons. An example of a linker molecule is formaldehyde. For example, amino groups on two synthons may undergo Mannich reaction in the presence of formaldehyde as the linker molecule to produce the linkage —$NHCH_2NH$—.

The macrocyclic module compositions may comprise, for example, from three to about twenty-four cyclic synthons coupled to form a closed ring; at least two functional groups for coupling the closed ring to complementary functional groups on at least two other closed rings; wherein each functional group and each complementary functional group comprises a functional group containing atoms selected from the group consisting of C, H, N, O, Si, P, S, B, Al, halogens, and metals from the alkali and alkaline earth groups. In some embodiments, the macrocyclic module may comprise at least two closed rings coupled through said functional groups. In another embodiment, the macrocyclic module comprises at least three closed rings coupled through said functional groups.

In another embodiment, the macrocyclic modules may comprise from three to about twenty-four cyclic synthons coupled to form a closed ring defining a pore; the closed ring having a first pore dimension in a first conformation when a first group of substituents is located at the pore and a second pore dimension in a second conformation when a second group of substituents is located at the pore; wherein each substituent of each group comprises a functional group containing atoms selected from the group consisting of C, H, N, O, Si, P, S, B, Al, halogens, and metals from the alkali and alkaline earth groups.

In another example, the macrocyclic module comprises (a) from three to about twenty-four cyclic synthons coupled to form a closed ring defining a pore; (b) at least one functional group coupled to the closed ring at the pore and selected to transport a selected species through the pore, wherein the at least one functional group comprises a functional group containing atoms selected from the group consisting of C, H, N, O, Si, P, S, B, Al, halogens, and metals from the alkali and alkaline earth groups; (c) a selected species to be transported through the pore. In some embodiments, the selected species is selected from the group of ovalbumin, glucose, creatinine, $H_2PO_4^-$, $HPO_4^{-2}$, $HCO_3^-$, urea, $Na^+$, $Li^+$, and $K^+$.

In some embodiments, the macrocyclic module composition is coupled to a solid support selected from the group of Wang resins, hydrogels, aluminas, metals, ceramics, polymers, silica gels, sepharose, sephadex, agarose, inorganic solids, semiconductors, and silicon wafers. In other embodiments, the macrocyclic module composition retains at least 85% of film area after thirty minutes on a Langmuir trough at 5-15 mN/m. In other embodiments, the macrocyclic module composition retains at least 95% of film area after thirty minutes on a Langmuir trough at 5-15 mN/m. In another embodiment, the macrocyclic module retains at least 98% of film area after thirty minutes on a Langmuir trough at 5-15 mN/m.

In some embodiments, the cyclic synthons are each independently selected from the group consisting of benzene, cyclohexadiene, cyclohexene, cyclohexane, cyclopentadiene, cyclopentene, cyclopentane, cycloheptane, cycloheptene, cycloheptadiene, cycloheptatriene, cyclooctane, cyclooctene, cyclooctadiene, cyclooctatriene, cyclooctatetraene, naphthalene, anthracene, phenylene, phenanthracene, pyrene, triphenylene, phenanthrene, pyridine, pyrimidine, pyridazine, biphenyl, bipyridyl, decalin, piperidine, pyrrolidine, morpholine, piperazine, pyrazolidine, quinuclidine, tetrahydropyran, dioxane, tetrahydrothiophene, tetrahydrofuran, pyrrole, triptycene, adamantane, bicyclo[2.2.1]heptane, bicyclo[2.2.1]heptene, bicyclo[2.2.2]octane, bicyclo[2.2.2]octene, bicyclo[3.3.0]octane, bicyclo[3.3.0]octene, bicyclo[3.3.1]nonane, bicyclo[3.3.1]nonene, bicyclo[3.2.2]nonane, bicyclo[3.2.2]nonene, bicyclo[4.2.2]decane, 7-azabicyclo[2.2.1]heptane, 1,3-diazabicyclo[2.2.1]heptane, and spiro[4.4]nonane.

In other embodiments, each coupled cyclic synthon is independently coupled to two adjacent synthons by a linkage selected from the group consisting of (a) a condensed linkage, and (b) a linkage selected from the group consisting of —NRC(O)—, —OC(O)—, —O—, —S—S—, —S—, —NR—, —(CRR')$_p$—, —$CH_2NH$—, —C(O)S—, —C(O)O—, —C≡C—, —C≡C—C≡C—, —CH(OH)—, —HC=CH—, —NHC(O)NH—, —NHC(O)O—, —$NHCH_2NH$—, —$NHCH_2CH(OH)CH_2NH$—, —N=CH($CH_2$)$_p$CH=N—, —$CH_2CH(OH)CH_2$—, —N=CH($CH_2$)$_h$CH=N— where h is 1-4, —CH=N—NH—, —OC(O)O—, —OP(O)(OH)O—, —CH(OH)$CH_2$NH—, —CH(OH)$CH_2$—, —CH(OH)C($CH_3$)$_2$C(O)O—,

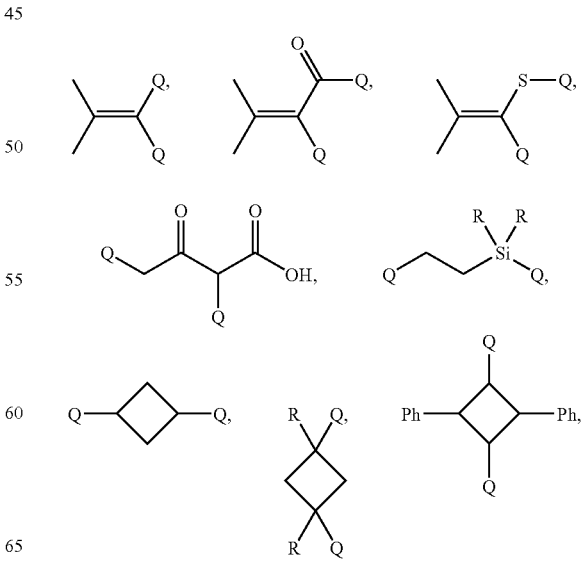

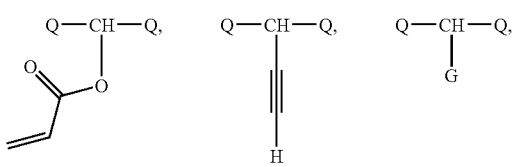

where G is halogen,

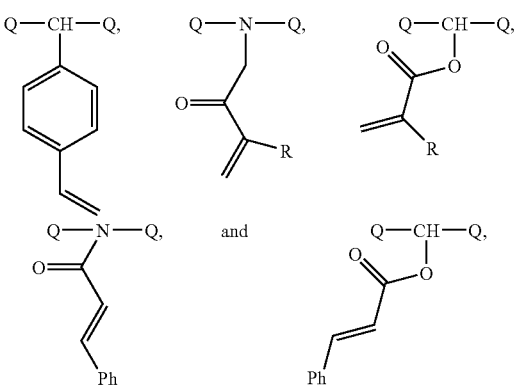

wherein p is 1-6;
wherein R and R' are each independently selected from the group of hydrogen and alkyl; wherein the linkage is independently configured in either of two possible configurations, forward and reverse, with respect to the synthons it couples together, if the two configurations are different structures; wherein Q is one of the synthons connected by the linkage.

In other embodiment, a closed ring composition may be comprised of the formula:

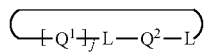

wherein: J is 2-23; $Q^1$ are synthons each independently selected from the group consisting of (a) phenyl synthons coupled to linkages L at 1,2-phenyl positions, (b) phenyl synthons coupled to linkages L at 1,3-phenyl positions, (c) aryl synthons other than phenyl synthons, (d) heteroaryl synthons other than pyridinium synthons, (e) saturated cyclic hydrocarbon synthons, (f) unsaturated cyclic hydrocarbon synthons, (g) saturated bicyclic hydrocarbon synthons, (h) unsaturated bicyclic hydrocarbon synthons, (i) saturated multicyclic hydrocarbon synthons, and (j) unsaturated multicyclic hydrocarbon synthons; wherein ring positions of each $Q^1$ which are not coupled to a linkage L are substituted with hydrogen or functional groups containing atoms selected from the group of C, H, N, O, Si, P, S, B, Al, halogens, and metals from the alkali and alkaline earth groups; $Q^2$ is a synthon independently selected from the group consisting of (a) aryl synthons other than phenyl synthons and naphthalene synthons coupled to linkages L at 2,7-naphthyl positions, (b) heteroaryl synthons other than pyridine synthons coupled to linkages L at 2,6-pyridino positions, (c) saturated cyclic hydrocarbon synthons other than cyclohexane synthons coupled to linkages L at 1,2-cyclohexyl positions, (d) unsaturated cyclic hydrocarbon synthons other than pyrrole synthons coupled to linkages L at 2,5-pyrrole positions, (e) saturated bicyclic hydrocarbon synthons, (f) unsaturated bicyclic hydrocarbon synthons, (g) saturated multicyclic hydrocarbon synthons, and (h) unsaturated multicyclic hydrocarbon synthons; wherein ring positions of $Q^2$ which are not coupled to an L are substituted with hydrogen or functional groups containing atoms selected from the group consisting of C, H, N, O, Si, P, S, B, Al, halogens, and metals from the alkali and alkaline earth groups; L are linkages between the synthons each independently selected from the group consisting of (a) a condensed linkage, and (b) a linkage selected from the group consisting of —NRC(O)—, —OC(O)—, —O—, —S—S—, —S—, —NR—, —(CRR')$_p$—, —CH$_2$NH—, —C(O)S—, —C(O)O—, —C=C—, —C≡C—C≡C—, —CH(OH)—, —HC=CH—, —NHC(O)NH—, —NHC(O)O—, —NHCH$_2$NH—, —NHCH$_2$CH(OH)CH$_2$NH—, —N=CH(CH$_2$)$_p$CH=N—, —CH$_2$CH(OH)CH$_2$—, —N=CH(CH$_2$)$_h$CH=N— where h is 1-4, —CH=N—NH—, —OC(O)O—, —OP(O)(OH)O—, —CH(OH)CH$_2$NH—, —CH(OH)CH$_2$—, —CH(OH)C(CH$_3$)$_2$C(O)O—,

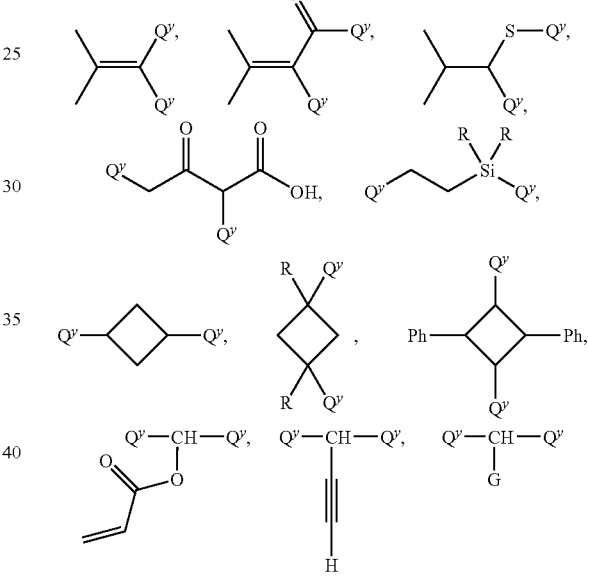

where G is halogen,

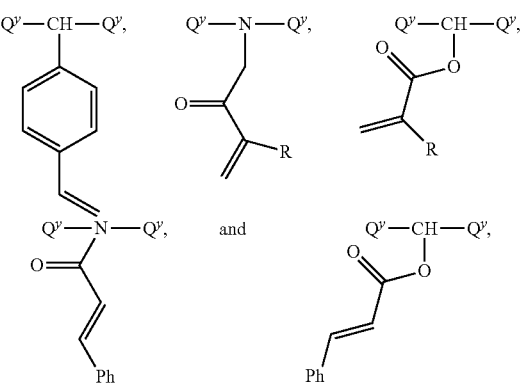

wherein p is 1-6; wherein R and R' are each independently selected from the group of hydrogen and alkyl; wherein linkages L are each independently configured in either of two possible configurations, forward and reverse, with respect to the synthons it couples together, if the two configurations are different structures; wherein y is 1 or 2, and $Q^y$ are each independently one of the $Q^1$ or $Q^2$ synthons connected by the linkage.

In some embodiments, the functional groups are each independently selected from the group consisting of hydrogen, an activated acid, —OH, —C(O)OH, —C(O)H, —C(O)OCH$_3$, —C(O)Cl, —NRR, —NRR$^+$, —MgX, —Li, —OLi, —OK, —ONa, —SH, —C(O)(CH$_2$)$_2$C(O)OCH$_3$, —NH-alkyl-C(O)CH$_2$CH(NH$_2$)CO$_2$-alkyl, —CH═CH$_2$, —CH═CHR, —CH═CR$_2$, 4-vinylaryl, —C(O)CH═CH$_2$, —NHC(O)CH═CH$_2$, —C(O)CH═CH(C$_6$H$_5$),

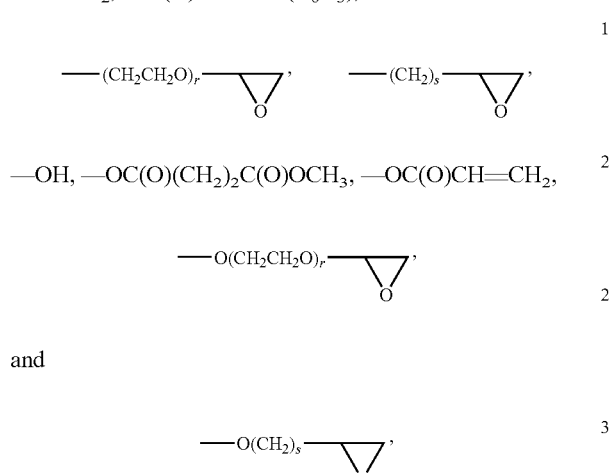

—OH, —OC(O)(CH$_2$)$_2$C(O)OCH$_3$, —OC(O)CH═CH$_2$, and

—P(O)(OH)(OX), —P(═O)(O$^-$)O(CH$_2$)$_s$NR$_3$$^+$; wherein R are each independently selected from the group consisting of hydrogen and 1-6C alkyl; X is selected from the group consisting of Cl, Br, and I; r is 1-50; and s is 1-4.

In another example, a closed ring composition comprises the formula:

$$(\text{-}Q^1\text{-})_J\text{-}L\text{-}Q^2\text{-}L'$$

wherein: J is 2-23; $Q^1$ are synthons each independently selected from the group consisting of (a) phenyl synthons coupled to linkages L at 1,2-phenyl positions, (b) phenyl synthons coupled to linkages L at 1,3-phenyl positions, and (c) cyclohexane synthons coupled to linkages L at 1,2-cyclohexyl positions; wherein ring positions of each $Q^1$ which are not coupled to a linkage L are substituted with hydrogen or functional groups containing atoms selected from the group of C, H, N, O, Si, P, S, B, Al, halogens, and metals from the alkali and alkaline earth groups; $Q^2$ is a cyclohexane synthon coupled to linkages L at 1,2-cyclohexyl positions; wherein ring positions of $Q^2$ which are not coupled to an L are substituted with functional groups containing atoms selected from the group consisting of C, H, N, O, Si, P, S, B, Al, halogens, and metals from the alkali and alkaline earth groups; L are linkages between the synthons each independently selected from the group consisting of (a) a condensed linkage, and (b) a linkage selected from the group consisting of —NRC(O)—, —OC(O)—, —O—, —S—S—, —S—, —NR—, —(CRR')$_p$—, —CH$_2$NH—, —C(O)S—, —C(O)O—, —C≡C—, —C≡C—C≡C—, —CH(OH)—, —HC═CH—, —NHC(O)NH—, —NHC(O)O—, —NHCH$_2$NH—, —NHCH$_2$CH(OH)CH$_2$NH—, —N═CH(CH$_2$)$_p$CH═N—, —CH$_2$CH(OH)CH$_2$—, —N═CH(CH$_2$)$_h$CH═N— where h is 1-4, —CH═N—NH—, —OC(O)O—, —OP(O)(OH)O—, —CH(OH)CH$_2$NH—, —CH(OH)CH$_2$—, —CH(OH)C(CH$_3$)$_2$C(O)O—,

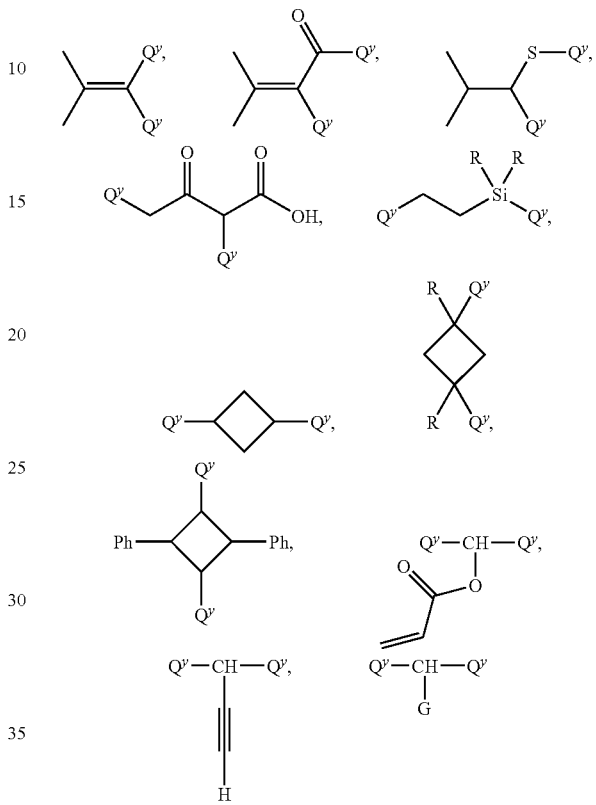

where G is halogen,

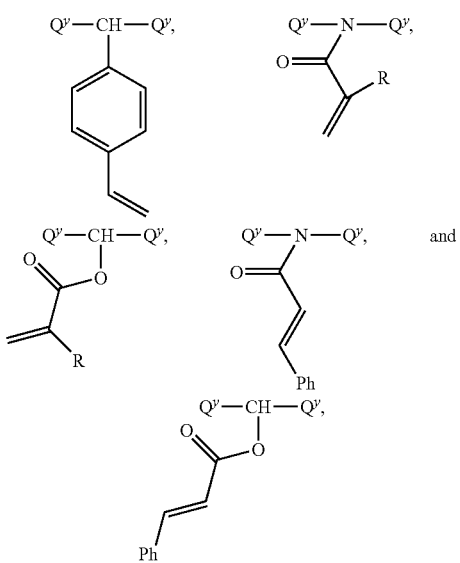

wherein p is 1-6; wherein R and R' are each independently selected from the group of hydrogen and alkyl; wherein linkages L are each independently configured in either of two possible configurations, forward and reverse, with respect to the synthons it couples together, if the two configurations are different structures; wherein y is 1 or 2, and $Q^y$ are each independently one of the $Q^1$ or $Q^2$ synthons connected by the linkage.

In some cases, the functional groups are each independently selected from the group consisting of hydrogen, an activated acid, —OH, —C(O)OH, —C(O)H, —C(O)OCH$_3$, —C(O)Cl, —NRR, —NRRR$^+$, —MgX, —Li, —OLi, —OK, —ONa, —SH, —C(O)(CH$_2$)$_2$C(O)OCH$_3$, —NH-alkyl-C(O)CH$_2$CH(NH$_2$)CO-alkyl, —CH=CH$_2$, —CH=CHR, —CH=CR$_2$, 4-vinylaryl, —C(O)CH=CH$_2$, —NHC(O)CH=CH$_2$, —C(O)CH=CH(C$_6$H$_5$),

—OH, —OC(O)(CH$_2$)$_2$C(O)OCH$_3$, —OC(O)CH=CH$_2$,

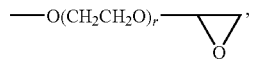

and

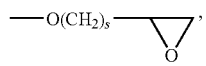

—P(O)(OH)(OX), —P(=O)(O$^-$)O(CH$_2$)$_s$NR$_3^+$;
wherein R are each independently selected from the group consisting of hydrogen and 1-6C alkyl; X is selected from the group consisting of Cl, Br, and I; r is 1-50; and s is 1-4.

In another embodiment is a closed ring composition of the formula:

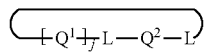

wherein: J is 2-23; $Q^1$ are synthons each independently selected from the group consisting of (a) phenyl synthons coupled to linkages L at 1,4-phenyl positions, (b) aryl synthons other than phenyl synthons, (c) heteroaryl synthons, (d) saturated cyclic hydrocarbon synthons, (e) unsaturated cyclic hydrocarbon synthons, (f) saturated bicyclic hydrocarbon synthons, (g) unsaturated bicyclic hydrocarbon synthons, (h) saturated multicyclic hydrocarbon synthons, and (i) unsaturated multicyclic hydrocarbon synthons; wherein at least one of $Q^1$ is a phenyl synthon coupled to linkages L at 1,4-phenyl positions, and wherein ring positions of each $Q^1$ which are not coupled to a linkage L are substituted with functional groups containing atoms selected from the group of C, H, N, O, Si, P, S, B, Al, halogens, and metals from the alkali and alkaline earth groups; $Q^2$ is a synthon independently selected from the group consisting of (a) aryl synthons other than phenyl synthons and naphthalene synthons coupled to linkages L at 2,7-naphthyl positions, (b) heteroaryl synthons, (c) saturated cyclic hydrocarbon synthons other than cyclohexane synthons coupled to linkages L at 1,2-cyclohexyl positions, (d) unsaturated cyclic hydrocarbon synthons, (e) saturated bicyclic hydrocarbon synthons, (f) unsaturated bicyclic hydrocarbon synthons, (g) saturated multicyclic hydrocarbon synthons, and (h) unsaturated multicyclic hydrocarbon synthons; wherein ring positions of $Q^2$ which are not coupled to an L are substituted with hydrogen or functional groups containing atoms selected from the group consisting of C, H, N, O, Si, P, S, B, Al, halogens, and metals from the alkali and alkaline earth groups; L are linkages between the synthons each independently selected from the group consisting of (a) a condensed linkage, and (b) a linkage selected from the group consisting of —NRC(O)—, —OC(O)—, —O—, —S—S—, —S—, —NR—, —(CRR')$_p$—, —CH$_2$NH—, —C(O)S—, —C(O)O—, —C≡C—, —C≡C—C≡C—, —CH(OH)—, —HC=CH—, —NHC(O)NH—, —NHC(O)O—, —NHCH$_2$NH—, —NHCH$_2$CH(OH)CH$_2$NH—, —N=CH(CH$_2$)$_p$CH=N—, —CH$_2$CH(OH)CH$_2$—, —N=CH(CH$_2$)$_h$CH=N— where h is 1-4, —CH=N—NH—, —OC(O)O—, —OP(O)(OH)O—, —CH(OH)CH$_2$NH—, —CH(OH)CH$_2$—, —CH(OH)C(CH$_3$)$_2$C(O)O—,

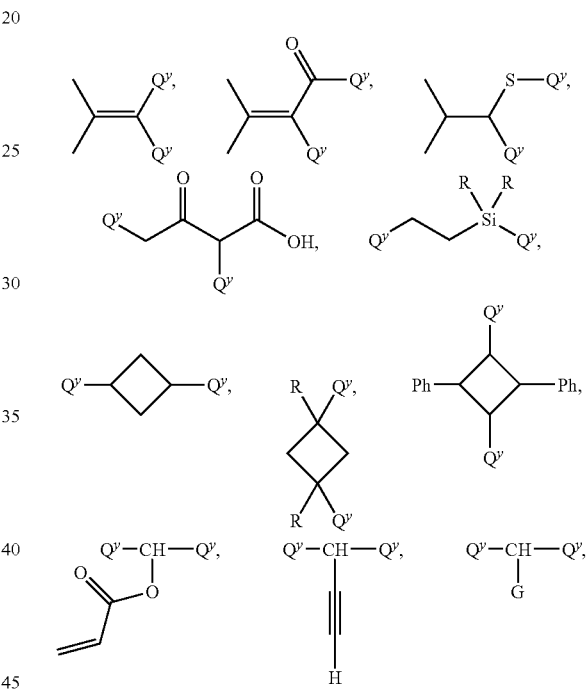

where G is halogen,

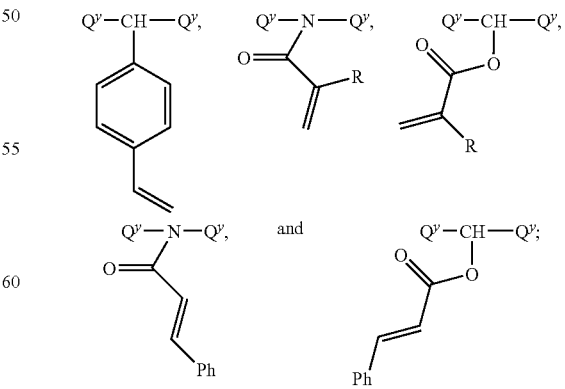

wherein p is 1-6; wherein R and R' are each independently selected from the group of hydrogen and alkyl; wherein linkages L are each independently configured in either of two possible configurations, forward and reverse, with respect to the synthons it couples together, if the two configurations are different structures; wherein y is 1 or 2, and $Q^y$ are each independently one of the $Q^1$ or $Q^2$ synthons connected by the linkage.

In other embodiment is a closed ring composition of the formula:

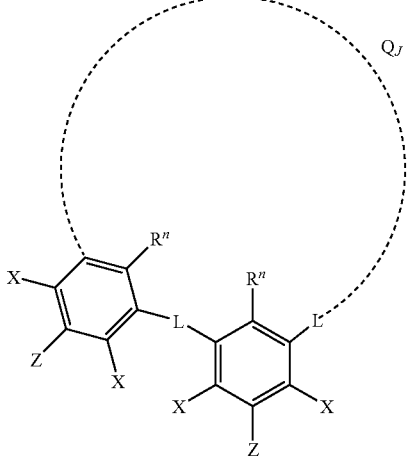

wherein: Q is

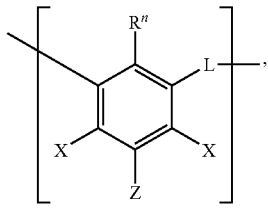

J is from 1-22, and n is from 1-24; X and $R''$ are each independently selected from the group consisting of functional groups containing atoms selected from the group consisting of C, H, N, O, Si, P, S, B, Al, halogens, and metals from the alkali and alkaline earth groups; Z are each independently hydrogen or a lipophilic group; L are linkages between synthons each independently selected from the group consisting of (a) a condensed linkage, and (b) a linkage selected from the group consisting of —N=CR—, —NRC(O)—, —OC(O)—, —O—, —S—S—, —S—, —NR—, —(CRR')$_p$—, —CH$_2$NH—, —C(O)S—, —C(O)O—, —C≡C—, —C≡C—C≡C—, —CH(OH)—, —HC=CH—, —NHC(O)NH—, —NHC(O)O—, —NHCH$_2$NH—, —NHCH$_2$CH(OH)CH$_2$NH—, —N=CHCH$_2$CH=N— —N=CH(CH$_2$)$_h$CH=N— where h is 1-4, —CH=N—NH—, —OC(O)O—, —P(O)(OH)$_2$O—, —CH(OH)CH$_2$NH—, —CH(OH)CH$_2$—, —CH(OH)C(CH$_3$)$_2$C(O)O—,

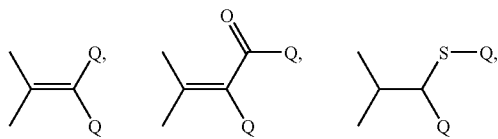

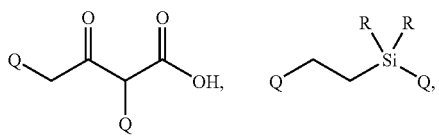

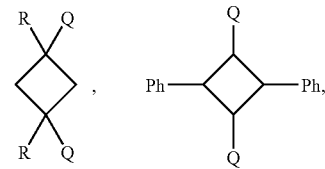

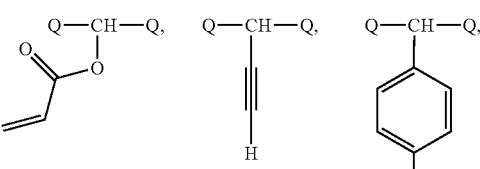

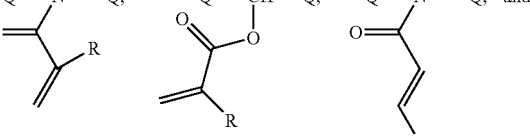

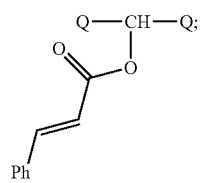

wherein p is 1-6; wherein R and R' are each independently selected from the group of hydrogen and alkyl; wherein linkages L are each independently configured in either of two possible configurations, forward and reverse, with respect to the synthons it couples together, if the two configurations are different structures.

In one embodiment, X and $R''$ are each independently selected from the group consisting of hydrogen, an activated acid, —OH, —C(O)OH, —C(O)H, —C(O)OCH$_3$, —C(O)Cl, —NRR, —NRRR$^+$, —MgX, —Li, —OLi, —OK, —ONa, —SH, —C(O)(CH$_2$)$_2$C(O)OCH$_3$, —NH-alkyl-C(O)CH$_2$CH(NH$_2$)CO$_2$-alkyl, —CH=CH$_2$, —CH=CHR, —CH=CR$_2$, 4-vinylaryl, —C(O)CH=CH$_2$, —NHC(O)CH=CH$_2$, —C(O)CH=CH(C$_6$H$_5$),

—OH, —OC(O)(CH$_2$)$_2$C(O)OCH$_3$, —OC(O)CH=CH$_2$,

and

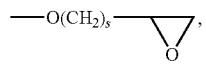

—P(O)(OH)(OX), —P(=O)(O⁻)O(CH₂)ₛNR₃⁺;
wherein R are each independently selected from the group consisting of hydrogen and 1-6C alkyl; X is selected from the group consisting of Cl, Br, and I; r is 1-50; and s is 1-4.

In another embodiment is a closed ring composition of the formula:

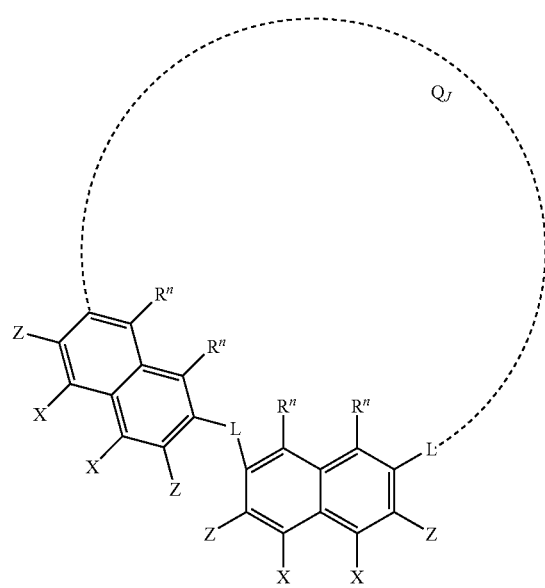

wherein: Q is

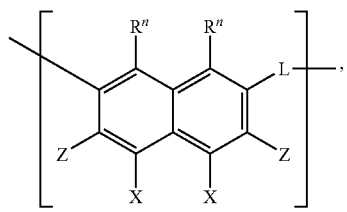

J is from 1-22, and n is from 1-48; X and R″ are each independently selected from the group consisting of functional groups containing atoms selected from the group consisting of C, H, N, O, Si, P, S, B, Al, halogens, and metals from the alkali and alkaline earth groups; Z are each independently hydrogen or a lipophilic group; L are linkages between the synthons each independently selected from the group consisting of (a) a condensed linkage, and (b) a linkage selected from the group consisting of —NRC(O)—, —OC(O)—, —O—, —S—S—, —S—, —NR—, —(CRR')ₚ—, —CH₂NH—, —C(O)S—, —C(O)O—, —C≡C—, —C≡C—C≡C—, —CH(OH)—, —HC=CH—, —NHC(O)NH—, —NHC(O)O—, —NHCH₂NH—, —NHCH₂CH(OH)CH₂NH—, —N=CH(CH₂)ₚCH=N—, —CH₂CH(OH)CH₂—, —N=CH(CH₂)ₕCH=N— where h is 1-4, —CH=N—NH—, —OC(O)O—, —OP(O)(OH)O—, —CH(OH)CH₂NH—, —CH(OH)CH₂—, —CH(OH)C(CH₃)₂C(O)O—,

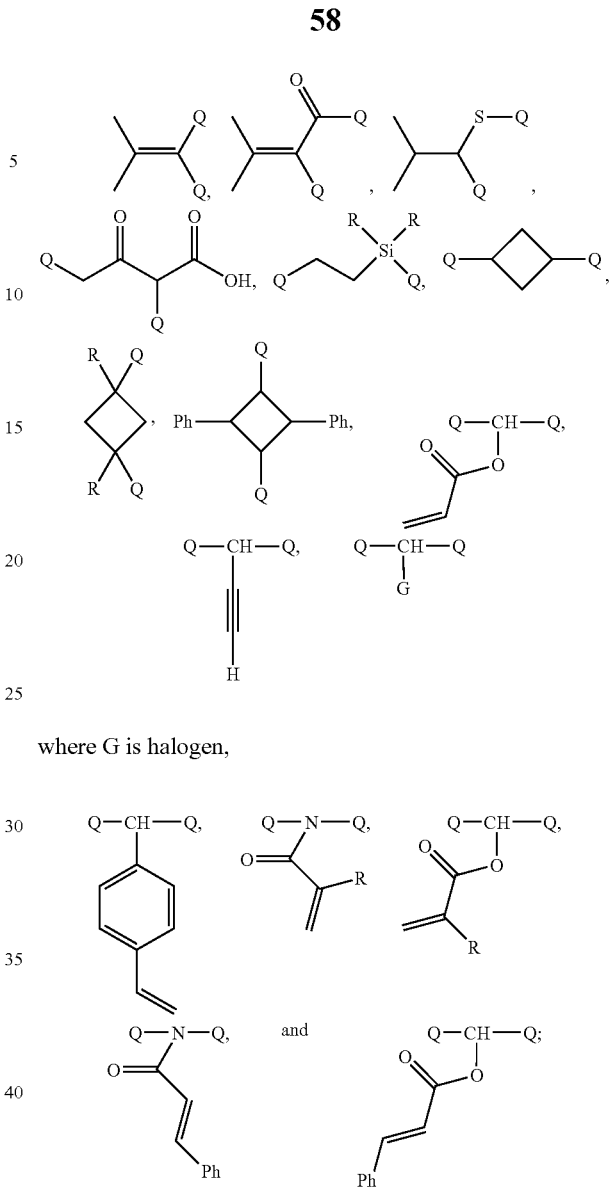

where G is halogen, wherein p is 1-6; wherein R and R' are each independently selected from the group of hydrogen and alkyl; wherein linkages L are each independently configured in either of two possible configurations, forward and reverse, with respect to the synthons it couples together, if the two configurations are different structures.

In another embodiment, X and R″ are each independently selected from the group consisting of hydrogen, an activated acid, —OH, —C(O)OH, —C(O)H, —C(O)OCH₃, —C(O)Cl, —NRR, —NRRR⁺, —MgX, —Li, —OLi, —OK, —ONa, —SH, —C(O)(CH₂)₂C(O)OCH₃, —NH-alkyl-C(O)CH₂CH(NH₂)CO₂-alkyl, —CH=CH₂, —CH=CHR, —CH=CR₂, 4-vinylaryl, —C(O)CH=CH₂, —NHC(O)CH=CH₂, —C(O)CH=CH(C₆H₅),

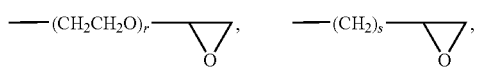

—OH, —OC(O)(CH₂)₂C(O)OCH₃, —OC(O)CH=CH₂,

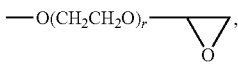

and

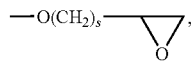

—P(O)(OH)(OX), —P(=O)(O⁻)O(CH₂)ₛNR₃⁺; wherein R are each independently selected from the group consisting of hydrogen and 1-6C alkyl; X is selected from the group consisting of Cl, Br, and I; r is 1-50; and s is 1-4.

In another embodiment, the closed ring composition may have the formula:

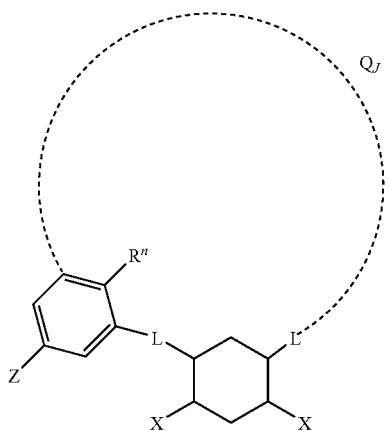

wherein:

Q is

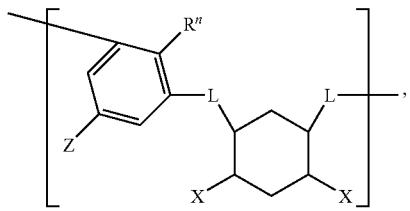

J is from 1-11, and n is from 1-12; X and R″ are each independently selected from the group consisting of hydrogen, an activated acid, —OH, —C(O)OH, —C(O)H, —C(O)OCH₃, —C(O)Cl, —NRR, —NRRR⁺, —MgX, —Li, —OLi, —OK, —ONa, —SH, —C(O)(CH₂)₂C(O)OCH₃, —NH-alkyl-C(O)CH₂CH(NH₂)CO₂-alkyl, —CH=CH₂, —CH=CHR, —CH=CR₂, 4-vinylaryl, —C(O)CH=CH₂, —NHC(O)CH=CH₂, —C(O)CH=CH(C₆H₅),

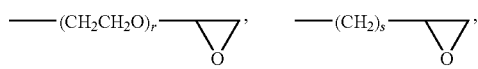

—OH, —OC(O)(CH₂)₂C(O)OCH₃, —OC(O)CH=CH₂,

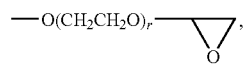

and

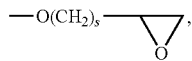

—P(O)(OH)(OX), —P(O)(O⁻)O(CH₂)ₛNR₃⁺;

wherein R are each independently selected from the group consisting of hydrogen and 1-6C alkyl; X is selected from the group consisting of Cl, Br, and I; r is 1-50; and s is 1-4; Z are each independently hydrogen or a lipophilic group; L are linkages between synthons each independently selected from the group consisting of (a) a condensed linkage, and (b) a linkage selected from the group consisting of —NRC(O)—, —OC(O)—, —O—, —S—S—, —S—, —NR—, —(CRR')ₚ—, —CH₂NH—, —C(O)S—, —C(O)O—, —C≡C—, —C≡C—C≡C—, —CH(OH)—, —HC=CH—, —NHC(O)NH—, —NHC(O)O—, —NHCH₂NH—, —NHCH₂CH(OH)CH₂NH—, —N=CH(CH₂)ₚCH=N—, —CH₂CH(OH)CH₂—, —N=CH(CH₂)ₕCH=N— where h is 1-4, —CH=N—NH—, —OC(O)O—, —OP(O)(OH)O—, —CH(OH)CH₂NH—, —CH(OH)CH₂—, —CH(OH)C(CH₃)₂C(O)O—,

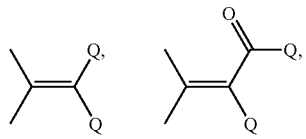
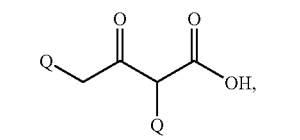
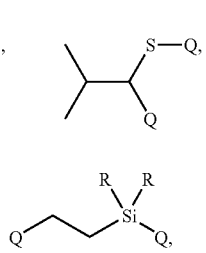
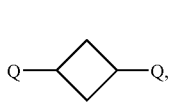
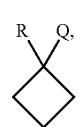
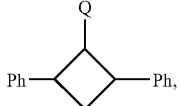
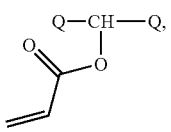
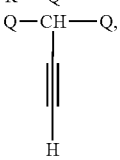
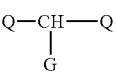

where G is halogen,

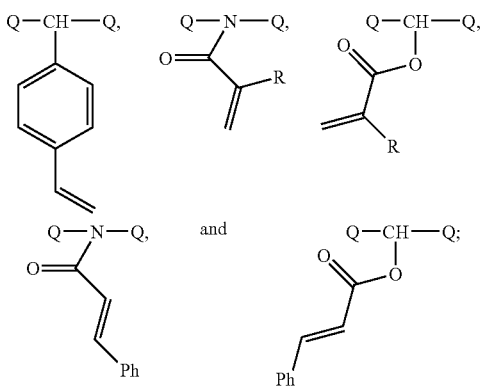

wherein p is 1-6; wherein R and R' are each independently selected from the group of hydrogen and alkyl; wherein linkages L are each independently configured in either of two possible configurations, forward and reverse, with respect to the synthons it couples together, if the two configurations are different structures.

In another embodiment the closed ring composition may have the formula:

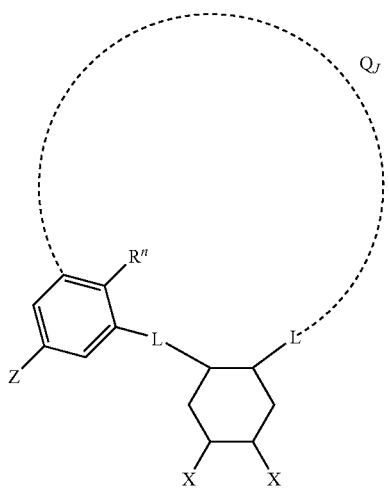

wherein:
Q is

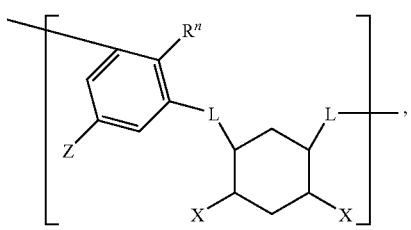

J is from 1-11, and n is from 1-12;
X and $R^n$ are each independently selected from the group consisting of hydrogen, an activated acid, —OH, —C(O)OH, —C(O)H, —C(O)OCH$_3$, —C(O)Cl, —NRR, —NRRR$^+$, —MgX, —Li, —OLi, —OK, —ONa, —SH, —C(O)(CH$_2$)$_2$ C(O)OCH$_3$, —NH-alkyl-C(O)CH$_2$CH(NH$_2$)CO$_2$-alkyl, —CH=CH$_2$, —CH=CHR, —CH=CR$_2$, 4-vinylaryl, —C(O)CH=CH$_2$, —NHC(O)CH=CH$_2$, —C(O)CH=CH (C$_6$H$_5$),

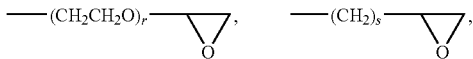

—OH, —OC(O)(CH$_2$)$_2$C(O)OCH$_3$, —OC(O)CH=CH$_2$,

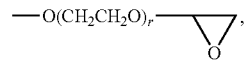

and

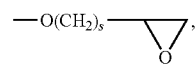

—P(O)(OH)(OX), —P(=O)(O$^-$)O(CH$_2$)$_s$NR$_3^+$; wherein R are each independently selected from the group consisting of hydrogen and 1-6C alkyl; X is selected from the group consisting of Cl, Br, and I; r is 1-50; and s is 1-4; Z are each independently hydrogen or a lipophilic group; L are linkages between the synthons each independently selected from the group consisting of (a) a condensed linkage, and (b) a linkage selected from the group consisting of —NRC(O)—, —OC (O)—, —O—, —S—S—, —S—, —NR—, —(CRR')$_p$—, —CH$_2$NH—, —C(O)S—, —C(O)O—, —C=C—, —C≡C—C≡C—, —CH(OH)—, —HC=CH—, —NHC (O)NH—, —NHC(O)O—, —NHCH$_2$NH—, —NHCH$_2$CH (OH)CH$_2$NH—, —N=CH(CH$_2$)$_p$CH=N—, —CH$_2$CH (OH)CH$_2$—, —N=CH(CH$_2$)$_h$CH=N— where h is 1-4, —CH=N—NH—, —OC(O)O—, —OP(O)(OH)O—, —CH(OH)CH$_2$NH—, —CH(OH)CH$_2$—, —CH(OH)C (CH$_3$)$_2$C(O)O—,

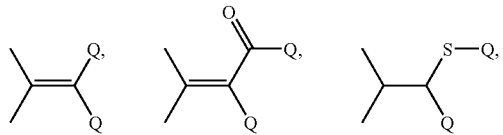

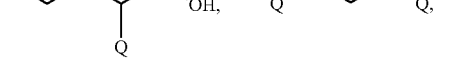

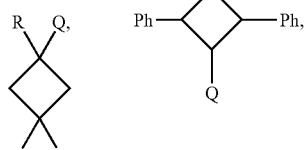

-continued

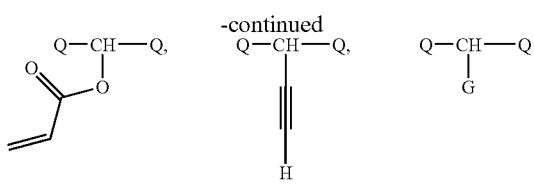

where G is halogen,

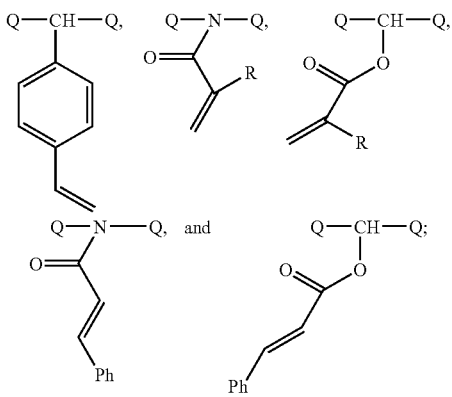

wherein p is 1-6; wherein R and R' are each independently selected from the group of hydrogen and alkyl; wherein linkages L are each independently configured in either of two possible configurations, forward and reverse, with respect to the synthons it couples together, if the two configurations are different structures.

In another embodiment, the closed ring composition may have the formula:

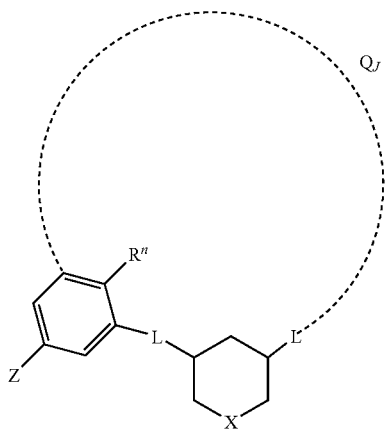

wherein:
Q is

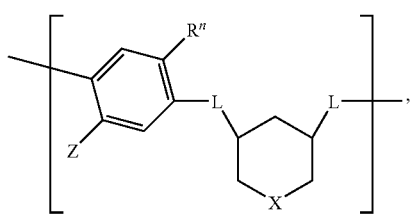

J is from 1-11, and n is from 1-12; X is $-NX^1-$ or $-CX^2X^3$, where $X^1$ is selected from the group consisting of an amino acid residue, $-CH_2C(O)CH_2CH(NH_2)CO_2$-alkyl, and $-C(O)CH=CH_2$; $X^2$ and $X^3$ are each independently selected from the group consisting of hydrogen, $-OH$, $-NH_2$, $-SH$, $-(CH_2)_tOH$, $-(CH_2)_tNH_2$ and $-(CH_2)_tSH$, wherein t is 1-4, and $X^2$ and $X^3$ are not both hydrogen; R" are each independently selected from the group consisting of hydrogen, an activated acid, $-OH$, $-C(O)OH$, $-C(O)H$, $-C(O)OCH_3$, $-C(O)Cl$, $-NRR$, $-NRRR^+$, $-MgX$, $-Li$, $-OLi$, $-OK$, $-ONa$, $-SH$, $-C(O)(CH_2)_2C(O)OCH_3$, $-NH$-alkyl-$C(O)CH_2CH(NH_2)CO_2$-alkyl, $-CH=CH_2$, $-CH=CHR$, $-CH=CR_2$, 4-vinylaryl, $-C(O)CH=CH_2$, $-NHC(O)CH=CH_2$, $-C(O)CH=CH(C_6H_5)$,

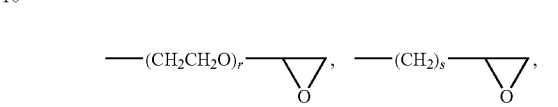

$-OH$, $-OC(O)(CH_2)_2C(O)OCH_3$, $-OC(O)CH=CH_2$,

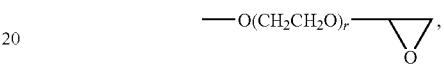

and

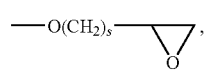

$-P(O)(OH)(OX)$, $-P(=O)(O^-)O(CH_2)_sNR_3^+$;

wherein R are each independently selected from the group consisting of hydrogen and 1-6C alkyl; X is selected from the group consisting of Cl, Br, and I; r is 1-50; and s is 1-4; Z are each independently hydrogen or a lipophilic group; L are linkages between synthons each independently selected from the group consisting of (a) a condensed linkage, and (b) a linkage selected from the group consisting of $-NRC(O)-$, $-OC(O)-$, $-O-$, $-S-S-$, $-S-$, $-NR-$, $-(CRR')_p-$, $-CH_2NH-$, $-C(O)S-$, $-C(O)O-$, $-C\equiv C-$, $-C\equiv C-C\equiv C-$, $-CH(OH)-$, $-HC=CH-$, $-NHC(O)NH-$, $-NHC(O)O-$, $-NHCH_2NH-$, $-NHCH_2CH(OH)CH_2NH-$, $-N=CH(CH_2)_pCH=N-$, $-CH_2CH(OH)CH_2-$, $-N=CH(CH_2)_hCH=N-$ where h is 1-4, $-CH=N-NH-$, $-OC(O)O-$, $-OP(O)(OH)O-$, $-CH(OH)CH_2NH-$, $-CH(OH)CH_2-$, $-CH(OH)C(CH_3)_2C(O)O-$,

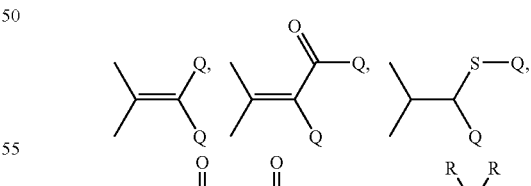

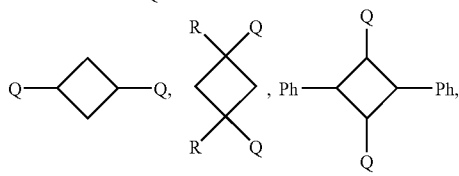

-continued

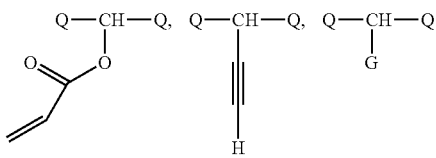

where G is halogen,

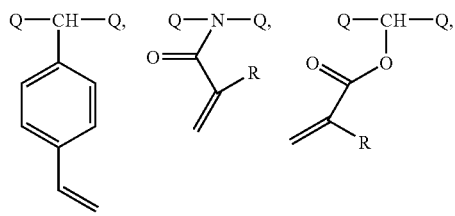

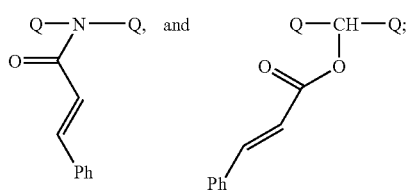

wherein p is 1-6; wherein R and R' are each independently selected from the group of hydrogen and alkyl; wherein linkages L are each independently configured in either of two possible configurations, forward and reverse, with respect to the synthons it couples together, if the two configurations are different structures.

In another embodiment the closed ring structure may have the formula:

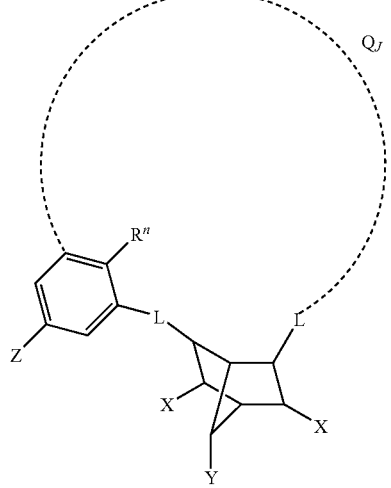

wherein:

Q is

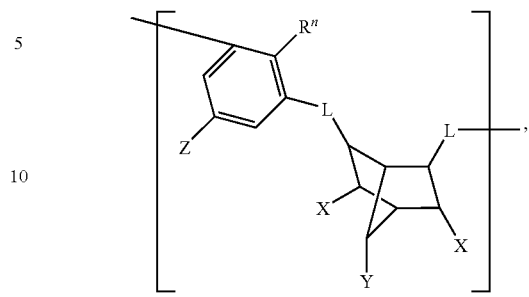

J is from 1-11, and n is from 1-12; X and R″ are each independently selected from the group consisting of hydrogen, an activated acid, —OH, —C(O)OH, —C(O)H, —C(O)OCH$_3$, —C(O)Cl, —NRR, —NRRR$^+$, —MgX, —Li, —OLi, —OK, —ONa, —SH, —C(O)(CH$_2$)$_2$C(O)OCH$_3$, —NH-alkyl-C(O)CH$_2$CH(NH$_2$)CO$_2$-alkyl, —CH=CH$_2$, —CH=CHR, —CH=CR$_2$, 4-vinylaryl, —C(O)CH=CH$_2$, —NHC(O)CH=CH$_2$, —C(O)CH=CH(C$_6$H$_5$), $$—(CH_2CH_2O)_r\text{-}\underset{O}{\triangle}, \quad —(CH_2)_s\text{-}\underset{O}{\triangle},$$

—OH, —OC(O)(CH$_2$)$_2$C(O)OCH$_3$, —OC(O)CH=CH$_2$, $$—O(CH_2CH_2O)_r\text{-}\underset{O}{\triangle},$$

and $$—O(CH_2)_s\text{-}\underset{O}{\triangle},$$

—P(O)(OH)(OX), —P(=O)(O$^-$)O(CH$_2$)$_s$NR$_3^+$; wherein R are each independently selected from the group consisting of hydrogen and 1-6C alkyl; X is selected from the group consisting of Cl, Br, and I; r is 1-50; and s is 1-4; Z and Y are each independently hydrogen or a lipophilic group; L are linkages between the synthons each independently selected from the group consisting of (a) a condensed linkage, and (b) a linkage selected from the group consisting of —NRC(O)—, —OC(O)—, —O—, —S—S—, —S—, —NR—, —(CRR')$_p$—, —CH$_2$NH—, —C(O)S—, —C(O)O—, —C≡C—, —C≡C—C≡C—, —CH(OH)—, —HC=CH—, —NHC(O)NH—, —NHC(O)O—, —NHCH$_2$NH—, —NHCH$_2$CH(OH)CH$_2$NH—, —N=CH(CH$_2$)$_p$CH=N—, —CH$_2$CH(OH)CH$_2$—, —N=CH(CH$_2$)$_h$CH=N— where h is 1-4, —CH=N—NH—, —OC(O)O—, —OP(O)(OH)O—, —CH(OH)CH$_2$NH—, —CH(OH)CH$_2$—, —CH(OH)C(CH$_3$)$_2$C(O)O—,

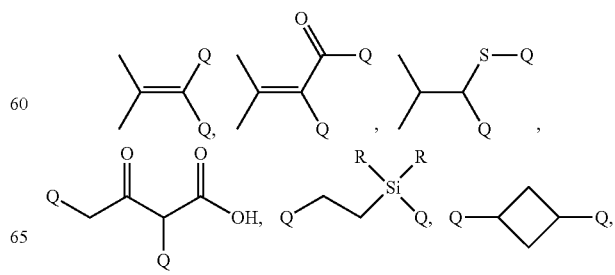

-continued

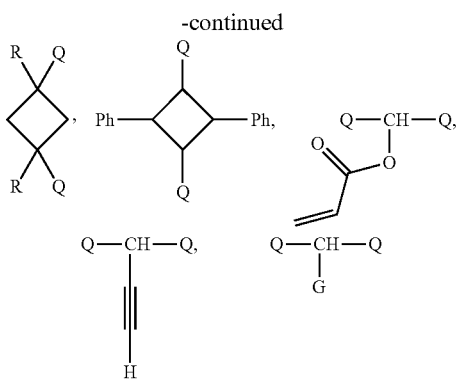

where G is halogen,

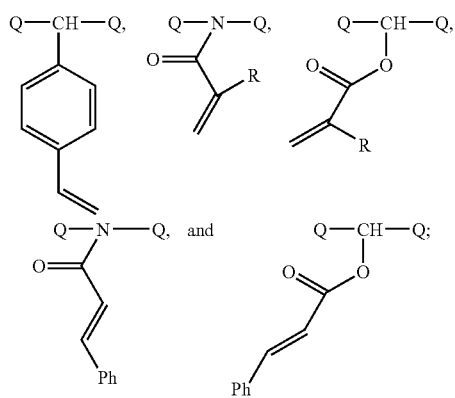

wherein p is 1-6;

wherein R and R' are each independently selected from the group of hydrogen and alkyl; wherein linkages L are each independently configured in either of two possible configurations, forward and reverse, with respect to the synthons it couples together, if the two configurations are different structures.

In another embodiment, the closed ring structure may have the formula:

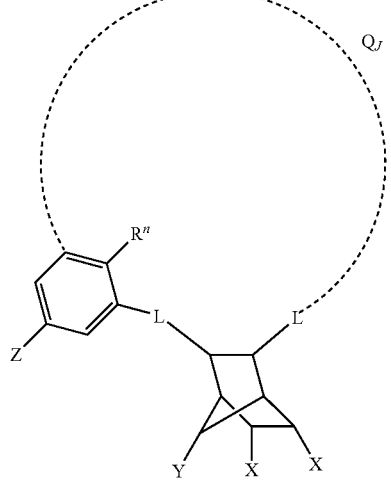

wherein:
Q is

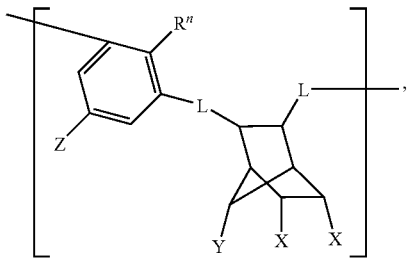

J is from 1-11, and n is from 1-12; X and R" are each independently selected from the group consisting of hydrogen, an activated acid, —OH, —C(O)OH, —C(O)H, —C(O)OCH$_3$, —C(O)Cl, —NRR, —NRRR$^+$, —MgX, —Li, —OLi, —OK, —ONa, —SH, —C(O)(CH$_2$)$_2$C(O)OCH$_3$, —NH-alkyl-C(O)CH$_2$CH(NH$_2$)CO$_2$-alkyl, —CH=CH$_2$, —CH=CHR, —CH=CR$_2$, 4-vinylaryl, —C(O)CH=CH$_2$, —NHC(O)CH=CH$_2$, —C(O)CH=CH(C$_6$H$_5$), —(CH$_2$CH$_2$O)$_r$—[epoxide], —(CH$_2$)$_s$—[epoxide],

—OH, —OC(O)(CH$_2$)$_2$C(O)OCH$_3$, —OC(O)CH=CH$_2$,

—O(CH$_2$CH$_2$O)$_r$—[epoxide], and

—O(CH$_2$)$_s$—[epoxide],

—P(O)(OH)(OX), —P(=O)(O$^-$)O(CH$_2$)$_s$NR$_3^+$;

wherein R are each independently selected from the group consisting of hydrogen and 1-6C alkyl; X is selected from the group consisting of Cl, Br, and I; r is 1-50; and s is 1-4; Z and Y are each independently hydrogen or a lipophilic group; L are linkages between synthons each independently selected from the group consisting of (a) a condensed linkage, and (b) a linkage selected from the group consisting of —NRC(O)—, —OC(O)—, —O—, —S—S—, —S—, —NR—, —(CRR')$_p$—, —CH$_2$NH—, —C(O)S—, —C(O)O—, —C≡C—, —C≡C—C≡C—, —CH(OH)—, —HC=CH—, —NHC(O)NH—, —NHC(O)O—, —NHCH$_2$NH—, —NHCH$_2$CH(OH)CH$_2$NH—, —N=CH(CH$_2$)$_p$CH=N—, —CH$_2$CH(OH)CH$_2$—, —N=CH(CH$_2$)$_h$CH=N— where h is 1-4, —CH=N—NH—, —OC(O)O—, —OP(O)(OH)O—, —CH(OH)CH$_2$NH—, —CH(OH)CH$_2$—, —CH(OH)C(CH$_3$)$_2$C(O)O—,

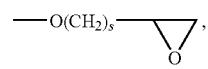

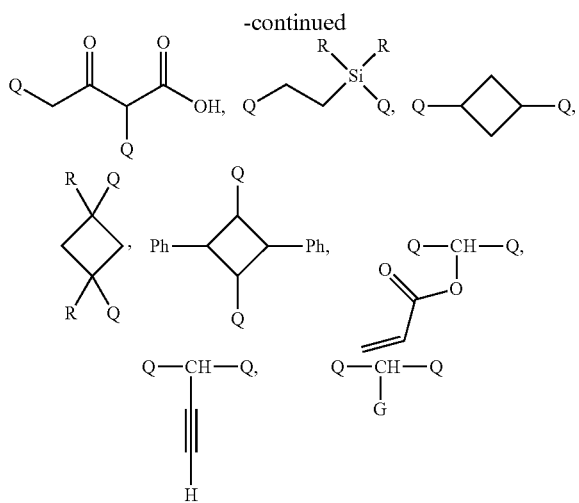

where G is halogen,

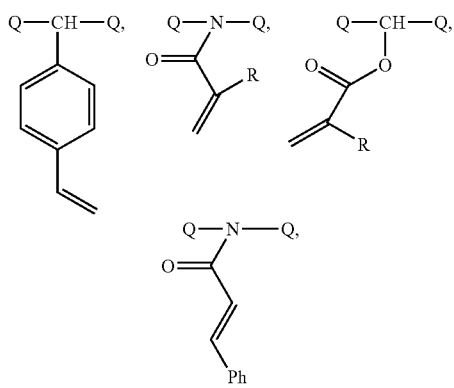

and

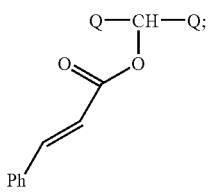

wherein p is 1-6; wherein R and R' are each independently selected from the group of hydrogen and alkyl; wherein linkages L are each independently configured in either of two possible configurations, forward and reverse, with respect to the synthons it couples together, if the two configurations are different structures.

In one variation, a macrocyclic module may be a closed ring composition of the formula:

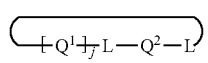

wherein: the closed ring comprises a total of from three to twenty-four synthons Q; J is 2-23; $Q^1$ are synthons each independently selected from the group consisting of (a) aryl synthons, (b) heteroaryl synthons, (c) saturated cyclic hydrocarbon synthons, (d) unsaturated cyclic hydrocarbon synthons, (e) saturated bicyclic hydrocarbon synthons, (f) unsaturated bicyclic hydrocarbon synthons, (g) saturated multicyclic hydrocarbon synthons, and (h) unsaturated multicyclic hydrocarbon synthons; wherein ring positions of each $Q^1$ which are not coupled to a linkage L are substituted with hydrogen or functional groups containing atoms selected from the group of C, H, N, O, Si, P, S, B, Al, halogens, and metals from the alkali and alkaline earth groups; $Q^2$ is a synthon independently selected from the group consisting of (a) aryl synthons, (b) heteroaryl synthons, (c) saturated cyclic hydrocarbon synthons, (d) unsaturated cyclic hydrocarbon synthons, (e) saturated bicyclic hydrocarbon synthons, (f) unsaturated bicyclic hydrocarbon synthons, (g) saturated multicyclic hydrocarbon synthons, and (h) unsaturated multicyclic hydrocarbon synthons; wherein ring positions of $Q^2$ which are not coupled to an L are substituted with hydrogen or functional groups containing atoms selected from the group consisting of C, H, N, O, Si, P, S, B, Al, halogens, and metals from the alkali and alkaline earth groups; L are linkages between the synthons each independently selected from the group consisting of synthon-synthon, —NRC(O)—, —OC(O)—, —O—, —S—S—, —S—, —NR—, —(CRR')$_p$—, —CH$_2$NH—, —C(O)S—, —C(O)O—, —C≡C—, —C≡C—C≡C—, —CH(OH)—, —HC=CH—, —NHC(O)NH—, —NHC(O)O—, —NHCH$_2$NH—, —NHCH$_2$CH(OH)CH$_2$NH—, —N=CH(CH$_2$)$_p$CH=N—, —CH$_2$CH(OH)CH$_2$—, —N=CH(CH$_2$)$_h$CH=N— where h is 1-4, —CH=N—NH—, —OC(O)O—, —OP(O)(OH)O—, —CH(OH)CH$_2$NH—, —CH(OH)CH$_2$—, —CH(OH)C(CH$_3$)$_2$C(O)O—,

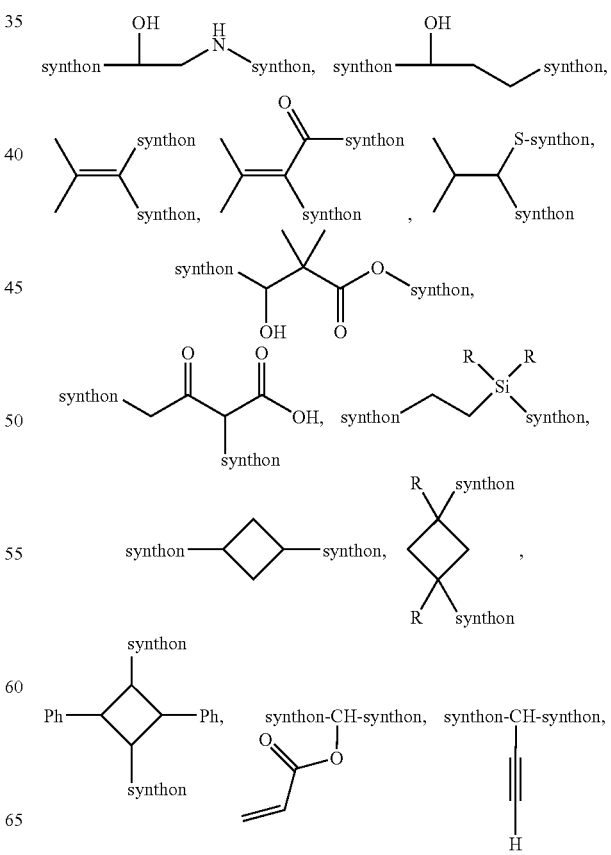

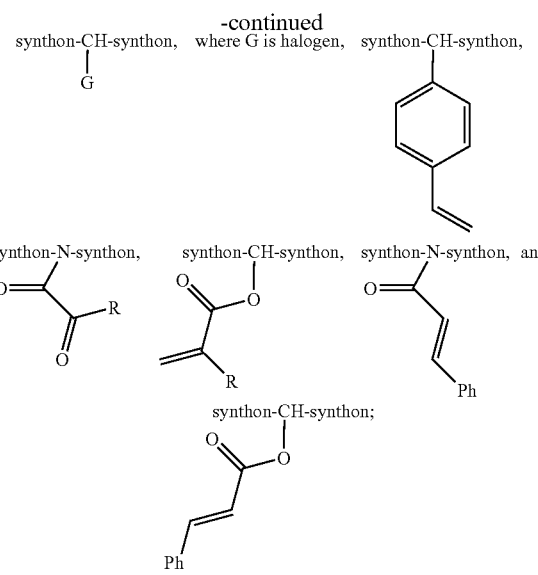

wherein p is 1-6; wherein R and R' are each independently selected from the group of hydrogen and alkyl; wherein the linkages L are each independently configured with respect to the $Q^1$ and $Q^2$ synthons, each L having either of its two possible configurations with respect to the synthons it couples together, the forward and reverse configurations of the linkage with respect to the immediately adjacent synthons to which it couples, for example, $Q^1_a$-NHC(O)-$Q^1_b$ and $Q^1_a$-C(O)NH-$Q^1_b$, if the two configurations are isomerically different structures. Synthons $Q^1$, when independently selected, may be any cyclic synthon as described, so that the J synthons $Q^1$ may be found in the closed ring in any order, for example, cyclohexyl-1,2-phenyl-piperidinyl-1,2-phenyl-1,2-phenyl-cyclohexyl, and so on, and the J linkages L may also be independently selected and configured in the closed ring. The macrocyclic modules represented and encompassed by the formula include all stereoisomers of the synthons involved, so that a wide variety of stereoisomers of the macrocyclic module are included for each closed ring composition of synthons.

Methods for making a macrocyclic module composition may comprise, for example: (a) providing a plurality of a first cyclic synthon; (b) contacting a plurality of a second cyclic synthon with the first cyclic synthons; (c) isolating the macrocyclic module composition. In some embodiments, the method may further comprise contacting a linker molecule with the mixture in (a) or (b).

Another method of preparing a composition for transporting a selected species through the composition comprises: selecting a first cyclic synthon, wherein the first cyclic synthon is substituted with at least one functional group comprising an functional group containing atoms selected from the group consisting of C, H, N, O, Si, P, S, B, Al, halogens, and metals from the alkali and alkaline earth groups; selecting from two to about twenty-three additional cyclic synthons; incorporating the first cyclic synthon and the additional cyclic synthons into a macrocyclic module composition comprising: from three to about twenty-four cyclic synthons coupled to form a closed ring defining a pore; wherein the at least one functional group of the first cyclic synthon is located at the pore of the macrocyclic module composition and is selected to transport the selected species through the pore.

Another method for making a macrocyclic module composition comprises: (a) providing a plurality of a first cyclic synthon; (b) contacting a plurality of a second cyclic synthon with the first cyclic synthons; (c) contacting a plurality of the first cyclic synthon with the mixture from (b).

Another method for making a macrocyclic module composition comprises: (a) providing a plurality of a first cyclic synthon; (b) contacting a plurality of a second cyclic synthon with the first cyclic synthons; (c) contacting a plurality of a third cyclic synthon with the mixture from (b).

In some embodiments, the method may further comprise supporting a cyclic synthon or coupled synthons on a solid phase.

Another method for making a macrocyclic module composition comprises: (a) contacting a plurality of cyclic synthons with a metal complex template; (b) isolating the macrocyclic module composition.

A macrocyclic module may include functional groups for coupling the macrocyclic module to a solid surface, substrate, or support. Examples of functional groups of macrocyclic modules which can be used to couple to a substrate or surface include amine, carboxylic acid, carboxylic ester, benzophenone and other light activated crosslinkers, alcohol, glycol, vinyl, styryl, olefin styryl, epoxide, thiol, magnesium halo or Grignard, acrylate, acrylamide, diene, aldehyde, and mixtures thereof. These functional groups may be coupled to the closed ring of the macrocyclic module, and may optionally be attached by a spacer group. Examples of solid surfaces include metal surfaces, ceramic surfaces, polymer surfaces, semiconductor surfaces, silicon wafer surfaces, alumina surfaces, and so on. Examples of functional groups of macrocyclic modules which can be used to couple to a substrate or surface further include those described in the left hand column of Tables 5 and 6. Methods of initiating coupling of the modules to the substrate include chemical, thermal, photochemical, electrochemical, and irradiative methods.

Examples of spacer groups include polyethylene oxides, polypropylene oxides, polysaccharides, polylysines, polypeptides, poly(amino acids), polyvinylpyrrolidones, polyesters, polyvinylchlorides, polyvinylidene fluorides, polyvinylalcohols, polyurethanes, polyamides, polyimides, polysulfones, polyethersulfones, polysulfonamides, and polysulfoxides.

Macrocyclic Module Pores

An individual macrocyclic module may include a pore in its structure. The size of the pore may determine the size of molecules or other species which can pass through the macrocyclic module. The size of a pore in a macrocyclic module may depend on the structure of the synthons used to make the macrocyclic module, the linkages between synthons, the number of synthons in a module, the structure of any linker molecules used to make the macrocyclic module, and other structural features of the macrocyclic module whether inherent in the preparation of the macrocyclic module or added in later steps or modifications. Stereoisomerism of macrocyclic modules may also be used to regulate the size of a pore of a macrocyclic module by variation of the stereoisomer of each synthon used to prepare the closed ring of the macrocyclic module.

The dimension of a pore in a macrocyclic module may be varied by changing the combination of synthons used to form the macrocyclic module, or by varying the number of synthons in the closed ring. The dimension of a pore may also be varied by substituents on the synthons or linkages. The pore may therefore be made large enough or small enough to achieve an effect on transport of species through the pore. Species which may be transported through the pore of a macrocyclic module include atoms, molecules, biomolecules, ions, charged particles, and photons.

The size of a species may not be the sole determinant of whether it will be able to pass through a pore of a macrocyclic module. Groups or moieties located in or near the pore structure of a macrocyclic module may regulate or affect transport of a species through the pore by various mechanisms. For example, transport of a species through the pore may be affected by groups of the macrocyclic module which interact with the species, by ionic or other interaction, such as chelating groups, or by complexing the species. For example, a charged group such as a carboxylate anion or ammonium group may couple an oppositely-charged species and affect its transport. Substituents of synthons in a macrocyclic module may affect the passage of a species through the pore of the macrocyclic module. Groups of atoms which render the pore of a macrocyclic module more or less hydrophilic or lipophilic may affect transport of a species through the pore. An atom or group of atoms may be located within or proximate to a pore to sterically slow or block the passage of a species through the pore. For example, hydroxyl or alkoxy groups may be coupled to a cyclic synthon and located in the pore of the structure of the macrocyclic module, or may be coupled to a linkage between synthons and located in the pore. A wide range of functional groups may be used to sterically slow or block the passage of a species through the pore, including functional groups containing atoms selected from the group consisting of C, H, N, O, Si, P, S, B, Al, halogens, and metals from the alkali and alkaline earth groups. Blocking and slowing passage of a species through the pore may involve reducing the dimension of the pore by steric blocking, as well as slowing the passage of species by creating a path through the pore which is not linear, and providing interaction between the functional group and the species to slow transport. The stereochemical structure of the portion of the macrocyclic module which defines the pore and its interior may also affect transport. Any groups or moieties which affect transport of a species through the pore of a macrocyclic module may be introduced as part of the synthons used to prepare the macrocyclic module, or may be added later by various means. For example, S7-1 could be reacted with $ClC(O)(CH_2)_2C(O)OCH_2CH_3$ to convert the phenol groups to succinyl ester groups. Further, molecular dynamical motion of the synthons and linkages of a partly flexible macrocyclic module may affect transport of a species through the pore of the module. Transport behavior may not be described solely by the structure of the macrocyclic module itself since the presence of the species which is to be transported through the pore affects the flexibility, conformation, and dynamical motions of a macrocyclic module. In general, solvent may also affect transport of solutes through a pore.

Macrocyclic modules and arrays of macrocyclic modules may be useful in size exclusion separations, ion separation, gas separation, separation of enantiomers, small molecule separation, water purification, filtration of bacteria, fungi, or viruses, sewage treatment, and toxin removal, among other uses.

The following examples further describe and demonstrate variations within the scope of the present invention. All examples described in this specification, both in the description above and the examples below, are given solely for the purpose of illustration and are not to be construed as limiting the present invention. While there have been described illustrative variations of this invention, those skilled in the art will recognize that they may be changed or modified without departing from the spirit and scope of this invention, and it is intended to cover all such changes, modifications, and equivalent arrangements that fall within the true scope of the invention as set forth in the appended claims.

All documents referenced herein, including applications for patent, patent references, publications, articles, books, and treatises, are specifically incorporated by reference herein in their entirety.

EXAMPLES

Reagents were obtained from Aldrich Chemical Company and VWR Scientific Products. Reactions were carried out under nitrogen or argon atmosphere unless otherwise noted. Solvent extracts of aqueous solutions were dried over anhydrous $Na_2SO_4$. Solutions were concentrated under reduced pressure using a rotary evaporator.

Example 1

Derivatization of Silicon Substrates with (3-aminopropyl)triethoxysilane (APTES)

$SiO_2$ substrates were first sonicated in a piranha solution (3:1 ratio of $H_2SO_4$:30% $H_2O_2$) for 15 minutes. This was followed by a 15 min sonication in Milli-Q water (>18 MΩ-cm). The derivatization step was done in a glove bag under a $N_2$ atmosphere. 0.05 mL APTES and 0.05 mL pyridine were added to 9 mL of toluene. Immediately following mixing, the freshly cleaned $SiO_2$ substrates were immersed in the APTES solution for 10 min. Substrates were washed with copious amounts of toluene and then dried with $N_2$. Deposited APTES films showed a range of thickness values from 0.8 to 1.3 nm.

Example 2

Amphiphilic modules Hexamer 1a were dissolved in HPLC-grade chloroform at a concentration of approximately 1 mg/ml. The chloroform solution was applied to a water (Millipore Milli-Q) surface in an L-B trough (KSV, Helsinki). The chloroform was allowed to evaporate, leaving the amphiphilic modules on the surface of the water with their hydrophilic groups immersed in the water and their lipophilic groups in the air. The temperature in the system was controlled (approximately ±0.2° C.). The barriers of the L-B trough were slowly compressed (1-10 mm/min). The surface pressure was monitored using the Wilhelmy procedure during film compression. The shape of the isotherm confirmed that the module formed a Langmuir film on the surface of the water.

Figure 6A:
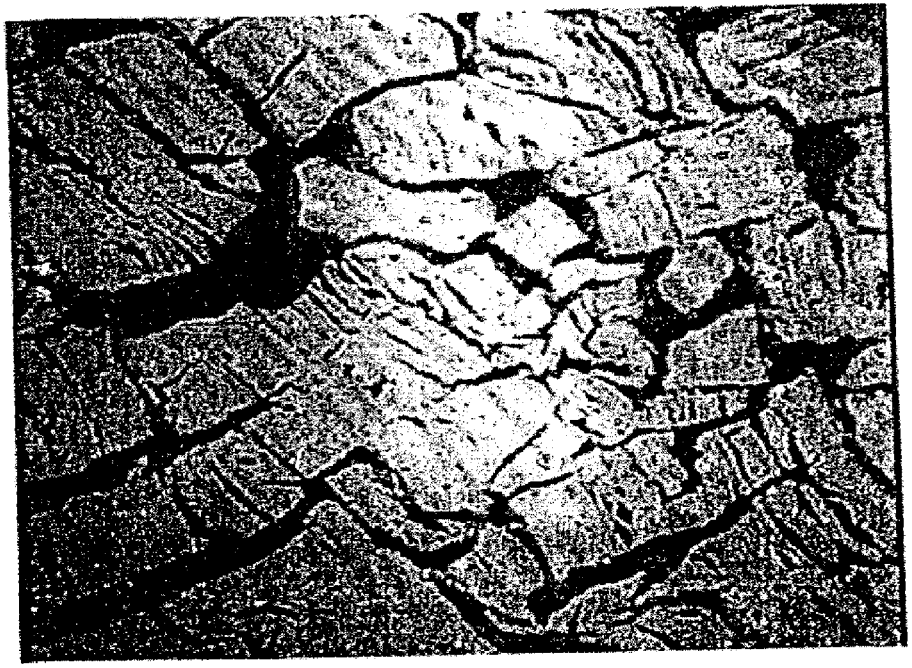
FIGS. 6A and 6B illustrate examples of the ellipsometric images of the preparation of a nanofilm of Hexamer 1 dh.

The scheme for this preparation is illustrated in FIGS. 1A and 1B. 25 μl of a 1 mg/ml solution of Hexamer 1 dh in chloroform were spread on a 2 mg/ml diethyl malonimidate (DEM) in water subphase (pH 8.8, T=22° C.). After waiting for 19 minutes to allow for spreading solvent evaporation, the monolayer was compressed and held at 5 mN/m. The subphase was then heated to 40° C. and held for approximately 60 minutes. A rigidified solid nanofilm was formed on the surface of the subphase, which appeared uniform and homogeneous in a Brewster Angle microscope image. When touched with a probe, the film was cracked, as shown by the Brewster Angle microscope image obtained for the film directly on the surface of the subphase, illustrated in FIG. 6A. This indicates that the nanofilm was highly cross-linked. Mass spectral analysis of the rigid nanofilm could not be performed because the solid nanofilm clogged the input of the instrument.

Example 3

Hexamer 1 dh with DEM (Langmuir-Blodgett Deposition)

The scheme for this preparation is illustrated in FIGS. 1A and 1B. 25 μl of a 1 mg/ml solution of Hexamer 1 dh in chloroform were spread on a 2 mg/ml diethyl malonimidate (DEM) in water subphase (pH 8.8, T=22° C.). After waiting for 19 minutes to allow for spreading solvent evaporation, the monolayer was compressed and held at 5 mN/m. The subphase was then heated to 40° C. and held for approximately 60 minutes. A rigidified solid nanofilm was formed on the surface of the subphase, which appeared uniform and homogeneous in a Brewster Angle microscope image. When touched with a probe, the film was cracked, as shown by the Brewster Angle microscope image obtained for the film directly on the surface of the subphase, illustrated in FIG. 6A. This indicates that the nanofilm was highly cross-linked. Mass spectral analysis of the rigid nanofilm could not be performed because the solid nanofilm clogged the input of the instrument.

Figure 6B:

Another monolayer prepared as above was transferred to a Si wafer (made hydrophilic by treating with piranha solution, 3:1 ratio of $H_2SO_4$/30% $H_2O_2$, for 10 min) by Langmuir-Blodgett deposition. The substrate was translated through the air-water interface at a speed of 0.3 mm/min. Imaging ellipsometry, illustrated in FIG. 6B, revealed shattered solid islands of film on the silicon substrate with heights of approximately 35 Å, which includes the nanofilm and an APTES coating of the substrate.

Figure 7:
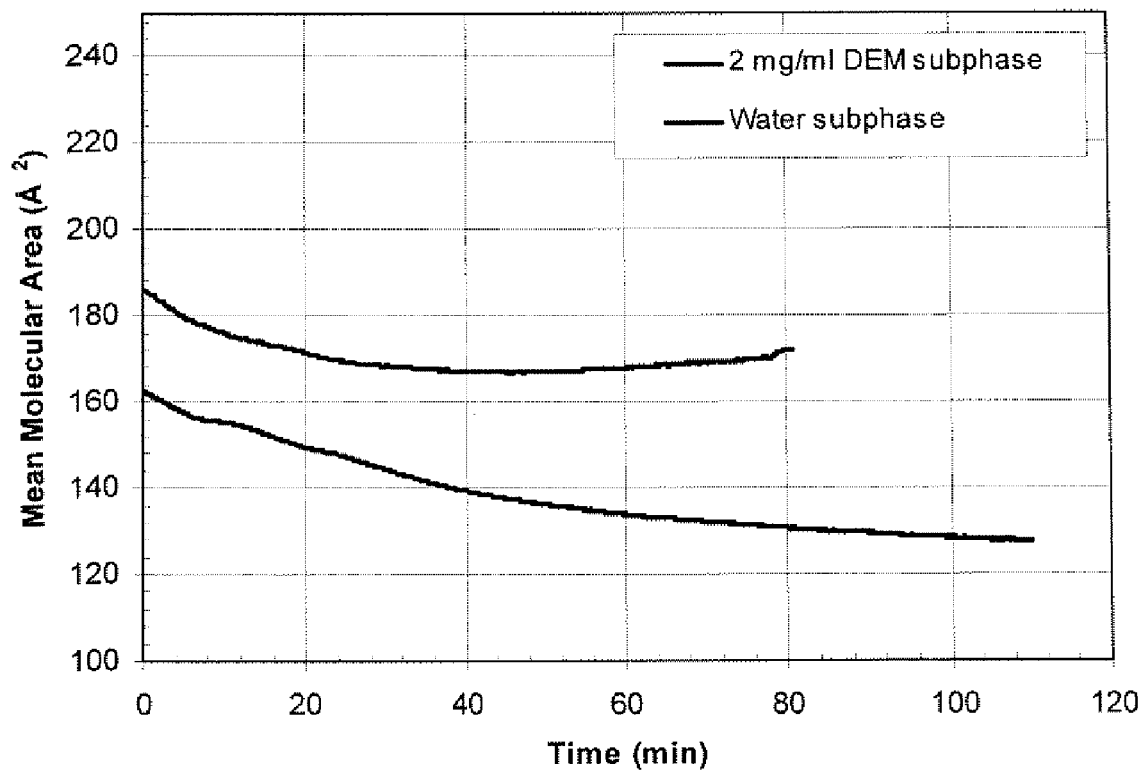
FIG. 7 illustrates an example of isobaric creep of a nanofilm of Hexamer 1 dh.

The isobaric creep of the solid nanofilm is illustrated in FIG. 7. A Langmuir film which has individual molecules oriented on a surface in a condensed state, but in which there is no coupling between the molecules will spread out or decompress when the force of compression is released. By comparison, the solid nanofilm of coupled modules retained its shape and film strength over time, even in the presence of solvent, as shown in FIG. 7. The upper line shows the isobaric creep of the nanofilm prepared in the presence of DEM crosslinker, and the lower line shows the isobaric creep of the nanofilm prepared without crosslinker.

Example 4

Hexamer 1 dh with DEM (Langmuir-Blodgett Deposition)

Figure 8A:
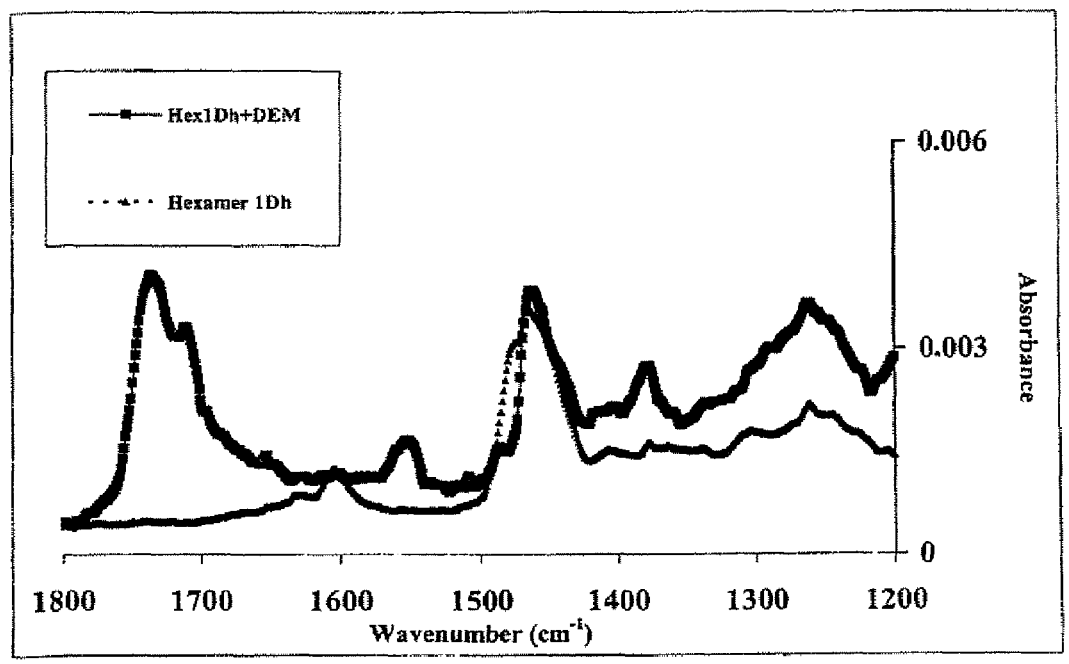
FIGS. 8A and 8B illustrate examples of FTIR spectra of the preparation of a nanofilm of Hexamer 1 dh.
Figure 8B:
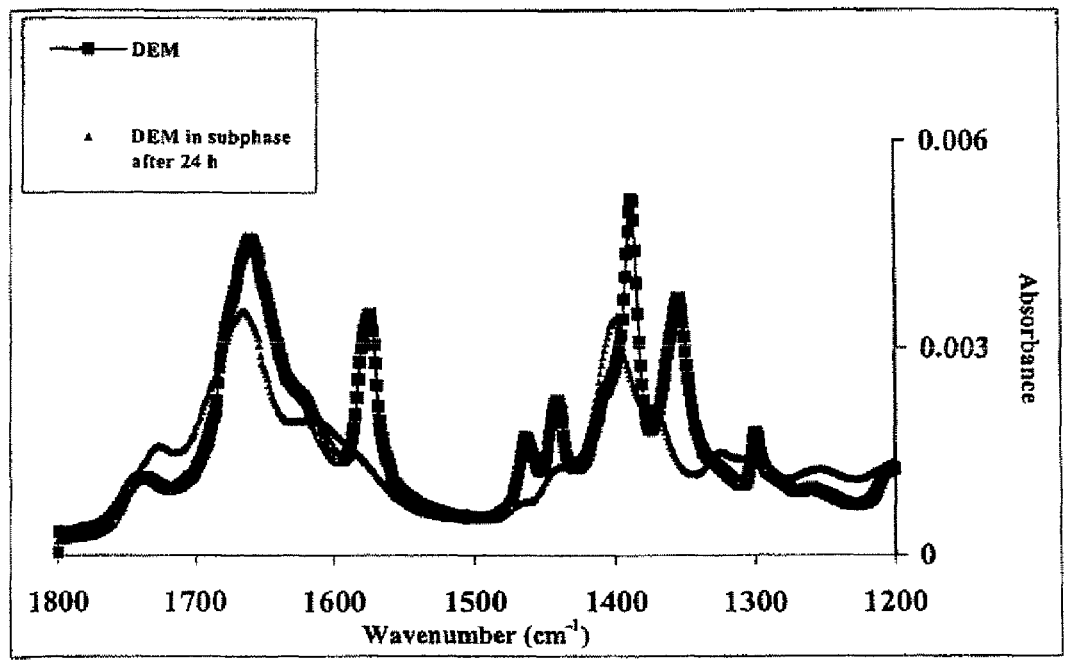

The presence of interlinking of modules was detected by Fourier Transform Infrared Spectroscopy (FTIR). The FTIR spectra of the nanofilm of Example 3 are illustrated in FIG. 8. In FIG. 8A, the FTIR spectra of the nanofilm and the Hexamer 1 dh are illustrated. In FIG. 8B, the FTIR spectra of DEM and DEM in the subphase after 24 hours are illustrated. Changes in the FTIR show that there was coupling between Hexamer 1 dh and DEM.

Example 5

Hexamer 1 dh with DEM (Langmuir-Schaefer Deposition)

Figure 9:
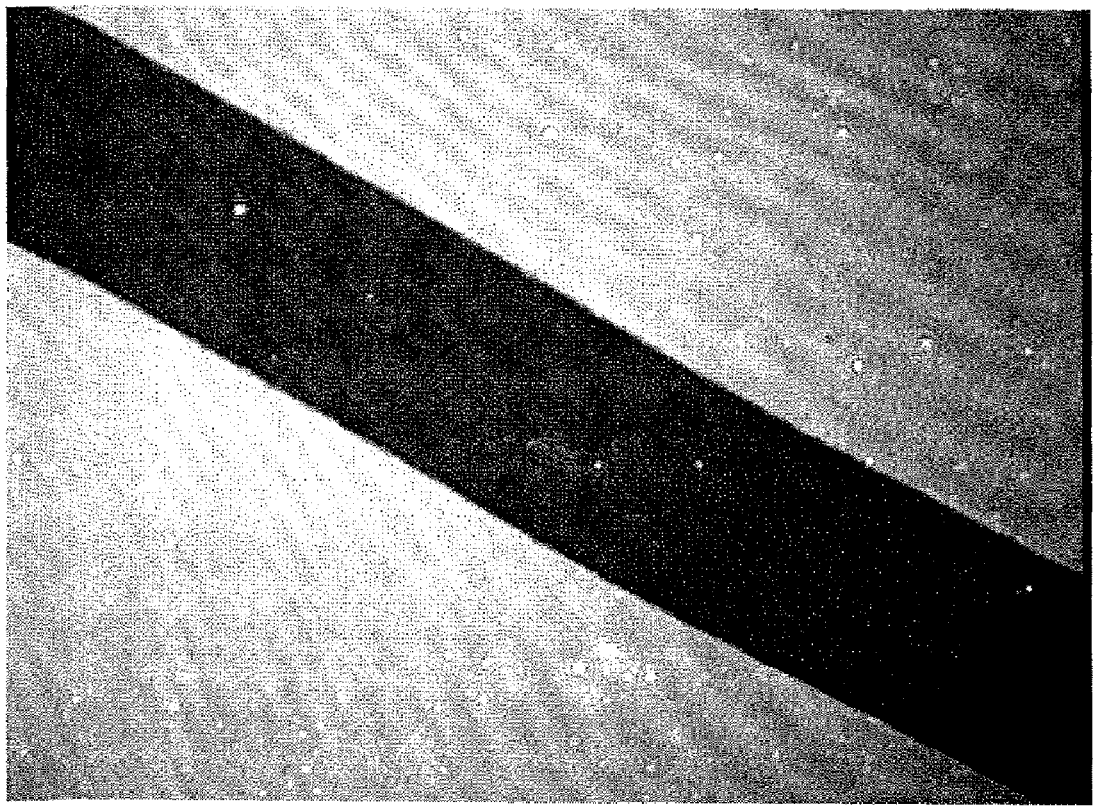
FIG. 9 illustrates an example of the ellipsometric image of the preparation of a nanofilm of Hexamer 1 dh.

25 μl of a 1 mg/ml solution of Hexamer 1 dh in chloroform were spread on a 2 mg/ml diethyl malonimidate subphase (pH 8.8, T=22° C.). After waiting 15 minutes to allow for spreading solvent evaporation, the monolayer was compressed and held at 5 mN/m. The monolayer was transferred to a Si wafer (made hydrophilic by treating with piranha solution for 10 minutes) by a Langmuir-Schaefer deposition. Imaging ellipsometry revealed an intact film on the silicon substrate with a height of approximately 21 Å, as illustrated in FIG. 9, in which a single fracture of the nanofilm is illustrated.

Example 6

Mannich Reaction with Octadecylamine

35 μl of a 1 mg/ml solution of octadecylamine in chloroform were spread on a 1% formaldehyde subphase (pH 3, T=22° C.). After waiting 15 minutes to allow for spreading solvent evaporation, the monolayer was compressed and held at 20 mN/m. At this surface pressure, the film exhibited a steady loss in area for approximately 80 minutes, after which the film area increased. After a total of 130 minutes at the air-water interface, the film was extracted by manual Langmuir-Blodgett depositions. Briefly, after dipping a Si wafer through the air-water interface, the wafer was shaken in chloroform to remove the deposited material, and the process was repeated. Mass spectrometry (ESI mode) was then performed on the chloroform solution. The structures of the linkages formed in the nanofilm upon coupling the amphiphiles as detected in the mass spectrum are illustrated FIGS. 4B, 4D and 4F.

Example 7

Surface Attachment with Reactive Ester Groups

First, the APTES modified silicon substrates were lowered into a pH 7, 22° C. aqueous subphase. 160 mL of methylheptadecanoate (MHD) (1 mg/mL $CHCl_3$ solution) was spread at the air/water interface. After 10 min the film was compressed to 38 mN/m at a rate of 3 mm/min. Upon reaching 38 mN/m the substrates were raised out of the subphase (while maintaining the surface pressure at 38 mN/m) at a rate of 1 mm/min resulting in deposition of one layer of MHD. Following deposition, some samples were heated at 70° C. for 3.5 hr to induce reaction between the surface amine groups (APTES) and the ester groups of MHD to form amide linkages. Samples were sonicated in $CHCl_3$ following the thermal cure to determine the extent of surface attachment. If the film did not react with the surface this treatment should result in the removal of the film.

Figure 10A:
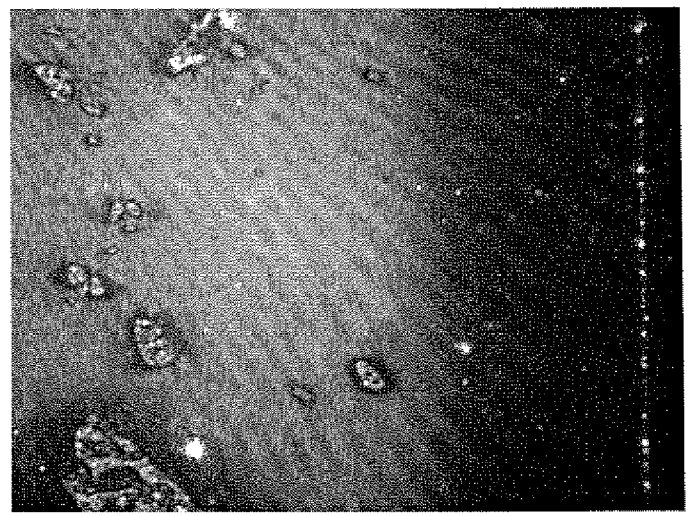
FIGS. 10A, 10B and 10C illustrate example of ellipsometric images of the preparation of a nanofilm of methylheptadecanoate attached to a substrate.
Figure 10B:
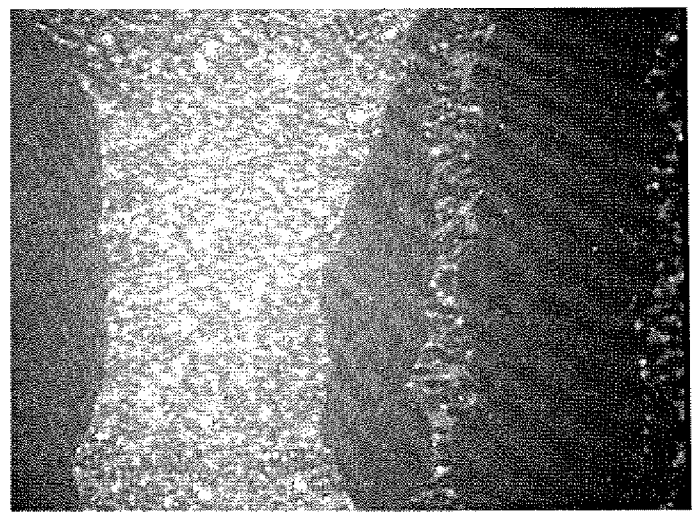
Figure 10C:
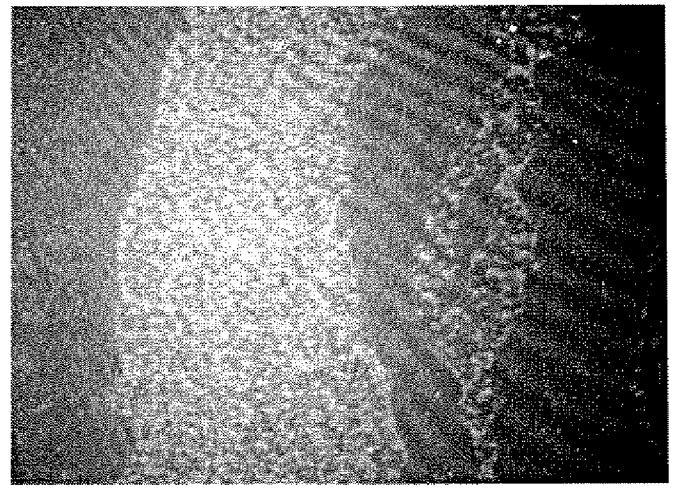

Ellipsometric images of the substrate are shown in FIG. 10. In FIG. 10A is shown the substrate after film deposition. In FIG. 10B is shown the substrate after film deposition and heating at 70° C. FIG. 10B indicates that some dewetting occurred during heating, and that nanofilm remained on the substrate. In FIG. 10C is shown the substrate after film deposition, after heating at 70° C., and after treatment with $CHCl_3$, again indicating that nanofilm remained on the substrate.

Example 8

Surface Attachment with Reactive Acryl Groups

First, $SiO_2$ substrates were derivatized with a layer of methylacryloxymethyltrimethoxysilane (MAOMTMOS) using the same procedure as described in the derivatization with APTES (Example 6). The substrates were then lowered into a pH 5, 22° C. aqueous subphase. 170 mL of N-octadecylacrylamide (ODAA) (1 mg/mL $CHCl_3$ solution) was spread at the air/water interface. After 10 min the film was compressed to 35 mN/m at a rate of 2 mm/min. Upon reaching 35 mN/m the substrates were raised out of the subphase at a rate of 2 mm/min resulting in the deposition of one layer of ODAA. Following deposition some samples were irradiated (254 nm) for 40 or 220 min. to induce coupling between the surface acryl groups (MAOMTMOS) and the acryl groups of ODAA. Samples were sonicated in $CHCl_3$ following the UV cure to determine the extent of surface attachment. If the film did not react with the surface this treatment would have resulted in removal of the film.

Figure 11A:
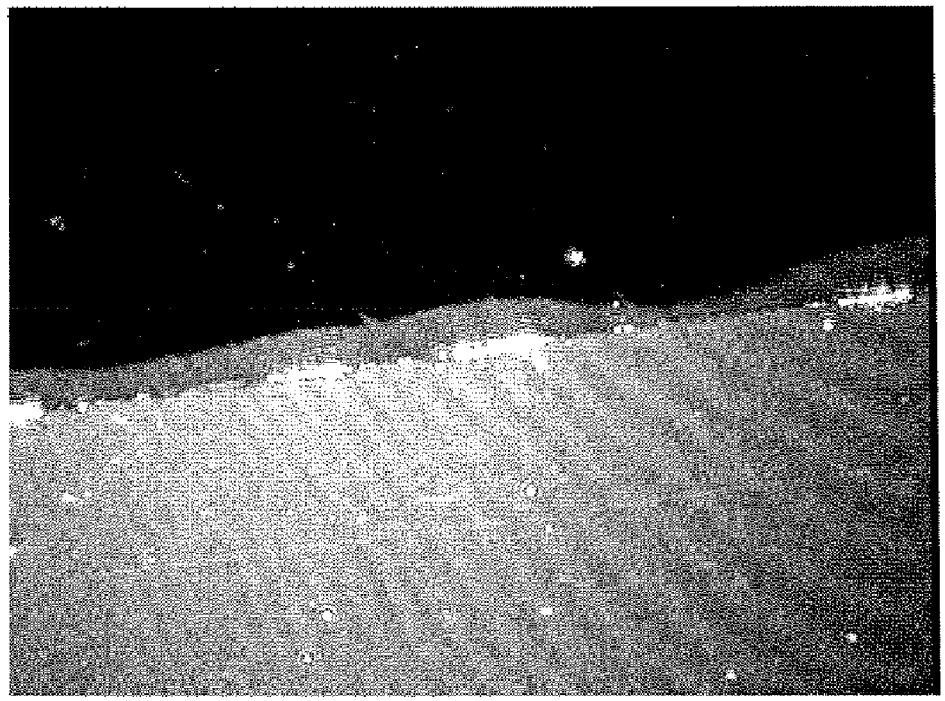
FIGS. 11A and 11B illustrate examples of ellipsometric images of the preparation of a nanofilm of N-octadecylacrylamide attached to a substrate.
Figure 11B:
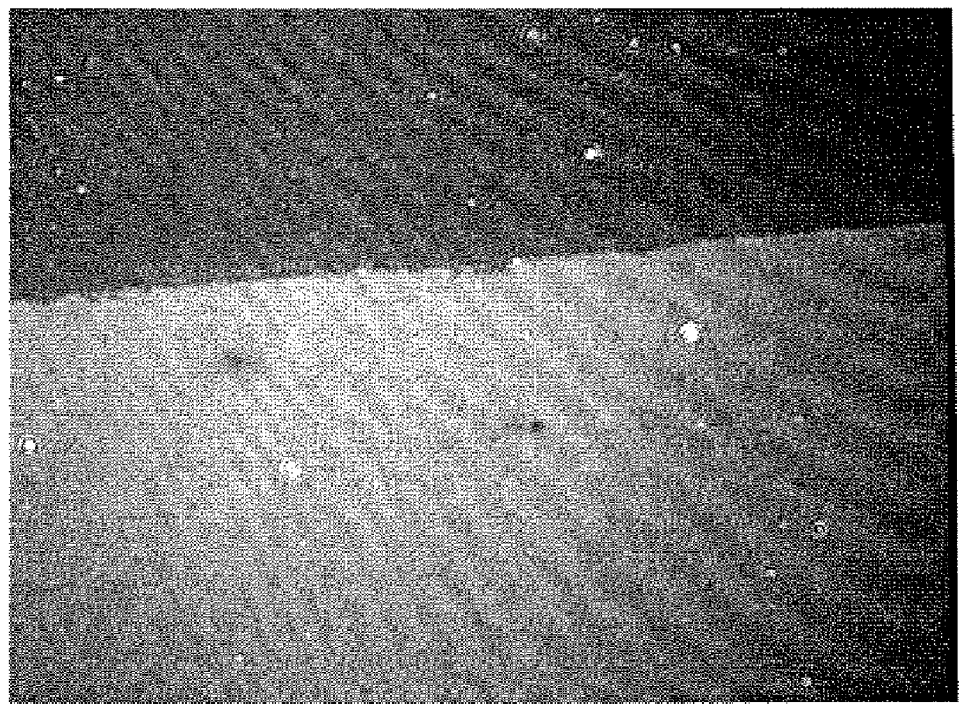

Ellipsometric images of the substrate are shown in FIG. 11. In FIG. 11A is shown the substrate after film deposition and exposure to UV irradiation at 254 nm for 40 minutes. In FIG. 11B is shown the substrate after film deposition, irradiation, and after treatment with $CHCl_3$. FIG. 11B shows that there was monolayer coupling to the substrate.

Example 9

Figure 12:
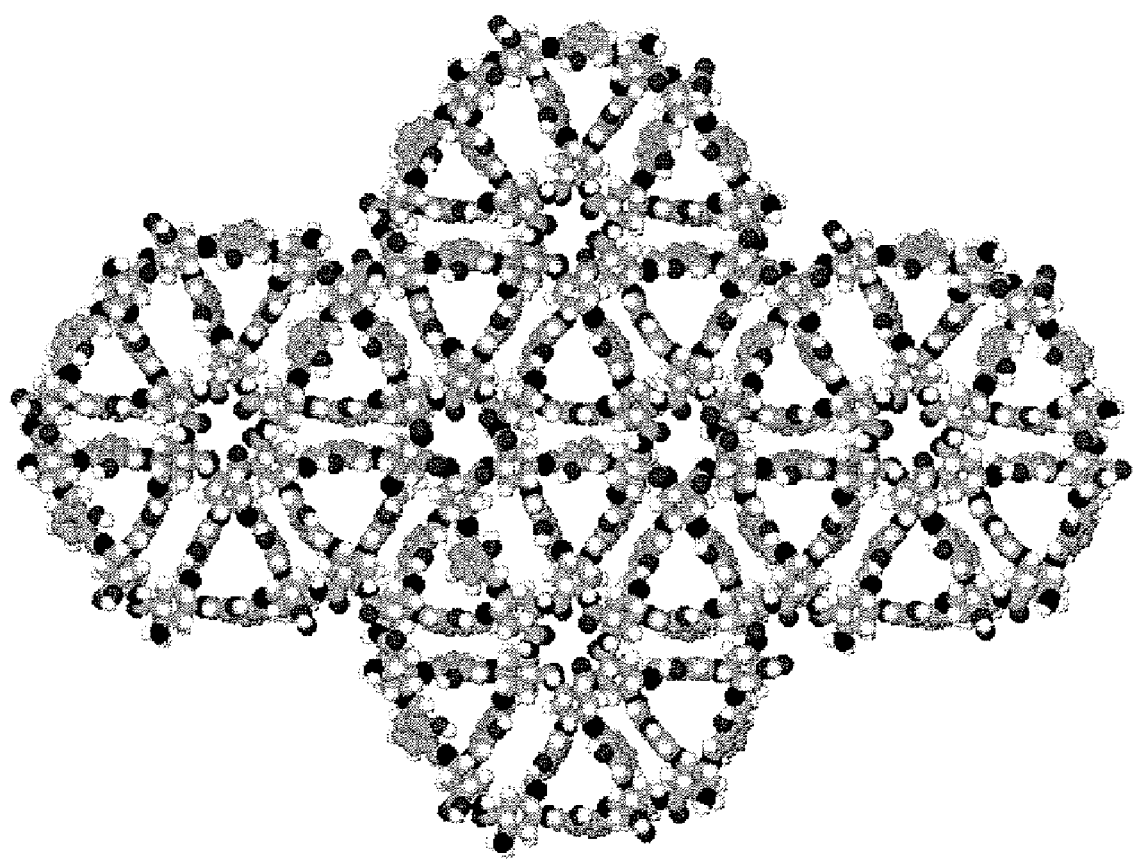
FIG. 12 illustrates a representation of the structure of a nanofilm of Hexamer 1 dh.

A unique structure of the nanofilm of Hexamer 1 dh of Example 3 is illustrated in FIG. 12, in which interlinking is by amide linkages of the modules through the cyclohexyl synthons. The approximate dimensions of the modular and interstitial pores of the structure are 14 Å$^2$, 25 Å$^2$ and 40 Å$^2$. The fully minimized structure was obtained by MM+ molecular mechanics.

Example 10

Figure 13:
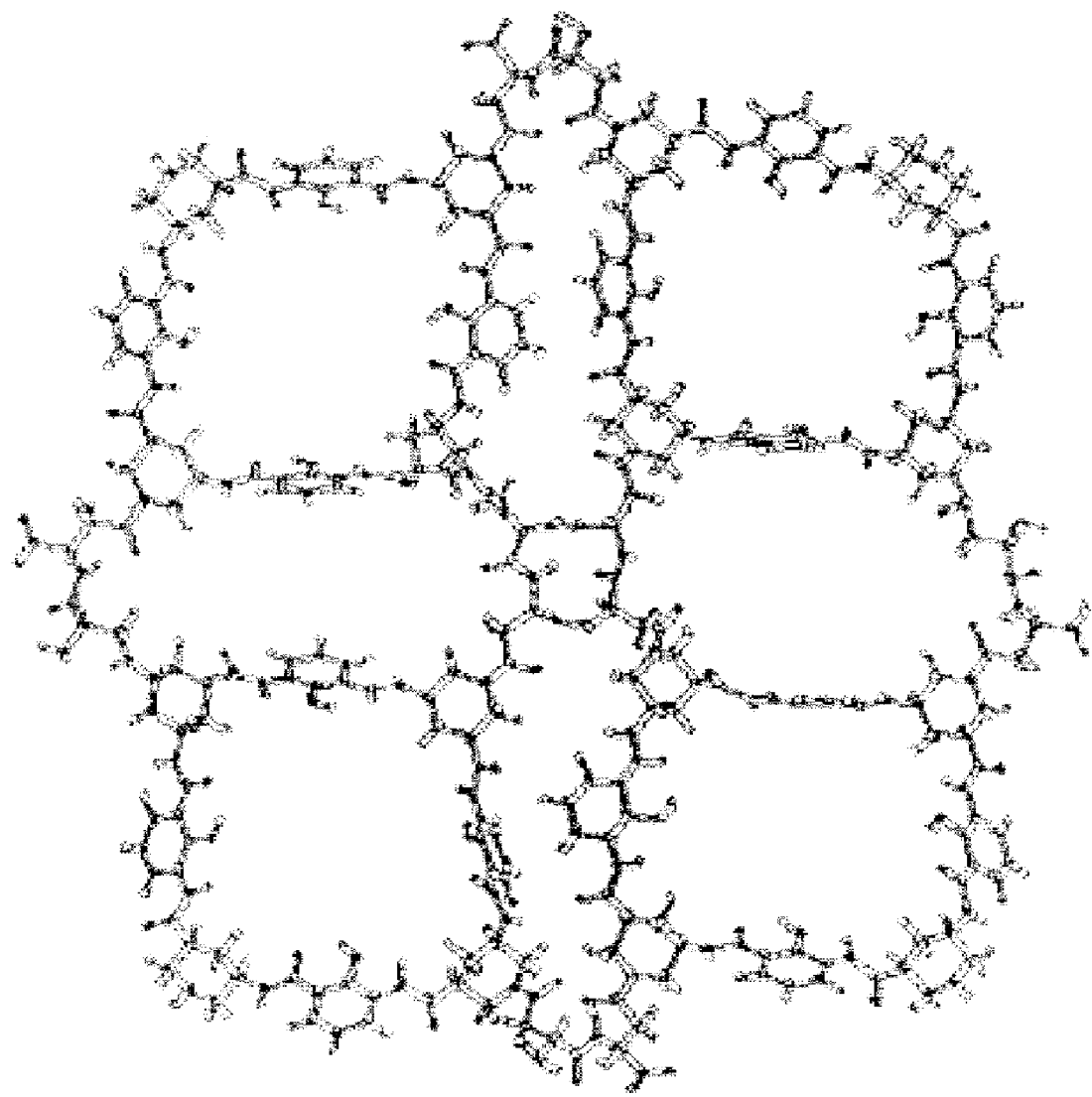
FIG. 13 illustrates a representation of the structure of a nanofilm of Octamer 5jh-aspartic.

Octamer 5jh-aspartic is formed in a condensed Langmuir film and heated to a temperature sufficient to initiate coupling of the modules through amide linkages to form a nanofilm. A unique structure of a nanofilm of octamer 5jh-aspartic is illustrated in FIG. 13, in which interlinking is by aspartic amide linkages of the modules through the piperidine synthons. The approximate dimensions of the pores of the structure are from 119 Å$^2$ to 200 Å$^2$. The fully minimized structure was obtained by MM+ molecular mechanics.

Example 11

Figure 14:
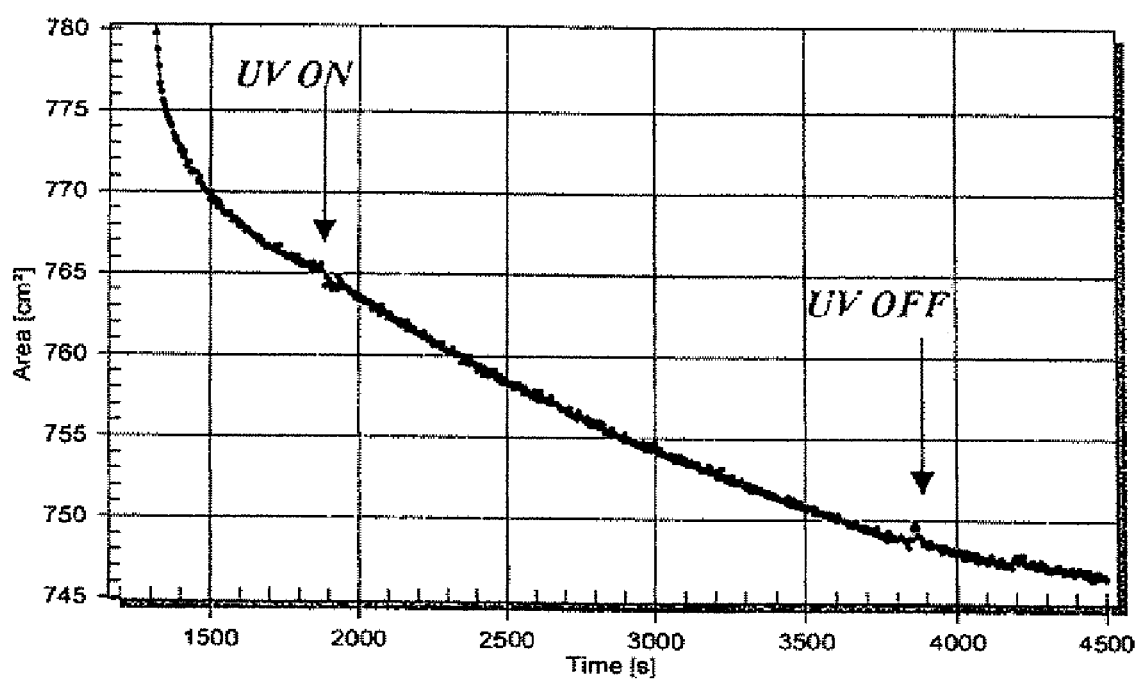
FIG. 14 illustrates the Langmuir trough area versus time for a nanofilm prepared from Hexamer 1jh-AC.
Figure 15:
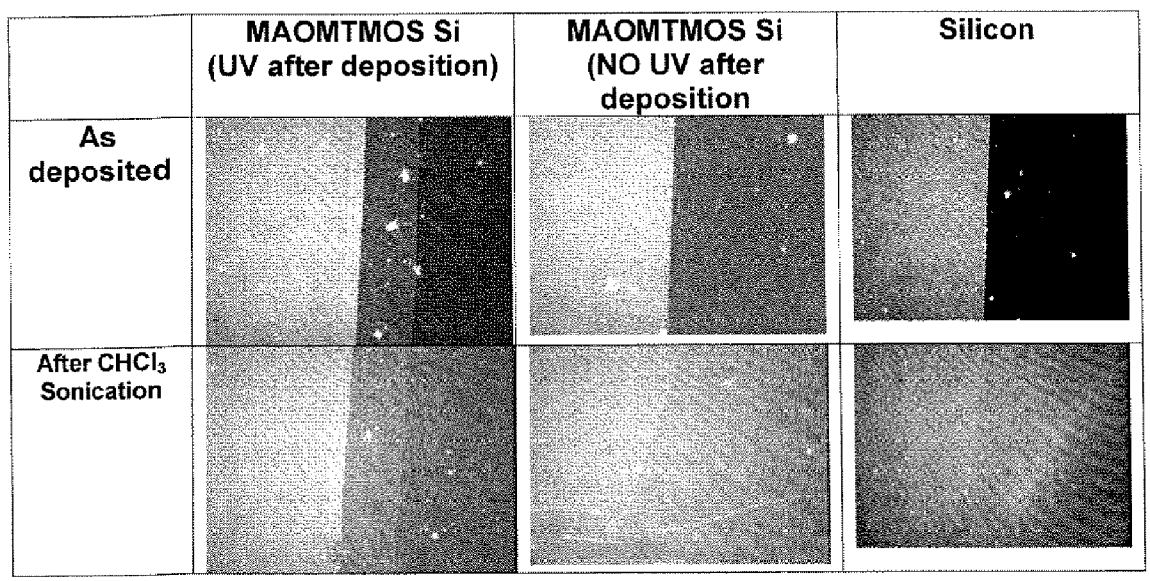
FIG. 15 illustrates an example of the ellipsometric image of a nanofilm prepared from Hexamer 1jh-AC.

First, two $SiO_2$ substrate were derivatized with a layer of acryloxy-propyltrimethoxysilane (AOPTMOS) using the same procedure as described in the derivatization with APTES (see example 1). These substrates, as well as an unmodified $SiO_2$ substrate, were then lowered into a $H_2O$ subphase that was maintained at 22° C. Subsequently, the Hexamer 1jh-AC (1 mg/mL $CHCl_3$ solution) was spread at the air/water interface. After 10 min the film was compressed to 30 mN/m at a rate of 4 mm/min. Upon reaching a surface pressure of 30 mN/m, the Langmuir film was irradiated with 254 nm light from a distance of 1.5 inches (1350 μW/cm$^2$ at 3 inches) for 30 min. Subsequently, the substrates were raised out of the subphase at a rate of 1 mm/min resulting in the deposition of one layer of cross-linked Hexamer 1jh-AC. Following deposition, the sample deposited on the AOPTMOS substrate was irradiated (254 nm) for 30 min to induce coupling between the surface acryl groups (AOPTMOS) and the acryl groups of Hexamer 1jh-AC. All samples were then examined by ellipsometry to determine film thickness values. Finally, all samples were sonicated in $CHCl_3$ to determine the extent of surface attachment. If the film did not react with the surface this treatment should result in removal of the film. The corresponding Langmuir trough area vs. time (during irradiation) graph and ellipsometric images of the deposited films are shown in FIGS. 14 and 15, respectively. The ellipsometric images for the film deposited on the MAOMTMOS modified substrate clearly shows that the films are still present after $CHCl_3$ sonication, and therefore indicate that surface attachment occurred. Conversely, when UV light was not used after deposition on the MAOMTMOS modified substrate or when the film was deposited on silicon, the ellipsometric images indicate that surface attachment did not occur.

Figure 16:
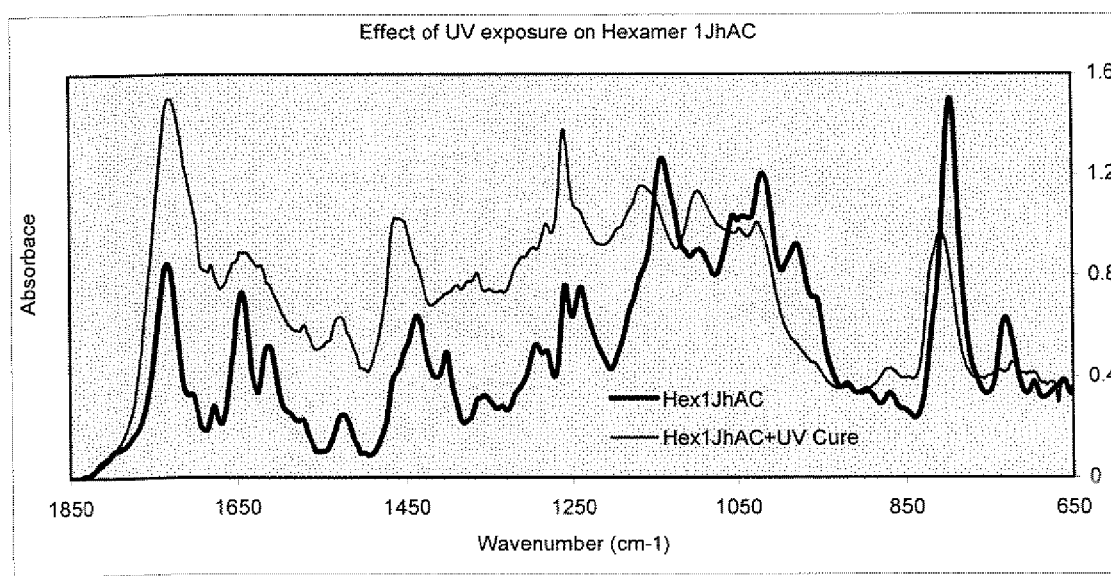
FIG. 16 illustrates an example of the FTIR spectra of the preparation of a nanofilm of Hexamer 1jh-AC.

Additionally, FTIR data reveal the loss of vinyl bands upon UV exposure of the Hexamer 1jh-AC (FIG. 16), indicating crosslinking between Hexamer 1jh-AC and the AOPTMOS-derivatized substrate.

Example 12

The filtration function of a membrane may be described in terms of its solute rejection profile. The filtration function of some nanofilm membranes is exemplified in Tables 7-8.

TABLE 7

Example filtration function of a G-membrane

| SOLUTE | MOLECULAR WEIGHT | PASS/NO PASS |
|---|---|---|
| Albumin | 68 kDa | NP |
| Ovalbumin | 44 kDa | P |
| Myoglobin | 17 kDa | P |
| $β_2$-Microglobulin | 12 kDa | P |
| Insulin | 5.2 kDa | P |
| Vitamin $B_{12}$ | 1350 Da | P |
| Urea, $H_2O$, ions | <1000 Da | P |

TABLE 8

Example filtration function of a T-membrane

| SOLUTE | MOLECULAR WEIGHT | PASS/NO PASS |
|---|---|---|
| $β_2$-Microglobulin | 12 kDa | NP |
| Insulin | 5.2 kDa | NP |
| Vitamin $B_{12}$ | 1350 Da | NP |
| Glucose | 180 Da | NP |
| Creatinine | 131 Da | NP |
| $H_2PO_4^-$, $HPO_4^{2-}$ | ≈97 Da | NP |
| $HCO_3^-$ | 61 Da | NP |
| Urea | 60 Da | NP |
| K+ | 39 Da | P |
| Na+ | 23 Da | P |

The passage or exclusion of a solute is measured by its clearance, which reflects the portion of solute that actually passes through the membrane. The no pass symbol in Tables 7-8 indicates that the solute is partly excluded by the nanofilm, sometimes less than 90% rejection, often at least 90% rejection, sometimes at least 98% rejection. The pass symbol indicates that the solute is partly cleared by the nanofilm, sometimes less than 90% clearance, often at least 90% clearance, sometimes at least 98% clearance.

A membrane is impermeable to a species if it has a very low clearance (for example, less than about 5%, less than about 3%) for the species, or if it has very high rejection for the species (for example, greater than about 95%, greater than about 98%).

Example 13

The dimensions of module pores may be measured by electrical conductance in a voltage-clamped lipid bilayer test. Modules are dissolved into a phosphatidylcholine-phosphatidylethanolamine lipid bilayer. On one side of the bilayer is placed a solution containing a test cationic species. On the other side is placed a solution containing a cationic species known to be able to pass through the module pore. Anions required for charge neutrality are selected such that they will not pass through the module pore. When a positive potential is created in the solution on the side of the lipid bilayer containing the test species, if the test cations are of such a size that they cannot pass through the pores in the modules, no current will be detected. The voltage is then reversed to create a positive potential on the side of the lipid bilayer having the solution containing the cationic species known to be able to traverse the pore. Observation of the expected current confirms the integrity of the lipid bilayer and the availability of the module pores as transporters of cations of the known size and smaller.

The selective permeability of macrocyclic modules was tested using the voltage-clamped bilayer method, as shown in Table 9. The "+" symbol indicates permeation of the solute, the "−" symbol indicates rejection of the solute. Permeation and rejection are indicators of clearance. The clamp voltage was 50 mV.

TABLE 9

Examples of permeation of macrocyclic modules

| Solute | Radius (VdW, Å) | Hexamer 1a | Hexamer 1jh |
|---|---|---|---|
| $Li^+$ | 0.8 | − | + |
| $Na^+$ | 1.0 | + | + |
| $K^+$ | 1.3 | + | + |
| $Cs^+$ | 1.7 | + | + |
| $Ca^{2+}$ | 1.0 | + | + |
| $Mg^{2+}$ | 0.7 | − | + |
| $NH_4^+$ | 1.9 | + | + |
| $MeNH_3^+$ | 2.0 | + | + |
| $EtNH_3^+$ | 2.6 | − | + |
| $NMe_4^+$ | 2.6 | − | + |
| Aminoguanidinium | 3.1 | − | + |
| $NEt_4^+$ | 3.9 | − | + |
| Choline | 3.8 | − | + |
| Glucosamine | 4.2 | − | + |
| $N(n-Pr)_4^+$ | | − | + |
| $N(n-Bu)_4^+$ | | − | + |

Example 14

Selective filtration and relative clearance of solutes is exemplified in Table 10. In Table 10, the heading "high permeability" indicates a clearance of greater than about 70-90% of the solute. The heading "medium permeability" indicates a clearance of less than about 50-70% of the solute. The heading "low permeability" indicates a clearance of less than about 10-30% of the solute.

TABLE 10

Clearance of solutes by nanofilms

| Nanofilm | high permeability | medium permeability | low permeability |
|---|---|---|---|
| Hexamer 1a | $H_2O$, $Na^+$, $K^+$, $Cs^+$ | $Ca^{2+}$, $Mg^{2+}$, phosphate | Glucose, $Li^-$, urea, creatinine |
| water nanofilm | $H_2O$ | Glucose, $Na^+$, $K^+$, phosphate | $Ca^{2+}$, $Mg^{2-}$, $Li^-$, urea, creatinine |
| ion nanofilm | $H_2O$, $Na^+$, $K^+$, phosphate | Glucose | $Ca^{2+}$, $Mg^{2+}$, $Li^-$, urea, creatinine |
| glucose nanofilm | $H_2O$, $Na^+$, $K^+$, Glucose | Phosphate | $Ca^{2+}$, $Mg^{2-}$, $Li^+$, urea, creatinine |
| G nanofilm | $H_2O$, $Na^+$, $K^+$, phosphate, Glucose, $Ca^{2+}$, $Mg^{2+}$, $Li^+$, urea, creatinine | Vitamin $B_{12}$, Insulin, $\beta_2$ Microglobulin | Myglobin, Ovalbumin, Albumin, |
| gas nanofilm | He, $H_2$ | — | $H_2O$ and larger, liquids in general |
| anion nanofilm | $Cl^-$ | $HCO_3^-$, Phosphate | — |

Example 15

The approximate diameter of various species to be considered in a filtration process are illustrated in Table 11:

| solute | molecular weight (Da) | diameter (Å) |
|---|---|---|
| virus | $10^6$ | 133 |
| immunoglobulin G (IgG) | $10^5$ | 60 |
| albumin | $50 \times 10^4$ | 50 |
| $\beta_2$-Microglobulin | $10^3$ | 13 |
| urea | 60 | — |
| $Na^+$ | 23 | — |

Synthon and Macrocyclic Module Synthesis Methods

All chemical structures illustrated and described in this specification, both in the description above and the examples below, as well as in the figures, are intended to encompass and include all variations and isomers of the structure which are foreseeable, including all stereoisomers and constitutional or configurational isomers when the illustration, description, or figure is not explicitly limited to any particular isomer.

Methods for Preparing Cyclic Synthons

To avoid the need to separate single configurational or enantiomeric isomers from complex mixtures resulting from non-specific reactions, stereospecific or at least stereoselective coupling reactions may be employed in the preparation of the synthons of this invention. The following are examples of synthetic schemes for several classes of synthons useful in the preparation of macrocyclic modules of this invention. In general, the core synthons are illustrated, and lipophilic moieties are not shown on the structures, however, it is understood that all of the following synthetic schemes might encompass additional lipophilic or hydrophilic moieties used to prepare amphiphilic and other modified macrocyclic modules. Species are numbered in relation to the scheme in which they appear; for example, "S1-1" refers to the structure 1 in Scheme 1.

An approach to preparing synthons of 1,3-Diaminocyclohex-5-ene is shown in Scheme 1. Enzymatically assisted partial hydrolysis of the

SCHEME 1

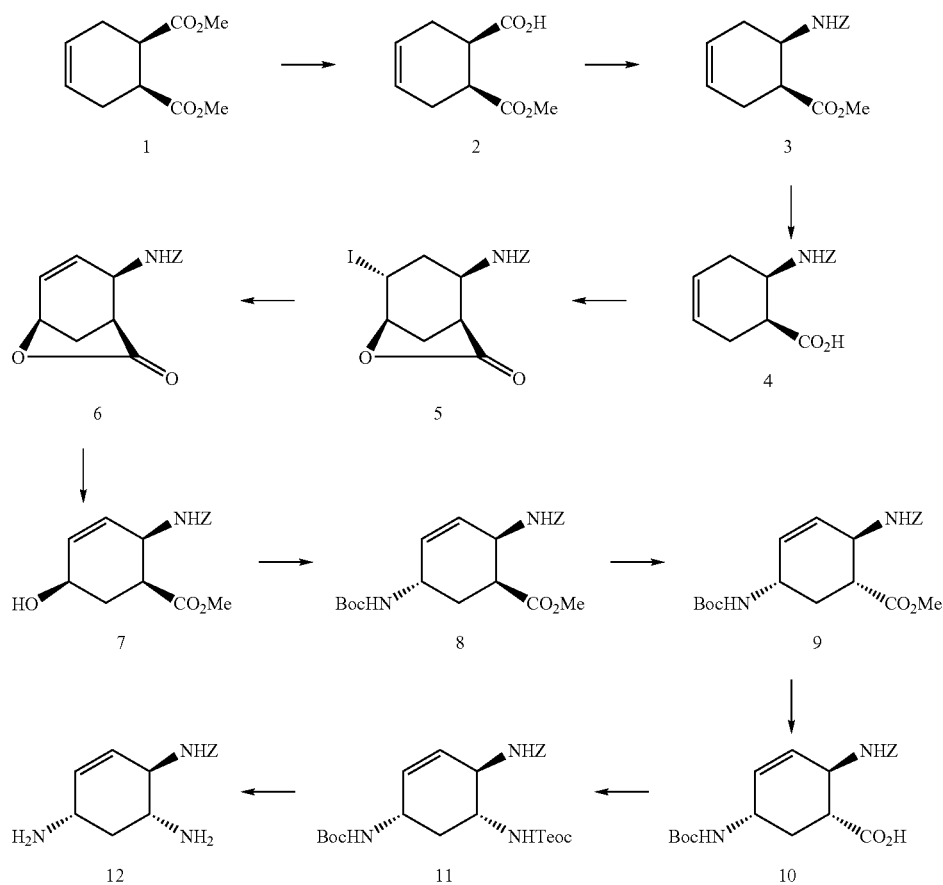

symmetrical diester S1-1 is used to give enantiomerically pure S1-2. S1-2 is subjected to the Curtius reaction and then quenched with benzyl alcohol to give protected amino acid S1-3. Iodolactonization of carboxylic acid S1-4 followed by dehydrohalogenation gives unsaturated lactone S1-6. Opening of the lactone ring with sodium methoxide gives alcohol S1-7, which is converted with inversion of configuration to S1-8 in a one-pot reaction involving mesylation, $SN_2$ displacement with azide, reduction and protection of the resulting amine with di-tert-butyl dicarbonate. Epimerization of S1-8 to the more stable diequatorial configuration followed by saponification gives carboxylic acid S1-10. S1-10 is subjected to the Curtius reaction. A mixed anhydride is prepared using ethyl chloroformate followed by reaction with aqueous $NaN_3$ to give the acyl azide, which is thermally rearranged to the isocyanate in refluxing benzene. The isocyanate is quenched with 2-trimethylsilylethanol to give differentially protected tricarbamate S1-11. Reaction with trifluoroacetic acid (TFA) selectively deprotects the 1,3-diamino groups to provide the desired synthon S1-12.

In another variation, an approach to preparing synthons of 1,3-Diaminocyclohexane is shown in Scheme 1a.

SCHEME 1a

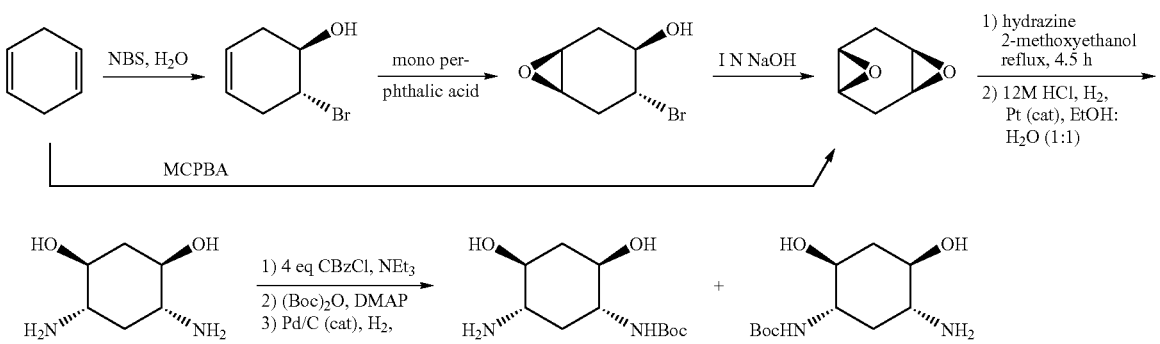

Some aspects of these preparations are given in Suami et al., *J. Org. Chem.* 1975, 40, 456 and Kavadias et al. *Can. J. Chem.* 1978, 56, 404.

In another variation, an approach to preparing synthons of 1,3-substituted cyclohexane is shown in Scheme 1b.

SCHEME 1b

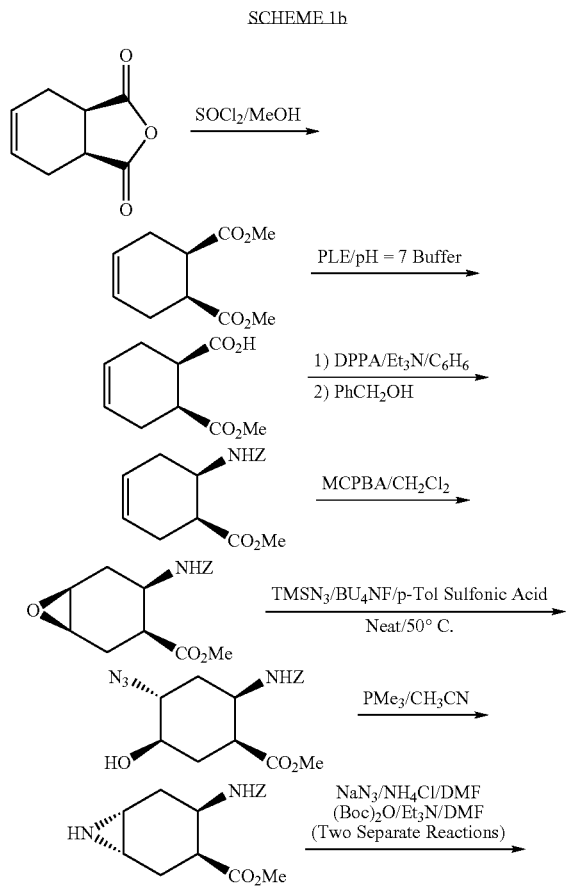

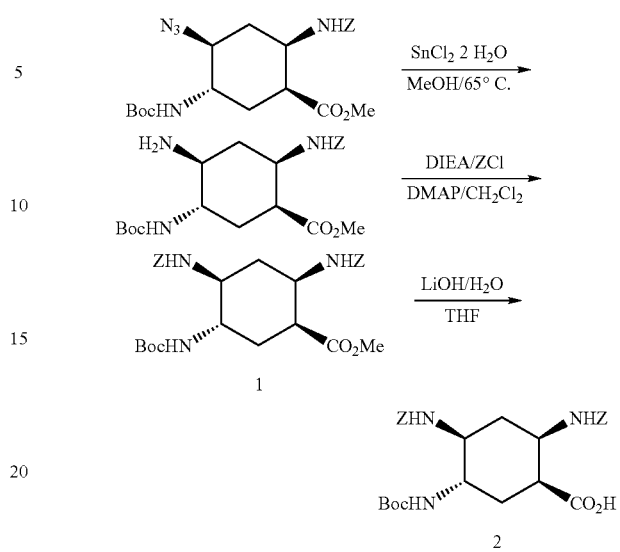

This synthon will remain "Z-protected" until the macrocyclic module has been cyclized. Subsequent deprotection to yield a macrocyclic module with amine functional groups is done by a hydrogenation protocol.

Norbornanes (bicycloheptanes) may be used to prepare synthons of this invention, and stereochemically controlled multifunctionalization of norbornanes can be achieved. For example, Diels-Alder cycloaddition may be used to form norbornanes incorporating various functional groups having specific, predictable stereochemistry. Enantiomerically enhanced products may also be obtained through the use of appropriate reagents, thus limiting the need for chiral separations.

An approach to preparing synthons of 1,2-Diaminonorbornane is shown in Scheme 2. 5-(Benzyloxy-methyl)-1,3-cyclopentadiene (S2-13) is reacted with

SCHEME 2

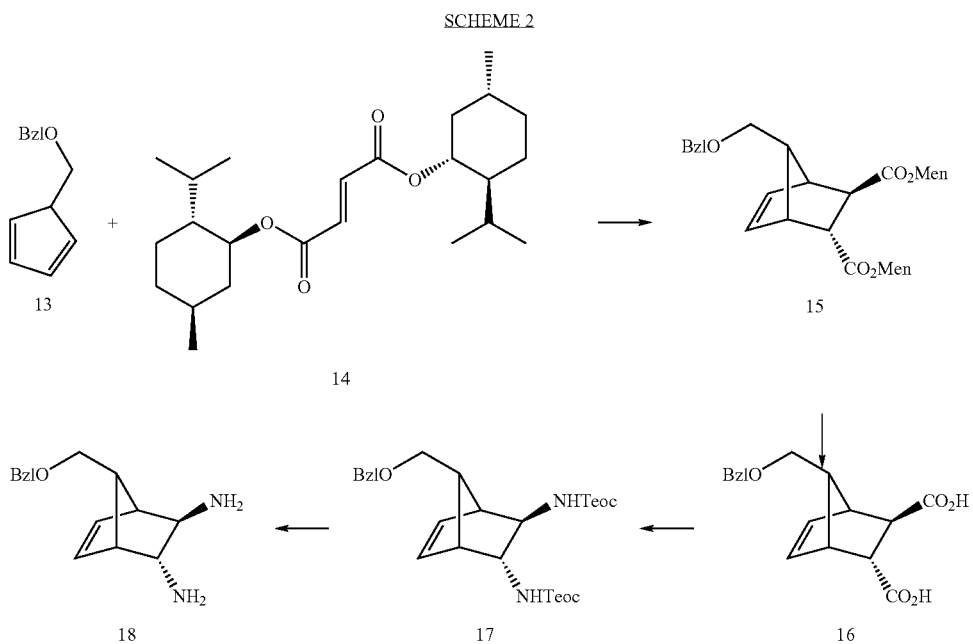

diethylaluminum chloride Lewis acid complex of di-(l)-menthyl fumarate (S2-14) at low temperature to give the diastereomerically pure norbornene S2-15. Saponification with potassium hydroxide in aqueous ethanol gives the diacid S2-16, which is subjected to a tandem Curtius reaction with diphenylphosphoryl azide (DPPA), the reaction product is quenched with 2-trimethylsilylethanol to give the biscarbamate S2-17. Deprotection with TFA gives diamine S2-18.

Another approach to this synthon class is outlined in Scheme 3. Opening of anhydride S3-19 with methanol in the presence of quinidine gives the enantiomerically pure ester acid S3-20. Epimerization of the ester group with sodium methoxide (NaOMe) gives S3-21. A Curtius reaction with DPPA followed by quenching with trimethylsilylethanol gives carbamate S3-22. Saponification with NaOH gives the acid S3-23, which undergoes a Curtius reaction, An approach to preparing synthons of endo,endo-1,3-Diaminonorbornane is shown in Scheme 4. 5-Trimethylsilyl-1,3-cyclopentadiene (S4-25) is reacted with the diethylaluminum chloride Lewis acid complex of di-(l)-menthyl fumarate at low temperature to give nearly diastereomerically pure norbornene S4-26. Crystallization of S4-26 from alcohol results in recovery of greater than 99% of the single diastereomer. Bromolactonization followed by silver mediated rearrangement gives mixed diester S4-28 with an alcohol moiety at the 7-position. Protection of the alcohol with benzyl bromide and selective deprotection of the methyl ester gives the free carboxylic acid S4-30. A Curtius reaction results in trimethylsilylethyl carbamate norbornene S4-31. Biscarbonylation of the olefin in methanol, followed by a single-step deprotection and dehydration gives the mono-anhydride

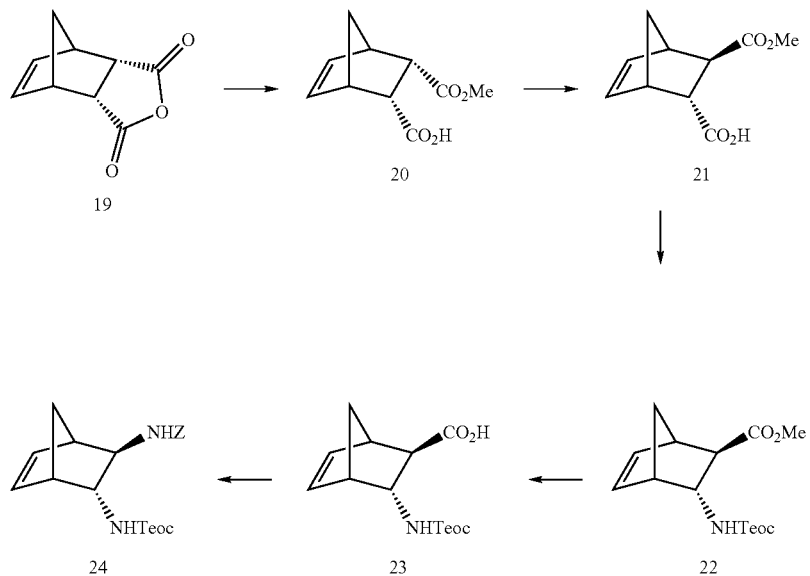

then quenched with benzyl alcohol to give differentially protected biscarbamate S3-24. Compound S3-24 can be fully deprotected to provide the diamine or either of the carbamates can be selectively deprotected.

S4-33. Quinidine mediated opening of the anhydride with methanol gives S4-34. Curtius transformation of S4-34 gives the biscarbamate S4-35, which is deprotected with TFA or tetrabutylammonium fluoride (TBAF) to give diamine S4-36.

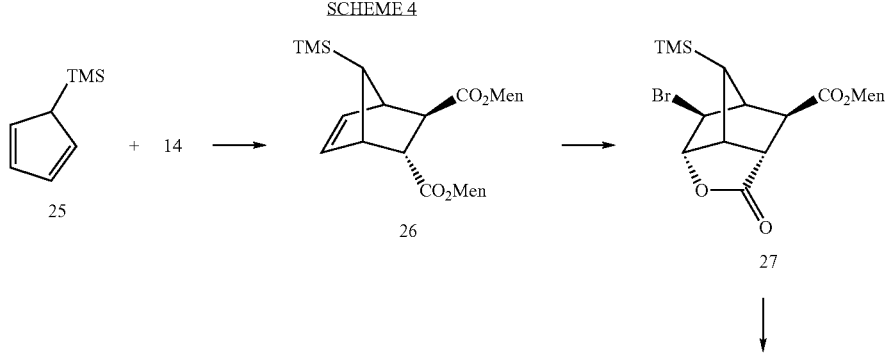

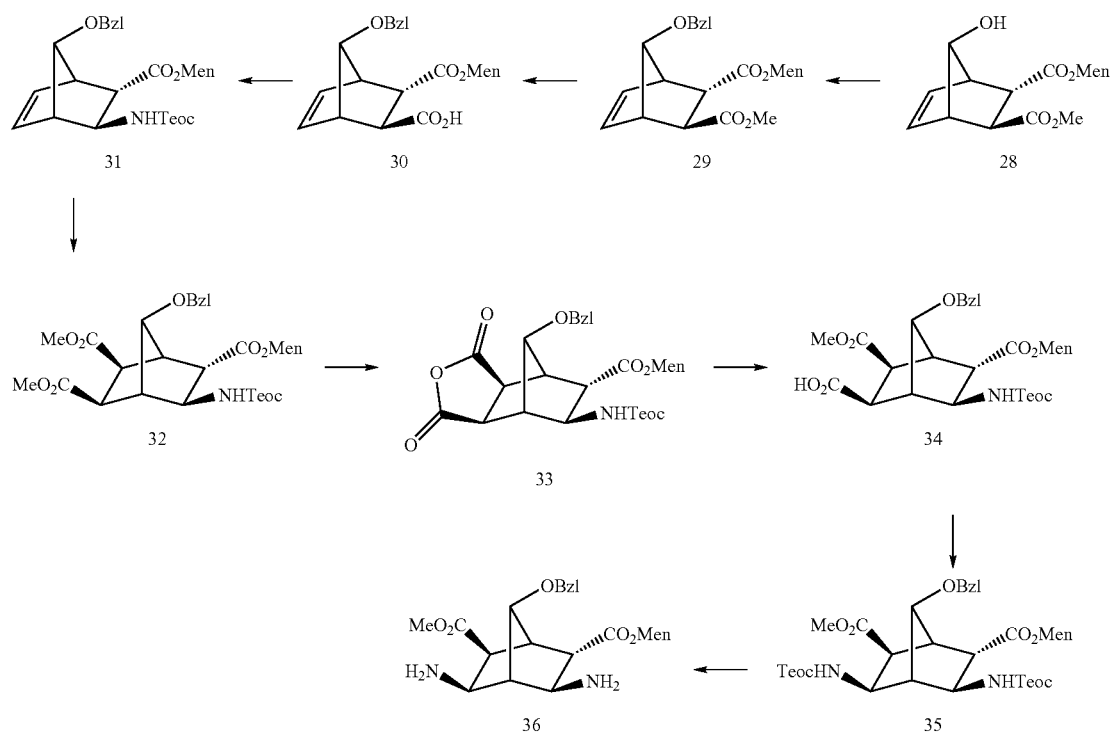

Another approach to this class of synthons is outlined in Scheme 5. Benzyl alcohol opening of S3-19 in the presence of quinidine gives S5-37 in high enantiomeric excess. Iodolactonization followed by NaBT$_4$ reduction gives lactone S5-39. Treatment with NaOMe liberates the methyl ester and the free alcohol to generate S5-40. Transformation of the alcohol S5-40 to the inverted t-butyl carbamate protected amine S5-41 is accomplished in a one-pot reaction by azide displacement of the mesylate S5-40 followed by reduction to the amine, which is protected with di-tert-butyl dicarbonate. Hydrogenolytic cleavage of the benzyl ester and epimerization of the methyl ester to the exo configuration is followed by protection of the free acid with benzyl bromide to give S5-44. Saponification of the methyl ester followed by a trimethylsilylethanol quenched Curtius reaction

SCHEME 5

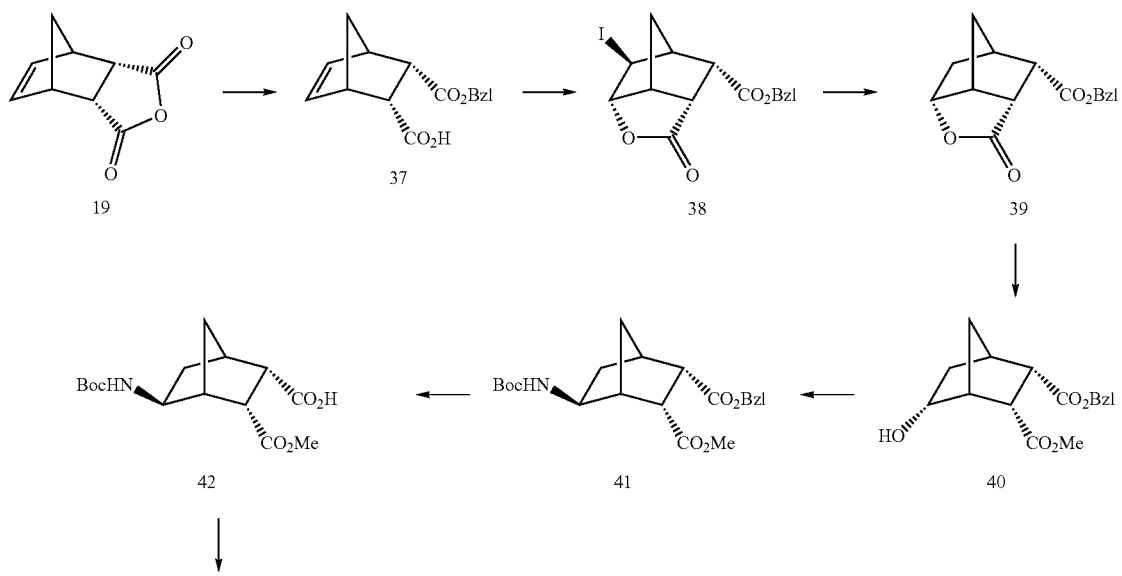

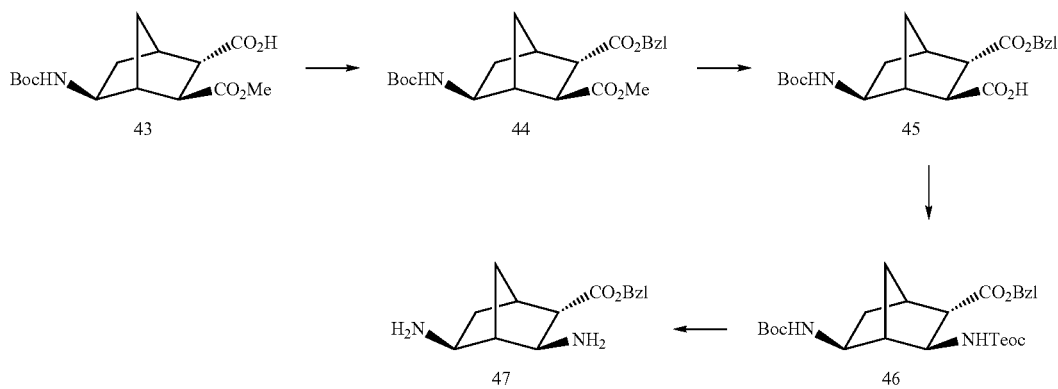

gives the biscarbamate S5-46, which is cleaved with TFA to give the desired diamine S5-47.

An approach to preparing synthons of exo,endo-1,3-Diaminonorbornane is shown in Scheme 6. p-Methoxybenzyl alcohol opening of norbornene anhydride S3-19 in the presence of quinidine gives monoester S6-48 in high enantiomeric excess. Curtius reaction of the free acid gives protected all endo monoacid-monoamine S6-49. Biscarbonylation and anhydride formation gives exo-monoanhydride S6-51. Selective methanolysis in the presence of quinine gives S6-52. A trimethylsilylethanol quenched Curtius reaction gives biscarbamate S6-53. Epimerization of the two esters results in the more sterically stable S6-54. Cleavage of the carbamate groups provides synthon S6-55.

Methods to Prepare Macrocyclic Modules

Synthons may be coupled to one another to form macrocyclic modules. In one variation, the coupling of synthons may be accomplished in a concerted scheme. Preparation of a macrocyclic module by the concerted route may be performed using, for example, at least two types of synthons, each type having at least two functional groups for coupling to other synthons. The functional groups may be selected so that a functional group of one type of synthon can couple only to a functional group of the other type of synthon. When two types of synthons are used, a macrocyclic module may be formed having alternating synthons of different types. Scheme 7 illustrates a concerted module synthesis.

SCHEME 6

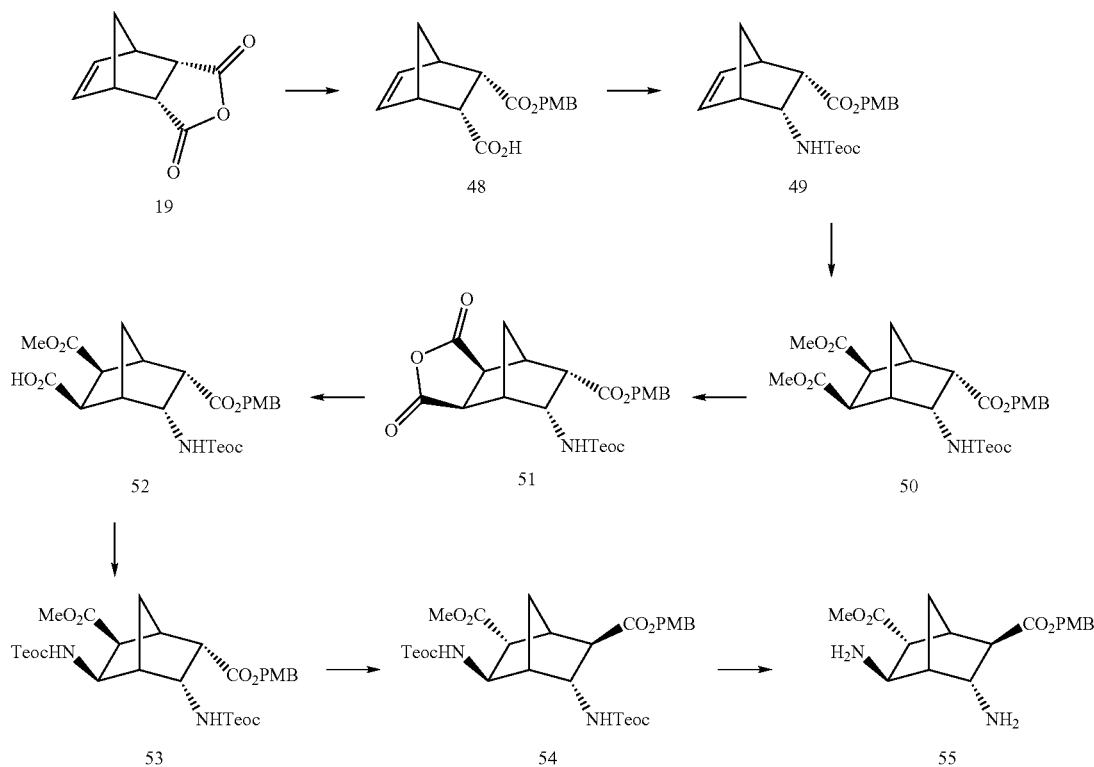

Referring to Scheme 7, 1,2-Diaminocyclohexane, S7-1, is a synthon having two amino functional groups for coupling to other synthons, and 2,6-diformyl-4-dodec-1-ynylphenol, S7-2, is a synthon having two formyl groups for coupling to other synthons. An amino group may couple with a formyl group to form an imine linkage. In Scheme 7, a concerted product hexamer macrocyclic module is shown.

In one variation, a mixture of tetramer, hexamer, and octamer macrocyclic modules may be formed in the concerted scheme. The yields of these macrocyclic modules can be varied by changing the concentration of various synthons in the reagent mixture, and among other factors, by changing the solvent, temperature, and reaction time.

out using 2,6-di(chlorocarbonyl)-4-dodec-1-ynylphenol instead of 2,6-diformyl-4-dodec-1-ynylphenol, the resulting module will contain amide linkages. Similarly, if 1,2-dihydroxycyclohexane is reacted with 2,6-di(chlorocarbonyl)-4-dodec-1-ynylphenol, the resulting module will contain ester linkages.

In some variations, the coupling of synthons may be accomplished in a stepwise scheme. In an example of the stepwise preparation of macrocyclic modules, a first type of synthon is substituted with one protected functional group and one unprotected functional group. A second type of synthon is substituted with an unprotected functional group that will couple with the unprotected functional group on the first

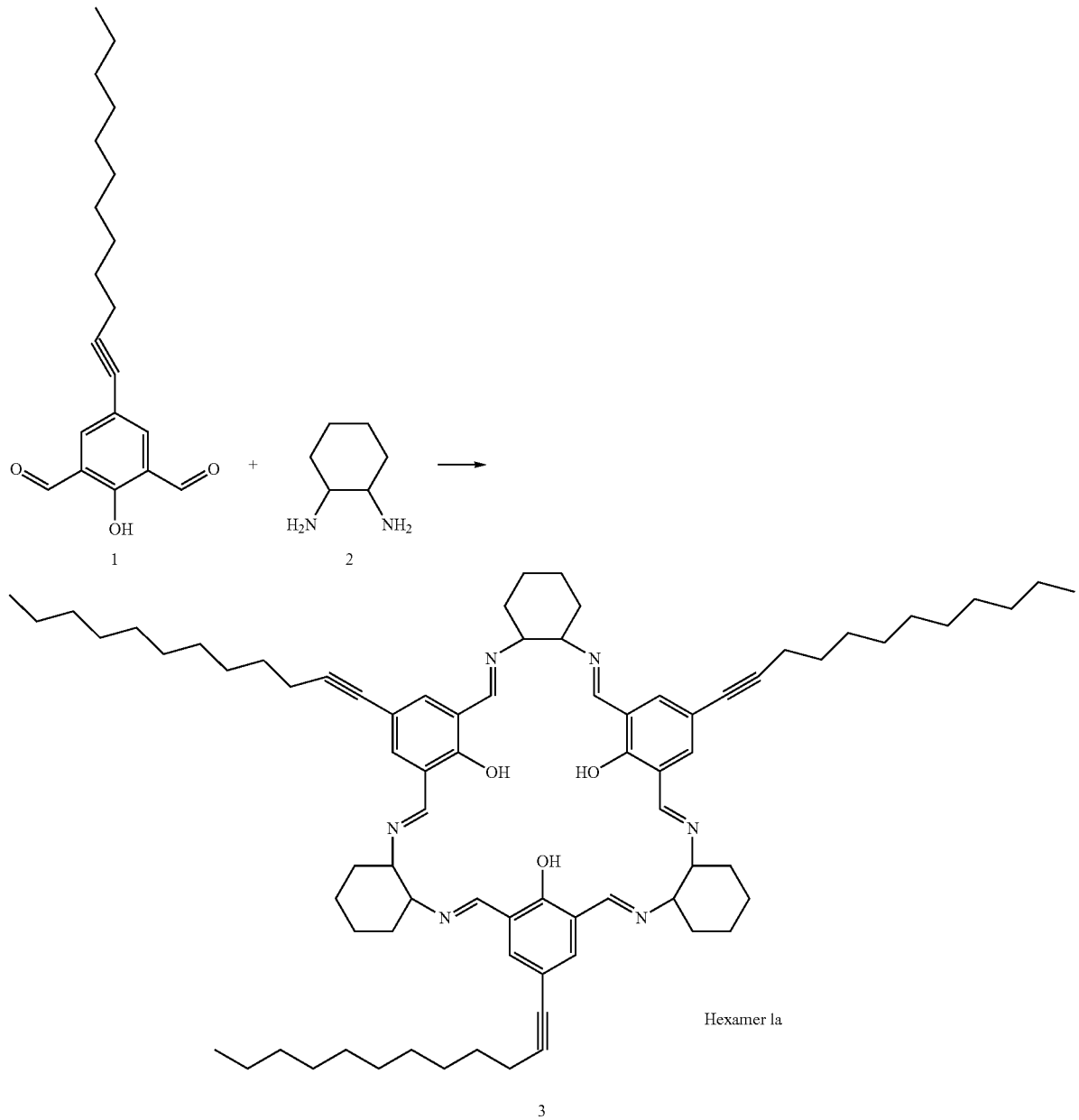

SCHEME 7

The imine groups of S7-3 can be reduced, e.g. with sodium borohydride, to give amine linkages. If the reaction is carried synthon. The product of contacting the first type of synthon with the second type of synthon may be a dimer, which is made of two coupled synthons. The second synthon may also be substituted with another functional group which is either protected, or which does not couple with the first synthon when the dimer is formed. The dimer may be isolated and purified, or the preparation may proceed as a one-pot method. The dimer may be contacted with a third synthon having two functional groups, only one of which may couple with the remaining functional group of either the first or second synthons to form a trimer, which is made of three coupled synthons. Such stepwise coupling of synthons may be repeated to form macrocyclic modules of various ring sizes. To cyclize or close the ring of the macrocyclic module, the $n^{th}$ synthon which was coupled to the product may be substituted with a second functional group which may couple with the second functional group of a previously coupled synthon that has not been coupled, which may be deprotected for that step. The stepwise method may be carried out with synthons on solid phase support. Scheme 8 illustrates a stepwise preparation of module SC8-1.

Compound S8-2 is reacted with S8-3, in which the phenol is protected as the benzyl ether and the nitrogen is shown as protected with a group "P," which can be any of a large number of protecting groups well-known in the art, in the presence of methanesulfonyl chloride (Endo, K.; Takahashi, H. *Heterocycles,* 1999, 51, 337), to give S8-4. Removal of the N-protecting group give the free amine S8-5, which can be coupled with synthon S8-6 using any standard peptide coupling reaction such as BOP/HOBt to give S8-7. Deprotection/coupling is repeated, alternating synthons S8-3 and S8-6 until a linear construct with eight residues is obtained. The remaining acid and amine protecting groups on the 8-mer are removed and the oligomer is cyclized, see e.g., Caba, J. M., et al., *J. Org. Chem.,* 2001, 66:7568 (PyAOP cyclization) and Tarver, J. E. et al., *J. Org. Chem.,* 2001, 66:7575 (active ester cyclization). The R group is H or an alkyl group linked via a functional group to the benzene ring, and X is N, O, or S. Examples of solid supports include Wang resin, hydrogels, silica gels, sepharose, sephadex, agarose, and inorganic solids. Using a solid support might simplify the procedure by obviating purification of intermediates along the way. The final cyclization may be done in a solid phase mode. A "safety-catch linker" approach (Bourne, G. T., et al., *J. Org. Chem.,* 2001, 66:7706) may be used to obtain cyclization and resin cleavage in a single operation.

SCHEME 8

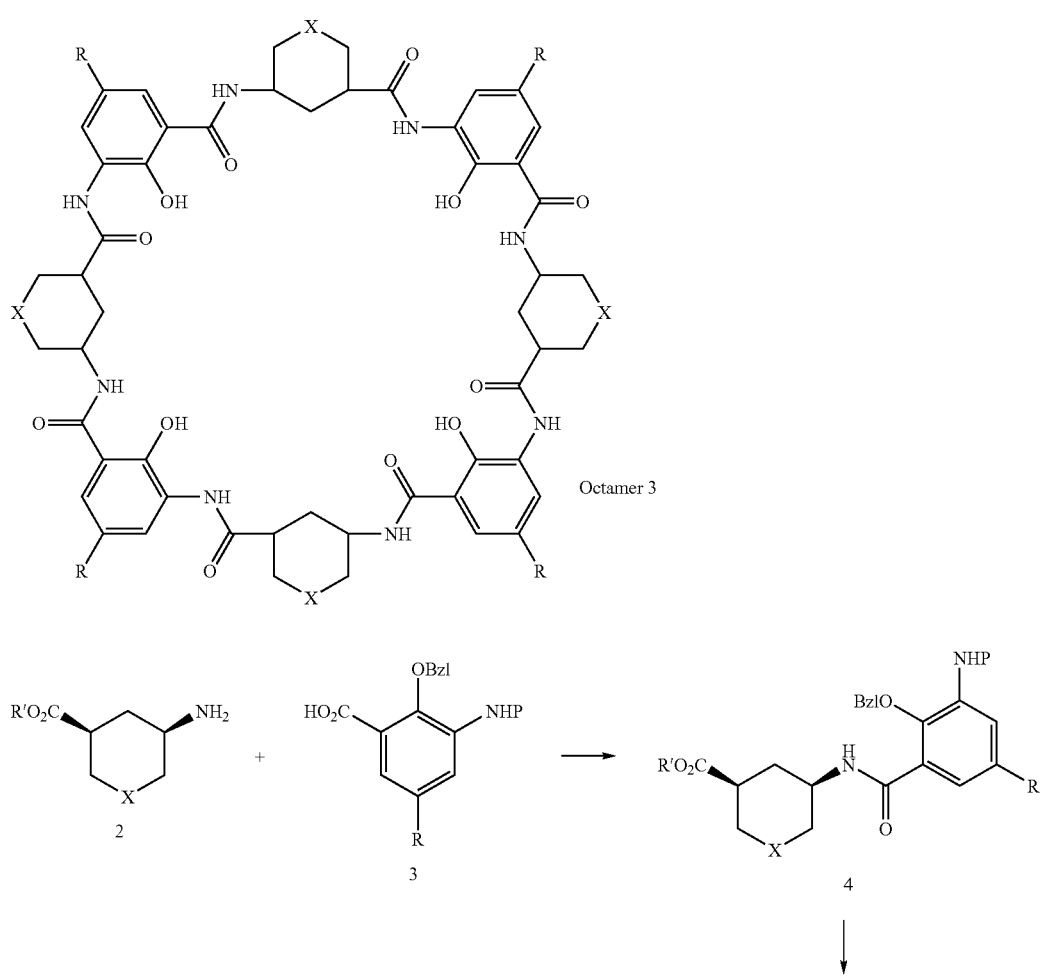

-continued

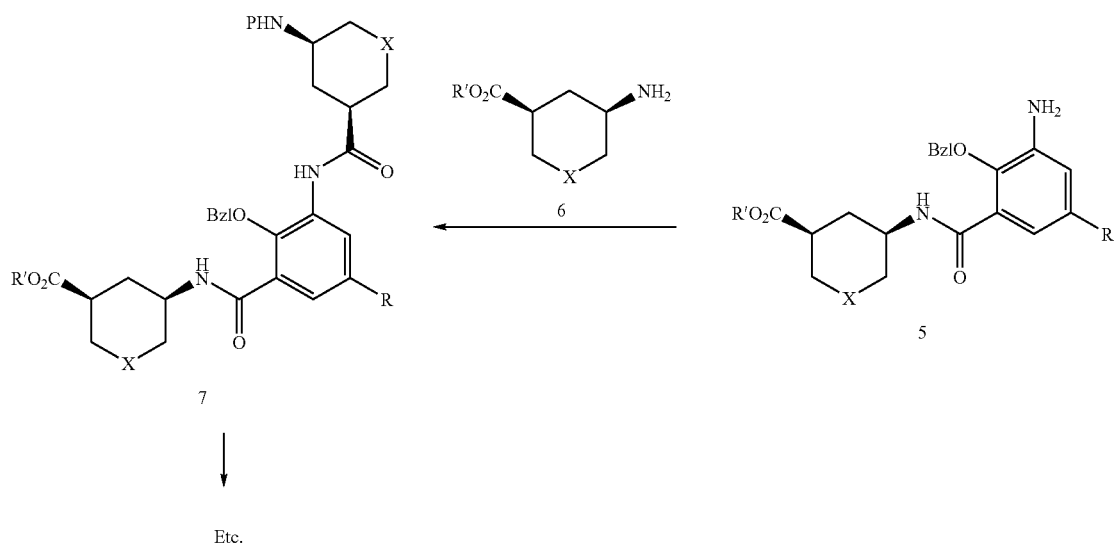

In another variation, a concerted method involves contacting two or more different synthons and a linker molecule as shown in Scheme 9, where R may be an alkyl group or other lipophilic group.

SCHEME 9

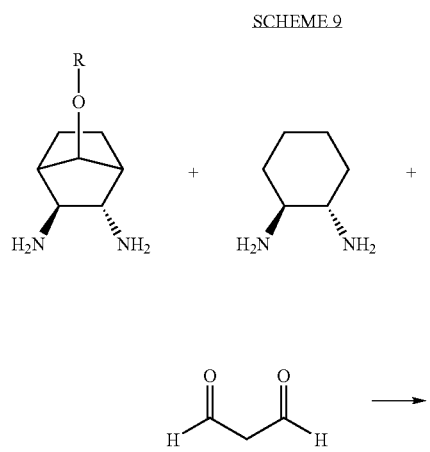

-continued

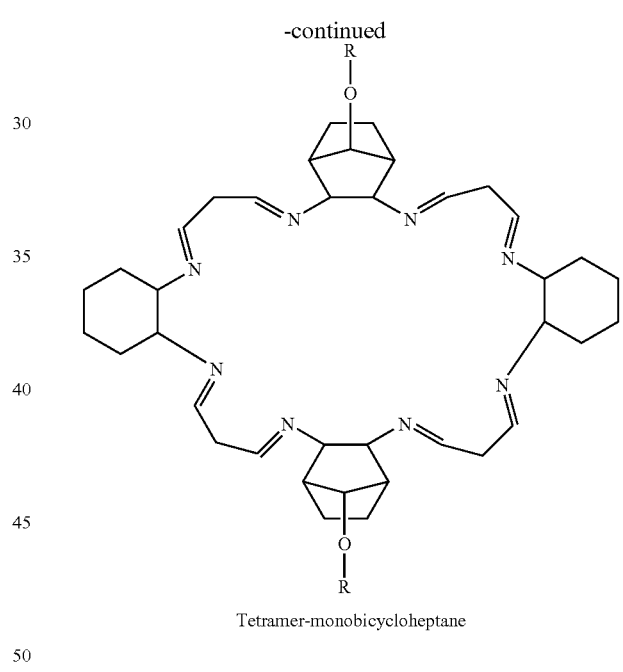

Tetramer-monobicycloheptane

In another variation, a stepwise linear method involves various synthons and a solid phase support as shown in Scheme 10.

SCHEME 10

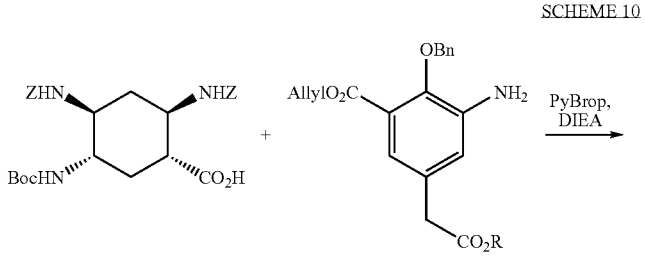

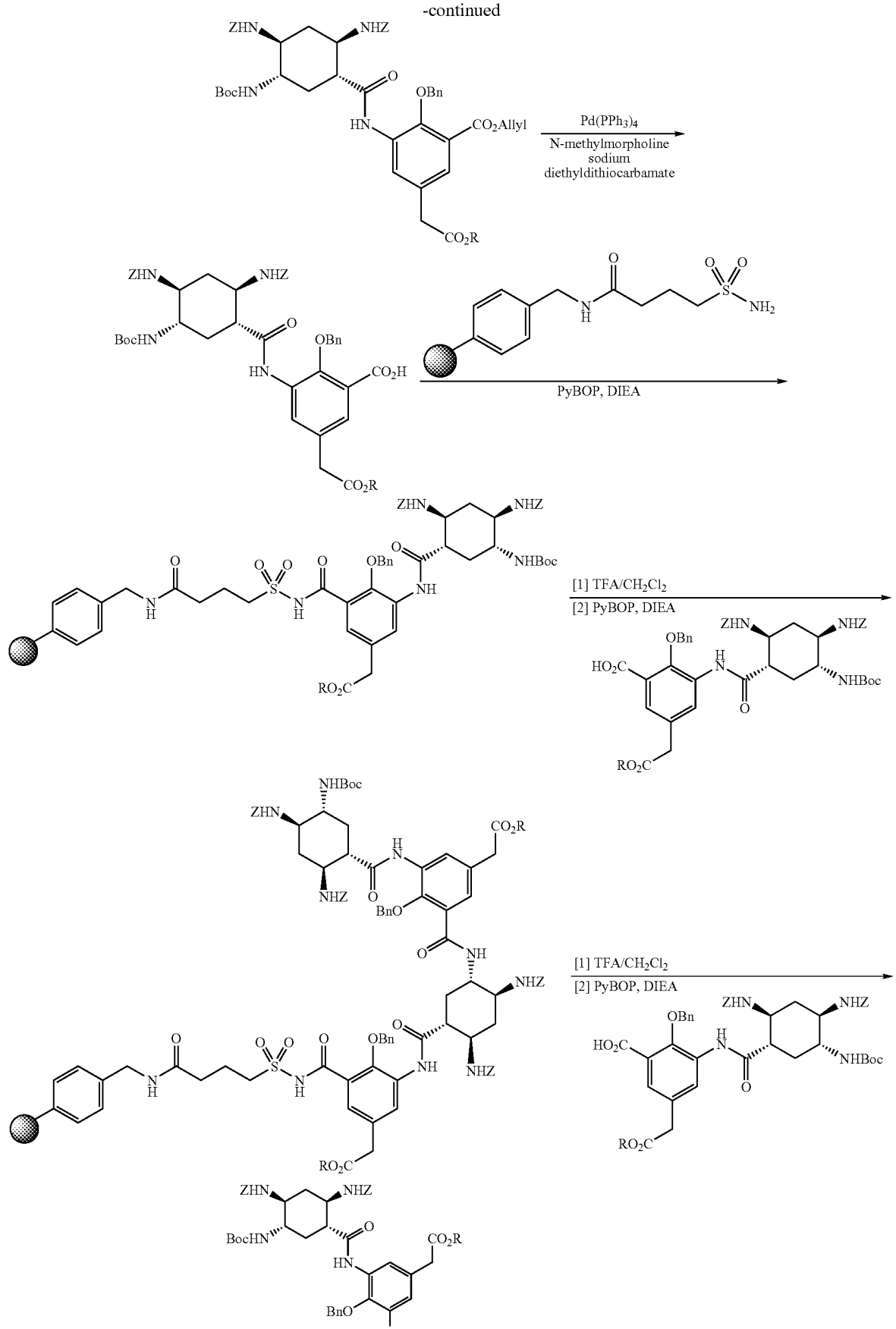

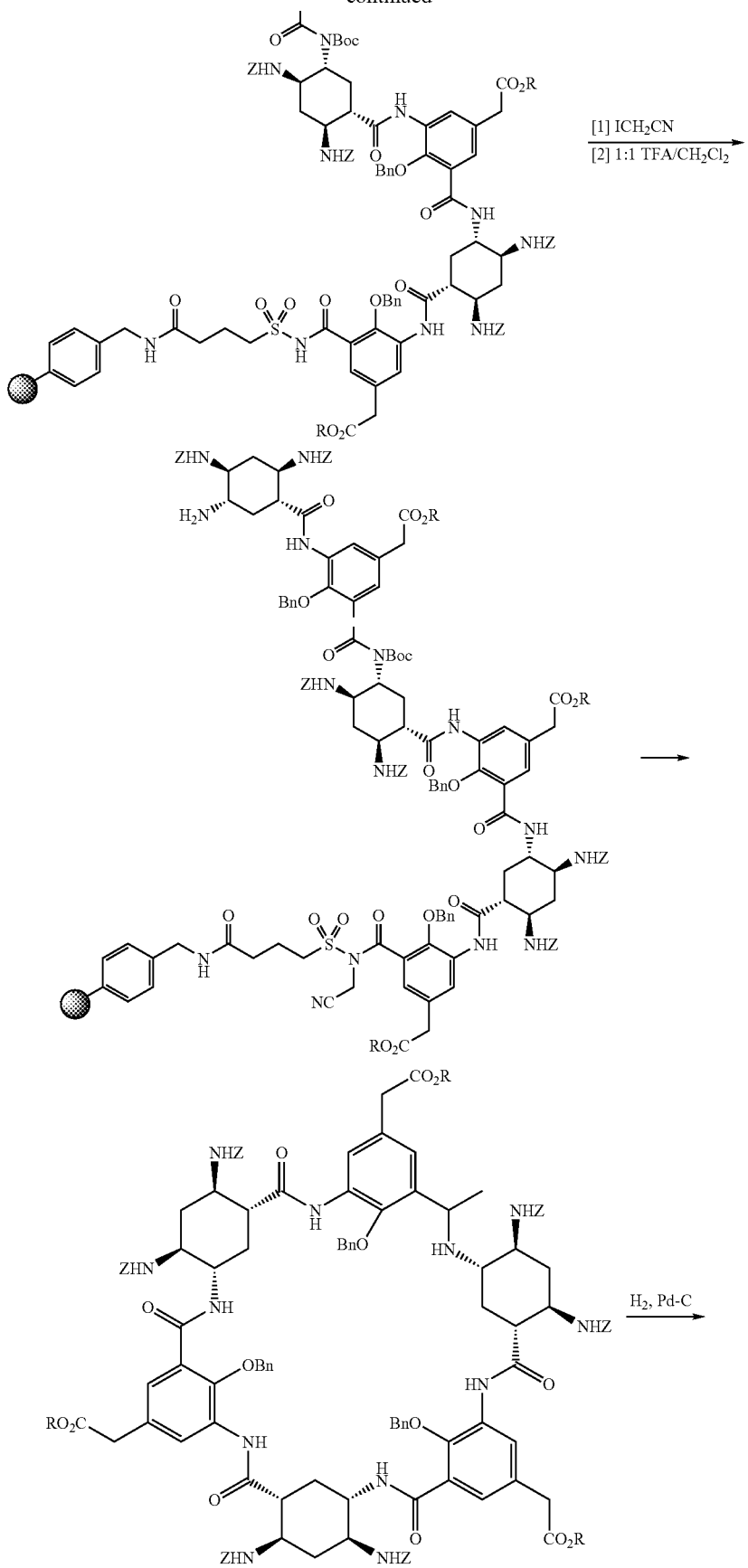

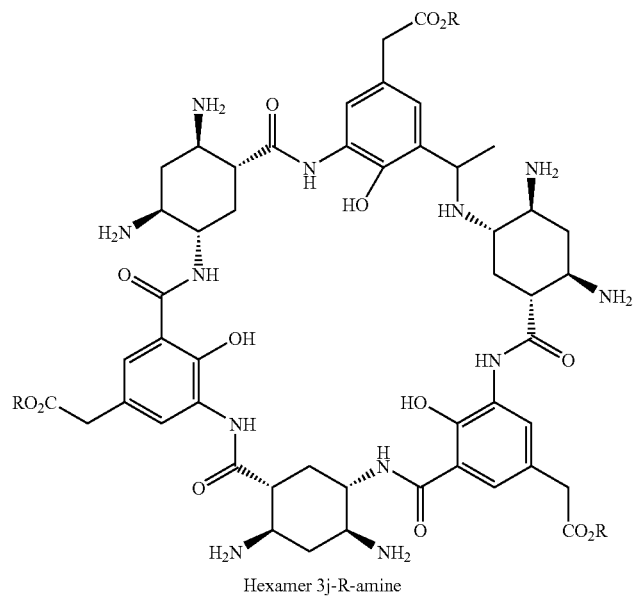

Hexamer 3j-R-amine

In another variation, a stepwise convergent method involves synthon trimers and a solid phase support as shown in Scheme 11. This method can also be done without the solid phase support using trimers in solution.

SCHEME 11

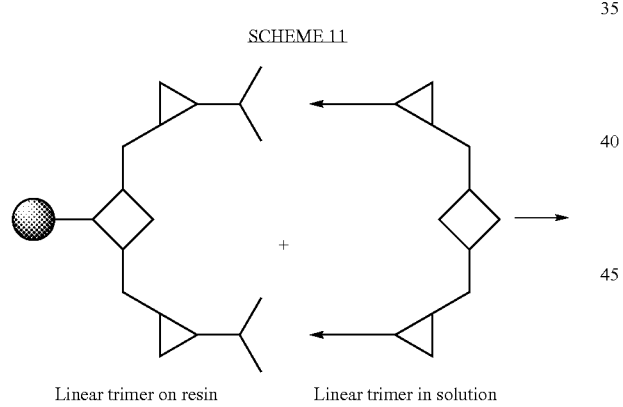

Linear trimer on resin     Linear trimer in solution

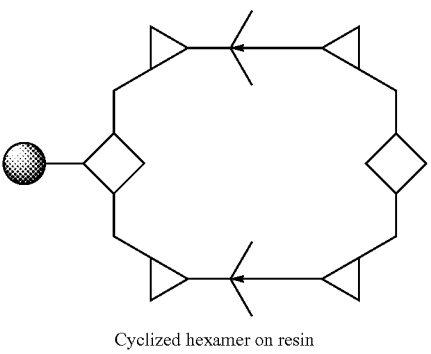

Cyclized hexamer on resin

In another variation, a template method involves synthons brought together by a template as shown in Scheme 12. Some aspects of this approach (and an $Mg^{2+}$ template) are given in Dutta et al. *Inorg. Chem.* 1998, 37, 5029.

SCHEME 12

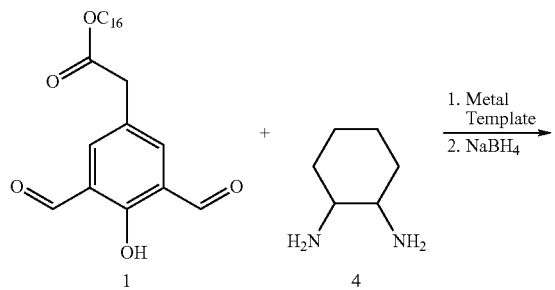

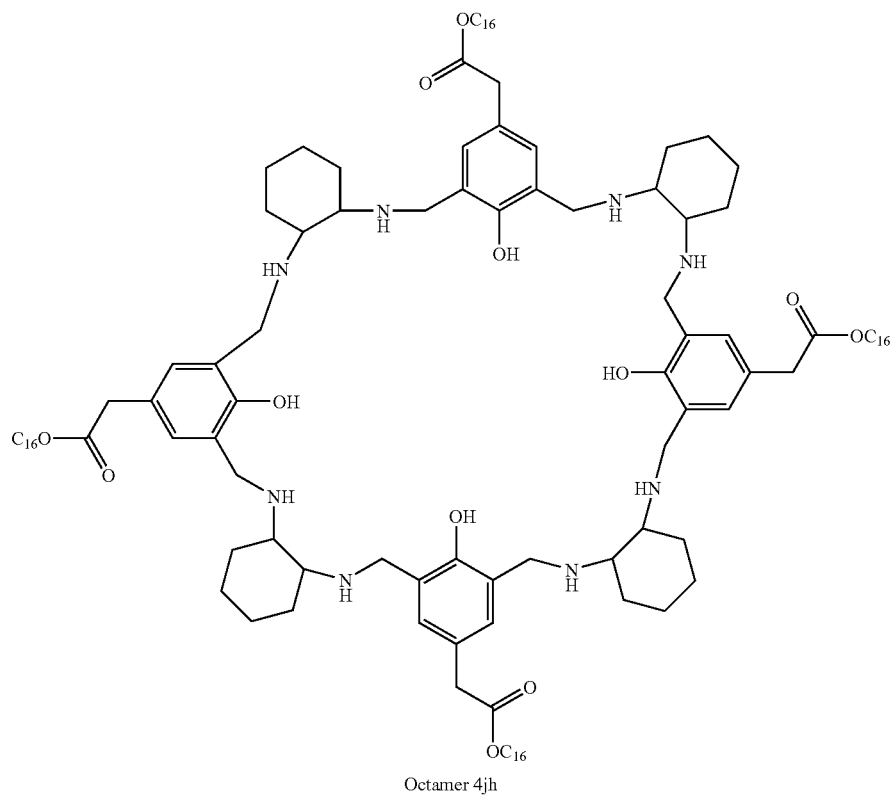
Octamer 4jh
In another variation, a linker molecule method involves cyclizing synthons in solution as shown in Scheme 13.
SCHEME 13
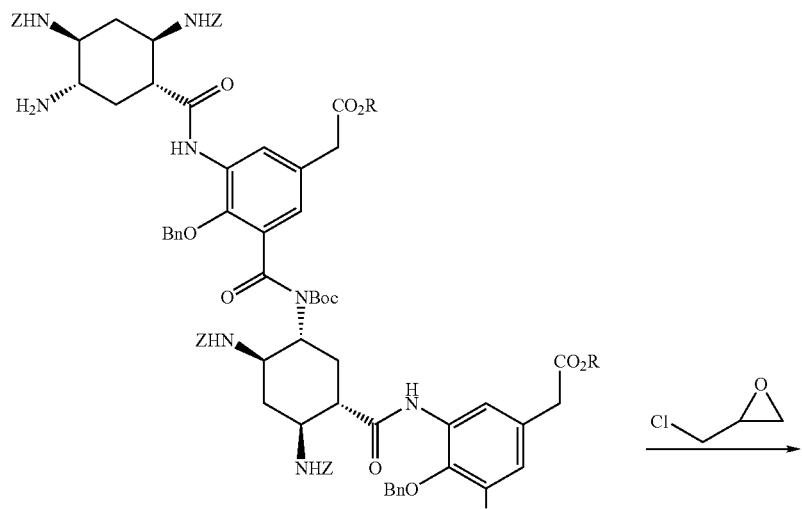

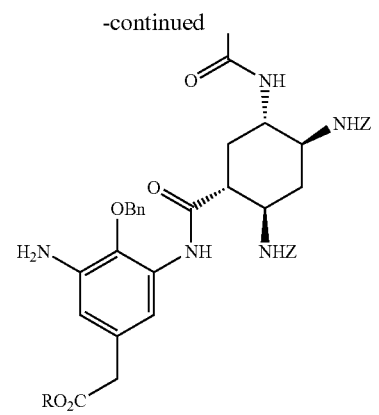

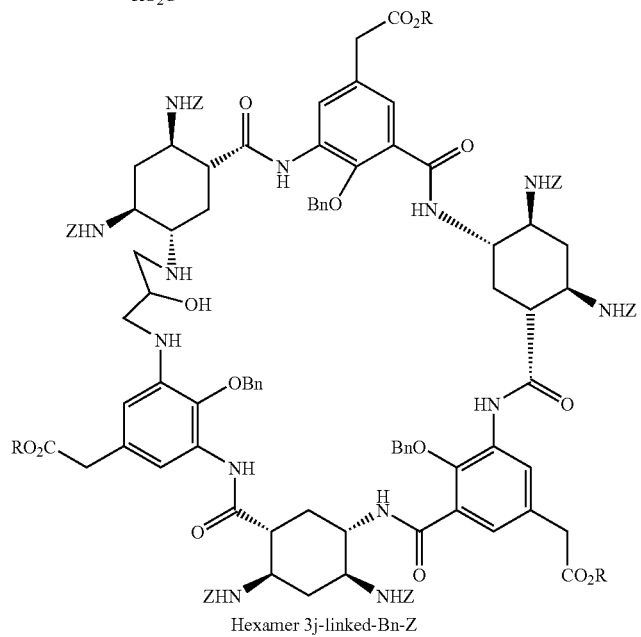

Hexamer 3j-linked-Bn-Z

Reagents for the following examples were obtained from Aldrich Chemical Company and VWR Scientific Products. All reactions were carried out under nitrogen or argon atmosphere unless otherwise noted. Solvent extracts of aqueous solutions were dried over anhydrous $Na_2SO_4$. Solutions were concentrated under reduced pressure using a rotary evaporator. Thin layer chromatography (TLC) was done on Analtech Silica gel GF (0.25 mm) plates or on Machery-Nagel Alugram Sil G/UV (0.20 mm) plates. Chromatograms were visualized with either UV light, phosphomolybdic acid, or $KMnO_4$. All compounds reported were homogenous by TLC unless otherwise noted. HPLC analyses were performed on a Hewlett Packard 1100 system using a reverse phase C-18 silica column. Enantiomeric excess was determined by HPLC using a reverse phase (l)-leucine silica column from Regis Technologies. All $^1$[H] and $^{13}$[C] NMR spectra were collected at 400 MHz on a Varian Mercury system. Electrospray mass spectra were obtained by Synpep Corp., or on a Thermo Finnigan LC-MS system.

Example 16

2,6-Diformyl-4-bromophenol

Hexamethylenetetramine (73.84 g, 526 mmol) was added to TFA (240 mL) with stirring. 4-Bromophenol (22.74 g, 131 mmol) was added in one portion and the solution heated in an oil bath to 120° C. and stirred under argon for 48 h. The reaction mixture was then cooled to ambient temperature. Water (160 mL) and 50% aqueous $H_2SO_4$ (80 mL) were added and the solution stirred for an additional 2 h. The reaction mixture was poured into water (1600 mL) and the resulting precipitate collected on a Büchner funnel. The precipitate was dissolved in ethyl acetate (EtOAc) and the solution was dried over $MgSO_4$. The solution was filtered and the solvent removed on a rotary evaporator. Purification by column chromatography on silica gel (400 g) using a gradient of 15-40% ethyl acetate in hexanes resulted in a isolation of the product as a yellow solid (18.0 g, 60%).

$^1$H NMR (400 MHz, CDCl$_3$) δ 11.54 (s, 1H, OH), 10.19 (s, 2H, CHO), 8.08 (s, 2H, ArH).

Example 17

2,6-Diformyl-4-(dodecyn-1-yl)phenol 2,6-Diformyl-4-bromophenol (2.50 g, 10.9 mmol), 1-dodecyne (2.00 g, 12.0 mmol), CuI (65 mg, 0.33 mmol), and bis(triphenylphosphine)palladium)II) dichloride were suspended in degassed acetonitrile (MeCN) (5 mL) and degassed benzene (1 mL). The yellow suspension was sparged with argon for 30 min and degassed Et$_3$N (1 mL) was added. The resulting brown suspension was sealed in a pressure vial, warmed to 80° C. and held there for 12 h. The mixture was then partitioned between EtOAc and KHSO$_4$ solution. The organic layer was separated, washed with brine, dried (MgSO$_4$) and concentrated under reduced pressure. The dark yellow oil was purified by column chromatography on silica gel (25% Et$_2$O in hexanes) to give 1.56 g (46%) of the title compound.

$^1$H NMR (400 MHz, CDCl$_3$) δ 11.64 (s, 1H, OH), 10.19 (s, 2H, CHO), 7.97 (s, 2H, ArH), 2.39 (t, 2H, J=7.2 Hz, propargylic), 1.59 (m, 3H, aliphatic), 1.43, (m, 2H, aliphatic), 1.28 (m, 11H, aliphatic), 0.88 (t, 3H, J=7.0 Hz, CH$_3$).

$^{13}$C NMR (400 MHz, CDCl$_3$) δ 192.5, 162.4, 140.3, 122.8, 116.7, 91.4, 77.5, 31.9, 29.6, 29.5, 29.3, 29.1, 28.9, 28.5, 22.7, 19.2, 14.1.

MS (FAB): Calcd. for C$_{20}$H$_{27}$O$_3$, 315.1960. found 315.1958 [M+H]$^+$.

Example 18

2,6-Diformyl-4-(dodecen-1-yl)phenol 2,6-Diformyl-4-bromophenol (1.00 g, 4.37 mmol), 1-dodecene (4.8 mL, 21.7 mmol), 1.40 g tetrabutylammonium bromide (4.34 mmol), 0.50 g NaHCO$_3$ (5.95 mmol), 1.00 g LiCl (23.6 mmol) and 0.100 g palladium diacetate (Pd(OAc)$_2$) (0.45 mmol) were combined in 30 mL degassed anhydrous dimethylformamide (DMF). The mixture was sparged with argon for 10 min and then sealed in a pressure vial which was warmed to 82° C. and held for 40 h. The crude reaction mixture was partitioned between CH$_2$Cl$_2$ and 0.1 M HCl solution. The organic layer was washed with 0.1 M HCl (2×), brine (2×), and saturated aqueous NaHCO$_3$ (2×), dried over MgSO$_4$ and concentrated under reduced pressure. The dark yellow oil was purified by column chromatography on silica gel (25% hexanes in Et$_2$O) to give 0.700 g (51%) of the title compound as primarily the Z isomer.

$^1$H NMR (400 MHz, CDCl$_3$) δ 11.50 (s, 1H, OH), 10.21 (s, 2H, CHO), 7.95 (s, 2H, ArH), 6.38 (d, 1H, vinyl), 6.25 (m, 1H, vinyl), 2.21 (m, 2H, allylic), 1.30-1.61 (m, 16H, aliphatic), 0.95 (t, 3H, J=7.0 Hz, CH$_3$).

MS (FAB): Calcd. for C$_{20}$H$_{27}$O$_3$, 315.20. found 315.35 [M−H]$^-$.

Example 19

(1R,6S)-6-Methoxycarbonyl-3-cyclohexene-1-carboxylic Acid (S1-2)

S1-1 (15.0 g, 75.7 mmol) was suspended in pH 7 phosphate buffer (950 mL). Pig liver esterase (2909 units) was added, and the mixture stirred at ambient temperature for 72 h with the pH maintained at 7 by addition of 2M NaOH. The reaction mixture was washed with ethyl acetate (200 mL), acidified to pH 2 with 2M HCl, and extracted with ethyl acetate (3×200 mL). The extracts were combined, dried, and evaporated to afford 13.8 g (99%) of S1-2.

$^1$H NMR: (CDCl$_3$) δ 2.32 (dt, 2H, 2$_{ax}$- and 5$_{ax}$-H's), 2.55 (dt, 2H, 2$_{eq}$- and 5$_{eq}$-H's), 3.00 (m, 2H, 1- and 6-H's), 3.62 (s, 3H, CO$_2$Me), 5.61 (m, 2H, 3- and 4-H's).

Example 20

Methyl (1S,6R)-6-Benzyloxycarbonylaminocyclohex-3-enecarboxylate (S1-3)

S1-2 (10.0 g, 54.3 mmol) was dissolved in benzene (100 mL) under N$_2$. Triethylamine (13.2 g, 18.2 mL, 130.3 mmol) was added followed by DPPA (14.9 g, 11.7 mL, 54.3 mmol). The solution was refluxed for 20 h. Benzyl alcohol (5.9 g, 5.6 mL, 54.3 mmol) was added and reflux continued for 20 h. The solution was diluted with EtOAc (200 mL), washed with saturated aqueous NaHCO$_3$ (2×50 mL), water (20 mL), and saturated aqueous NaCl (20 mL), dried and evaporated to give 13.7 g (87%) of S1-3.

$^1$H NMR: (CDCl$_3$) δ 2.19 (dt, 1H, 5$_{ax}$-H), 2.37 (tt, 2H, 2$_{ax}$- and 5$_{eq}$-H's), 2.54 (dt, 1H, 2$_{eq}$-H), 2.82 (m, 1H, 1-H), 3.65 (s, 3H, CO$_2$Me), 4.28 (m, 1H, 6-H), 5.08 (dd, 2H, CH$_2$Ar), 5.42 (d, 1H, NH), 5.62 (ddt, 2H, 3- and 4-H's), 7.35 (m, 5H, Ar H's).

Example 21

(1S,6R)-6-Benzyloxycarbonylaminocyclohex-3-enecarboxylic acid (S1-4)

S1-3 (23.5 g, 81.3 mmol) was dissolved in MeOH (150 mL) and the solution cooled to 0° C. 2M NaOH (204 mL, 0.41 mol) was added, the mixture allowed to come to ambient temperature and then it was stirred for 48 h. The reaction mixture was diluted with water (300 mL), acidified with 2M HCl, and extracted with dichloromethane (250 mL), dried, and evaporated. The residue was recrystallized from diethyl ether to give 21.7 (97%) of S1-4.

$^1$H NMR: (CDCl$_3$) δ 2.20 (d, 1H, 5$_{ax}$-H), 2.37 (d, 2H, 2$_{ax}$- and 5$_{eq}$-H's), 2.54 (d, 1H, 2$_{eq}$-H), 2.90 (br s, 1H, 1-H), 4.24 (br s, 1H, 6-H), 5.08 (dd, 2H, CH$_2$Ar), 5.48 (d, 1H, NH), 5.62 (dd, 2H, 3- and 4-H's), 7.35 (m, 5H, Ar H's).

Example 22

(1S,2R,4R,5R)-2-Benzyloxycarbonylamino-4-iodo-7-oxo-6-oxabicyclo[3.2.1]octane (S1-5)

S1-4 (13.9 g, 50.5 mmol) was dissolved in dichloromethane (100 mL) under N$_2$, 0.5 M NaHCO$_3$ (300 mL), KI (50.3 g, 303.3 mmol), and iodine (25.6 g, 101 mmol) were added and the mixture stirred at ambient temperature for 72 h. The mixture was diluted with dichloromethane (50 mL) and the organic phase separated. The organic phase was washed with saturated aqueous Na$_2$S$_2$O$_3$ (2×50 mL), water (30 mL), and saturated aqueous NaCl (20 mL), dried and evaporated to afford 16.3 g (80%) of S1-5.

$^1$H NMR: (CDCl$_3$) δ 2.15 (m, 1H, 8$_{ax}$-H), 2.42 (m, 2H, 3$_{ax}$- and 8$_{eq}$-H's), 2.75 (m, 2H, 1- and 3$_{eq}$-H's), 4.12 (br s, 1H, 2-H), 4.41 (t, 1H, 4-H), 4.76 (dd, 1H, 5-H), 4.92 (d, 1H, NH), 5.08 (dd, 2H, CH$_2$Ar), 7.35 (m, 5H, Ar H's).

Example 23

(1S,2R,5R)-2-Benzyloxycarbonylamino-7-oxo-6-oxabicyclo[3.2.1]oct-3-ene (S1-6)

S1-5 (4.0 g, 10 mmol) was dissolved in benzene (50 mL) under N$_2$. 1,8-Diazabicyclo[5.4.0]undec-7-ene (DBU) (1.8 g, 12 mmol) was added and the solution refluxed for 16 h. The precipitate was filtered and the filtrate was diluted with EtOAc (200 mL). The filtrate was washed with 1M HCl (20 mL), saturated aqueous Na$_2$S$_2$O$_3$ (20 mL), water (20 mL), and saturated aqueous NaCl (20 mL), dried and evaporated to give 2.2 g (81%) S1-6.

$^1$H NMR: (CDCl$_3$) δ 2.18 (d, 1H, 8$_{ax}$-H), 2.39 (m, 1H, 8$_{eq}$-H), 3.04 (t, 1H, 1-H), 4.70 (m, 1H, 5-H), 4.82 (t, 1H, 2-H), 5.15 (dd, 3H, CH$_2$Ar and NH), 5.76 (d, 1H, 4-H), 5.92 (m, 1H, 3-H), 7.36 (s, 5H, Ar H's).

Example 24

(1S,2R,5R)-Methyl 2-Benzyloxycarbonylamino-5-hydroxycyclohex-3-enecarboxylate (S1-7)

S1-6 (9.0 g, 33 mmol) was suspended in MeOH (90 mL) and cooled to 0° C. NaOMe (2.8 g, 52.7 mmol) was added and the mixture stirred for 3 h during which time a solution gradually formed. The solution was neutralized with 2M HCl, diluted with saturated aqueous NaCl (200 mL), and extracted with dichloromethane (2×100 mL). The extracts were combined, washed with water (20 mL) and saturated aqueous NaCl (20 ml), dried, and evaporated. The residue was flash chromatographed (silica gel (250 g), 50:50 hexane/EtOAc) to give 8.5 g (85%) of S1-7.

$^1$H NMR: (CDCl$_3$) δ 1.90 (m, 1H, 6$_{ax}$-H), 2.09 (m, 1H, 6$_{eq}$-H), 2.81 (m, 1H, 1-H), 3.55 (s, 3H, CO$_2$Me), 4.15 (m, 1H, 5-H), 4.48 (t, 1H, 2-H), 5.02 (dd, 2H, CH$_2$Ar), 5.32 (d, 1H, NH), 5.64 (dt, 1H, 4-H), 5.82 (dt, 1H, 3-H), 7.28 (s, 5H, Ar H's).

Example 25

(1S,2R,5S)-Methyl 2-Benzyloxycarbonylamino-5-t-butoxycarbonylaminocyclohex-3-enecarboxylate (S1-8)

S1-7 (7.9 g, 25.9 mmol) was dissolved in dichloromethane (150 mL) and cooled to 0° C. under N$_2$. Triethylamine (6.3 g, 8.7 mL, 62.1 mmol) and methanesulfonyl chloride (7.1 g, 62.1 mmol) were added and the mixture stirred at 0° C. for 2 h. (n-Bu)$_4$NN$_3$ (14.7 g, 51.7 mmol) in dichloromethane (50 mL) was added and stirring continued at 0° C. for 3 h followed by 15 h at ambient temperature. The mixture was cooled to 0° C. and P(n-Bu)$_3$ (15.7 g, 19.3 mL, 77.7 mmol) and water (1 mL) were added and the mixture stirred at ambient temperature for 24 h. Di-tert-butyl dicarbonate (17.0 g, 77.7 mmol) was added and stirring continued for 24 h. The solvent was removed, the residue dissolved in 2:1 hexane/EtOAc (100 mL), the solution filtered, and evaporated. The residue was flash chromatographed (silica gel (240 g), 67:33 hexane/EtOAc) to give 5.9 g (56%) of S1-8.

$^1$H NMR: (CDCl$_3$) δ 1.40 (s, 9H, Boc H's), 1.88 (m, 1H, 6$_{ax}$-H), 2.21 (m, 1H, 6$_{eq}$-H), 2.95 (m, 1H, 1-H), 3.60 (s, 3H, CO$_2$Me), 4.15 (d, 1H, Boc NH), 4.50 (m, 2H, 2- and 5-H's), 5.02 (s, 2H, CH$_2$Ar), 5.38 (d, 1H, Z NH), 5.65 (m, 2 H, 3- and 4-H's), 7.30 (s, 5H, Ar H's).

Example 26

(1R,2R,3S)-Methyl 2-Benzyloxycarbonylamino-5-t-butoxycarbonylaminocyclohex-3-enecarboxylate (S1-9)

S1-8 (1.1 g, 2.7 mmol) was suspended in MeOH (50 mL). NaOMe (0.73 g, 13.6 mmol) was added and the mixture refluxed for 18 h after which 0.5 M NH$_4$Cl (50 mL) was added and the resulting precipitate collected. The filtrate was evaporated and the residue triturated with water (25 mL). The insoluble portion was collected and combined with the original precipitate to give 0.85 g (77%) of S1-9.

$^1$H NMR: (CDCl$_3$) δ 1.38 (s, 9H, Boc H's), 1.66 (m, 1H, 6$_{ax}$-H), 2.22 (d, 1H, 6$_{eq}$-H), 2.58 (t, 1H, 1-H), 3.59 (3, 3H, CO$_2$Me), 4.22 (br s, 1H, Boc NH), 4.50 (m, 2H, 2- and 5-H's), 4.75 (d, 1H, Z NH), 5.02 (s, 2H, CH$_2$Ar), 5.62 (s, 2H, 3- and 4-H's), 7.30 (s, 5H, Ar H's).

Example 27

(1R,2R,5S)-2-benzyloxycarbonylamino-5-t-butoxycarbonylaminocyclohex-3-enecarboxylic acid (S1-10)

S1-9 (0.85 g, 2.1 mmol) was suspended in 50:50 MeOH/dichloromethane (5 mL) and cooled to 0° C. under N$_2$ after which 2M NaOH (2.0 mL) was added and the mixture stirred at ambient temperature for 16 h. The mixture was acidified with 2M HCl upon which a white precipitate formed. The precipitate was collected, washed with water and hexane, and dried to give 0.74 g (90%) of S1-10.

$^1$H NMR: (CD$_3$OD) δ 1.42 (s, 9H, Boc H's), 1.66 (m, 1H, 6$_{ax}$-H), 2.22 (d, 1H, 6$_{eq}$-H), 2.65 (t, 1H, 1-), 4.18 (m, 1H, 5-H), 4.45 (m, 1H, 5-H), 5.04 (s, 2H, CH$_2$Ar), 5.58 (m, 2H, 3- and 4-H's), 7.35 (s, 5H, Ar H's).

Example 28

(1R,2R,5S)-2-Benzyloxycarbonylamino-5-t-butoxycarbonylamino-1-(2-trimethylsilyl)ethoxycarbonylaminocyclohex-3-ene (S1-11)

S1-10 (3.1 g, 7.9 mmol) was dissolved in THF (30 mL) under N$_2$ and cooled to 0° C. Triethylamine (1.6 g, 2.2 mL, 15.9 mmol) was added followed by ethyl chloroformate (1.3 g, 1.5 mL, 11.8 mmol). The mixture was stirred at 0° C. for 1 h. A solution of NaN$_3$ (1.3 g, 19.7 mmol) in water (10 mL) was added and stirring at 0° C. was continued for 2 h. The reaction mixture was partitioned between EtOAc (50 mL) and water (50 mL). The organic phase was separated, dried, and evaporated. The residue was dissolved in benzene (50 mL) and refluxed for 2 h. 2-Trimethylsilylethanol (1.0 g, 1.2 mL, 8.7 mmol) was added and reflux continued for 3 h. The reaction mixture was diluted with EtOAc (200 mL), washed with saturated aqueous NaHCO$_3$ (50 mL), water (20 mL), and saturated aqueous NaCl (20 mL), dried and evaporated. The residue was flash chromatographed (silica gel (100 g), 67:33 hexane/EtOAc) to give 3.1 g (77%) of S1-11.

$^1$H NMR: (CDCl$_3$) δ −0.02 (s, 9H, TMS), 0.90 (t, 3H, CH$_2$TMS), 1.40 (s, 9H, Boc H's), 2.38 (m, 1H, 6$_{eq}$-H), 3.62 (m, 1H, 1-H), 4.08 (m, 2H, OCH$_2$CH$_2$TMS), 4.18 (m, 1H), 4.38 (m, 1H), 4.62 (m, 1H), 5.07 (dd, 2H, CH$_2$Ar), 5.18 (m, 1H), 5.26 (m, 1H), 5.58 (d, 1H, olefinic H), 5.64 (d, 2H, olefinic H), 7.30 (s, 5, Ar H's).

Example 29

(1R,2R,5S)-2-Benzyloxycarbonylamino-1,5-diaminocyclohex-3-ene (S1-12)

S1-11 (2.5 g, 4.9 mmol) was added to TFA (10 mL) and the solution stirred at ambient temperature for 16 h after which the solution was evaporated. The residue was dissolved in water (20 mL), basified to pH 14 with KOH and extracted with dichloromethane (3×50 mL). The extracts were combined, washed with water (20 mL), dried and evaporated to give 1.1 g (85%) of S1-12.

$^1$H NMR: (CDCl$_3$) δ 1.30 (m, 1H, 61, —H), 2.15 (br d, 1H, 6$_{eq}$-H), 2.68 (m, 1H, 1-H), 3.42 (br s, 1H, 5-H), 3.95 (m, 1H, 2-H), 4.85 (d, 1H, Z NH), 5.08 (t, 2H, CH$_2$Ar), 5.45 (d, 1H, 4-H), 5.62 (d, 1H, 3-H), 7.32 (s, 5H, Ar H's). ESCI MS m/e 262 M+1.

Example 30

Isolation of S1b-2 was accomplished using the following procedure: Using Schlenk technique 5.57 g (10.0 mmol) of methyl ester compound, S1b-1, was dissolved in 250 mL of THF. In another flask LiOH (1.21 g, 50.5 mmol) was dissolved in 50 mL water and de-gassed by bubbling $N_2$ through the solution using a needle for 20 minutes. The reaction was started transferring the base solution into the flask containing S1b-1 over one minute with rapid stirring. The mixture was stirred at room temperature and work-up initiated when the starting material S1b-1 was completely consumed (Using a solvent system of 66% EtOAc/33% Hexane and developing with phosphomolybdic acid reagent (Aldrich #31, 927-9) the starting material S1b-1 has an Rf of 0.88 and the product streaks with an Rf of approx. 0.34 to 0.64.). The reaction usually takes 2 days. Work-Up: The THF was removed by vacuum transfer until about the same volume is left as water added to the reaction, in this case 50 mL. During this the reaction solution forms a white mass that adheres to the stir bar surrounded by clear yellow solution. As the THF is being removed a separatory funnel is set up including a funnel to pour in the reaction solution and an Erlenmeyer flask is placed underneath the separatory funnel. Into the Erlenmeyer flask is added some anhydrous $Na_2SO_4$. This apparatus should be set up before acidification is started. (It is important to set up the separatory funnel and Erlenmeyer flask etc. before acidification of the reaction solution to enable separation of phases and extraction of the product away from the acid quickly once the solution attains a pH close to 1. If the separation is not preformed rapidly the Boc functional group will be hydrolyzed significantly reducing the yield.) Once the volatiles are sufficiently removed, $CH_2Cl_2$ (125 mL) and water (65 mL) are added and the reaction flask cooled in an ice bath. The solution is stirred rapidly and 5 mL aliquots of 1N HCl are added by syringe and the reaction solution tested with pH paper. Acid is added until the spot on the pH paper shows red (not orange) around the edge indicating a pH is 1 to 2 has been achieved (The solution being tested is a mixture of $CH_2Cl_2$ and water so the pH paper will show the accurate measurement at the edge of the spot and not the center.) and the phases are separated by quickly pouring the solution into the separatory funnel. As the phases separate the stopcock is turned to release the $CH_2Cl_2$ phase (bottom) into the Erlenmeyer flask and swirl the flask to allow the drying agent to absorb water in the solution. (At this scale of this procedure 80 mL of 1N HCl was used.) Soon after phase separation the aqueous phase is extracted with $CH_2Cl_2$ (2×100 mL), dried over anhydrous $Na_2SO_4$ and the volatiles removed to produce 5.37 g/9.91 mmoles of a beautiful white microcrystals reflecting a 99.1% yield. This product can not be purified by chromatography since that process would also hydrolyze the Boc functional group on the column.

$^1$H NMR (400 MHz, $CDCl_3$) δ 7.33, 7.25 (5H, m, Ph), 6.30 (1H, d, NH), 5.97 (1H, d, Nm), 5.10 (2H, m, $CH_2Ph$), 4.90 (1H, d, NH), 3.92, 3.58, 3.49 (1H, m, CHNH), 2.96, 2.48, 2.04, 1.95, 1.63 (1H, m, $CH_2CHNH$), 1.34 (9H, s, $CCH_3$).

IR (crystalline, $cm^{-1}$) 3326 br w, 3066 w, 3033 w, 2975 w, 2940 w sh, 1695 vs, 1506 vs, 1454 m sh, 1391 w, 1367 m, 1300 m sh, 1278 m sh, 1236 s, 1213 w sh, 1163 vs, 1100 w, 1053 m, 1020 m, 981 w sh, 910 w, 870 m, 846 w, 817 w, 775 w sh, 739 m, 696 m.

Example 31

Di-(l)-menthyl bicyclo[2.2.1]hept-5-ene-7-anti-(trimethylsilyl)-2-endo-3-exo-dicarboxylate (S4-26)

To a solution of S4-25 (6.09 g, 0.0155 mol) in toluene (100 mL) was added diethylaluminum chloride (8.6 mL of a 1.8 M solution in toluene) at −78° C. under nitrogen and the mixture was stirred for 1 hour. To the resulting orange solution was added S2-14 (7.00 g, 0.0466 mol) dropwise as a −78° C. solution in toluene (10 mL). The solution was kept at −78° C. for 2 hours, followed by slow warming to room temperature overnight. The aluminum reagent was quenched with a saturated solution of ammonium chloride (50 mL). The aqueous layer was separated and extracted with methylene chloride (100 mL) which was subsequently dried over magnesium sulfate. Evaporation of the solvent left a yellow solid that was purified by column chromatography (10% ethyl acetate/hexanes) to give S4-26 as a while solid (7.19 g, 0.0136 mol, 87% yield).

$^1$H NMR: ($CDCl_3$) δ −0.09 (s, 9H, $SiMe_3$), 0.74-1.95 (multiplets, 36H, menthol), 2.72 (d, 1H, α-methyl carbonyl CH), 3.19 (bs, 1H, bridgehead CH), 3.30 (bs, 1H, bridgehead CH), 3.40 (t, 1H, α-methyl carbonyl CH), 4.48 (d of t, 1H, α-menthyl ester CH), 4.71 (d of t, 1H, α-menthyl ester CH), 5.92 (d of d, 1H, CH=CH), 6.19 (d of d, 1H, CH=CH).

Example 32

5-exo-Bromo-3-exo-l)-menthylcarboxybicyclo[2.2.1]heptane-7-anti-(trimethylsilyl)-2,6-carbolactone (S4-27)

A solution of bromine (3.61 g, 0.0226 mol) in methylene chloride (20 mL) was added to a stirring solution of S4-26 (4.00 g, 0.00754 mol) in methylene chloride (80 mL). Stirring was continued at room temperature overnight. The solution was treated with 5% sodium thiosulfate (150 mL), and the organic layer separated and dried over magnesium sulfate. The solvent was evaporated at reduced pressure, and the crude product purified by column chromatography (5% ethyl acetate/hexanes) to give S4-27 as a white solid (3.53 g, 0.00754 mol, 99% yield).

$^1$H NMR: ($CDCl_3$) δ −0.19 (s, 9H, $SiMe_3$), 0.74-1.91 (multiplets, 18H, menthol), 2.82 (d, 1H, α-lactone carbonyl CH), 3.14 (bs, 1H, lactone bridgehead CH), 3.19 (d of d, 1H, bridgehead CH), 3.29 (t, 1H, α-methyl carbonyl CH), 3.80 (d, 1H, α-lactone ester), 4.74 (d of t, 1H, α-menthyl ester CH), 4.94 (d, 1H, bromo CH).

Example 33

Bicyclo[2.2.1]hept-5-ene-7-syn-(hydroxy)-2-exo-methyl-3-endo-(l)-menthyl dicarboxylate (S4-28)

S4-27 (3.00 g, 0.00638 mol) was dissolved in anhydrous methanol (150 mL), silver nitrate (5.40 g, 0.0318 mol) added and the suspension refluxed for 3 days. The mixture was cooled, filtered through Celite and the solvent evaporated to give an oily residue. Purification by column chromatography gave S4-28 as a light yellow oil (1.72 g, 0.00491 mol, 77% yield).

$^1$H NMR: ($CDCl_3$) δ 0.75-2.02 (multiplets, 18H, menthol), 2.83 (d, 1 H, α-menthyl carbonyl CH), 3.03 (bs, 1H, bridgehead CH), 3.14 (bs, 1H, bridgehead CH), 3.53 (t, 1H, α-methyl carbonyl CH), 3.76 (s, 3H, $CH_3$), 4.62 (d of t, 1H, α-menthyl ester CH), 5.87 (d of d, 1H, CH=CH), 6.23 (d of d, 1H, CH=CH).

Example 34

2-exo-Methyl-3-endo-(l)-menthylbicyclo[2.2.1]hept-5-ene-7-syn-(benzyloxy)dicarboxylate (S4-29)

Benzyl bromide (1.20 g, 0.0070 mol) and silver oxide (1.62 g, 0.0070 mol) were added to a stirring solution of S4-28 (0.490 g, 0.00140 mol) in DMF (25 mL). The suspension was stirred overnight and then diluted with ethyl acetate (100 mL). The solution was washed repeatedly with water followed by 1 N lithium chloride. The organic layer was separated and dried with magnesium sulfate. The solvent was evaporated under reduced pressure and the crude product was purified by column chromatography on silica gel to give S4-29 as an oil (0.220 g, 0.000500 mol, 36% yield).

$^1$H NMR: (CDCl$_3$) δ 0.74-2.08 (multiplets, 18H, menthol), 2.83 (d, 1 H, α-methyl carbonyl CH), 3.18 (bs, 1H, bridgehead CH), 3.44 (bs, 1H, bridgehead CH), 3.52 (t, 1H, bridge CH), 3.57 (s, 3H, CH$_3$), 3.68 (t, 1H, α-methyl carbonyl CH), 4.42 (d of d, 2H, benzyl —CH$_2$—), 4.61 (d of t, 1H, α-menthyl ester CH), 5.89 (d of d, 1H, CH═CH), 6.22 (d of d, 1H, CH═CH), 7.25-7.38 (m, 5H, C$_6$H$_5$).

Example 35

Bicyclo[2.2.1]hept-5-ene-7-syn-(benzyloxy)-2-exo-carboxy-3-endo-(l)-menthyl carboxylate (S4-30)

S4-29 (0.220 g, 0.00050 mol) was added to a mixture of tetrahydrofuran (1.5 mL), water (0.5 mL), and methanol (0.5 mL). Potassium hydroxide (0.036 g, 0.00065 mol) was added and the solution stirred at room temperature overnight. The solvent was evaporated under reduced pressure and the residue purified by column chromatography (10% ethyl acetate/hexanes) to give S4-30 (0.050 g, 0.00012 mol, 23% yield).

$^1$H NMR: (CDCl$_3$) δ 0.73-2.01 (multiplets, 18H, menthol), 2.85 (d, 1 H, α-methyl carbonyl CH), 3.18 (bs, 1H, bridgehead CH), 3.98 (bs, 1H, bridgehead CH), 3.53 (bs, 1H, bridge CH), 3.66 (t, 1H, α-methyl carbonyl CH), 4.44 (d of d, 2H, benzyl —CH$_2$—), 4.63 (d of t, 1H, α-methyl ester CH), 5.90 (d of d, 1H, CH═CH), 6.23 (d of d, 1H, CH═CH), 7.25-7.38 (m, 5H, C$_6$H$_5$).

Mass Spec: calculated for C$_{26}$H$_{34}$O$_5$, 426.24. found 425.4 (M−1) and 851.3 (2M−1).

Example 36

Bicyclo[2.2.1]hept-5-ene-7-syn-(benzyloxy)-2-exo-(trimethylsilylethoxycarbonyl)-amino-3-endo-(l)-menthyl carboxylate (S4-31)

To a solution of S4-30 in benzene is added triethylamine and diphenylphosphoryl azide. The solution is refluxed for 24 hours then cooled to room temperature. Trimethylsilylethanol is added, and the solution refluxed for an additional 48 hours. The benzene solution is partitioned between ethyl acetate and 1 M sodium bicarbonate. The organic layers are combined, washed with 1 M sodium bicarbonate and dried over sodium sulfate. The solvent is evaporated under reduced pressure to give the crude Curtius reaction product.

Example 37

Bicyclo[2.2.1]heptane-7-syn-(benzyloxy)-2-exo-(trimethylsilylethoxycarbonyl)-amino-3-endo-(l)-menthyl-5-exo-methyl-6-exo-methyl tricarboxylate (S4-32)

S4-31, dry copper(II) chloride, 10% Pd/C, and dry methanol are added to a flask with vigorous stirring. After degassing, the flask is charged with carbon monoxide to a pressure just above 1 atm., which is maintained for 72 hours. The solids are filtered and the residue worked up in the usual way to afford the biscarbonylation product.

Example 38

Bicyclo[2.2.1]heptane-7-syn-(benzyloxy)-2-exo-(trimethylsilylethoxycarbonyl)-amino-3-endo-(l)-menthylcarbox-5-exo-6-exo-dicarboxylic anhydride (S4-33)

A mixture of S4-32, formic acid, and a catalytic amount of p-toluenesulfonic acid is stirred at 90° C. overnight. Acetic anhydride is added and the reaction mixture refluxed for 6 hours. Removal of the solvents and washing with ether gives the desired anhydride.

Example 39

Bicyclo[2.2.1]heptane-7-syn-(benzyloxy)-2-exo-(trimethylsilylethoxycarbonyl)-amino-3-endo-(l)-menthyl-6-exo-carboxy-5-exo-methyl dicarboxylate (S4-33)

To a solution of S4-32 in equal amounts of toluene and carbon tetrachloride is added quinidine. The suspension is cooled to −65° C. and stirred for 1 hour. Three equivalents of methanol are slowly added over 30 minutes. The suspension is stirred at −65° C. for 4 days followed by removal of the solvents under reduced pressure. The resulting white solid is partitioned between ethyl acetate and 2M HCl. The quinine is recovered from the acid layer and S4-33 obtained from the organic layer.

Example 40

Bicyclo[2.2.1]heptane-7-syn-(benzyloxy)-2-exo-(trimethylsilylethoxycarbonyl)-amino-3-endo-(l)-menthyl-6-exo-(trimethylsilylethoxycarbonyl)amino-5-exo-methyl dicarboxylate (S4-35)

To a solution of S4-34 in benzene is added triethylamine and diphenylphosphoryl azide. The solution is refluxed for 24 hours. After cooling to room temperature, 2-trimethylsilylethanol is added and the solution refluxed for 48 hours. The benzene solution is partitioned between ethyl acetate and 1M sodium bicarbonate. The organic layers are combined, washed with 1M sodium bicarbonate, and dried over sodium sulfate. The solvent is evaporated under reduced pressure to give the crude Curtius reaction product.

Example 41 endo-Bicyclo[2.2.1]hept-5-ene-2-benzylcarboxylate-3-carboxylic acid (S5-37)

Compound S3-19 (4.00 g, 0.0244 mol) and quinidine (8.63 g, 0.0266 mol) were suspended in equal amounts of toluene (50 mL) and carbon tetrachloride (50 mL). The suspension was cooled to −55° C. after which benzyl alcohol (7.90 g, 0.0732 mol) was added over 15 minutes. The reaction mixture became homogenous after 3 hours and was stirred at −55° C. for an additional 96 hours. After removal of the solvents, the residue was partitioned between ethyl acetate (300 mL) and 2M hydrochloric acid (100 mL). The organic layer was washed with water (2×50 mL) and saturated aqueous sodium chloride (1×50 mL). Drying over magnesium sulfate and evaporation of the solvent gave S5-37 (4.17 g, 0.0153 mol, 63% yield).

$^1$H NMR: (CDCl$_3$) δ 1.33 (d, 1H, bridge CH$_2$), 1.48 (d of t, 1H, bridge CH$_2$), 3.18 (bs, 1H, bridgehead CH), 3.21 (bs, 1H, bridgehead CH), 3.33 (t, 2H, α-acid CH), 4.98 (d of d, 2H, CH$_2$Ph), 6.22 (d of d, 1H, CH═CH), 6.29 (d of d, 1H, CH═CH), 7.30 (m, 5H, C$_6$H$_5$).

Example 42

2-endo-Benzylcarboxy-6-exo-iodobicyclo[2.2.1] heptane-3,5-carbolactone (S5-38)

S5-37 (4.10 g, 0.0151 mol) was dissolved in 0.5 M sodium bicarbonate solution (120 mL) and cooled to 0° C. Potassium iodide (15.0 g, 0.090 mol) and iodine (7.66 g, 0.030 mol) were added followed by methylene chloride (40 mL). The solution was stirred at room temperature overnight. After dilution with methylene chloride (100 mL), sodium thiosulfate was added to quench the excess iodine. The organic layer was separated and washed with water (100 mL) and sodium chloride solution (100 mL). Drying over magnesium sulfate and evaporation of the solvent gave S5-38 (5.44 g, 0.0137 mol, 91% yield).

$^1$H NMR: (CDCl$_3$) δ 1.86 (d of q, 1H, bridge —CH$_2$—), 2.47 (d of t, 1H, bridge —CH$_2$—), 2.83 (d of d, 1H, α-lactone carbonyl CH), 2.93 (bs, 1H, lactone bridgehead CH), 3.12 (d of d, 1H, α-benzyl ester CH), 3.29 (m, 1H, bridgehead CH), 4.63 (d, 1H, α-lactone ester CH), 5.14 (d of d, 2H, CH$_2$Ph), 5.19 (d, 1H, iodo CH), 7.38 (m, 5H, C$_6$H$_5$).

Example 43

2-endo-Bezylcarboxy-bicylo[2.2.1]heptane-3,5-carbolactone (S5-39)

S5-38 (0.30 g, 0.75 mmol) was placed in DMSO under N$_2$, NaBH$_4$ (85 mg, 2.25 mmol) added and the solution stirred at 85° C. for 2 h. The mixture was cooled, diluted with water (50 mL) and extracted with dichloromethane (3×20 mL). The extracts were combined, washed with water (4×15 mL) and saturated aqueous NaCl (10 mL), dried, and evaporated to give 0.14 g (68%) of S5-39.

Example 44

5-endo-hydroxybicyclo[2.2.1]heptane-2-endo-benzyl-3-endo-methyl dicarboxylate (S5-40)

Compound S5-39 is dissolved in methanol and sodium methoxide added with stirring. Removal of the solvent gives S5-40.

Example 45

Bicyclo[2.2.1]heptane-2-endo-benzyl-3-endo-methyl-5-exo-(t-butoxycarbonyl)-amino dicarboxylate (S5-41)

In a one-pot reaction S5-40 is converted to the corresponding mesylate with methanesulfonyl chloride, sodium azide added to displace the mesylate to give exo-azide, which is followed by reduction with tributyl phosphine to give the free amine, which is protected as the t-Boc derivative to give S5-41.

Example 46

Bicyclo[2.2.1]heptane-2-endo-carboxy-3-exo-methyl-5-exo-(t-butoxycarbonyl)-amino carboxylate (S5-42)

The benzyl ether protecting group is removed by catalytic hydrogenolysis of S5-41 with 10% Pd/C in methanol at room temperature for 6 hours. Filtration of the catalyst and removal of the solvent yields crude S5-42.

Example 47

Bicyclo[2.2.1]heptane-2-endo-carboxy-3-exo-methyl-5-exo-(t-butoxycarbonyl)-amino carboxylate (S5-43)

Sodium is dissolved in methanol to generate sodium methoxide. S5-42 is added and the mixture stirred at 62° C. for 16 hr. The mixture is cooled and acetic acid added with cooling to neutralize the excess sodium methoxide. The mixture is diluted with water and extracted with ethyl acetate. The extract is dried and evaporated to give S5-43.

Example 48

Bicyclo[2.2.1]heptane-2-endo-benzyl-3-exo-methyl-5-exo-(t-butoxycarbonyl)amino dicarboxylate (S5-44)

Compound S5-43 is reacted with benzyl bromide and cesium carbonate in tetrahydrofuran at room temperature to give benzyl ester S5-44, which is isolated by acid work-up of the crude reaction mixture.

Example 49

Bicyclo[2.2.1]heptane-2-endo-benzyl-3-exo-carboxy-5-exo-(t-butoxycarbonyl)-amino carboxylate (S5-45)

Compound S5-44 is dissolved in methanol and cooled to 0° C. under N$_2$. 2M NaOH (2 equivalents) is added dropwise, the mixture allowed to come to ambient temperature and is stirred for 5 h. The solution is diluted with water, acidified with 2M HCl and extracted with ethyl acetate. The extract is washed with water, saturated aqueous NaCl, dried and evaporated to give S5-45.

Example 50

Bicyclo[2.2.1]heptane-2-endo-benzyl-3-exo-(trimethylsilylethoxycarbonyl)amino-5-exo-(t-butoxycarbonyl)amino carboxylate (S5-46)

To a solution of S5-45 in benzene is added triethylamine and diphenylphosphoryl azide. The solution is refluxed for 24 hours and then cooled to room temperature. Trimethylsilylethanol is added and the solution refluxed for 48 hours. The solution is partitioned between ethyl acetate and 1M sodium bicarbonate. The organic layer is washed with 1M sodium bicarbonate and dried over sodium sulfate. The solvent is evaporated under reduced pressure to give crude Curtius product S5-46.

Example 51 endo-Bicyclo[2.2.1]hept-5-ene-2-(4-methoxy)benzylcarboxylate-3-carboxylic acid (S6-48)

Compound S3-19 and quinidine are suspended in equal amounts of toluene and carbon tetrachloride and cooled to −55° C. p-Methoxybenzyl alcohol is added over 15 minutes and the solution stirred at −55° C. for 96 hours. After removal of the solvents, the residue is partitioned between ethyl acetate and 2 M hydrochloric acid. The organic layer is washed with water and saturated aqueous sodium chloride. Drying over magnesium sulfate and removal of the solvent gives S6-48.

Example 52 endo-Bicyclo[2.2.1]hept-5-ene-2-(4-methoxy)benzyl-3-(trimethylsilylethoxy-carbonyl)amino carboxylate (S6-49)

To a solution of S6-48 in benzene is added triethylamine and diphenylphosphoryl azide. The solution is refluxed for 24 hours, cooled to room temperature, trimethylsilylethanol is added, and the solution is refluxed for an additional 48 hours. The benzene solution is partitioned between ethyl acetate and 1 M sodium bicarbonate. The organic layers are combined, washed with 1 M sodium bicarbonate, and dried with sodium sulfate. The solvent is evaporated under reduced pressure to give crude Curtius product S6-49.

Example 53

Bicyclo[2.2.1]heptane-2-endo-(4-methoxy)benzyl-3-endo-(trimethylsilylethoxycarbonyl)amino-5-exo-methyl-6-exo-methyl tricarboxylate (S6-50)

S6-49, copper(II) chloride, 10% Pd/C, and dry methanol are added to a flask with vigorous stirring. After degassing the suspension, the flask is charged with carbon monoxide to a pressure just above 1 atm. The pressure of carbon monoxide is maintained over 72 hours. The solids are filtered off, and the crude reaction mixture worked up in the usual way to afford S6-50.

Example 54

Bicylo[2.2.1]heptane-2-endo-(4-methoxy)benzyl-3-endo-(trimethylsilylethoxycarbonyl)amino-5-exo-6-exo-dicarboxylic anhydride (S6-51)

S6-50, formic acid, and a catalytic amount of p-toluenesulfonic acid is heated at 90° C. overnight. Acetic anhydride is added to the reaction mixture, and it is refluxed for an additional 6 hours. Removal of the solvents and washing with ether affords S6-51.

Example 55

Bicyclo[2.2.1]heptane-2-endo-(4-methoxy)benzyl-3-endo-(trimethylsilylethoxycarbonyl)amino-5-exo-carboxy-6-exo-methyl dicarboxylate (S6-52)

To a solution of S6-51 in equal amounts of toluene and carbon tetrachloride is added quinine. The suspension is cooled to −65° C. and stirred for 1 hour. Three equivalents of methanol are added slowly over 30 minutes. The suspension is stirred at −65° C. for 4 days followed by removal of the solvents. The resulting white solid is partitioned between ethyl acetate and 2 M HCl, with S6-52 worked up from the organic layer.

Example 56

Bicyclo[2.2.1]heptane-2-endo-(4-methoxy)benzyl-3-endo-(trimethylsilylethoxycarbonyl)amino-5-exo-(trimethylsilylethoxycarbonyl)amino-6-exo-methyl dicarboxylate (S6-53)

To a solution of S6-52 in benzene is added triethylamine and diphenylphosphoryl azide. The solution is refluxed for 24 hours then cooled to room temperature. 2-Trimethylsilylethanol is added, and the solution is refluxed for an additional 48 hours. The benzene solution is partitioned between ethyl acetate and 1 M sodium bicarbonate. The organic layers are combined, washed with 1 M sodium bicarbonate, and dried with sodium sulfate. The solvent is evaporated under reduced pressure to give S6-53.

Example 57

Bicyclo[2.2.1]heptane-2-exo-(4-methoxy)benzyl-3-endo-(trimethylsilylethoxycarbonyl)amino-5-exo-(trimethylsilylethoxycarbonyl)amino-6-endo-methyl dicarboxylate (S6-54)

To a solution of S6-53 in tetrahydrofuran is carefully added potassium tert-butoxide. The basic solution is refluxed for 24 hours followed by addition of acetic acid. Standard extraction methods give the double epimerized product S6-54.

Example 58

Preparation of Hexamer

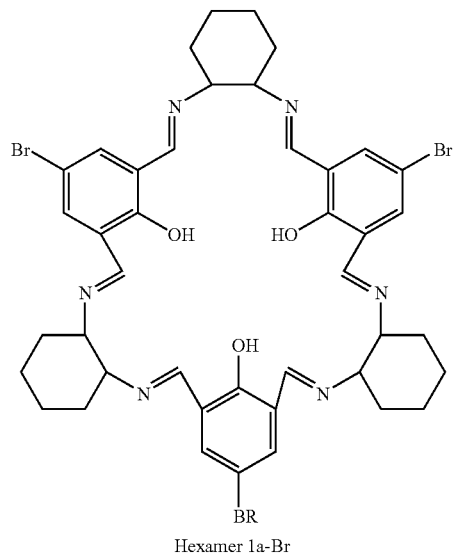

Hexamer 1a-Br

To 0.300 g (1R,2R)-(−)-trans-1,2-diaminocyclohexane (2.63 mmol) in 5 mL $CH_2Cl_2$ at 0° C. was added 0.600 g of 2,6-diformyl-4-bromophenol (2.62 mmol) in 5 mL of $CH_2Cl_2$. The yellow solution was allowed to warm to room temperature and stirred for 48 hours. The reaction solution was decanted, and added to 150 mL of methanol. After standing for 30 minutes, the yellow precipitate was collected, washed with methanol, and air-dried (0.580 g; 72% yield).

$^1$H NMR (400 MHz, $CDCl_3$) δ 14.31 (s, 3H, OH), 8.58 (s, 3H, CH=N), 8.19 (s, 3H, CH=N), 7.88 (d, 3H, J=2.0 Hz, ArH), 7.27 (d, 3H, J=2.0 Hz, ArH), 3.30-3.42 (m, 6H, $CH_2$—CH—N), 1.41-1.90 (m, 24H, aliphatic).

MS (FAB): Calcd for $C_{42}H_{46}N_6O_3Br_3$, 923.115. found 923.3 [M+H]$^+$.

Example 59

Preparation of Hexamer

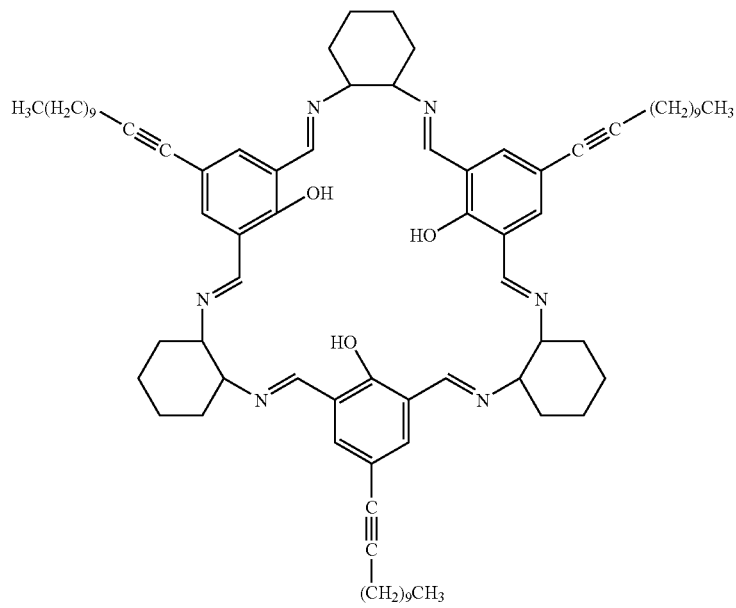

Hexamer 1a

To 0.300 g (1R,2R)-(−)-trans-1,2-diaminocyclohexane (2.63 mmol) in 6 mL $CH_2Cl_2$ at 0° C. was added 0.826 g of 2,6-diformyl-4-(1-dodec-1-yne)phenol (2.63 mmol) in 6 mL of $CH_2Cl_2$. The orange solution was stirred at 0° C. for 1 hour and then allowed to warm to room temperature after which stirring was continued for 16 hours. The reaction solution was decanted and added to 150 mL of methanol. A sticky yellow solid was obtained after decanting the methanol solution. Chromatographic cleanup of the residue gave a yellow powder.

$^1$H NMR (400 MHz, $CDCl_3$) δ 14.32 (s, 3H, OH), 8.62 (s, 3H, CH═N), 8.18 (s, 3H, CH═N), 7.84 (d, 3H, J=2.0 Hz, ArH), 7.20 (d, 3H, J=2.0 Hz, ArH), 3.30-3.42 (m, 6H, $CH_2$—CH—N), 2.25 (t, 6H, J=7.2 Hz, propargylic), 1.20-1.83 (m, 72H, aliphatic), 0.85 (t, 9H, J=7.0 Hz, $CH_3$).

$^{13}$C NMR (400 MHz, $CDCl_3$) δ 163.4, 161.8, 155.7, 136.9, 132.7, 123.9, 119.0, 113.9, 88.7, 79.7, 75.5, 73.2, 33.6, 33.3, 32.2, 29.8, 29.7, 29.6, 29.4, 29.2, 29.1, 24.6, 24.5, 22.9, 19.6, 14.4.

MS (FAB): Calcd for $C_{78}H_{109}N_6O_3$, 1177.856. found: 1177.8 $[M+H]^+$.

Example 60

Preparation of Hexamer

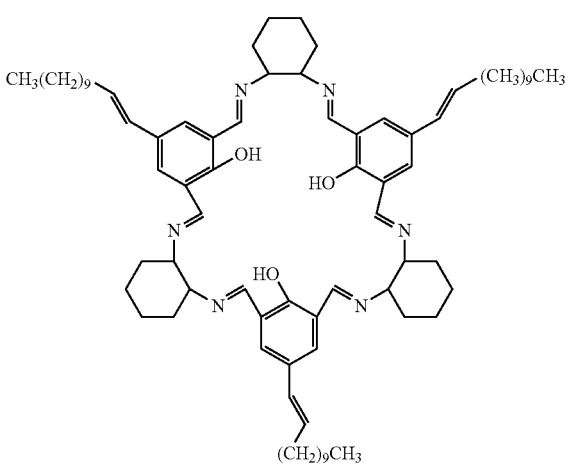

Hexamer 1d-C12

To 0.240 g of 2,6-diformyl-4-(1-dodecene)phenol (0.76 mmol) in 10 mL of benzene was added a 10 mL benzene solution of (1R,2R)-(−)-trans-1,2-diaminocyclohexane (0.087 g, 0.76 mmol). The solution was stirred at room temperature for 48 hours shielded from the light. The orange solution was taken to dryness and chromatographed (silica, 50/50 acetone/Et$_2$O) to give a yellow sticky solid (33% yield).

$^1$H NMR (400 MHz, CDCl$_3$) δ 14.12 (s, 3H, OH), 8.62 (s, 3H, CH=N), 8.40 (s, 3H, CH=N), 7.82 (d, 3H, J=2.0 Hz, ArH), 7.28 (d, 3H, J=2.0 Hz, ArH), 6.22 (d, 3H, vinyl), 6.05 (d, 3H, vinyl), 3.30-3.42 (m, 6H, CH$_2$—CH—N), 1.04-1.98 (m, 87H, aliphatic).

MS (FAB): Calcd for C$_{78}$H$_{115}$N$_6$O$_3$, 1183.90. found: 1184.6 [M+H]$^+$.

Example 61

Preparation of Tetramer

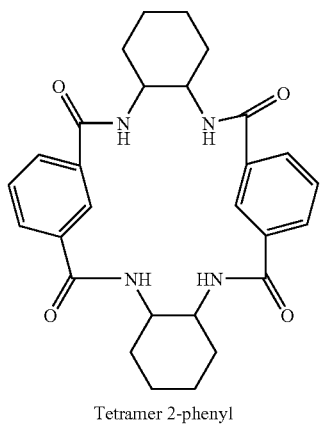

Tetramer 2-phenyl

Preparation of hexamer:

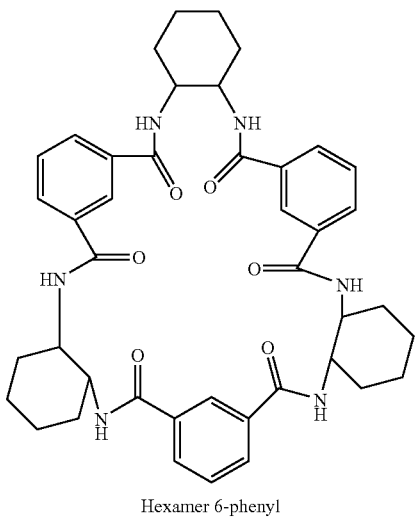

Hexamer 6-phenyl

Triethylamine (0.50 mL, 3.59 mmol) and (1R,2R)-(–)-trans-1,2-diaminocyclohexane (0.190 g, 1.66 mmol) were combined in 150 mL EtOAc and purged with N$_2$ for 5 minutes. To this solution was added 0.331 g isophthaloyl chloride (1.66 mmol) dissolved in 100 mL EtOAc dropwise over six hours. The solution was filtered and the filtrate taken to dryness. TLC (5% methanol/CH$_2$Cl$_2$) shows the product mixture to be primarily composed of two macrocyclic compositions. Chromatographic separation (silica, 5% methanol/CH$_2$Cl$_2$) gave the above tetramer (0.020 g, 5% yield) and hexamer (about 10%).

Tetramer:
$^1$H NMR (400 MHz, CDCl$_3$) δ 7.82 (s, 1H), 7.60 (br s, 2H), 7.45 (br s, 2H), 7.18 (br s, 1H), 3.90 (br s, 2H), 2.22 (d, 2H), 1.85 (m, 4H), 1.41 (m, 4H).

MS (ESI): Calcd for C$_{28}$H$_{33}$N$_4$O$_4$, 489.25. found 489.4 [M+H]$^+$.

Hexamer:
MS (ESI): Calcd for C$_{42}$H$_{49}$N$_6$O$_6$, 733.37. found 733.5 [M+H]$^+$.

Example 62

Preparation of Macrocyclic Modules from Benzene and Cyclohexane Cyclic Synthons

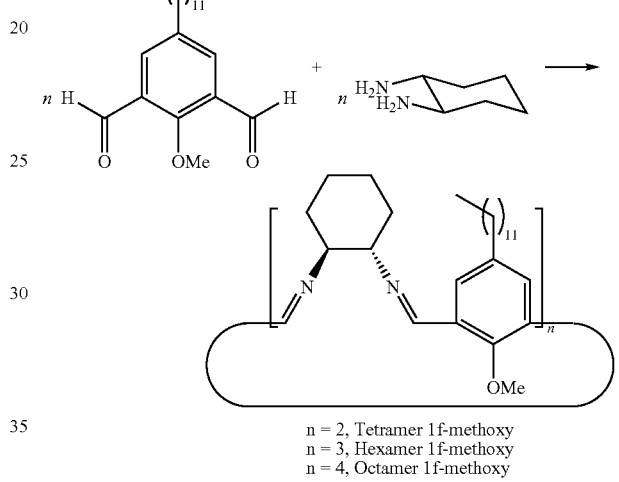

n = 2, Tetramer 1f-methoxy
n = 3, Hexamer 1f-methoxy
n = 4, Octamer 1f-methoxy

To a 5 mL dichloromethane solution of 4-dodecyl-2,6-diformyl anisole (24 mg; 0.072 mmol) was added a 5 mL dichloromethane solution of (1R,2R)-(–)-trans-1,2-diaminocyclohexane (8.5 mg; 0.074 mmol). This solution was stirred at room temperature for 16 hours and then added to the top of a short silica column. Elution with diethyl ether and then removal of solvent led to the isolation of 22 mg of an off-white solid. Positive ion electrospray mass spectrometry demonstrated the presence of the tetramer (m/z 822, MH$^+$), hexamer (m/z 1232, MH$^+$), and the octamer (m/z 1643, MH$^+$) in the off-white solid. Calculated molecular weights were as follows: tetramer+H(C$_{54}$H$_{85}$N$_4$O$_2$, 821.67); hexamer+H (C$_{81}$H$_{127}$N$_6$O$_3$, 1232.00); octamer+H(C$_{108}$H$_{169}$N$_8$O$_4$, 1643.33).

Example 63

Without intending to be bound by any one particular theory, one method to approximate pore size of a macrocyclic module is quantum mechanical (QM) and molecular mechanical (MM) computations. In this example, macrocyclic modules having two types of synthons, "A" and "B," were used and all linkages between synthons were assumed to be the same. For the purposes of QM and MM computations, the root mean square deviations in the pore areas were computed over dynamic runs.

For QM, each module was first optimized using the MM+ force field approach of Allinger (JACS, 1977, 99:8127) and Burkert, et al., (Molecular Mechanics, ACS Monograph 177, 1982). They were then re-optimized using the AM1 Hamiltonian (Dewar, et al., JACS, 1985, 107:3903; Dewar, et al., JACS, 1986, 108:8075; Stewart, J. Comp. Aided Mol. Design, 1990, 4:1). To verify the nature of the potential energy surface in the vicinity of the optimized structures, the associated Hessian matrices were computed using numerical double-differencing.

For MM, the OPLS-AA force field approach (Jorgensen, et al., JACS, 1996, 118:11225) was used. For imine linkages, the dihedral angle was confined to 180°±10°. The structures were minimized and equilibrated for one picosecond using 0.5 femtosecond time steps. Then a 5 nanosecond dynamics run was carried out with a 1.5 femtosecond time step. Structures were saved every picosecond. The results are shown in Tables 12 and 13.

Macrocyclic module pore areas derived from QM and MM computations for various linkages and macrocyclic module pore size are shown in Table 12. In Table 12, the macrocyclic modules had alternating synthons "A" and "B." Synthon "A" is a benzene synthon coupled to linkages L at 1,3-phenyl positions, and Synthon "B" is shown in the left-hand column of the table.

In Table 13, Synthon "A" is a naphthalene synthon coupled to linkages L at 2,7-naphthyl positions, and Synthon "B" is shown in the left-hand column of the table.

TABLE 13

PORE AREAS FOR VARIOUS MACROCYCLIC MODULES ($Å^2$)

| SYNTHON B | HEXAMER QM | HEXAMER MM |
|---|---|---|
| Trans-1,2-cyclohexane | imine (trans) 23.5 $Å^2$ | imine (trans) 25.4 ± 4.9 $Å^2$ |
| Endo-endo-1,3-bicycloheptane | imine (trans) 30.1 $Å^2$ | imine (trans) 30.0 ± 3.6 $Å^2$ |

Figure 17A:
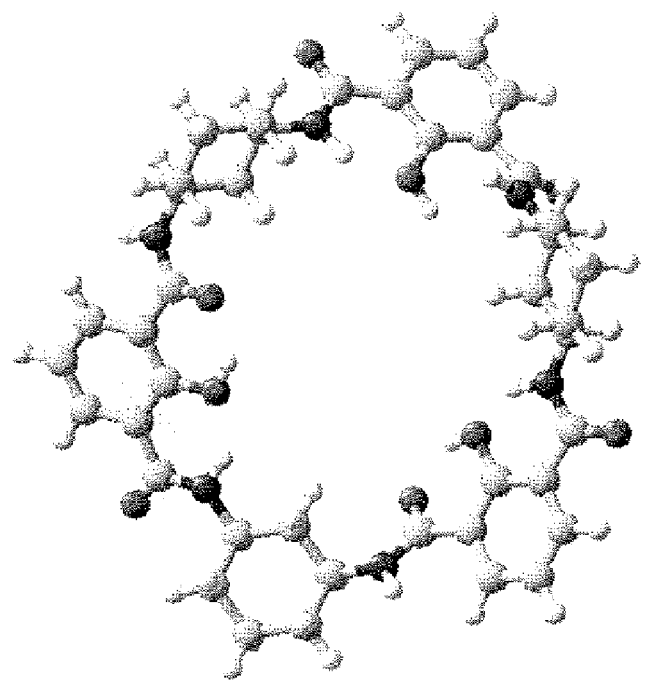
FIGS. 17A and 17B show representations of examples of the structure of embodiments of a hexamer macrocyclic module.
Figure 17B:
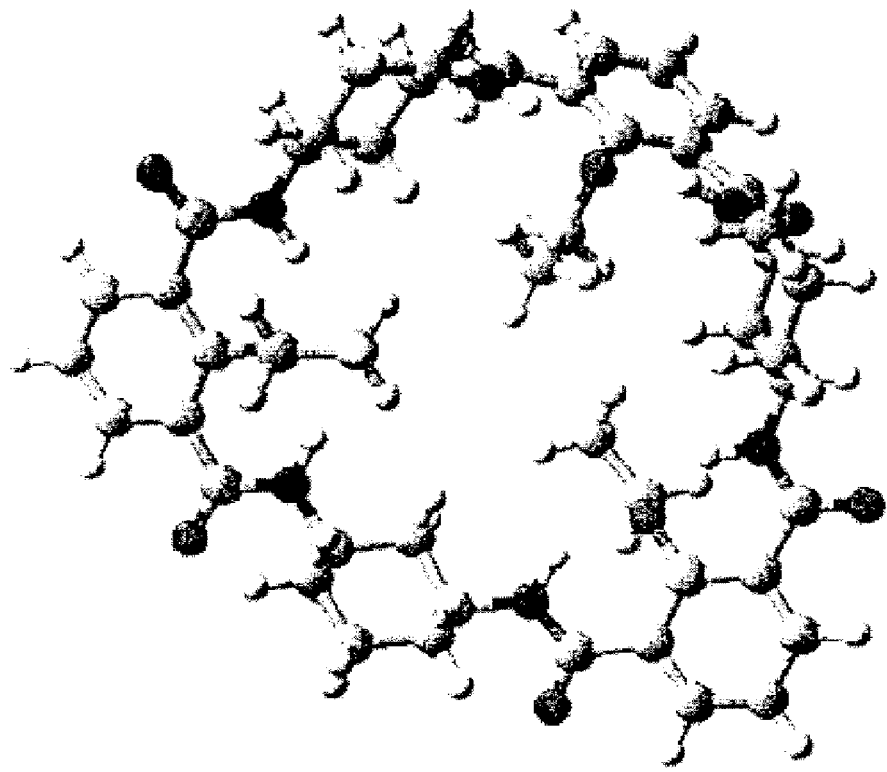

An example of the energy-minimized conformations of some hexamer macrocyclic modules having groups of substituents are shown in FIGS. 17A and 17B. Referring to FIG. 17A, a Hexamer 1-h-(OH)$_3$ is shown having a group of —OH substituents. Referring to FIG. 17B, a Hexamer 1-h-(OEt)$_3$ is shown having a group of —OEt substituents. The differences in pore structure and area between these two examples, which

TABLE 12

PORE AREAS FOR VARIOUS MACROCYCLIC MODULES ($Å^2$)

| SYNTHON B | TETRAMER QM | TETRAMER MM | HEXAMER QM | HEXAMER MM | OCTAMER QM | OCTAMER MM |
|---|---|---|---|---|---|---|
| trans-1,2-cyclohexane | | | imine (trans) 14.3 $Å^2$ | Imine (trans) 13.2 ± 1.4 $Å^2$ | | |
| trans-1,2-cyclohexane | | | Acetylene 14.3 $Å^2$ | | | |
| trans-1,2-cyclohexane | | | Amine 23.1 $Å^2$ | Amine 13.9 ± 1.9 $Å^2$ | | |
| trans-1,2-cyclohexane | | | Amide 19.7 $Å^2$ | Amide 17.5 ± 2.0 $Å^2$ | | |
| trans-1,2-cyclohexane | | | Ester 18.9 $Å^2$ | Ester 19.6 ± 2.0 $Å^2$ | | |
| Equatorial-1,3-cyclohexane | | | imine (trans) 18.1 $Å^2$ | Imine (trans) 21.8 ± 1.6 $Å^2$ | imine (trans) 66.2 $Å^2$ | Imine (trans) 74.5 ± 7.7 $Å^2$ |
| Equatorial-1,3-cyclohexane | | | Amine 14.7 $Å^2$ | Amine 19.9 ± 2.6 $Å^2$ | | |
| Equatorial-1,3-cyclohexane | | | Amide 24.8 $Å^2$ | Amide 21.7 ± 1.8 $Å^2$ | | |
| Equatorial-1,3-cyclohexane | | | Ester 22.9 $Å^2$ | Ester 22.8 ± 2.4 $Å^2$ | | |
| Equatorial-3-amino-cyclohexene | imine (trans) oxygen-oxygen distance 2.481 Å | imine (trans) oxygen-oxygen distance 3.7 ± .3 Å | imine (trans) 18.4 $Å^2$ | Imine (trans) 21.0 ± 1.5 $Å^2$ | imine (trans) 56.7 $Å^2$ | Imine (trans) 60.5⁺ – 8.3 $Å^2$ |
| trans-1,2-pyrrolidine | | | imine (trans) 10.4 $Å^2$ | Imine (trans) 9.2 ± 1.4 $Å^2$ | | |
| Equatorial-1,3-piperidene | | | imine (trans) 19.2 $Å^2$ | Imine (trans) 20.9 ± 1.1 $Å^2$ | | |
| Endo-exo-1,2-bicycloheptane | | | imine (trans) 11.1 $Å^2$ | Imine (trans) 14.1 ± +–11 $Å^2$ | | |
| Endo-endo-1,3-bicycloheptane | | | imine (trans) 18.8 $Å^2$ | Imine (trans) 20.7 ± 1.4 $Å^2$ | | |
| Endo-exo-1,3-bicycloheptane | | | Imine 19.5 $Å^2$ | Imine 10.1 ± +4.9 $Å^2$ | | |
| Equatorial-1,3-cyclohexane | | | Amine 9.8 $Å^2$ | Amine 9.9 ± 2.4 $Å^2$ | | |
| Endo-endo-1,3-bicyclooctene | | | imine (trans) 18.9 $Å^2$ | Imine (trans) 21.6 ± 1.5 $Å^2$ | | |
| Endo-exo-1,3-bicyclooctene | | | imine (trans) 15.6 $Å^2$ | Imine (trans) 18.7 ± 1.6 $Å^2$ | | |
| Equatorial-3,9-decalin | | | imine (trans) 35.4 $Å^2$ | Imine (trans) 40.0 ± 2.2 $Å^2$ | | |

Further macrocyclic module pore areas derived from QM and MM computations for various linkages and macrocyclic module pore size are shown in Table 13. In Table 13, the macrocyclic modules had alternating synthons "A" and "B."

also reflect conformational and flexibility differences, are evident. This macrocyclic module results in a composition which may be used to regulate pores. Selection of ethoxy synthon substituents over hydroxy synthon substituents for this hexamer composition is a method which may be used for transporting selected species.

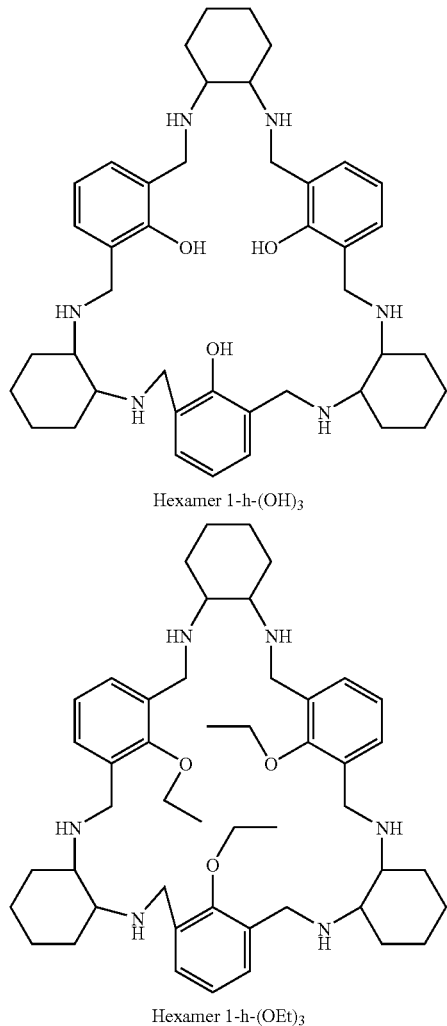

Hexamer 1-h-(OH)$_3$

Hexamer 1-h-(OEt)$_3$

The pore size of macrocyclic modules was determined experimentally using a voltage-clamped bilayer procedure. A quantity of a macrocyclic module was inserted into a lipid bilayer formed by phosphatidylcholine and phosphatidylethanolamine. On one side of the bilayer was placed a solution containing the cationic species to be tested. On the other side was a solution containing a reference cationic species known to be able to pass through the pore of the macrocyclic module. Anions required for charge balance were selected which could not pass through the pores of the macrocyclic module. When a positive electrical potential was applied to the solution on the side of the lipid bilayer containing the test species, if the test species passed through the pores in the macrocyclic modules, a current was detected. The voltage was then reversed to detect current due to transport of the reference species through the pores, thereby confirming that the bilayer is a barrier to transport and that the pores of the macrocyclic modules provide transport of species.

Using the above technique, a hexameric macrocyclic module comprised of 1R,2R-(−)-transdiaminocyclohexane and 2,6-diformal-4-(1-dodec-1-ynyl)phenol synthons, having imine groups as the linkages (the first module in Table 1) was tested for transport of various ionic species. The results are shown in Table 14.

TABLE 14

VOLTAGE-CLAMPED BILAYER TEST FOR MACROCYCLIC MODULE PORE SIZE

| Ionic species | Calculated van der Waals radius of ionic species (Å) | Calculated van der Waals radius of ionic species with one water shell (Å) | Does ionic species pass through pore? |
|---|---|---|---|
| Na$^+$ | 1.0 | 2.2 | Yes |
| K$^+$ | 1.3 | 2.7 | Yes |
| Ca$^{2+}$ | 1.0 | 2.7 | Yes |
| NH$_4^+$ | 1.9 | 2.9 | Yes |
| Cs$^+$ | 1.7 | 3.0 | Yes |
| MeNH$_3^+$ | 2.0 | 3.0 | Yes |
| EtNH$_3^+$ | 2.6 | 3.6 | No |
| NMe$_4^+$ | 2.6 | 3.6 | No |
| Aminoguanidinium | 3.1 | 4.1 | No |
| NEt$_4^+$ | 3.9 | 4.4 | No |
| Choline | 3.8 | 4.8 | No |
| Glucosamine | 4.2 | 5.2 | No |

The results in Table 14 show that the cut-off for passage through the pore in the selected module is a van der Waals radius of between 2.0 and 2.6 Å. In Table 12, the QM and MM computed pore sizes are given as areas. Using the equation for area of a circle, $A=\pi r^2$, the computed area of the pore in the first module of Table 12, 14.3 Å$^2$, gives a value for r of 2.13 Å. Ions having van der Waals radii of less than 2.13 Å would be expected to traverse the pore and those with larger radii would not, and that is what was observed. CH$_3$NH$_3^+$, having a radius of 2.0 Å, passed through the pore while CH$_3$CH$_2$NH$_3^+$, with a radius of 2.6 Å, did not. Without being held to a particular theory, and recognizing that several factors influence pore transport, the observed ability of hydrated ions to pass through the pore may be due to partial dehydration of the species to enter the pore, transport of water molecules and ions through the pore separately or with reduced interaction during transport, and re-coordination of water molecules and ions after transport. The details of pore structure, composition, and chemistry, the flexibility of the macrocyclic module, and other interactions may affect the transport process.

Example 64

Pore properties of 1,2-imine-linked and 1,2-amine-linked hexamer macrocyclic modules are illustrated in Table 15. Referring to Table 15, the bilayer clamp data indicates that the passage and exclusion of certain species through the pore of the modules correlates with the computational size of the pores. Further, these surprising data show that a very small change in the placement of atoms and/or structural features can lead to a discrete change in transport properties and allow regulation of transport through the pore by variation of synthons and linkages, among other factors.

TABLE 15

VOLTAGE-CLAMPED BILAYER TEST FOR MACROCYCLIC MODULE PORE SIZE

| Solute species | Radius of Solute | Radius of solute with $H_2O$ (radius of $2^{nd}$ hydration shell in parentheses) | Hexamer 1a (1,2-imine) Radius = 3.3 Å | Hexamer 1jh (1,2-amine) Radius = 3.9 Å |
|---|---|---|---|---|
| $Li^+$ | 0.6 | 2.0 (5.6) | No | Yes |
| $Na^+$ | 1.0 | 2.2 | Yes | Yes |
| $K^+$ | 1.3 | 2.7 | Yes | Yes |
| $Ca^{2+}$ | 1.0 | 2.7 | Yes | Yes |
| $Mg^{2+}$ | 0.7 | 2.8 (5.5) | No | Yes |
| $NH_3^+$ | 1.9 | 2.9 | Yes | Yes |
| $Cs^+$ | 1.7 | 3 | Yes | Yes |
| $MeNH_3^+$ | 2 | 3 | Yes | Yes |
| $EtNH_3^+$ | 2.6 | 3.6 | No | Yes |
| $NMe_4^+$ | 2.6 | 3.6 | No | Yes |
| Aminoguanidine | 3.1 | 4.1 | No | Yes |
| Choline | 3.8 | 4.8 | No | Yes |
| $NEt_4^+$ | 3.9 | 4.4 | No | No |
| Glucosamine | 4.2 | 5.2 | No | No |
| $NPr_4^+$ | — | — | — | No |

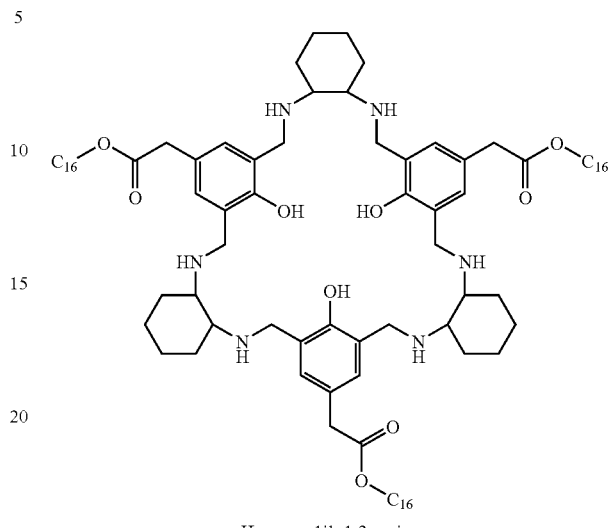

Hexamer 1jh-1,2-amine

Example 65

Figure 18A:
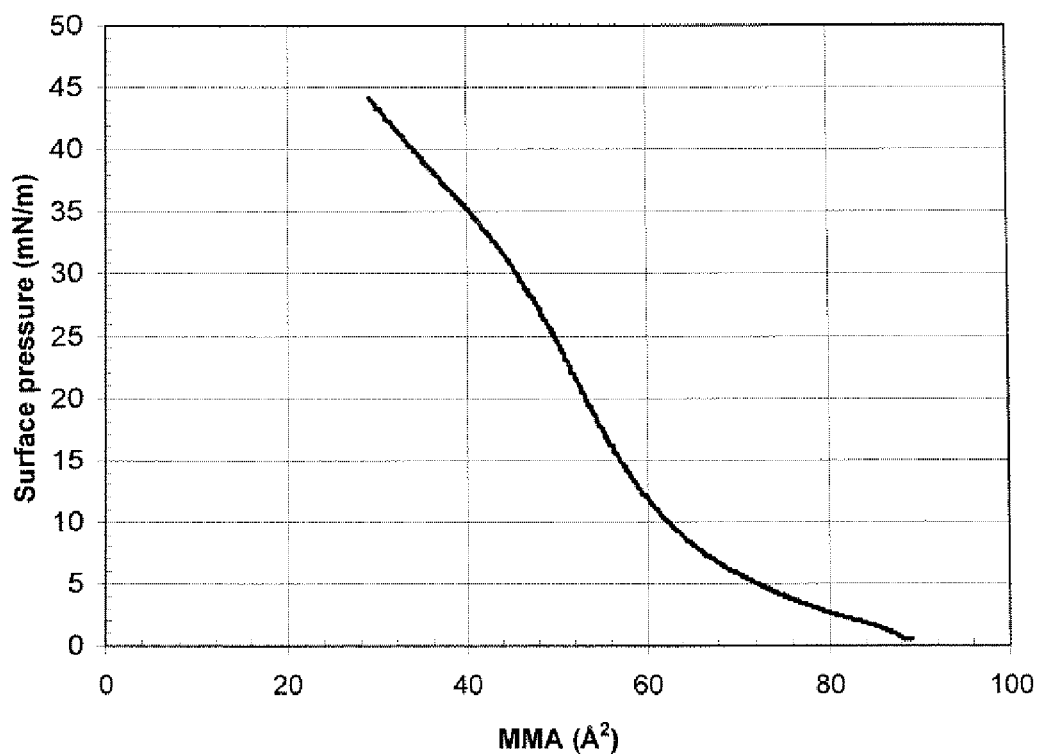
FIG. 18A shows an example of the Langmuir isotherm of an embodiment of a hexamer macrocyclic module.
Figure 18B:
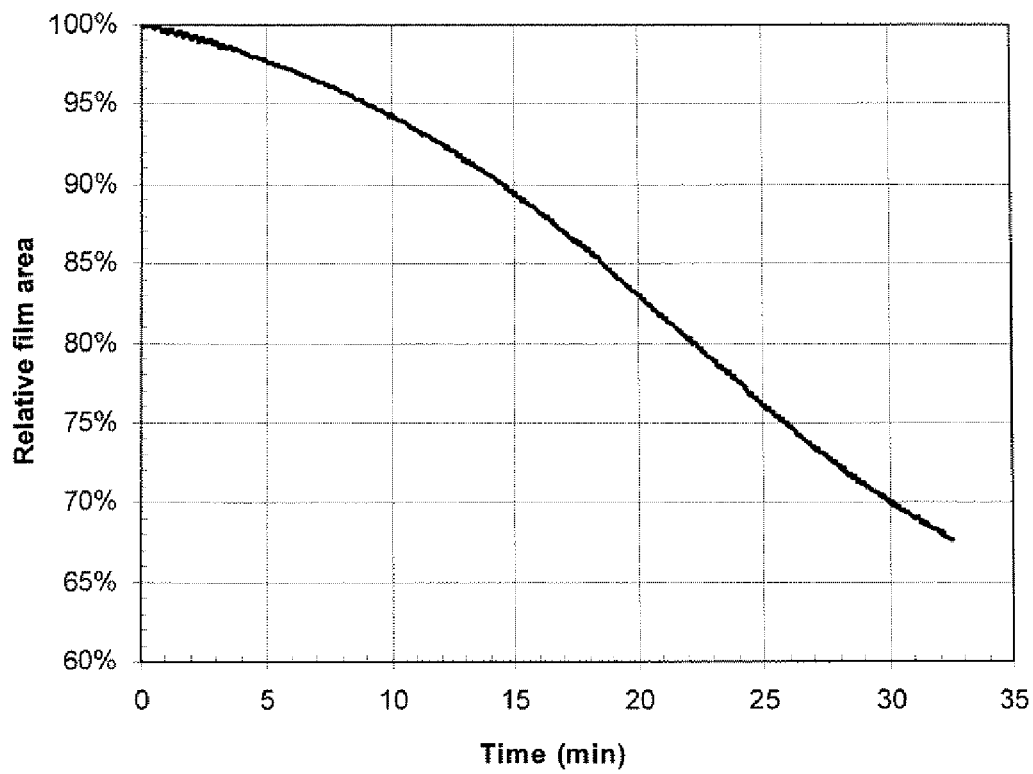
FIG. 18B shows an example of the isobaric creep of an embodiment of a hexamer macrocyclic module.

The Langmuir isotherm and isobaric creep for hexamer 1a-Me are shown in FIGS. 18A and 18B, respectively.

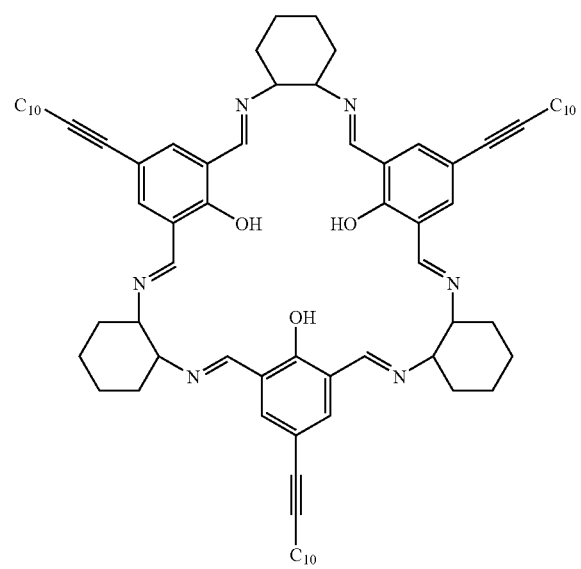

Hexamer 1a-1,2-imine

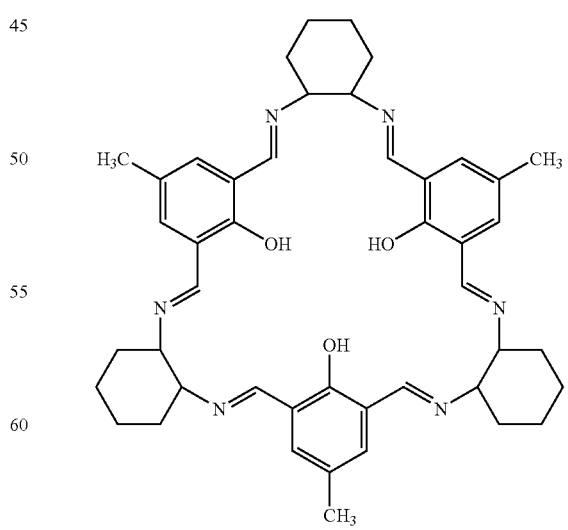

Hexamer 1a-Me

-continued

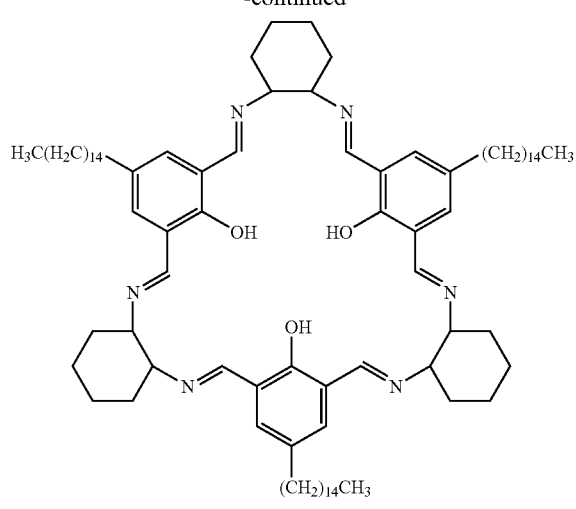
Hexamer 1a-C15

Figure 19A:
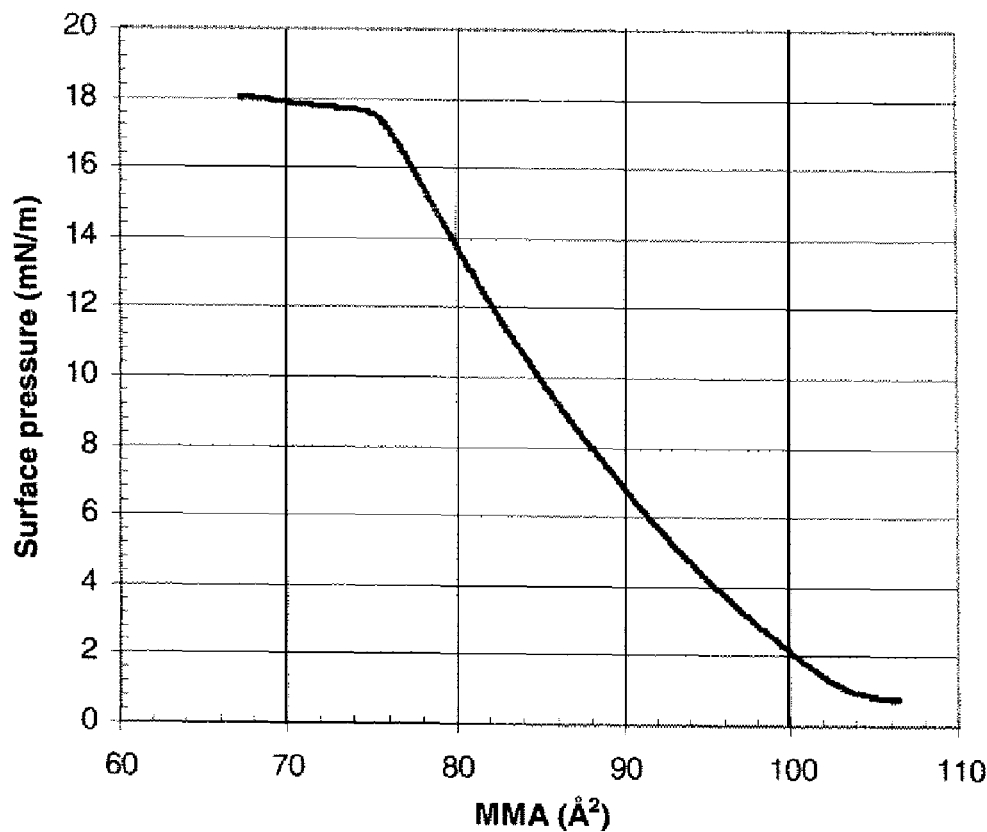
FIG. 19A shows an example of the Langmuir isotherm of an embodiment of a hexamer macrocyclic module.
Figure 19B:
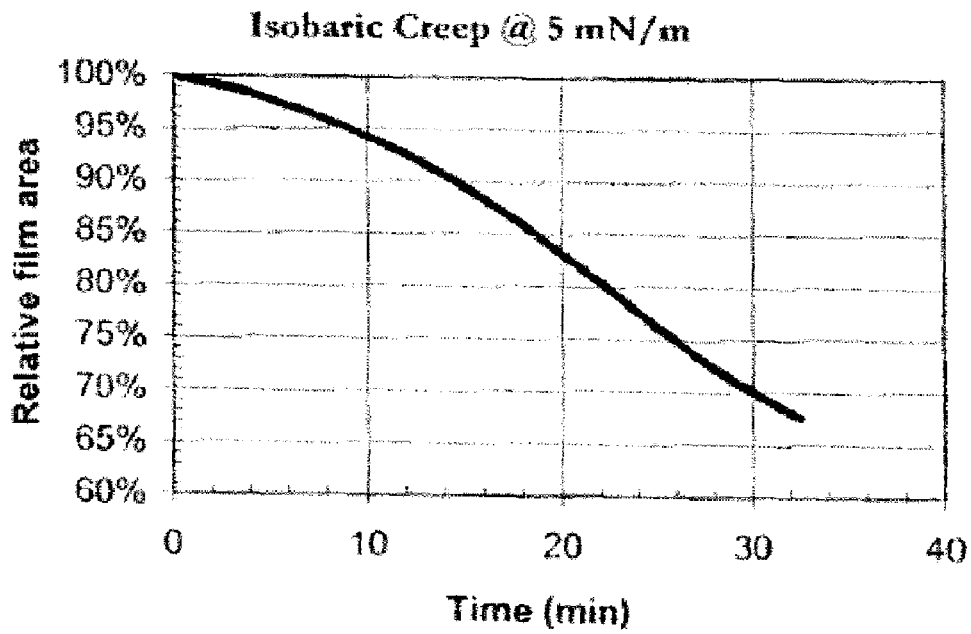
FIG. 19B shows an example of the isobaric creep of an embodiment of a hexamer macrocyclic module.

The relative stability of the Langmuir film of Hexamer 1a-Me is illustrated by the isobaric creep data shown in FIG. 18B. The area of the film decreased by about 30% after about 30 min at 5 mN/m surface pressure. The Langmuir isotherm and isobaric creep for Hexamer 1a-C15 are shown in FIGS. 19A and 19B, respectively. The relative stability of the Langmuir film of Hexamer 1a-C15 is illustrated by the isobaric creep data shown in FIG. 19B. The area of the film decreased by about 1-2% after about 30 min at 10 mN/m surface pressure, and by about 2% after about 60 min. The collapse pressure was about 18 mN/m for Hexamer 1a-C15.

Example 66

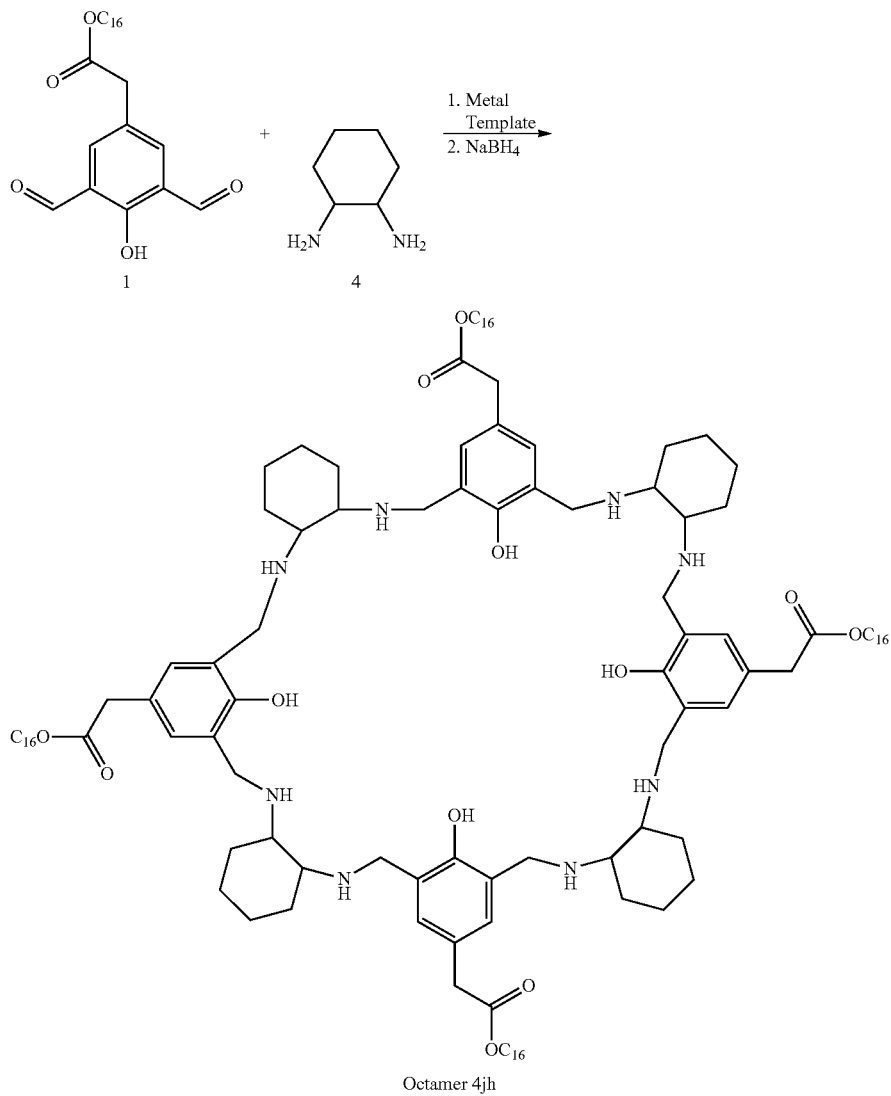
Octamer 4jh

Templated Imine Octamer. To a 3 neck 100 mL round bottomed flask with stirbar, fitted with condenser and addition funnel under argon, amphiphilic dialdehyde phenol 1 (500 mg, 1.16 mmol) was added. Next, $Mg(NO_3)_2 \cdot 6H_2O$ (148 mg, 0.58 mmol) 2 and $Mg(OAc)_2 \cdot 4H_2O$ (124 mg, 0.58 mmol) were successively added. The flask was put under vacuo and backfilled with argon 3 X. Anhydrous methanol was transferred to the flask via syringe under argon and the resulting suspension stirred. The mixture was then refluxed for 10 min affording a homogeneous solution. The reaction was allowed to cool to room temperature under positive argon pressure. (1R,2R)-(−)-trans-1,2-diaminocyclohexane 4 was added to the addition funnel followed by cannula transfer of anhydrous MeOH (11.6 mL) under argon. The diamine/MeOH solution was added to the stirred homogeneous metal template/dialdehyde solution drop wise over a period of 1 h affording an orange oil. The addition funnel was replaced with a glass stopper and the mixture was refluxed for 3 days. The solvent was removed in vacuo affording a yellow crystalline solid that was used without further purification.

Amine Octamer. To a 50 mL schlenk flask with stirbar under argon Imine Octamer (314 mg, 0.14 mmol) was added. Next anhydrous THF (15 mL) and MeOH (6.4 mL) were added via syringe under argon and the suspension stirred at room temperature. To the homogeneous solution, $NaBH_4$ (136 mg, 3.6 mmol) was added in portions and the mixture stirred at room temperature for 12 h. The solution was filtered, followed by addition of 19.9 mL $H_2O$. The pH was adjusted to ca. 2 by addition of 4 M HCl, then 6.8 mL of an ethylenediamine tetraaceticacid disodium salt dihydrate (0.13 M in $H_2O$) was added and the mixture stirred for 5 min. To the solution, 2.0% ammonium hydroxide was added and stirring continued for an additional 5 min. The solution was extracted with ethyl acetate (3×100 mL) the organic layer separated, dried over $Na_2SO_4$ and the solvent removed via rotoevaporation affording a pale yellow solid. Recrystallization from chloroform and hexanes afforded the Amine Octamer. Molecular weight was confirmed by ESIMS M+H=experimental=2058.7 m/z, calcd=2058.7 m/z.

Example 67

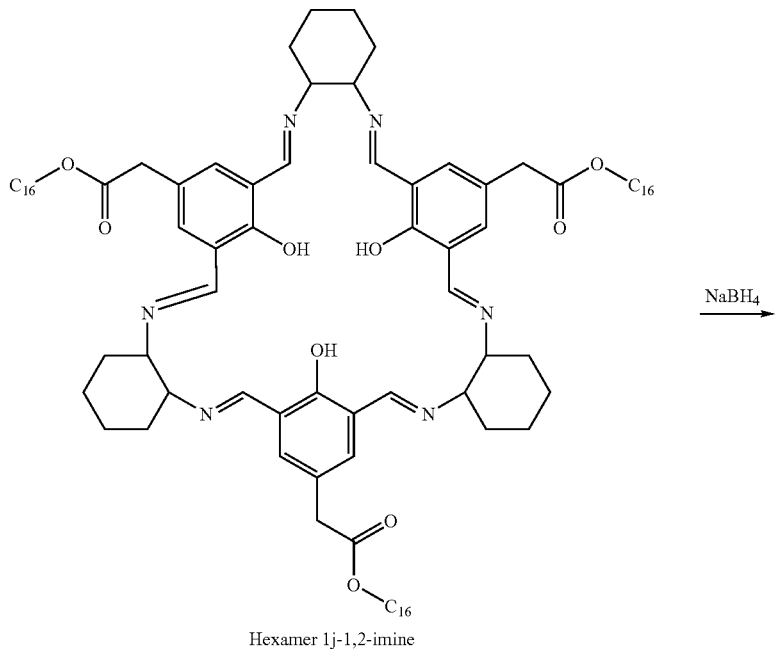

Hexamer 1j-1,2-imine

-continued

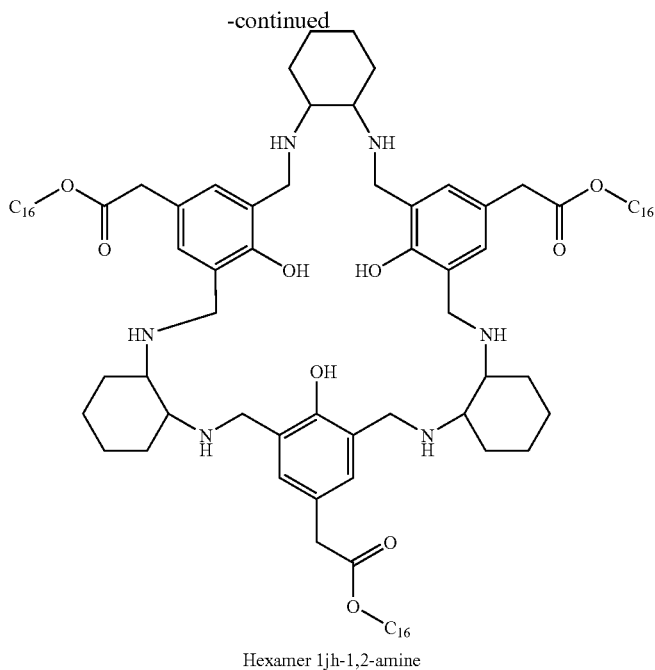

Hexamer 1jh-1,2-amine

Hexamer 1j. The two substrates, (−)—R,R-1,2-trans-diaminocyclohexane (0.462 mmol, 0.053 g) and 2,6-diformyl-4-hexadecyl benzylphenol carboxylate (0.462 mmol, 0.200 g) were added to a 10 mL vial containing a magnetic stirbar followed by the addition of 2 mL of $CH_2Cl_2$. The yellow solution was stirred at room temperature. After 24 h the reaction solution was plugged through silica gel with diethyl ether, and the solvent removed via roto-evaporation. (232 mg; 98% yield). $^1$H NMR (400 MHz, $CDCl_3$): δ 14.11 (s, 3H, OH), 8.67 (s, 3H, CH=N), 8.23 (s, 3H, CH=N), 7.70 (s, 3H, ArH), 7.11 (s, 3H, ArH), 4.05-3.90 (t, 6H, $^3J$=6.6 Hz, $CH_2C(O)OCH_2(CH_2)_{14}CH_3$), 3.44 (s, 6H, $CH_2C(O)OCH_2(CH_2)_{14}CH_3$), 3.30-3.42 (m, 6H, $CH_2$—CH—N), 1.21-1.90 (m, 108H, aliphatic) 0.92-0.86 (t, 9H, $^3J$=6.6 Hz. ESIMS (+) Calcd for $C_{96}H_{151}N_6O_9$, 1533. Found: 1534 $[M+H]^+$.

Hexamer 1jh. To a 100 mL pear-shaped flask with magnetic stirbar under argon, Hexamer 1j (0.387 mmol, 0.594 g) was added and dissolved in THF:MeOH (7:3, 28:12 mL, respectively). Next, $NaBH_4$ (2.32 mmol, 0.088 g) was added slowly in portions at room temperature for 6.5 h. The solvent was removed by roto-evaporation, the residue dissolved in 125 mL ethyl acetate and washed 3×50 mL of $H_2O$. The organic layer was separated, dried over $Na_2SO_4$ and the solvent removed by roto-evaporation. The resulting residue was recrystallized from $CH_2Cl_2$ and MeOH affording a white solid (0.440 g; 74% yield). $^1$H NMR (400 MHz, $CDCl_3$): δ 6.86 (s, 6H, ArH), 4.10-4.00 (t, 6H, $^3J$=6.6 Hz, $CH_2C(O)OCH_2(CH_2)_{14}CH_3$), 3.87-3.69 (dd, 6H, $^3J$=13.7 Hz, $^3J$ (CNH)=42.4 Hz $CH_2$—CH—N), 3.43 (s, 6H, $CH_2C(O)OCH_2(CH_2)_{14}CH_3$), 2.40-2.28 (m, 6H, aliphatic), 2.15-1.95 (m, 6H, aliphatic), 1.75-1.60 (m, 6H, aliphatic), 1.60-1.55 (m, 6H, aliphatic) 1.37-1.05 (m, 84H, aliphatic) 0.92-0.86 (t, 9H, $^3J$=6.8 Hz. ESIMS (+) Calcd for $C_{96}H_{163}N_6O_9$, 1544. Found: 1545 $[M+H]^+$.

Example 68

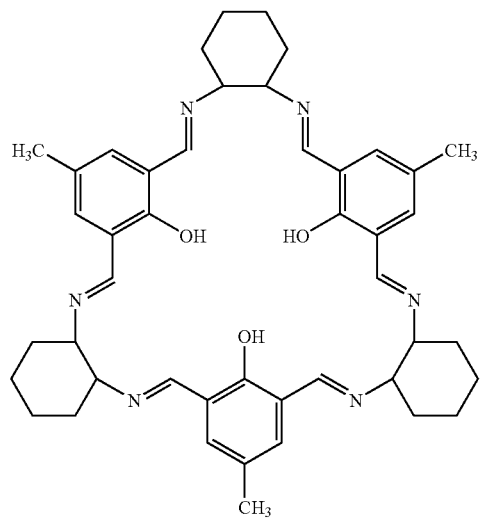

Hexamer 1a-Me-1,2-imine

Hexamer 1A-Me. A solution of 2-hydroxy-5-methyl-1,3-benzenedicarboxaldehye (53 mg, 0.32 mmol) in dichloromethane (0.6 mL) was added to a solution of (1R,2R)-(−)-1,2-diaminocyclohexane (37 mg, 0.32 mmol) in dichloromethane (0.5 mL). The mixture was stirred at ambient temperature for 16 h, added dropwise to methanol (75 mL) and chilled (4° C.) for 4 h. The precipitate was collected to afford 71 mg (92%) of hexamer 1A-Me. $^1$H NMR ($CDCl_3$): δ 13.88 (s, 3H, OH), 8.66 (s, 3H, ArCH=N), 8.19 (s, 3H, ArCH=N), 7.52 (d, 3H, J=2 Hz, Ar H), 6.86 (d, 3H, J=2 Hz, Ar H), 3.35 (m, 6H, cyclohexane 1,2-H's), 2.03 (3, 9H, Me), 1.6-1.9 (m, 18H, cyclohexane 3,6-$H_2$ and $4_{eq},5_{eq}$-H's), 1.45 (m, 6H, cyclohexane $4_{ax},5_{ax}$-H's); $^{13}$C NMR δ 63.67, 159.55, 156.38, 134.42, 129.75, 127.13, 119.00, 75.68, 73.62, 33.68, 33.41, 24.65, 24.57, 20.22; ESI(+) MS m/e (%) 727 M+H (100); IR 1634 $cm^{−1}$.

Example 69

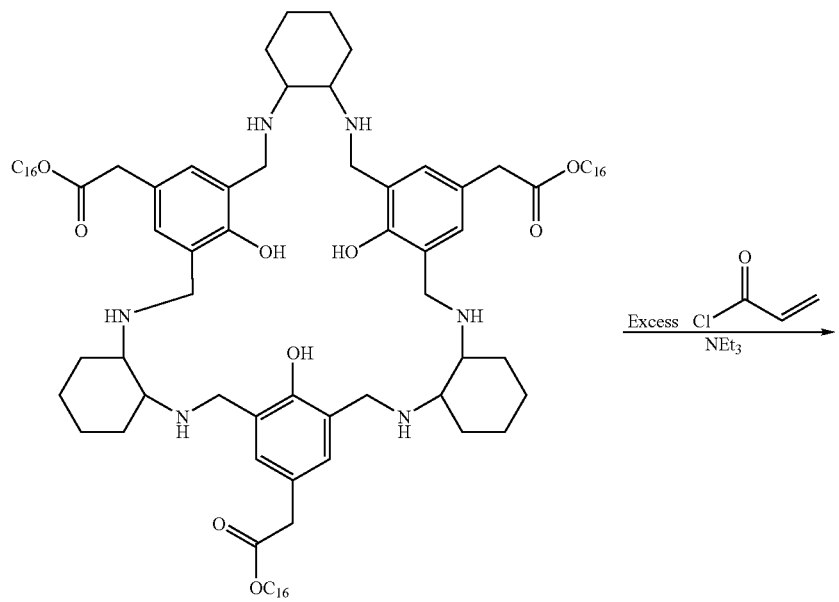

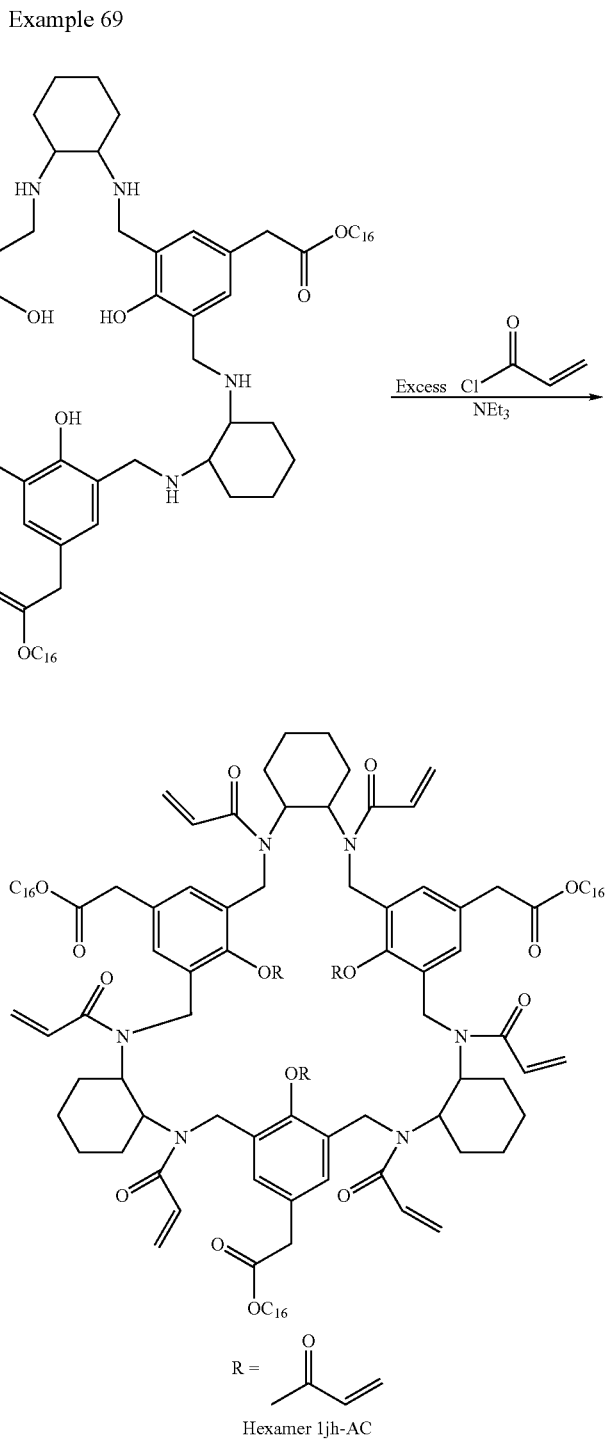

Hexamer 1jh-AC 32.7 mg Hexamer 1jh (recrystallized times) was added to 30 mL dry THF. 100 μL triethylamine and 100 μL acryloyl chloride (freshly distilled) were added subsequently to the THF mixture using Schlenk technique. Solution was stirred for 18 hrs in an acetone/dry ice bath. After removal of solvent a white precipitate remained. The precipitate was redissolved in $CH_2Cl_2$ and filtered through a fritted funnel. $CH_2Cl_2$ solution was added to the separatory funnel and washed one time with water followed by two brine (NaCl) washes. The $CH_2Cl_2$ solution was dried over $MgSO_4$ and then filtered to remove $MgSO_4$. A yellow precipitate remained after solvent removal.

$^1$H NMR ($CDCl_3$): δ −0.867-0.990 (3H), 1.259 (21.8H), 1.39 (1.86H), 1.64 (12.7H), 2.8 (1.25H), 3.46-3.62 (2.47H), 3.71 (0.89H), 3.99 (2.46H), 5.06 (0.71H), 5.31 (3.80H), 5.71 (1.43H), 5.90 (0.78H), 6.2-6.4 (2.49H), 6.59 (0.80H), 6.78 (0.47H), 6.98 (0.28H). FTIR-ATR: 3340, 2926 (—$CH_2$—), 2854 (—$CH_2$—), 1738 (Ester Carbonyl), 1649 and 1613 (Acrylate), 983 (=CH), 959 sh (=$CH_2$). ESI-MS: 1978.5 (Hex1JhAC+8-AC), 1948.8 (Hex1JhAC+7-AC+Na$^+$), 1923.3 (Hex1JhAC+7-AC), 1867.6 (Hex1JhAC+6-AC), 1842.6, 1759.7 (Hex1JhAC+4-AC).

What is claimed is:

1. A method for filtration comprising
    contacting a nanofilm with a fluid to provide a filtered fluid,
        wherein said nanofilm comprises amphiphilic macrocyclic modules, wherein at least one of said amphiphilic macrocyclic modules comprises three to about twenty-four cyclic synthons coupled into a closed ring by one or more coupling linkages between said cyclic synthons including at least one linkage other than —$CH_2$—;
        wherein said fluid comprises one or more components for which said nanofilm has low permeability and one or more components for which said nanofilm is permeable; and
        wherein said nanofilm retains at least some of said one or more low permeability components and wherein at least some of said permeable components traverse the nanofilm.

2. The method of claim 1, wherein said fluid is selected from at least one gas, at least one liquid, and mixtures thereof.

3. The method of claim 1, wherein at least some of said amphiphilic macrocyclic modules define a pore having a radius of about 0.5 Å to about 5 Å.

4. The method of claim 3, wherein the pore has a radius of about 2.13 Å.

5. The method of claim 3, wherein the pore has a radius of about 3.3 Å.

6. The method of claim 3, wherein the pore has a radius of about 3.9 Å.

7. The method of claim 3, wherein said one or more low permeability components and said one or more permeable components may be solvated.

8. The method of claim 3, wherein said one or more low permeability components and said one or more permeable components may be non-solvated.

9. The method of claim 7, wherein said one or more solvated low permeability components have a radius greater than that of the pore.

10. The method of claim 8, wherein said one or more non-solvated low permeability components have a radius greater than that of the pore.

11. The method of claim 9, wherein said one or more solvated low permeability components will not traverse the pore.

12. The method of claim 10, wherein said one or more non-solvated low permeability components will not traverse the pore.

13. The method of claim 1, wherein said one or more low permeability components have a molecular weight greater than about 50 Da.

14. The method of claim 1, wherein said one or more low permeability components have a molecular weight greater than about 100 Da.

15. The method of claim 1, wherein said one or more low permeability components have a molecular weight greater than about 400 Da.

16. The method of claim 1, wherein said one or more low permeability components have a molecular weight greater than about 600 Da.

17. The method of claim 1, wherein said one or more low permeability components have a molecular weight greater than about 800 Da.

18. The method of claim 1, wherein said one or more low permeability components have a molecular weight greater than about 1 kDa.

19. The method of claim 1 wherein said one or more low permeability components have a clearance through the nanofilm of less than about 10%.

20. The method of claim 1 wherein said one or more low permeability components have a clearance through the nanofilm of less than about 20%.

21. The method of claim 1 wherein said one or more low permeability components have a clearance through the nanofilm of less than about 30%.

22. The method of claim 1 wherein said nanofilm is permeable to water.

23. The method of claim 22 wherein said one or more low permeability components comprise one or more of immunoglobulin G, albumin, $\beta_2$-Microglobulin, myoglobin, ovalbumin, glucose, urea, creatinine, $Li^+$, $Ca^{2+}$, $Mg^{2+}$, and viruses.

24. The method of claim 22 wherein said nanofilm is permeable to $Cl^-$.

25. The method of claim 22 wherein said nanofilm is permeable to $K^+$.

26. The method of claim 22 wherein said one or more low permeability components comprise $Na^+$.

27. The method of claim 25 wherein said one or more low permeability components comprise $Na^+$.

28. The method of claim 22 wherein said nanofilm is permeable to $Na^+$.

29. The method of claim 22 wherein said one or more low permeability components comprise $K^+$.

30. The method of claim 28 wherein said one or more low permeability components comprise $K^+$.

31. The method of claim 28 wherein said nanofilm is permeable to $K^+$ and glucose.

32. The method of claim 22, wherein said nanofilm is permeable to $Na^+$, $K^+$, hydrogen phosphate and dihydrogen phosphate.

33. The method of claim 1, wherein at least one of said amphiphilic macrocyclic modules is coupled to at least one second amphiphilic macrocyclic module through at least one reactive functional group.

34. The method of claim 1, wherein said amphiphilic macrocyclic modules are independently selected from Hexamer 1a, Hexamer 1dh, Hexamer 3j- amine, Hexamer 1jh, Hexamer 1jh-AC, Hexamer 2j-amine/ester, Hexamer 1dh-acryl, Octamer 5jh-aspartic, and Octamer 4jh-acryl.

35. The method of claim 1 wherein said nanofilm further comprises one or more surface attachment groups.

36. The method of claim 35 wherein said one or more surface attachment groups are independently selected from amino, hydroxyl, halo, thiol, alkynyl, magnesium halo, aldehyde, —CH═C($CH_3$)$_2$, vinyl, —(CH═CH)—CH═$CH_2$, —OC(O)CH($CH_3$)$_2$, —OC(O)CH═$CH_2$, —N(C(O)CH═$CH_2$, carboxylate, isocyanate, epoxide, and streptavidin.

37. The method of claim 1 wherein at least one of said amphiphilic macrocyclic modules has one or more hydrophobic tails that are cleavable from said at least one of said macrocyclic modules by at least one method chosen from chemical, thermal, photochemical, electrochemical, and irradiative.

38. The method of claim 1 wherein at least one of said amphiphilic macrocyclic modules has one or more hydrophilic groups.

39. The method of claim 38 wherein said one or more hydrophilic groups are independently selected from hydroxyl, methoxy, phenol, carboxylic acids and salts thereof, methyl- ethyl-, and vinyl-esters of carboxylic acids, amides, amino, cyano, ammonium salts, sulfonium salts, phosphonium salts, polyethylene glycols, epoxy groups, acrylates, sulfonamides, nitro, —OP(O)(O CH$_2$CH$_2$N$^+$ RR'R")O$^-$, guanidinium, aminate, acrylamide, pyridinium, and piperidine, wherein R, R', and R" are each independently selected from H and alkyl.

40. The method of claim 1 wherein at least one of said amphiphilic macrocyclic modules comprises one or more functional groups to impart amphiphilic character wherein said one or more functional groups are attached to said amphiphilic macrocyclic modules via a linkage chosen from carboxylate and amide.

41. The method of claim 40 wherein said one or more functional groups to impart amphiphilic character are independently selected from

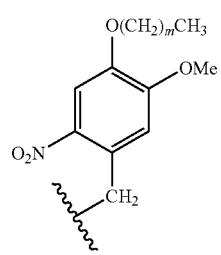

and

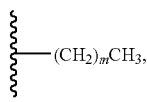

wherein m is seven to twenty-seven.

42. The method of claim 33 wherein said at least one of said amphiphilic macrocyclic modules and said at least one second amphiphilic macrocyclic module are coupled to at least one linker molecule.

43. The method of claim 42 wherein said at least one linker molecule is selected from

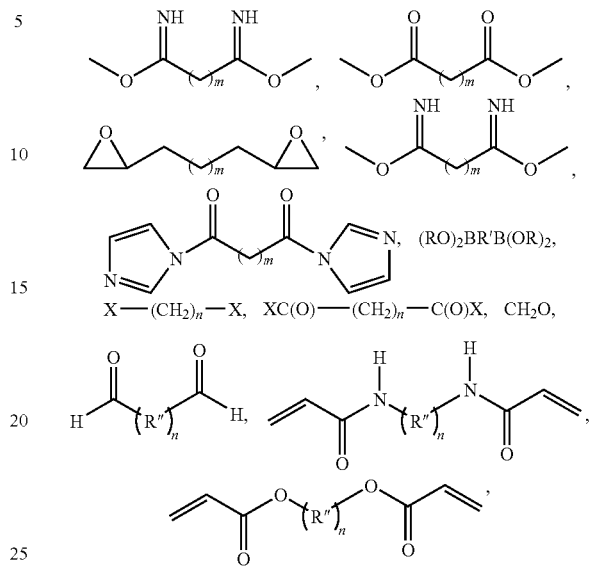

and mixtures thereof; wherein m is one to ten, n is one to six, each R is independently chosen from H and CH$_3$, each R' is independently chosen from —(CH$_2$)$_n$— and phenylene, each R" is independently chosen from —(CH$_2$)$_n$—, polyethylene glycol (PEG), and polypropylene glycol (PPG), and each X is independently chosen from Br, Cl, and I.

44. The method of claim 1 wherein one or more of said amphiphilic macrocyclic modules have at least one reactive functional group independently selected from Table 2.

* * * * *